US011339367B2

(12) United States Patent
Gerke et al.

(10) Patent No.: US 11,339,367 B2
(45) Date of Patent: May 24, 2022

(54) **HYPERBLEBBING *SHIGELLA* STRAINS**

(71) Applicant: GLAXOSMITHKLINE BIOLOGICALS SA, Rixensart (BE)

(72) Inventors: Christiane Gerke, Siena (IT); Francesco Berlanda Scorza, Siena (IT); Allan Saul, Siena (IT); Luana Maggiore, Siena (IT)

(73) Assignee: GLAXOSMITHKLINE BIOLOGICALS SA, Rixensart (BE)

(*) Notice: Subject to any disclaimer, the term of this patent is extended or adjusted under 35 U.S.C. 154(b) by 421 days.

(21) Appl. No.: 15/094,077

(22) Filed: Apr. 8, 2016

(65) Prior Publication Data

US 2016/0289632 A1 Oct. 6, 2016

Related U.S. Application Data

(63) Continuation of application No. 13/498,723, filed as application No. PCT/IB2010/002582 on Sep. 28, 2010, now abandoned.

(30) Foreign Application Priority Data

Sep. 28, 2009 (GB) ..................................... 0917002

(51) Int. Cl.

| | |
|---|---|
| *C12N 1/20* | (2006.01) |
| *C07K 14/25* | (2006.01) |
| *A61K 39/00* | (2006.01) |
| *A61K 35/12* | (2015.01) |

(52) U.S. Cl.
CPC ................ *C12N 1/20* (2013.01); *C07K 14/25* (2013.01); *A61K 39/00* (2013.01); *A61K 2035/122* (2013.01); *Y02A 50/30* (2018.01)

(58) Field of Classification Search
None
See application file for complete search history.

(56) References Cited

U.S. PATENT DOCUMENTS

| | | | |
|---|---|---|---|
| 5,057,540 | A | 10/1991 | Kensil et al. |
| 5,681,736 | A | 10/1997 | Pace et al. |
| 5,916,588 | A | 6/1999 | Popescu et al. |
| 6,080,725 | A | 6/2000 | Marciani |
| 6,090,406 | A | 7/2000 | Popescu et al. |
| 6,207,646 | B1 | 3/2001 | Krieg et al. |
| 6,239,116 | B1 | 5/2001 | Krieg et al. |
| 6,429,199 | B1 | 8/2002 | Krieg et al. |
| 8,062,644 | B2 | 11/2011 | Pizza et al. |
| 2007/0014805 | A1 | 1/2007 | Dalencon et al. |

FOREIGN PATENT DOCUMENTS

| | | | |
|---|---|---|---|
| AU | 20122207041 | A1 | 8/2012 |
| EP | 109942 | A2 | 5/1984 |
| EP | 626169 | A2 | 11/1994 |
| EP | 689454 | A1 | 1/1996 |
| EP | 735898 | A1 | 10/1996 |
| EP | 761231 | A1 | 3/1997 |
| EP | 835318 | A2 | 4/1998 |
| WO | 9014837 | A1 | 12/1990 |
| WO | 9511700 | A1 | 5/1995 |
| WO | 9517211 | A1 | 6/1995 |
| WO | 9611711 | A1 | 4/1996 |
| WO | 9633739 | A1 | 10/1996 |
| WO | WO/1997/019688 | | 6/1997 |
| WO | 9840100 | A1 | 9/1998 |
| WO | 9842375 | A1 | 10/1998 |
| WO | 9857659 | A1 | 12/1998 |
| WO | 9911241 | A1 | 3/1999 |
| WO | 9927960 | A1 | 6/1999 |
| WO | 9940936 | A2 | 8/1999 |
| WO | 9944636 | A2 | 9/1999 |
| WO | 9962923 | A2 | 12/1999 |
| WO | 0007621 | A3 | 6/2000 |
| WO | WO 2001/25254 | | 4/2001 |
| WO | 0195935 | A1 | 12/2001 |
| WO | 0226757 | A2 | 4/2002 |
| WO | 02062378 | A2 | 8/2002 |
| WO | 03035836 | A2 | 5/2003 |
| WO | 2004014419 | A1 | 2/2004 |
| WO | 2004084938 | A1 | 10/2004 |
| WO | 2005097181 | A1 | 10/2005 |
| WO | 2006113373 | A2 | 10/2006 |

OTHER PUBLICATIONS

Bernadac et al (Journal of Bacteriology 180(18):4875-4878, 1998).*
Berlanda, "Outer Membrane Blebs Vaccine Against Shigella," Meeting of the European Initiative for Basic Research in Microbiology and Infectious Diseases (EIMID), Potsdam, Germany, Sep. 30-Oct. 2, 2009, Abstract, <http://www.eimid.org/documents/EIMID_meeting_2009_Book_of_abstracts.pdf> [retrieved Jan. 20, 2011], 36 pages.
Bernadac et al., "*Escherichia coli* tol-pal Mutants Form Outer Membrane Vesicles," Journal of Bacteriology 180(18):4872-4878, Sep. 1998.
D'Hauteville et al., Two msbB Genes Encoding Maximal Acylation of Lipid A Are Required for Invasive Shigella flexneri to Mediate Inflammatory Rupture and Destruction of the Intestinal Epithelium, J. Immunol, 168:5240-51, 2002.
Dutta et al, "Release of Shiga Toxin by Membrane Vesicles in Shigella dysenteriae Serotype 1 Strains and In Vitro Effects of Antimicrobials on Toxin Production and Release," Microbia. Immunol. 48(12):965-969, 2004.
Habib and Jackson, "Identification of a B Subunit Gene Promoter in the Shiga Toxin Operon of Shigella dysenteriae 1," Journal of Bacteriology, 1992, vol. 174, No. 20, pp. 6498-6507.
Henry et al., "Improved Methods for Producing Outer Membrane Vesicles in Gram-Negative Bacteria," Research in Microbiology 155(6):437-446, Jul./Aug. 2004.
International Preliminary Report on Patentability and Written Opinion dated Apr. 3, 2012, in corresponding International Application No. PCT/IB2010/002582, filed Sep. 28,2010, 10 pages.

(Continued)

*Primary Examiner* — Patricia Duffy

(74) *Attorney, Agent, or Firm* — Loza & Loza, LLP; Michelle L. Lewis

(57) ABSTRACT

Hyperblebbing *Shigella* strains are generated by disrupting one or more components of the Tol-Pal system. The blebs from these strains are useful immunogens for vaccination. The individual proteins found in these blebs can also be used as immunogens.

12 Claims, 12 Drawing Sheets

Specification includes a Sequence Listing.

(56) References Cited

OTHER PUBLICATIONS

International Search Report dated Jun. 8, 2011, issued in corresponding International Application No. PCT/B2010/002582, filed Sep. 28, 2010, 7 pages.
Jemal et al., "Analysis of Shiga Toxin Subunit Association by Using Hybrid a Polypeptides and Site-Specific Mutagenesis," Journal of Bacteriology, Jun. 1995, vol. 177, No. 11, pp. 3128-3132.
Kadurugamuwa et al, "Delivery of the Non-Membrane-Permeative Antibiotic Gentamicin into Mammalian Cells by Using Shigella flexneriMembrane Vesicles," Antimicrobioal Agents and Chemotherapy, 42(6):1476-1483, 1998.
Köhler et al., "Shigella flexneri Interactions with the Basolateral Membrane Domain of Polarized Model Intestinal Epithelium: Role of Lipopolysaccharide in Cell Invasion and in Activation of the Mitogen-Activated Protein Kinase ERK," Infection and Immunity, 2002, vol. 70, No. 3, pp. 1150-1158.
Liu et al., "Structure and genetics of Shigella O antigens" FEMS Microbiol Rev., 32:627-653, Apr. 17, 2008.
McKenzie et al, "Safety and immunogenicity of WRSd1, a live attenuated Shigella dysenteriae type 1 vaccine candidate," Vaccine 26:3291-3296, Apr. 16, 2008.
Nagy et al., "Strategies for the development of vaccines conferring broad-spectrum protection," International Journal of Medical Microbiology, 298:379-395, Jul. 2008).
Nichols et al, "htrB of Haemophilus influenzae: determination of biochemical activity and effects on virulence and lipooligosaccharide toxicity," Journal of Endotoxin Research, 4:163-72, 1997.
Nie et al., "Complete genome sequence of Shigella flexneri 5b and comparison with Shigella flexneri 2a," BMC Genomics, BioMed Central, 2006, 7:173, pp. 1-9.
Nucleotide Sequence Accession No. Q0T0M2, deposited in UniProtKB/ TrEMBL on Sep. 5, 2006, Description: Outer Membrane Channel Protein, <http://www.uniprot.org>, 1 page.
Sandlin, "A virulence of Rough Mutants of Shigella flexneri: Requirement of O Antigen for Correct Unipolar Localization of IcsA in the Bacterial Outer Membrane," Infection and Immunity 63(1):229-237, Jan. 1995.
Scorza et al., "Proteomics Characterization of Outer Membrane Vesicles from the Extraintestinal Pathogenic Escherichia coli ?tolR IHE3034 Mutant," Molecular and Cellular Proteomics, 7:473-485, 2008.
Yamamoto & Shinoda, "Iron Uptake Mechanisms of Pathogenic Bacteria," Japanese Journal of Bacteriology, 1996, vol. 51, No. 2, pp. 523-547.
Yang et al., "Human and animal pathogenic bacteriology," Hebei Science & Technology Press, 2003, pp. 489-493, with partial English translation.
European Patent Office, Partial Search Report and accompanying Provisional Opinion dated Nov. 15, 2017 for EP3279313; 10 total pages.
Wessel et al., *Role of Pseudomonas aeruginosa Peptidoglycan-Associated Outer Membrane Proteins in Vesicle Formation*, 2013 J. Bacteriology 195(2):213-219.
Dennis et al., *Identification and Characterization of the tolQRA Genes of Pseudomonas aeruginosa*, 1996 J. Bacteriology 178(24):7059-7068.
Allison et al., Res Immunol, vol. 143, 1992, pp. 519-525.
Ausubel et al., Current Protocols in Molecular Biology, 2010, 30.0.1.
Barr et al., Advanced Drug Delivery Reviews, vol. 32, 1998, pp. 247-271.
Beignon et al., Infect Immun, vol. 70, 2002, pp. 3012-3019.
Beloin et al., Mol Genet Genomics, vol. 270, No. 1, 2003, pp. 66-77.
Bhagat et al., BBRC, vol. 300, 2003, pp. 853-861.
Blackwell et al., JLMMUNOL, vol. 170, 2003, pp. 4061-4068.
Brusic et al., Bioinformatics, vol. 14, No. 2, 1998, pp. 121-130.
Bublil et al., Proteins, vol. 68, No. 1, 2007, pp. 294-304.
Carter, Methods Mol Biol, vol. 36, 1994, pp. 207-223.
Chen et al., Amino Acids, vol. 33, No. 3, 2007, pp. 423-428.
Clementz et al., J. Biol. Chem., vol. 16, 1997, pp. 10353-10360.
Davenport et al., Immunogenetics, vol. 42, 1995, pp. 392-297.
Day et al., Infect Immun, vol. 69, 2001, pp. 7471-7480.
De Lalla et al., J. Immunol., vol. 163, 1999, pp. 1725-1729.
D'Hauteville et al., J Immunol., vol. 168, 2002, pp. 5240-5251.
Domenighini et al., Mol Microbiol, vol. 15, 1995, pp. 1165-1167.
Edwards-Jones et al., Microbiol, vol. 150, 2004, pp. 1079-1084.
Erlandson; Mackey, J Bacteriol, vol. 75, No. 3, 1958, pp. 253-257.
Evans et al., Expert Rev Vaccines, vol. 2, 2003, pp. 219-229.
Feller; De La Cruz, Nature, vol. 349, No. 6311, 1991, pp. 720-721.
Geysen et al., PNAS USA, vol. 81, 1984, pp. 3998-4002.
Hariharan et al., Cancer Res, vol. 55, 1995, pp. 3486-3489.
Henry et al., Res Microbiol, vol. 155, 2004, pp. 437-446.
Hopp, Peptide Research, vol. 6, 1993, pp. 183-190.
Jameson, Ba et al., CABIOS, vol. 4, No. 1, 1988, pp. 181-186.
Johnson et al., Bioorg Med Chem Lett, vol. 9, 1999, pp. 2273-2278.
Kandimalla et al., Biochemical Society Transactions, vol. 31, 2003, pp. 654-658.
Kandimalla et al., BBRC, vol. 306, 2003, pp. 948-953.
Kandimalla et al., Nucleic Acids Research, vol. 31, 2003, pp. 2393-2400.
Köhler et al., Infect Immun, vol. 70, 2002, pp. 1150-1158.
Krieg, Nature Medicine, vol. 9, 2003, pp. 831-835.
Krieg, Trends Immunol, vol. 23, 2002, pp. 64-65.
Kweon, Curr Opin Infect Dis., vol. 21, No. 3, 2008, pp. 313-318.
Kwok et al., Trends Immunol, vol. 22, 2001, pp. 583-588.
Lingnau et al., Expert Rev Vaccines, vol. 6, 2007, pp. 741-746.
Liu et al., Sci China C Life Sci., vol. 48, No. 3, 2005, pp. 228-240.
Maksyutov et al., Comput Appl Biosci, vol. 9, No. 3, 1993, pp. 291-297.
McCluskie et al., FEMS Immunology and Medical Microbiology, vol. 32, 2002, pp. 179-185.
Meister etal, Vaccine, vol. 13, No. 6, 1995, pp. 581-591.
Meraldi et al., Vaccine, vol. 21, 2003, pp. 2485-2491.
Murphy et al., BMC Molecular Biology, vol. 4, 2003, pp. 11.
Nichols et al., J. Endotoxin Res., vol. 4, 1997, pp. 163-172.
Pajak et al., Vaccine, vol. 21, 2003, pp. 836-842.
Partidos et al., Immunol Lett, vol. 67, 1999, pp. 209-216.
Peppoloni et al., Expert Rev Vaccines, vol. 2, 2003, pp. 285-293.
Pine et al., J Control Release, vol. 85, 2002, pp. 263-270.
Pizza et al., Int J Med Microbiol, vol. 290, 2000, pp. 455-461.
Pizza et al., Vaccine, vol. 19, 2001, pp. 2534-2541.
Podda; Del Giudice, Expert Rev Vaccines, vol. 2, 2003, pp. 197-203.
Ferrari et al. "Outer membrane vesicles from group B Neisseria meningitidis ⁻gna33 mutant: Proteomic and immunological comparison with detergent-derived outer membrane vesicles" Proteomics 2006, 6 (1856-1866).
Podda, Vaccine, vol. 19, 2001, pp. 2673-2680.
Raddrizzani; Hammer, Brief Bioinform, vol. 1, No. 2, 2000, pp. 179-189.
Roberts et al., AIDS Res Hum Retroviruses, vol. 12, No. 7, 1996, pp. 593-610.
Ryan et al., Infect Immun, vol. 67, 1999, pp. 6270-6280.
Sandlin et al., Infect. Immun., vol. 63, 1995, pp. 229-237.
Scharton-Kersten et al., Infect Immun, vol. 68, 2000, pp. 5306-5313.
Schellack et al., Vaccine, vol. 24, 2006, pp. 5461-5472.
Singh, J Cont Release, vol. 70, 2001, pp. 267-276.
Sjolanderet et al., Advanced Drug Delivery Reviews, vol. 32, 1998, pp. 321-338.
Smith; Waterman, Adv. Appl. Math., vol. 2, 1981, pp. 482-489.
Stanley, Clin Exp Dermatol, vol. 27, 2002, pp. 571-577.
Tebbey et al., Vaccine, vol. 18, 2000, pp. 2723-2734.
Uyttendaele et al., International Journal Offood Microbiology, vol. 70, No. 3, 2001, pp. 255-265.
Welling et al., FEBS Lett., vol. 188, 1985, pp. 215-218.
Jones (2003) Curr Opin Investig Drugs 4:214-218.

\* cited by examiner

*S. flexneri2a*

SEQUENCE LISTING

<160> NUMBER OF SEQ ID NOS: 136

<210> SEQ ID NO 1
<211> LENGTH: 413
<212> TYPE: PRT
<213> ORGANISM: Shigella flexneri

<400> SEQUENCE: 1

```
Met Ser Lys Ala Thr Glu Gln Asn Asp Lys Leu Lys Arg Ala Ile Ile
1               5                   10                  15
Ile Ser Ala Val Leu His Val Ile Leu Phe Ala Ala Leu Ile Trp Ser
                20                  25                  30
Ser Phe Asp Glu Asn Ile Glu Ala Ser Ala Gly Gly Gly Gly Gly Ser
            35                  40                  45
Ser Ile Asp Ala Val Met Val Asp Ser Gly Ala Val Val Glu Gln Tyr
        50                  55                  60
Lys Arg Met Gln Ser Gln Glu Ser Ser Ala Lys Arg Ser Asp Glu Gln
65                  70                  75                  80
Arg Lys Met Lys Glu Gln Gln Ala Ala Glu Glu Leu Arg Glu Lys Gln
                85                  90                  95
Ala Ala Glu Gln Glu Arg Leu Lys Gln Leu Glu Lys Glu Arg Leu Ala
            100                 105                 110
Ala Gln Glu Gln Lys Lys Gln Ala Glu Ala Ala Lys Gln Ala Glu
        115                 120                 125
Leu Lys Gln Lys Gln Ala Glu Val Ala Ala Lys Ala Ala Ala Asp
    130                 135                 140
Ala Lys Ala Ala Glu Glu Ala Ala Lys Lys Ala Ala Asp Ala Lys
145                 150                 155                 160
Lys Lys Ala Glu Ala Glu Ala Lys Ala Ala Glu Ala Gln Lys
                165                 170                 175
Lys Ala Glu Val Ala Ala Ala Ala Leu Lys Lys Ala Glu Ala Ala
            180                 185                 190
Glu Ala Ala Ala Glu Ala Arg Lys Lys Ala Thr Glu Ala Ala
        195                 200                 205
Glu Lys Ala Lys Ala Glu Glu Lys Lys Ala Ala Glu Lys Ala
    210                 215                 220
Ala Ala Asp Lys Lys Ala Ala Glu Lys Ala Ala Asp Lys Lys
225                 230                 235                 240
Ala Ala Glu Lys Ala Ala Ala Asp Lys Ala Ala Asp Lys Lys Ala
                245                 250                 255
Ala Ala Glu Lys Ala Ala Asp Lys Lys Ala Ala Ala Lys Ala
            260                 265                 270
Ala Ala Glu Lys Ala Ala Ala Lys Ala Ala Glu Ala Asp Asp
        275                 280                 285
Ile Phe Gly Glu Leu Ser Ser Gly Lys Asn Ala Pro Lys Thr Gly Gly
    290                 295                 300
Gly Ala Lys Gly Asn Asn Ala Ser Pro Ala Gly Ser Gly Asn Thr Lys
305                 310                 315                 320
Asn Asn Gly Ala Ser Gly Ala Asp Ile Asn Asn Tyr Ala Gly Gln Ile
                325                 330                 335
Lys Ser Ala Ile Glu Ser Lys Phe Tyr Asp Ala Ser Ser Tyr Ala Gly
            340                 345                 350
Lys Thr Cys Thr Leu Arg Ile Lys Leu Ala Pro Asp Gly Met Leu Leu
        355                 360                 365
Asp Ile Lys Pro Glu Gly Gly Asp Pro Ala Leu Cys Gln Ala Ala Leu
    370                 375                 380
Ala Ala Ala Lys Leu Ala Lys Ile Pro Lys Pro Ser Gln Ala Val
385                 390                 395                 400
Tyr Glu Val Phe Lys Asn Ala Pro Leu Asp Phe Lys Pro
                405                 410
```

<210> SEQ ID NO 2
<211> LENGTH: 430
<212> TYPE: PRT
<213> ORGANISM: Shigella flexneri

<400> SEQUENCE: 2

```
Met Lys Gln Ala Leu Arg Val Ala Phe Gly Phe Leu Ile Leu Trp Ala
1               5                   10                  15

Ser Val Leu His Ala Glu Val Arg Ile Val Ile Asp Ser Gly Val Asp
                20                  25                  30

Ser Gly Arg Pro Ile Gly Val Pro Phe Gln Trp Ala Gly Pro Gly
            35                  40                  45

Ala Ala Pro Glu Asp Ile Gly Gly Ile Val Ala Ala Asp Leu Arg Asn
        50                  55                  60

Ser Gly Lys Phe Asn Pro Leu Asp Arg Ala Arg Leu Pro Gln Gln Pro
65                  70                  75                  80

Gly Ser Ala Gln Glu Val Gln Pro Ala Ala Trp Ser Ala Leu Gly Ile
                85                  90                  95

Asp Ala Val Val Val Gly Gln Val Thr Pro Asn Pro Asp Gly Ser Tyr
                100                 105                 110

Asn Val Ala Tyr Gln Leu Val Asp Thr Gly Gly Ala Pro Gly Thr Val
            115                 120                 125

Leu Ala Gln Asn Ser Tyr Lys Val Asn Lys Gln Trp Leu Arg Tyr Ala
130                 135                 140

Gly His Thr Ala Ser Asp Glu Val Phe Glu Lys Leu Thr Gly Ile Lys
145                 150                 155                 160

Gly Ala Phe Arg Thr Arg Ile Ala Tyr Val Gln Thr Asn Gly Gly
                165                 170                 175

Gln Phe Pro Tyr Glu Leu Arg Val Ser Asp Tyr Asp Gly Tyr Asn Gln
            180                 185                 190

Phe Val Val His Arg Ser Pro Gln Pro Leu Met Ser Pro Ala Trp Ser
        195                 200                 205

Pro Asp Gly Ser Lys Leu Ala Tyr Val Thr Phe Glu Ser Gly Arg Ser
210                 215                 220

Ala Leu Val Ile Gln Thr Leu Ala Asn Gly Ala Val Arg Gln Val Ala
225                 230                 235                 240

Ser Phe Pro Arg His Asn Gly Ala Pro Ala Phe Ser Pro Asp Gly Ser
                245                 250                 255

Lys Leu Ala Phe Ala Leu Ser Lys Thr Gly Ser Leu Asn Leu Tyr Val
            260                 265                 270

Met Asp Leu Ala Ser Gly Gln Ile Arg Gln Val Thr Asp Gly Arg Ser
        275                 280                 285

Asn Asn Thr Glu Pro Thr Trp Phe Pro Asp Ser Gln Asn Leu Ala Phe
    290                 295                 300

Thr Ser Asp Gln Ala Gly Arg Pro Gln Val Tyr Lys Val Asn Ile Asn
305                 310                 315                 320

Gly Gly Ala Pro Gln Arg Ile Thr Trp Glu Gly Ser Gln Asn Gln Asp
                325                 330                 335

Ala Asp Val Ser Ser Asp Gly Lys Phe Met Val Met Ser Ser Asn
            340                 345                 350

Gly Gly Gln Gln His Ile Ala Lys Gln Asp Leu Ala Thr Gly Gly Val
        355                 360                 365

Gln Val Leu Ser Ser Thr Phe Leu Asp Glu Thr Pro Ser Leu Ala Pro
    370                 375                 380
```

Asn Gly Thr Met Val Ile Tyr Ser Ser Ser Gln Met Gly Ser Val
385                 390                 395                 400

Leu Asn Leu Val Ser Thr Asp Gly Arg Phe Lys Ala Arg Leu Pro Ala
            405                 410                 415

Thr Asp Gly Gln Val Lys Phe Pro Ala Trp Ser Pro Tyr Leu
        420                 425                 430

<210> SEQ ID NO 3
<211> LENGTH: 230
<212> TYPE: PRT
<213> ORGANISM: Shigella flexneri

<400> SEQUENCE: 3

Met Thr Asp Met Asn Ile Leu Asp Leu Phe Leu Lys Ala Ser Leu Leu
1               5                   10                  15

Val Lys Leu Ile Met Leu Ile Leu Ile Gly Phe Ser Ile Ala Ser Trp
            20                  25                  30

Ala Ile Ile Ile Gln Arg Thr Arg Ile Leu Asn Ala Ala Ala Arg Glu
        35                  40                  45

Ala Glu Ala Phe Glu Asp Lys Phe Trp Ser Gly Ile Glu Leu Ser Arg
    50                  55                  60

Leu Tyr Gln Glu Ser Gln Gly Lys Arg Asp Asn Leu Thr Gly Ser Glu
65                  70                  75                  80

Gln Ile Phe Tyr Ser Gly Phe Lys Glu Phe Val Arg Leu His Arg Ala
                85                  90                  95

Asn Ser His Ala Pro Glu Ala Val Val Glu Gly Ala Ser Arg Ala Met
            100                 105                 110

Arg Ile Ser Met Asn Arg Glu Leu Glu Asn Leu Glu Thr His Ile Pro
        115                 120                 125

Phe Leu Gly Thr Val Gly Ser Ile Ser Pro Tyr Ile Gly Leu Phe Gly
    130                 135                 140

Thr Val Trp Gly Ile Met His Ala Phe Ile Ala Leu Gly Ala Val Lys
145                 150                 155                 160

Gln Ala Thr Leu Gln Met Val Ala Pro Gly Ile Ala Glu Ala Leu Ile
                165                 170                 175

Ala Thr Ala Ile Gly Leu Phe Ala Ala Ile Pro Ala Val Met Ala Tyr
            180                 185                 190

Asn Arg Leu Asn Gln Arg Val Asn Lys Leu Glu Leu Asn Tyr Asp Asn
        195                 200                 205

Phe Met Glu Glu Phe Thr Ala Ile Leu His Arg Gln Ala Phe Thr Val
    210                 215                 220

Ser Glu Ser Asn Lys Gly
225                 230

<210> SEQ ID NO 4
<211> LENGTH: 142
<212> TYPE: PRT
<213> ORGANISM: Shigella flexneri

<400> SEQUENCE: 4

Met Ala Arg Ala Arg Gly Arg Gly Arg Arg Asp Leu Lys Ser Glu Ile
1               5                   10                  15

Asn Ile Val Pro Leu Leu Asp Val Leu Leu Val Leu Leu Ile Phe
            20                  25                  30

Met Ala Thr Ala Pro Ile Ile Thr Gln Ser Val Glu Val Asp Leu Pro
        35                  40                  45

```
Asp Ala Thr Glu Ser Gln Ala Val Ser Ser Asn Asp Asn Pro Pro Val
    50                  55                  60

Ile Val Glu Val Ser Gly Ile Gly Gln Tyr Thr Val Val Glu Lys
 65                  70                  75                  80

Asp Arg Leu Glu Arg Leu Pro Pro Gln Val Val Ala Glu Val Ser
                 85                  90                  95

Ser Arg Phe Lys Ala Asn Pro Lys Thr Val Phe Leu Ile Gly Gly Ala
                100                 105                 110

Lys Asp Val Pro Tyr Asp Glu Ile Ile Lys Ala Leu Asn Leu Leu His
                115                 120                 125

Ser Ala Gly Val Lys Ser Val Gly Leu Met Thr Gln Pro Ile
                130                 135                 140
```

<210> SEQ ID NO 5
<211> LENGTH: 173
<212> TYPE: PRT
<213> ORGANISM: Shigella flexneri

<400> SEQUENCE: 5

```
Met Gln Leu Asn Lys Val Leu Lys Gly Leu Met Ile Ala Leu Pro Val
 1               5                  10                  15

Met Ala Ile Ala Ala Cys Ser Ser Asn Lys Asn Ala Ser Asn Asp Gly
                20                  25                  30

Ser Glu Gly Met Leu Gly Ala Gly Thr Gly Met Asp Ala Asn Gly Gly
                35                  40                  45

Asn Gly Asn Met Ser Ser Glu Glu Gln Ala Arg Leu Gln Met Gln Gln
    50                  55                  60

Leu Gln Gln Asn Asn Ile Val Tyr Phe Asp Leu Asp Lys Tyr Asp Ile
 65                  70                  75                  80

Arg Ser Asp Phe Ala Gln Met Leu Asp Ala His Ala Asn Phe Leu Arg
                85                  90                  95

Ser Asn Pro Ser Tyr Lys Val Thr Val Glu Gly His Ala Asp Glu Arg
                100                 105                 110

Gly Thr Pro Glu Tyr Asn Ile Ser Leu Gly Glu Arg Arg Ala Asn Ala
                115                 120                 125

Val Lys Met Tyr Leu Gln Gly Lys Gly Val Ser Ala Asp Gln Ile Ser
                130                 135                 140

Ile Val Ser Tyr Gly Lys Glu Lys Pro Ala Val Leu Gly His Asp Glu
145                 150                 155                 160

Ala Ala Tyr Ser Lys Asn Arg Arg Ala Val Leu Val Tyr
                165                 170
```

<210> SEQ ID NO 6
<211> LENGTH: 11
<212> TYPE: PRT
<213> ORGANISM: Artificial Sequence
<220> FEATURE:
<223> OTHER INFORMATION: Cationic peptide

<400> SEQUENCE: 6

```
Lys Leu Lys Leu Leu Leu Leu Leu Lys Leu Lys
 1               5                  10
```

<210> SEQ ID NO 7
<211> LENGTH: 26
<212> TYPE: DNA
<213> ORGANISM: Artificial Sequence
<220> FEATURE:
<223> OTHER INFORMATION: Immunostimulatory oligonucleotide
<220> FEATURE:
<221> NAME/KEY: modified_base
<222> LOCATION: 1, 3, 5, 7, 9, 11, 13, 15, 17, 19, 21, 23, 25
<223> OTHER INFORMATION: 'n' is 'i' (Inosine)

<400> SEQUENCE: 7
ncncncncnc ncncncncnc ncncnc                                        26

<210> SEQ ID NO 8
<211> LENGTH: 493
<212> TYPE: PRT
<213> ORGANISM: Shigella flexneri

<400> SEQUENCE: 8

Met Lys Lys Leu Leu Pro Ile Leu Ile Gly Leu Ser Leu Ser Gly Phe
1               5                   10                  15

Ser Ser Leu Ser Gln Ala Glu Asn Leu Met Gln Val Tyr Gln Gln Ala
            20                  25                  30

Arg Leu Ser Asn Pro Glu Leu Arg Lys Ser Ala Ala Asp Arg Asp Ala
        35                  40                  45

Ala Phe Glu Lys Ile Asn Glu Ala Arg Ser Pro Leu Leu Pro Gln Leu
    50                  55                  60

Gly Leu Gly Ala Asp Tyr Thr Tyr Ser Asn Gly Tyr Arg Asp Ala Asn
65                  70                  75                  80

Gly Ile Asn Ser Asn Ala Thr Ser Ala Ser Leu Gln Leu Thr Gln Ser
                85                  90                  95

Ile Phe Asp Met Ser Lys Trp Arg Ala Leu Thr Leu Gln Glu Lys Ala
            100                 105                 110

Ala Gly Ile Gln Asp Val Thr Tyr Gln Thr Asp Gln Gln Thr Leu Ile
        115                 120                 125

Leu Asn Thr Ala Thr Ala Tyr Phe Asn Val Leu Asn Ala Ile Asp Val
    130                 135                 140

Leu Ser Tyr Thr Gln Ala Gln Lys Glu Ala Ile Tyr Arg Gln Leu Asp
145                 150                 155                 160

Gln Thr Thr Gln Arg Phe Asn Val Gly Leu Val Ala Ile Thr Asp Val
                165                 170                 175

Gln Asn Ala Arg Ala Gln Tyr Asp Thr Val Leu Ala Asn Glu Val Thr
            180                 185                 190

Ala Arg Asn Asn Leu Asp Asn Ala Val Glu Gln Leu Arg Gln Ile Thr
        195                 200                 205

Gly Asn Tyr Tyr Pro Glu Leu Ala Ala Leu Asn Val Glu Asn Phe Lys
    210                 215                 220

Thr Asp Lys Pro Gln Pro Val Asn Ala Leu Leu Lys Glu Ala Glu Lys
225                 230                 235                 240

Arg Asn Leu Ser Leu Leu Gln Ala Arg Leu Ser Gln Asp Leu Glu Arg
                245                 250                 255

Glu Gln Ile Arg Gln Ala Gln Asp Gly His Leu Pro Thr Leu Asp Leu
            260                 265                 270

Thr Ala Ser Thr Gly Ile Ser Asp Thr Ser Tyr Ser Gly Ser Lys Thr
        275                 280                 285

Arg Gly Ala Ala Gly Thr Gln Tyr Asp Asp Ser Asn Met Gly Gln Asn
    290                 295                 300

Lys Val Gly Leu Ser Phe Ser Leu Pro Ile Tyr Gln Gly Gly Met Val
305                 310                 315                 320

Asn Ser Gln Val Lys Gln Ala Gln Tyr Asn Phe Val Gly Ala Ser Glu
                325                 330                 335

```
Gln Leu Glu Ser Ala His Arg Ser Val Val Gln Thr Val Arg Ser Ser
                340                 345                 350

Phe Asn Asn Ile Asn Ala Ser Ile Ser Ser Ile Asn Ala Tyr Lys Gln
            355                 360                 365

Ala Val Val Ser Ala Gln Ser Ser Leu Asp Ala Met Glu Ala Gly Tyr
        370                 375                 380

Ser Val Gly Thr Arg Thr Ile Val Asp Val Leu Asp Ala Thr Thr Thr
385                 390                 395                 400

Leu Tyr Asn Ala Lys Gln Glu Leu Ala Asn Ala Arg Tyr Asn Tyr Leu
                405                 410                 415

Ile Asn Gln Leu Asn Ile Lys Ser Ala Leu Gly Thr Leu Asn Glu Gln
            420                 425                 430

Asp Leu Leu Ala Leu Asn Asn Ala Leu Ser Lys Pro Val Ser Thr Asn
        435                 440                 445

Pro Glu Asn Val Ala Pro Gln Thr Pro Glu Gln Asn Ala Ile Ala Asp
    450                 455                 460

Gly Tyr Ala Pro Asp Ser Pro Ala Pro Val Val Gln Gln Thr Ser Ala
465                 470                 475                 480

Arg Thr Thr Thr Ser Asn Gly His Asn Pro Phe Arg Asn
                485                 490

<210> SEQ ID NO 9
<211> LENGTH: 368
<212> TYPE: PRT
<213> ORGANISM: Shigella sonnei

<400> SEQUENCE: 9

Met Lys Val Lys Val Leu Ser Leu Leu Val Pro Ala Leu Leu Val Ala
1               5                   10                  15

Gly Ala Ala Asn Ala Ala Glu Val Tyr Asn Lys Asp Gly Asn Lys Leu
            20                  25                  30

Asp Leu Tyr Gly Lys Val Asp Gly Leu His Tyr Phe Ser Asp Asn Lys
        35                  40                  45

Ser Glu Asp Gly Asp Gln Thr Tyr Val Arg Leu Gly Phe Lys Gly Val
    50                  55                  60

Thr Gln Val Thr Asp Gln Leu Thr Gly Tyr Gly Gln Trp Glu Tyr Gln
65                  70                  75                  80

Ile Gln Gly Asn Thr Ser Glu Asp Asn Lys Glu Asn Ser Trp Thr Arg
                85                  90                  95

Val Ala Phe Ala Gly Leu Lys Phe Gln Asp Val Gly Ser Phe Asp Tyr
            100                 105                 110

Gly Arg Asn Tyr Gly Val Val Tyr Asp Val Thr Ser Trp Thr Asp Val
        115                 120                 125

Leu Pro Glu Phe Gly Gly Asp Thr Tyr Gly Ser Asp Asn Phe Met Gln
    130                 135                 140

Gln Arg Gly Asn Gly Phe Ala Thr Tyr Arg Asn Thr Asp Phe Phe Gly
145                 150                 155                 160

Leu Val Asp Gly Leu Asn Phe Ala Val Gln Tyr Gln Gly Lys Asn Gly
                165                 170                 175

Ser Val Ser Gly Glu Gly Met Thr Asn Asn Gly Arg Gly Ala Leu Arg
            180                 185                 190

Gln Asn Gly Asp Gly Val Gly Gly Ser Ile Thr Tyr Asp Tyr Glu Gly
        195                 200                 205

Phe Gly Ile Gly Gly Ala Ile Ser Ser Ser Lys Arg Thr Asp Asp Gln
    210                 215                 220
```

```
Asn Ser Pro Leu Tyr Ile Gly Asn Gly Asp Arg Ala Glu Thr Tyr Thr
225                 230                 235                 240

Gly Gly Leu Lys Tyr Asp Ala Asn Asn Ile Tyr Leu Ala Ala Gln Tyr
                245                 250                 255

Thr Gln Thr Tyr Asn Ala Thr Arg Val Gly Ser Leu Gly Trp Ala Asn
            260                 265                 270

Lys Ala Gln Asn Phe Glu Ala Val Ala Gln Tyr Gln Phe Asp Phe Gly
        275                 280                 285

Leu Arg Pro Ser Val Ala Tyr Leu Gln Ser Lys Gly Lys Asn Leu Gly
    290                 295                 300

Thr Ile Ala Gly Arg Asn Tyr Asp Asp Glu Asp Ile Leu Lys Tyr Val
305                 310                 315                 320

Asp Val Gly Ala Thr Tyr Tyr Phe Asn Lys Asn Met Ser Thr Tyr Val
                325                 330                 335

Asp Tyr Lys Ile Asn Leu Leu Asp Asp Asn Gln Phe Thr Arg Asp Ala
            340                 345                 350

Gly Ile Asn Thr Asp Asn Ile Val Ala Leu Gly Leu Val Tyr Gln Phe
        355                 360                 365

<210> SEQ ID NO 10
<211> LENGTH: 346
<212> TYPE: PRT
<213> ORGANISM: Shigella sonnei

<400> SEQUENCE: 10

Met Lys Lys Thr Ala Ile Ala Ile Ala Val Ala Leu Ala Gly Phe Ala
1               5                   10                  15

Thr Val Ala Gln Ala Ala Pro Lys Asp Asn Thr Trp Tyr Thr Gly Ala
                20                  25                  30

Lys Leu Gly Trp Ser Gln Tyr His Asp Thr Gly Phe Ile Asn Asn Asn
            35                  40                  45

Gly Pro Thr His Glu Asn Gln Leu Gly Ala Gly Ala Phe Gly Gly Tyr
        50                  55                  60

Gln Val Asn Pro Tyr Val Gly Phe Glu Met Gly Tyr Asp Trp Leu Gly
65                  70                  75                  80

Arg Met Pro Tyr Lys Gly Ser Val Glu Asn Gly Ala Tyr Lys Ala Gln
                85                  90                  95

Gly Val Gln Leu Thr Ala Lys Leu Gly Tyr Pro Ile Thr Asp Asp Leu
            100                 105                 110

Asp Ile Tyr Thr Arg Leu Gly Gly Met Val Trp Arg Ala Asp Thr Lys
        115                 120                 125

Ser Asn Val Tyr Gly Lys Asn His Asp Thr Gly Val Ser Pro Val Phe
130                 135                 140

Ala Gly Gly Val Glu Tyr Ala Ile Thr Pro Glu Ile Ala Thr Arg Leu
145                 150                 155                 160

Glu Tyr Gln Trp Thr Asn Asn Ile Gly Asp Ala His Thr Ile Gly Thr
                165                 170                 175

Arg Pro Asp Asn Gly Met Leu Ser Leu Gly Val Ser Tyr Arg Phe Gly
            180                 185                 190

Gln Gly Glu Ala Ala Pro Val Val Ala Pro Ala Pro Ala Pro Ala Pro
        195                 200                 205

Glu Val Gln Thr Lys His Phe Thr Leu Lys Ser Asp Val Leu Phe Asn
    210                 215                 220

Phe Asn Lys Ala Thr Leu Lys Pro Glu Gly Gln Ala Ala Leu Asp Gln
225                 230                 235                 240
```

-continued

```
Leu Tyr Ser Gln Leu Ser Asn Leu Asp Pro Lys Asp Gly Ser Val Val
                245                 250                 255

Val Leu Gly Tyr Thr Asp Arg Ile Gly Ser Asp Ala Tyr Asn Gln Gly
            260                 265                 270

Leu Ser Glu Arg Arg Ala Gln Ser Val Val Asp Tyr Leu Ile Ser Lys
        275                 280                 285

Gly Ile Pro Ala Asp Lys Ile Ser Ala Arg Gly Met Gly Glu Ser Asn
    290                 295                 300

Pro Val Thr Gly Asn Thr Cys Asp Asn Val Lys Gln Arg Ala Ala Leu
305                 310                 315                 320

Ile Asp Cys Leu Ala Pro Asp Arg Arg Val Glu Ile Glu Val Lys Gly
                325                 330                 335

Ile Lys Asp Val Val Thr Gln Pro Gln Ala
            340                 345

<210> SEQ ID NO 11
<211> LENGTH: 407
<212> TYPE: PRT
<213> ORGANISM: Shigella flexneri

<400> SEQUENCE: 11

Met Ser Ile Asp Phe Thr Pro Gly Ile Ile Asn Thr Tyr His Gly Asp
1               5                   10                  15

Ile Tyr Asn Cys Thr Thr Asn Thr Asp Asn Val Lys Thr Pro Asp Thr
            20                  25                  30

Pro Lys Trp Pro Cys Asp Asn Trp Glu Glu Gln Pro Ile Asn Ser
        35                  40                  45

Thr Phe Ser Gly Glu Gly Tyr Asn Pro Glu Gln Phe Asp Leu Ala Gln
    50                  55                  60

Gln Gln Leu Gln Gln Ile Asn Ala Cys His Thr Asn Thr Thr Tyr Thr
65                  70                  75                  80

Asn Ala Asp Tyr Ser Lys Val Val Val Gln Leu Val Ser Leu Ile Asn
                85                  90                  95

Asn Ile Glu Thr Ile Ser Ser Thr Pro Leu Thr Gln Gln Thr Gln Ser
            100                 105                 110

Ile Leu Asn Gln Ile His Asn Ile Arg Tyr Glu Lys Asp Lys Asp Ser
        115                 120                 125

Val Cys Gln Ile Ile Val Val Asn Pro Glu Pro Asn Asn Pro Ile
    130                 135                 140

Ile Thr Lys Ile Leu Val Glu Glu Gly Ile Pro Glu Arg Phe Ser Val
145                 150                 155                 160

Gln Thr Val Ser Ser Asp Asn Lys Asn Phe Ala Gly Gln Arg Ala Asp
                165                 170                 175

Leu Pro Thr Asp Ile Arg Asp Ile Gln Ser Leu Tyr Leu Lys Met Ala
            180                 185                 190

Lys Leu Tyr Ile Glu His Ser Lys Asn Glu Asn Arg Met Glu Ala Leu
        195                 200                 205

Ala Gly Cys Asp Phe Ile Asp Phe Asn Met Thr Gly Gln Asp Met Ser
    210                 215                 220

Lys Leu Val Leu Thr Leu Ser Lys Phe Tyr Phe Glu Asp Leu Leu Asn
225                 230                 235                 240

Ile Asn Phe Thr Asp Ala Asn Leu Phe Asn Thr Ile Phe Ser His Lys
                245                 250                 255

Glu Asn Pro Ile Pro Lys Leu His Lys Tyr Glu Gln His Leu Asp Lys
            260                 265                 270
```

-continued

```
Gln Ile Asn Gly Leu Phe Ser Thr Leu Leu Thr Ile Asn Asp Asn Ser
            275                 280                 285

Leu Arg Ala Lys Ala Glu Ile Ala Ser Arg Ile Ile Asp Phe Leu Glu
    290                 295                 300

Ala Lys Val Val Asn Leu Ser Phe Asp Asp Ile Leu Lys Tyr Lys Gln
305                 310                 315                 320

Glu Phe Lys Lys Ile Cys Tyr Lys Gln Leu Gln Glu Phe Thr Thr Pro
                325                 330                 335

Ser Leu Tyr Asn Lys Ile Gln Lys Trp Ala Thr Met Ser Lys Asn Glu
            340                 345                 350

Phe Ile Ala Phe His Tyr Glu Thr Leu Gln Pro Glu Lys Ile Ser Tyr
            355                 360                 365

Pro Phe Tyr Leu Lys Arg Asp Leu Pro Asn Glu Lys Asp Ile Asn Tyr
    370                 375                 380

Gly Val Glu Ile Glu Ile Pro Ser Gly Lys Arg Ile Arg Leu Ser Asn
385                 390                 395                 400

His Tyr Gln Asn Ile Ile Pro
                405
```

<210> SEQ ID NO 12
<211> LENGTH: 171
<212> TYPE: PRT
<213> ORGANISM: Shigella flexneri

<400> SEQUENCE: 12

```
Met Lys Lys Ile Ala Cys Leu Ser Ala Leu Ala Ala Val Leu Ala Phe
1               5                   10                  15

Thr Ala Gly Thr Ser Val Ala Ala Thr Ser Thr Val Thr Gly Gly Tyr
            20                  25                  30

Ala Gln Ser Asp Ala Gln Gly Gln Met Asn Lys Met Gly Gly Phe Asn
        35                  40                  45

Leu Lys Tyr Arg Tyr Glu Glu Asp Asn Ser Pro Leu Gly Val Ile Gly
    50                  55                  60

Ser Phe Thr Tyr Thr Glu Lys Ser Arg Thr Ala Ser Ser Gly Asp Tyr
65                  70                  75                  80

Asn Lys Asn Gln Tyr Tyr Gly Ile Thr Ala Gly Pro Ala Tyr Arg Ile
                85                  90                  95

Asn Asp Trp Ala Ser Ile Tyr Gly Val Val Gly Val Gly Tyr Gly Lys
            100                 105                 110

Phe Gln Thr Thr Glu Tyr Pro Thr Tyr Lys His Asp Thr Ser Asp Tyr
        115                 120                 125

Gly Phe Ser Tyr Gly Ala Gly Leu Gln Phe Asn Pro Met Glu Asn Val
    130                 135                 140

Ala Leu Asp Phe Ser Tyr Glu Gln Ser Arg Ile Arg Ser Val Asp Val
145                 150                 155                 160

Gly Thr Trp Ile Ala Gly Val Gly Tyr Arg Phe
                165                 170
```

<210> SEQ ID NO 13
<211> LENGTH: 155
<212> TYPE: PRT
<213> ORGANISM: Shigella flexneri

<400> SEQUENCE: 13

```
Met Ile Lys Arg Val Leu Val Ser Met Val Gly Leu Ser Leu Val
1               5                   10                  15

Gly Cys Val Asn Asn Asp Thr Leu Ser Gly Asp Val Tyr Thr Ala Ser
                20                  25                  30

Glu Ala Lys Gln Val Gln Asn Val Ser Tyr Gly Thr Ile Val Asn Val
            35                  40                  45

Arg Pro Val Gln Ile Gln Gly Gly Asp Asp Ser Asn Val Ile Gly Ala
        50                  55                  60

Ile Gly Gly Ala Val Leu Gly Gly Phe Leu Gly Asn Thr Val Gly Gly
65                  70                  75                  80

Gly Thr Gly Arg Ser Leu Ala Thr Ala Ala Gly Ala Val Ala Gly Gly
                85                  90                  95

Val Ala Gly Gln Gly Val Gln Ser Ala Met Asn Lys Thr Gln Gly Val
            100                 105                 110

Glu Leu Glu Ile Arg Lys Asp Asp Gly Asn Thr Ile Met Val Val Gln
        115                 120                 125

Lys Gln Gly Asn Thr Arg Phe Ser Pro Gly Gln Arg Val Val Leu Ala
    130                 135                 140

Ser Asn Gly Ser Gln Val Thr Val Ser Pro Arg
145                 150                 155
```

<210> SEQ ID NO 14
<211> LENGTH: 207
<212> TYPE: PRT
<213> ORGANISM: Shigella flexneri

<400> SEQUENCE: 14

```
Met Pro Leu Pro Asp Phe Arg Leu Ile Arg Leu Leu Pro Leu Ala Ala
1               5                   10                  15

Leu Val Leu Thr Ala Cys Ser Val Thr Thr Pro Lys Gly Pro Gly Lys
                20                  25                  30

Ser Pro Asp Ser Pro Gln Trp Arg Gln His Gln Gln Asp Val Arg Asn
            35                  40                  45

Leu Asn Gln Tyr Gln Thr Arg Gly Ala Phe Ala Tyr Ile Ser Asp Gln
        50                  55                  60

Gln Lys Val Tyr Ala Arg Phe Phe Trp Gln Gln Thr Gly Gln Asp Arg
65                  70                  75                  80

Tyr Arg Leu Leu Leu Thr Asn Pro Leu Gly Ser Thr Glu Leu Glu Leu
                85                  90                  95

Asn Ala Gln Pro Gly Asn Val Gln Leu Val Asp Asn Lys Gly Gln Arg
            100                 105                 110

Tyr Thr Ala Asp Asp Ala Glu Glu Met Ile Gly Lys Leu Thr Gly Met
        115                 120                 125

Pro Ile Pro Leu Asn Ser Leu Arg Gln Trp Ile Leu Gly Leu Pro Gly
    130                 135                 140

Asp Ala Thr Asp Tyr Lys Leu Asp Asp Gln Tyr Arg Leu Ser Glu Ile
145                 150                 155                 160

Thr Tyr Ser Gln Asn Gly Lys Asn Trp Lys Val Val Tyr Gly Gly Tyr
                165                 170                 175

Asp Thr Lys Thr Gln Pro Ala Met Pro Ala Asn Met Glu Leu Thr Asp
            180                 185                 190

Gly Gly Gln Arg Ile Lys Leu Lys Met Asp Asn Trp Ile Val Lys
        195                 200                 205
```

```
<210> SEQ ID NO 15
<211> LENGTH: 810
<212> TYPE: PRT
<213> ORGANISM: Shigella flexneri

<400> SEQUENCE: 15
```

| | | | | | | | | | | | | | | | |
|---|---|---|---|---|---|---|---|---|---|---|---|---|---|---|---|
| Met | Ala | Met | Lys | Lys | Leu | Leu | Ile | Ala | Ser | Leu | Leu | Phe | Ser | Ser | Ala |
| 1 | | | | 5 | | | | | 10 | | | | | 15 | |
| Thr | Val | Tyr | Gly | Ala | Glu | Gly | Phe | Val | Val | Lys | Asp | Ile | His | Phe | Glu |
| | | | 20 | | | | | 25 | | | | | 30 | | |
| Gly | Leu | Gln | Arg | Val | Ala | Val | Gly | Ala | Ala | Leu | Leu | Ser | Met | Pro | Val |
| | | | | 35 | | | | | 40 | | | | | 45 | |
| Arg | Thr | Gly | Asp | Thr | Val | Asn | Asp | Glu | Asp | Ile | Ser | Asn | Thr | Ile | Arg |
| | 50 | | | | | 55 | | | | | 60 | | | | |
| Ala | Leu | Phe | Ala | Thr | Gly | Asn | Phe | Glu | Asp | Val | Arg | Val | Leu | Arg | Asp |
| 65 | | | | | 70 | | | | | 75 | | | | | 80 |
| Gly | Asp | Thr | Leu | Leu | Val | Gln | Val | Lys | Glu | Arg | Pro | Thr | Ile | Ala | Ser |
| | | | | 85 | | | | | 90 | | | | | 95 | |
| Ile | Thr | Phe | Ser | Gly | Asn | Lys | Ser | Val | Lys | Asp | Asp | Met | Leu | Lys | Gln |
| | | | | 100 | | | | | 105 | | | | | 110 | |
| Asn | Leu | Glu | Ala | Ser | Gly | Val | Arg | Val | Gly | Glu | Ser | Leu | Asp | Arg | Thr |
| | | | | 115 | | | | | 120 | | | | | 125 | |
| Thr | Ile | Ala | Asp | Ile | Glu | Lys | Gly | Leu | Glu | Asp | Phe | Tyr | Tyr | Ser | Val |
| | | 130 | | | | | 135 | | | | | 140 | | | |
| Gly | Lys | Tyr | Ser | Ala | Ser | Val | Lys | Ala | Val | Val | Thr | Pro | Leu | Pro | Arg |
| 145 | | | | | 150 | | | | | 155 | | | | | 160 |
| Asn | Arg | Val | Asp | Leu | Lys | Leu | Val | Phe | Gln | Glu | Gly | Val | Ser | Ala | Glu |
| | | | | 165 | | | | | 170 | | | | | 175 | |
| Ile | Gln | Gln | Ile | Asn | Ile | Val | Gly | Asn | His | Ala | Phe | Thr | Thr | Asp | Glu |
| | | | | 180 | | | | | 185 | | | | | 190 | |
| Leu | Ile | Ser | His | Phe | Gln | Leu | Arg | Asp | Glu | Val | Pro | Trp | Trp | Asn | Val |
| | | | | 195 | | | | | 200 | | | | | 205 | |
| Val | Gly | Asp | Arg | Lys | Tyr | Gln | Lys | Gln | Lys | Leu | Ala | Gly | Asp | Leu | Glu |
| | | 210 | | | | | 215 | | | | | 220 | | | |
| Thr | Leu | Arg | Ser | Tyr | Tyr | Leu | Asp | Arg | Gly | Tyr | Ala | Arg | Phe | Asn | Ile |
| 225 | | | | | 230 | | | | | 235 | | | | | 240 |
| Asp | Ser | Thr | Gln | Val | Ser | Leu | Thr | Pro | Asp | Lys | Lys | Gly | Ile | Tyr | Val |
| | | | | 245 | | | | | 250 | | | | | 255 | |
| Thr | Val | Asn | Ile | Thr | Glu | Gly | Asp | Gln | Tyr | Lys | Leu | Ser | Gly | Val | Glu |
| | | | | 260 | | | | | 265 | | | | | 270 | |
| Val | Ser | Gly | Asn | Leu | Ala | Gly | His | Ser | Ala | Glu | Ile | Glu | Gln | Leu | Thr |
| | | | 275 | | | | | 280 | | | | | 285 | | |
| Lys | Ile | Glu | Pro | Gly | Glu | Leu | Tyr | Asn | Gly | Thr | Lys | Val | Thr | Lys | Met |
| | | 290 | | | | | 295 | | | | | 300 | | | |
| Glu | Asp | Asp | Ile | Lys | Lys | Leu | Leu | Gly | Arg | Tyr | Gly | Tyr | Ala | Tyr | Pro |
| 305 | | | | | 310 | | | | | 315 | | | | | 320 |
| Arg | Val | Gln | Ser | Met | Pro | Glu | Ile | Asn | Asp | Ala | Asp | Lys | Thr | Val | Lys |
| | | | | 325 | | | | | 330 | | | | | 335 | |
| Leu | Arg | Val | Asn | Val | Asp | Ala | Gly | Asn | Arg | Phe | Tyr | Val | Arg | Lys | Ile |
| | | | | 340 | | | | | 345 | | | | | 350 | |
| Arg | Phe | Glu | Gly | Asn | Asp | Thr | Ser | Lys | Asp | Ala | Val | Leu | Arg | Arg | Glu |
| | | | | 355 | | | | | 360 | | | | | 365 | |
| Met | Arg | Gln | Met | Glu | Gly | Ala | Trp | Leu | Gly | Ser | Asp | Leu | Val | Asp | Gln |
| | | 370 | | | | | 375 | | | | | 380 | | | |

```
Gly Lys Glu Arg Leu Asn Arg Leu Gly Phe Phe Glu Thr Val Asp Thr
385                 390                 395                 400

Asp Thr Gln Arg Val Pro Gly Ser Pro Asp Gln Val Asp Val Val Tyr
            405                 410                 415

Lys Val Lys Glu Arg Asn Thr Gly Ser Phe Asn Phe Gly Ile Gly Tyr
            420                 425                 430

Gly Thr Glu Ser Gly Val Ser Phe Gln Ala Gly Val Gln Gln Asp Asn
            435                 440                 445

Trp Leu Gly Thr Gly Tyr Ala Val Gly Ile Asn Gly Thr Lys Asn Asp
        450                 455                 460

Tyr Gln Thr Tyr Ala Glu Leu Ser Val Thr Asn Pro Tyr Phe Thr Val
465                 470                 475                 480

Asp Gly Val Ser Leu Gly Gly Arg Leu Phe Tyr Asn Asp Phe Gln Ala
            485                 490                 495

Asp Asp Ala Asp Leu Ser Asp Tyr Thr Asn Lys Ser Tyr Gly Thr Asp
            500                 505                 510

Val Thr Leu Gly Phe Pro Ile Asn Glu Tyr Asn Ser Leu Arg Ala Gly
        515                 520                 525

Leu Gly Tyr Val His Asn Ser Leu Ser Asn Met Gln Pro Gln Val Ala
        530                 535                 540

Met Trp Arg Tyr Leu Tyr Ser Met Gly Glu His Pro Ser Thr Ser Asp
545                 550                 555                 560

Gln Asp Asn Ser Phe Lys Thr Asp Asp Phe Thr Phe Asn Tyr Gly Trp
            565                 570                 575

Thr Tyr Asn Lys Leu Asp Arg Gly Tyr Phe Pro Thr Asp Gly Ser Arg
            580                 585                 590

Val Asn Leu Thr Gly Lys Val Thr Ile Pro Gly Ser Asp Asn Glu Tyr
        595                 600                 605

Tyr Lys Val Thr Leu Asp Thr Ala Thr Tyr Val Pro Ile Asp Asp Asp
        610                 615                 620

His Lys Trp Val Val Leu Gly Arg Thr Arg Trp Gly Tyr Gly Asp Gly
625                 630                 635                 640

Leu Gly Gly Lys Glu Met Pro Phe Tyr Glu Asn Phe Tyr Ala Gly Gly
            645                 650                 655

Ser Ser Thr Val Arg Gly Phe Gln Ser Asn Thr Ile Gly Pro Lys Ala
            660                 665                 670

Val Tyr Phe Pro His Gln Ala Ser Asn Tyr Asp Pro Asp Tyr Asp Tyr
        675                 680                 685

Glu Cys Ala Thr Gln Asp Gly Ala Lys Asp Leu Cys Lys Ser Asp Asp
        690                 695                 700

Ala Val Gly Gly Asn Ala Met Ala Val Ala Ser Leu Glu Phe Ile Thr
705                 710                 715                 720

Pro Thr Pro Phe Ile Ser Asp Lys Tyr Ala Asn Ser Val Arg Thr Ser
            725                 730                 735

Phe Phe Trp Asp Met Gly Thr Val Trp Asp Thr Asn Trp Asp Ser Ser
            740                 745                 750

Gln Tyr Ser Gly Tyr Pro Asp Tyr Ser Asp Pro Ser Asn Ile Arg Met
        755                 760                 765

Ser Ala Gly Ile Ala Leu Gln Trp Met Ser Pro Leu Gly Pro Leu Val
        770                 775                 780
```

```
Phe Ser Tyr Ala Gln Pro Phe Lys Lys Tyr Asp Gly Asp Lys Ala Glu
785                 790                 795                 800

Gln Phe Gln Phe Asn Ile Gly Lys Thr Trp
            805                 810

<210> SEQ ID NO 16
<211> LENGTH: 376
<212> TYPE: PRT
<213> ORGANISM: Shigella boydii

<400> SEQUENCE: 16

Met Lys Val Lys Val Leu Ser Leu Leu Val Pro Ala Leu Leu Val Ala
1               5                   10                  15

Gly Ala Ala Asn Ala Ala Glu Val Tyr Asn Lys Asp Gly Asn Lys Leu
            20                  25                  30

Asp Leu Tyr Gly Lys Val Asp Gly Leu His Tyr Phe Ser Asp Asn Lys
        35                  40                  45

Ser Glu Asp Gly Asp Gln Thr Tyr Val Arg Leu Gly Phe Lys Gly Glu
50                  55                  60

Thr Gln Val Thr Asp Gln Leu Thr Gly Tyr Gly Gln Trp Glu Tyr Gln
65                  70                  75                  80

Ile Gln Gly Asn Thr Ser Glu Asp Asn Lys Glu Asn Ser Trp Thr Arg
                85                  90                  95

Val Ala Phe Ala Gly Leu Lys Phe Gln Asp Val Gly Ser Phe Asp Tyr
            100                 105                 110

Gly Arg Asn Tyr Gly Val Val Tyr Asp Val Thr Ser Trp Thr Asp Val
        115                 120                 125

Leu Pro Glu Phe Gly Gly Asp Thr Tyr Gly Ser Asp Asn Phe Met Gln
130                 135                 140

Gln Arg Gly Asn Gly Phe Ala Thr Tyr Arg Asn Thr Asp Phe Phe Gly
145                 150                 155                 160

Leu Val Asp Gly Leu Asn Phe Ala Val Gln Tyr Gln Gly Lys Asn Gly
                165                 170                 175

Ser Val Ser Gly Glu Gly Met Thr Asn Asn Gly Arg Gly Ala Leu Arg
            180                 185                 190

Gln Asn Gly Asp Gly Val Gly Gly Ser Ile Thr Tyr Asp Tyr Glu Gly
        195                 200                 205

Phe Gly Ile Gly Ala Ala Val Ser Ser Ser Lys Arg Thr Asp Asp Gln
210                 215                 220

Asn Gly Ser Tyr Ile Ser Asn Gly Val Val Arg Asn Tyr Ile Gly Thr
225                 230                 235                 240

Gly Asp Arg Ala Glu Thr Tyr Thr Gly Gly Leu Lys Tyr Asp Ala Asn
                245                 250                 255

Asn Ile Tyr Leu Ala Ala Gln Tyr Thr Gln Thr Tyr Asn Ala Thr Arg
            260                 265                 270

Val Gly Ser Leu Gly Trp Ala Asn Lys Ala Gln Asn Phe Glu Ala Val
        275                 280                 285

Ala Gln Tyr Gln Phe Asp Phe Gly Leu Arg Pro Ser Val Ala Tyr Leu
290                 295                 300

Gln Ser Lys Gly Lys Asn Leu Gly Val Ile Asn Gly Arg Asn Tyr Asp
305                 310                 315                 320

Asp Glu Asp Ile Leu Lys Tyr Val Asp Val Gly Ala Thr Tyr Tyr Phe
                325                 330                 335

Asn Lys Asn Met Ser Thr Tyr Val Asp Tyr Lys Ile Asn Leu Leu Asp
            340                 345                 350
```

```
Asp Asn Gln Phe Thr Arg Asp Ala Gly Ile Asn Thr Asp Asn Ile Val
            355                 360                 365
Ala Leu Gly Leu Val Tyr Gln Phe
        370                 375

<210> SEQ ID NO 17
<211> LENGTH: 78
<212> TYPE: PRT
<213> ORGANISM: Shigella flexneri

<400> SEQUENCE: 17

Met Lys Ala Thr Lys Leu Val Leu Gly Ala Val Ile Leu Gly Ser Thr
1               5                   10                  15
Leu Leu Ala Gly Cys Ser Ser Asn Ala Lys Ile Asp Gln Leu Ser Ser
            20                  25                  30
Asp Val Gln Thr Leu Asn Ala Lys Val Asp Gln Leu Ser Asn Asp Val
        35                  40                  45
Asn Ala Met Arg Ser Asp Val Gln Ala Ala Lys Asp Asp Ala Ala Arg
    50                  55                  60
Ala Asn Gln Arg Leu Asp Asn Met Ala Thr Lys Tyr Arg Lys
65                  70                  75

<210> SEQ ID NO 18
<211> LENGTH: 173
<212> TYPE: PRT
<213> ORGANISM: Shigella flexneri

<400> SEQUENCE: 18

Met Gln Leu Asn Lys Val Leu Lys Gly Leu Met Ile Ala Leu Pro Val
1               5                   10                  15
Met Ala Ile Ala Ala Cys Ser Ser Asn Lys Asn Ala Ser Asn Asp Gly
            20                  25                  30
Ser Glu Gly Met Leu Gly Ala Gly Thr Gly Met Asp Ala Asn Gly Gly
        35                  40                  45
Asn Gly Asn Met Ser Ser Glu Glu Gln Ala Arg Leu Gln Met Gln Gln
    50                  55                  60
Leu Gln Gln Asn Asn Ile Val Tyr Phe Asp Leu Asp Lys Tyr Asp Ile
65                  70                  75                  80
Arg Ser Asp Phe Ala Gln Met Leu Asp Ala His Ala Asn Phe Leu Arg
                85                  90                  95
Ser Asn Pro Ser Tyr Lys Val Thr Val Glu Gly His Ala Asp Glu Arg
            100                 105                 110
Gly Thr Pro Glu Tyr Asn Ile Ser Leu Gly Glu Arg Arg Ala Asn Ala
        115                 120                 125
Val Lys Met Tyr Leu Gln Gly Lys Gly Val Ser Ala Asp Gln Ile Ser
    130                 135                 140
Ile Val Ser Tyr Gly Lys Glu Lys Pro Ala Val Leu Gly His Asp Glu
145                 150                 155                 160
Ala Ala Tyr Ser Lys Asn Arg Arg Ala Val Leu Val Tyr
                165                 170

<210> SEQ ID NO 19
<211> LENGTH: 48
<212> TYPE: PRT
<213> ORGANISM: Shigella flexneri
```

```
<400> SEQUENCE: 19

Met Val Lys Lys Thr Ile Ala Ala Ile Phe Ser Val Leu Val Leu Ser
1               5                   10                  15

Thr Val Leu Thr Ala Cys Asn Thr Thr Arg Gly Val Gly Glu Asp Ile
            20                  25                  30

Ser Asp Gly Gly Asn Ala Ile Ser Gly Ala Ala Thr Lys Ala Gln Gln
        35                  40                  45

<210> SEQ ID NO 20
<211> LENGTH: 137
<212> TYPE: PRT
<213> ORGANISM: Shigella flexneri

<400> SEQUENCE: 20

Met Lys Lys Leu Ala Ile Ala Gly Ala Leu Met Leu Ala Gly Cys
1               5                   10                  15

Ala Glu Val Glu Asn Tyr Asn Asn Val Val Lys Thr Pro Ala Pro Asp
            20                  25                  30

Trp Leu Ala Gly Tyr Trp Gln Thr Lys Gly Pro Gln Arg Ala Leu Val
        35                  40                  45

Ser Pro Glu Ala Ile Gly Ser Leu Ile Val Thr Lys Glu Gly Asp Thr
50                  55                  60

Leu Asp Cys Arg Gln Trp Gln Arg Gly Ile Ala Val Pro Gly Lys Leu
65                  70                  75                  80

Thr Leu Met Ser Asp Asp Leu Thr Asn Val Thr Val Lys Arg Glu Leu
                85                  90                  95

Tyr Glu Val Glu Arg Asp Gly Asn Thr Ile Glu Tyr Asp Gly Met Thr
            100                 105                 110

Met Glu Arg Val Asp Arg Pro Thr Ala Glu Cys Ala Ala Ala Leu Asp
        115                 120                 125

Lys Ala Pro Leu Pro Thr Pro Leu Pro
    130                 135

<210> SEQ ID NO 21
<211> LENGTH: 130
<212> TYPE: PRT
<213> ORGANISM: Shigella flexneri

<400> SEQUENCE: 21

Met Lys Lys Phe Ala Ala Val Ile Ala Val Met Ala Leu Cys Ser Ala
1               5                   10                  15

Pro Val Met Ala Ala Glu Gln Gly Gly Phe Ser Gly Pro Ser Val Thr
            20                  25                  30

Gln Ser Gln Ala Gly Gly Phe Gln Gly Pro Asn Gly Ser Val Thr Thr
        35                  40                  45

Val Glu Ser Ala Lys Ser Leu Arg Asp Asp Thr Trp Val Thr Leu Arg
    50                  55                  60

Gly Asn Ile Val Glu Arg Ile Ser Asp Asp Leu Tyr Val Phe Lys Asp
65                  70                  75                  80

Ala Ser Gly Thr Ile Asn Val Asp Ile Asp His Lys Arg Trp Asn Gly
                85                  90                  95

Val Thr Val Thr Pro Lys Asp Thr Val Glu Ile Gln Gly Glu Val Asp
            100                 105                 110
```

```
Lys Asp Trp Asn Ser Val Glu Ile Asp Val Lys Gln Ile Arg Lys Val
        115                 120                 125

Asn Pro
    130
```

<210> SEQ ID NO 22
<211> LENGTH: 128
<212> TYPE: PRT
<213> ORGANISM: Shigella flexneri

<400> SEQUENCE: 22

```
Met Ala Ser Ser Ser Leu Ile Met Gly Asn Asn Met His Val Lys Tyr
1               5                   10                  15

Leu Ala Gly Ile Val Gly Ala Ala Leu Leu Met Ala Gly Cys Ser Ser
            20                  25                  30

Ser Asn Glu Leu Ser Ala Ala Gly Gln Ser Val Arg Ile Val Asp Glu
        35                  40                  45

Gln Pro Gly Ala Glu Cys Gln Leu Ile Gly Thr Ala Thr Gly Lys Gln
    50                  55                  60

Ser Asn Trp Leu Ser Gly Gln His Gly Glu Glu Gly Gly Ser Met Arg
65                  70                  75                  80

Gly Ala Ala Asn Asp Leu Arg Asn Gln Ala Ala Met Gly Gly Asn
                85                  90                  95

Val Ile Tyr Gly Ile Ser Ser Pro Ser Gln Gly Met Leu Ser Ser Phe
            100                 105                 110

Val Pro Thr Asp Ser Gln Ile Ile Gly Gln Val Tyr Lys Cys Pro Asn
        115                 120                 125
```

<210> SEQ ID NO 23
<211> LENGTH: 190
<212> TYPE: PRT
<213> ORGANISM: Shigella flexneri

<400> SEQUENCE: 23

```
Met Lys Leu Val His Met Ala Ser Gly Leu Ala Val Ala Ile Ala Leu
1               5                   10                  15

Ala Ala Cys Ala Asp Lys Ser Ala Asp Ile Gln Thr Pro Ala Pro Ala
            20                  25                  30

Ala Asn Thr Ser Ile Ser Ala Thr Gln Gln Pro Ala Ile Gln Gln Pro
        35                  40                  45

Asn Val Ser Gly Thr Val Trp Ile Arg Gln Lys Val Ala Leu Pro Pro
    50                  55                  60

Asp Ala Val Leu Thr Val Thr Leu Ser Asp Ala Ser Leu Ala Asp Ala
65                  70                  75                  80

Pro Ser Lys Val Leu Ala Gln Lys Ala Val Arg Thr Glu Gly Lys Gln
                85                  90                  95

Ser Pro Phe Ser Phe Val Leu Pro Phe Asn Pro Ala Asp Val Gln Pro
            100                 105                 110

Asn Ala Arg Ile Leu Leu Ser Ala Ala Ile Thr Val Asn Asp Lys Leu
        115                 120                 125

Val Phe Ile Thr Asp Thr Val Gln Pro Val Ile Asn Gln Gly Gly Thr
    130                 135                 140

Lys Ala Asp Leu Thr Leu Val Pro Val Gln Gln Thr Ala Val Pro Val
145                 150                 155                 160
```

Gln Ala Ser Gly Gly Ala Thr Thr Val Pro Ser Thr Ser Pro Thr
            165                 170                 175

Gln Val Asn Pro Ser Ser Ala Val Pro Ala Pro Thr Gln Tyr
        180                 185                 190

<210> SEQ ID NO 24
<211> LENGTH: 191
<212> TYPE: PRT
<213> ORGANISM: Shigella flexneri

<400> SEQUENCE: 24

Met Lys Ser Leu Arg Leu Met Leu Cys Ala Met Pro Leu Met Leu Thr
1               5                   10                  15

Gly Cys Ser Thr Met Ser Ser Val Asn Trp Ser Ala Ala Asn Pro Trp
            20                  25                  30

Asn Trp Phe Gly Ser Ser Thr Lys Val Ser Glu Gln Gly Val Gly Glu
        35                  40                  45

Leu Thr Ala Ser Thr Pro Leu Gln Glu Gln Ala Ile Ala Asp Ala Leu
    50                  55                  60

Asp Gly Asp Tyr Arg Leu Arg Ser Gly Met Lys Thr Thr Asn Gly Asn
65                  70                  75                  80

Val Val Arg Phe Phe Glu Val Met Lys Gly Asp Asn Val Ala Met Val
                85                  90                  95

Ile Asn Gly Asp Gln Gly Thr Ile Ser Arg Ile Asp Val Leu Asp Ser
            100                 105                 110

Asp Ile Pro Ala Asp Thr Gly Val Lys Ile Gly Thr Pro Phe Ser Asp
        115                 120                 125

Leu Tyr Ser Lys Ala Phe Gly Asn Cys Gln Lys Ala Asp Gly Asp Asp
    130                 135                 140

Asn Arg Ala Val Glu Cys Lys Ala Glu Gly Ser Gln His Ile Ser Tyr
145                 150                 155                 160

Gln Phe Ser Gly Glu Trp Arg Gly Pro Glu Gly Leu Met Pro Ser Asp
                165                 170                 175

Asp Thr Leu Lys Asn Trp Lys Val Ser Lys Ile Ile Trp Arg Arg
            180                 185                 190

<210> SEQ ID NO 25
<211> LENGTH: 76
<212> TYPE: PRT
<213> ORGANISM: Shigella sonnei

<400> SEQUENCE: 25

Met Met Lys Lys Thr Ala Ala Ile Ile Ser Ala Cys Met Leu Thr Phe
1               5                   10                  15

Ala Leu Ser Ala Cys Ser Gly Ser Asn Tyr Val Met His Thr Asn Asp
            20                  25                  30

Gly Arg Thr Ile Val Ser Asp Gly Lys Pro Gln Thr Asp Asn Asp Thr
        35                  40                  45

Gly Met Ile Ser Tyr Lys Asp Ala Asn Gly Asn Lys Gln Gln Ile Asn
    50                  55                  60

Arg Thr Asp Val Lys Glu Met Val Glu Leu Asp Gln
65                  70                  75

<210> SEQ ID NO 26
<211> LENGTH: 344
<212> TYPE: PRT
<213> ORGANISM: Shigella flexneri

<400> SEQUENCE: 26

```
Met Ala Tyr Ser Val Gln Lys Ser Arg Leu Ala Lys Val Ala Gly Val
1               5                   10                  15

Ser Leu Val Leu Leu Ala Ala Cys Ser Ser Asp Ser Arg Tyr Lys
            20                  25                  30

Arg Gln Val Ser Gly Asp Glu Ala Tyr Leu Glu Ala Pro Leu Ala
        35                  40                  45

Glu Leu His Ala Pro Ala Gly Met Ile Leu Pro Val Thr Ser Gly Asp
    50                  55                  60

Tyr Ala Ile Pro Val Thr Asn Gly Ser Gly Ala Val Gly Lys Ala Leu
65                  70                  75                  80

Asp Ile Arg Pro Pro Ala Gln Pro Leu Ala Leu Val Ser Gly Ala Arg
                85                  90                  95

Thr Gln Phe Thr Gly Asp Thr Ala Ser Leu Leu Val Glu Asn Gly Arg
            100                 105                 110

Gly Asn Thr Leu Trp Pro Gln Val Ser Val Leu Gln Ala Lys Asn
        115                 120                 125

Tyr Thr Ile Thr Gln Arg Asp Asp Ala Gly Gln Thr Leu Thr Thr Asp
    130                 135                 140

Trp Val Gln Trp Asn Arg Leu Asp Glu Asp Gln Tyr Arg Gly Arg
145                 150                 155                 160

Tyr Gln Ile Ser Val Lys Pro Gln Gly Tyr Gln Gln Ala Val Thr Val
                165                 170                 175

Lys Leu Leu Asn Leu Glu Gln Ala Gly Lys Pro Val Ala Asp Ala Ala
            180                 185                 190

Ser Met Gln Arg Tyr Ser Thr Glu Met Met Asn Val Ile Ser Ala Gly
        195                 200                 205

Leu Asp Lys Ser Ala Thr Asp Ala Ala Asn Ala Gln Asn Arg Ala
    210                 215                 220

Ser Thr Thr Met Asp Val Gln Ser Ala Ala Asp Asp Thr Gly Leu Pro
225                 230                 235                 240

Met Leu Val Val Arg Gly Pro Phe Asn Val Val Trp Gln Arg Leu Pro
                245                 250                 255

Ala Ala Leu Glu Lys Val Gly Met Lys Val Thr Asp Ser Thr Arg Ser
            260                 265                 270

Gln Gly Asn Met Ala Val Thr Tyr Lys Pro Leu Ser Asp Ser Asp Trp
        275                 280                 285

Gln Glu Leu Gly Ala Ser Asp Pro Gly Leu Ala Ser Gly Asp Tyr Lys
    290                 295                 300

Leu Gln Val Gly Asp Leu Asp Asn Arg Ser Ser Leu Gln Phe Ile Asp
305                 310                 315                 320

Pro Lys Gly His Thr Leu Thr Gln Ser Gln Asn Asp Ala Leu Val Ala
                325                 330                 335

Val Phe Gln Ala Ala Phe Ser Lys
            340
```

<210> SEQ ID NO 27
<211> LENGTH: 139
<212> TYPE: PRT
<213> ORGANISM: Shigella sonnei -continued

<400> SEQUENCE: 27

Met Arg Arg Thr Gly Asn Lys Leu Cys Leu Ile Ala Met Ile Thr Ala
1 5 10 15

Thr Val Ala Leu Thr Ala Cys Thr Pro Lys Gly Ser Val Glu Gln His
20 25 30

Thr Arg His Tyr Val Tyr Ala Ser Asp Asp Gly Phe Asp Pro Asn Phe
35 40 45

Ser Thr Gln Lys Ala Asp Thr Thr Arg Met Met Val Pro Phe Phe Arg
50 55 60

Gln Phe Trp Asp Met Gly Ala Lys Asp Lys Ala Thr Gly Lys Ser Arg
65 70 75 80

Ser Asp Val Gln Gln Arg Ile Gln Gln Phe His Ser Gln Glu Phe Leu
85 90 95

Asn Ser Leu Arg Gly Thr Thr Gln Phe Ala Gly Thr Asp Tyr Arg Ser
100 105 110

Lys Asp Leu Thr Pro Lys Lys Ser Arg Leu Leu Ala Asp Thr Ile Ser
115 120 125

Ala Val Tyr Leu Asp Gly Tyr Glu Gly Arg Gln
130 135

<210> SEQ ID NO 28
<211> LENGTH: 193
<212> TYPE: PRT
<213> ORGANISM: Shigella dysenteriae

<400> SEQUENCE: 28

Met Arg Tyr Leu Ala Thr Leu Leu Leu Ser Leu Ala Val Leu Ile Thr
1 5 10 15

Ala Gly Cys Gly Trp His Leu Arg Asp Thr Thr Gln Val Pro Ser Thr
20 25 30

Met Lys Val Met Ile Leu Asp Ser Gly Asp Pro Asn Gly Pro Leu Ser
35 40 45

Arg Ala Val Arg Asn Gln Leu Arg Leu Asn Gly Val Glu Leu Leu Asp
50 55 60

Lys Glu Thr Thr Arg Lys Asp Val Pro Ser Leu Arg Leu Gly Lys Val
65 70 75 80

Ser Ile Ala Lys Asp Thr Ala Ser Val Phe Arg Asn Gly Gln Thr Ala
85 90 95

Glu Tyr Gln Met Ile Met Thr Val Asn Ala Thr Val Leu Ile Pro Gly
100 105 110

Ser Asp Ile Tyr Pro Ile Ser Ala Lys Val Phe Arg Ser Phe Phe Asp
115 120 125

Asn Pro Gln Met Ala Leu Ala Lys Asp Asn Glu Gln Asp Met Ile Val
130 135 140

Lys Glu Met Tyr Asp Arg Ala Ala Glu Gln Leu Ile Arg Lys Leu Pro
145 150 155 160

Ser Ile Arg Ala Ala Asp Ile Arg Ser Asp Glu Glu Gln Thr Ser Thr
165 170 175

Thr Thr Asp Thr Pro Ala Thr Pro Ala Arg Val Ser Thr Thr Leu Gly
180 185 190

Asn

<210> SEQ ID NO 29
<211> LENGTH: 427
<212> TYPE: PRT
<213> ORGANISM: Shigella sonnei

<400> SEQUENCE: 29

```
Met Asn Thr Phe Ser Val Ser Arg Leu Ala Leu Ala Leu Ala Phe Gly
1               5                   10                  15

Val Thr Leu Thr Ala Cys Ser Ser Thr Pro Pro Asp Gln Arg Pro Ser
            20                  25                  30

Asp Gln Thr Ala Pro Gly Thr Ser Ser Arg Pro Ile Leu Ser Ala Lys
        35                  40                  45

Glu Ala Gln Asn Phe Asp Ala Gln His Tyr Phe Ala Ser Leu Thr Pro
    50                  55                  60

Gly Ala Ala Ala Trp Asn Pro Ser Pro Ile Thr Leu Pro Ala Gln Pro
65                  70                  75                  80

Asp Phe Val Val Gly Pro Ala Gly Thr Gln Gly Val Thr His Thr Thr
                85                  90                  95

Ile Gln Ala Ala Val Asp Ala Ala Ile Ile Lys Arg Thr Asn Lys Arg
            100                 105                 110

Gln Tyr Ile Ala Val Met Pro Gly Glu Tyr Gln Gly Thr Val Tyr Val
        115                 120                 125

Pro Ala Ala Pro Gly Gly Ile Thr Leu Tyr Gly Thr Gly Glu Lys Pro
    130                 135                 140

Ile Asp Val Lys Ile Gly Leu Ser Leu Asp Gly Gly Met Ser Pro Ala
145                 150                 155                 160

Asp Trp Arg His Asp Val Asn Pro Arg Gly Lys Tyr Met Pro Gly Lys
                165                 170                 175

Pro Ala Trp Tyr Met Tyr Asp Ser Cys Gln Ser Lys Arg Ser Asp Ser
            180                 185                 190

Ile Gly Val Leu Cys Ser Ala Val Phe Trp Ser Gln Asn Asn Gly Leu
        195                 200                 205

Gln Leu Gln Asn Leu Thr Ile Glu Asn Thr Leu Gly Asp Ser Val Asp
    210                 215                 220

Ala Gly Asn His Pro Ala Val Ala Leu Arg Thr Asp Gly Asp Gln Val
225                 230                 235                 240

Gln Ile Asn Asn Val Asn Ile Leu Gly Arg Gln Asn Thr Phe Phe Val
                245                 250                 255

Thr Asn Ser Gly Val Gln Asn Arg Leu Glu Thr Asn Arg Gln Pro Arg
            260                 265                 270

Thr Leu Val Thr Asn Ser Tyr Ile Glu Gly Asp Val Asp Ile Val Ser
        275                 280                 285

Gly Arg Gly Ala Val Val Phe Asp Asn Thr Glu Phe Arg Val Val Asn
    290                 295                 300

Ser Arg Thr Gln Gln Glu Ala Tyr Val Phe Ala Pro Ala Thr Leu Ser
305                 310                 315                 320

Asn Met Tyr Tyr Gly Phe Leu Ala Val Asn Ser Arg Phe Asn Ala Phe
                325                 330                 335

Gly Asp Gly Val Ala Gln Leu Gly Arg Ser Leu Asp Val Asp Ala Asn
            340                 345                 350

Thr Asn Gly Gln Val Val Ile Arg Asp Ser Ala Ile Asn Glu Gly Phe
        355                 360                 365

Asn Thr Ala Lys Pro Trp Ala Asp Ala Val Ile Ser Asn Arg Pro Phe
    370                 375                 380
```

```
Ala Gly Asn Thr Gly Ser Val Asp Asp Asn Asp Glu Ile Gln Arg Asn
385                 390                 395                 400

Leu Asn Asp Thr Asn Tyr Asn Arg Met Trp Glu Tyr Asn Asn Arg Gly
            405                 410                 415

Val Gly Ser Lys Val Val Ala Glu Ala Lys Lys
            420                 425
```

<210> SEQ ID NO 30
<211> LENGTH: 270
<212> TYPE: PRT
<213> ORGANISM: Shigella flexneri

<400> SEQUENCE: 30

```
Met Lys Ser Leu Phe Lys Val Thr Leu Leu Ala Thr Thr Met Ala Val
1               5                   10                  15

Ala Leu His Ala Pro Ile Thr Phe Ala Ala Glu Ala Ala Lys Pro Ala
            20                  25                  30

Thr Thr Ala Asp Ser Lys Ala Ser Phe Lys Asn Asp Asp Gln Lys Ser
        35                  40                  45

Ala Tyr Ala Leu Gly Ala Ser Leu Gly Arg Tyr Met Glu Asn Ser Leu
50                  55                  60

Lys Glu Gln Glu Lys Leu Gly Ile Lys Leu Asp Lys Asp Gln Leu Ile
65                  70                  75                  80

Ala Gly Val Gln Asp Ala Phe Ala Asp Lys Ser Lys Leu Ser Asp Gln
                85                  90                  95

Glu Ile Glu Gln Thr Leu Gln Ala Phe Glu Ala Arg Val Lys Ser Ser
            100                 105                 110

Ala Gln Ala Lys Met Glu Lys Asp Ala Ala Asp Asn Glu Ala Lys Gly
        115                 120                 125

Lys Glu Tyr Arg Glu Lys Phe Ala Lys Glu Lys Gly Val Lys Thr Ser
130                 135                 140

Ser Thr Gly Leu Val Tyr Gln Val Val Glu Ala Gly Lys Gly Glu Ala
145                 150                 155                 160

Pro Lys Asp Ser Asp Thr Val Val Val Asn Tyr Lys Gly Thr Leu Ile
                165                 170                 175

Asp Gly Lys Glu Phe Asp Asn Ser Tyr Thr Arg Gly Glu Pro Leu Ser
            180                 185                 190

Phe Arg Leu Asp Gly Val Ile Pro Gly Trp Thr Glu Gly Leu Lys Asn
        195                 200                 205

Ile Lys Lys Gly Gly Lys Ile Lys Leu Val Ile Pro Pro Glu Leu Ala
210                 215                 220

Tyr Gly Lys Ala Gly Val Pro Gly Ile Pro Pro Asn Ser Thr Leu Val
225                 230                 235                 240

Phe Asp Val Glu Leu Leu Asp Val Lys Pro Ala Pro Lys Ala Asp Ala
                245                 250                 255

Lys Pro Glu Ala Asp Ala Lys Ala Ala Asp Ser Ala Lys Lys
            260                 265                 270
```

<210> SEQ ID NO 31
<211> LENGTH: 260
<212> TYPE: PRT
<213> ORGANISM: Shigella sonnei

<400> SEQUENCE: 31

Met Lys Lys Leu Val Leu Ser Leu Ser Leu Val Leu Ala Phe Ser Ser
1               5                   10                  15

Ala Thr Ala Ala Phe Ala Ala Ile Pro Gln Asn Ile Arg Ile Gly Thr
            20                  25                  30

Asp Pro Thr Tyr Ala Pro Phe Glu Ser Lys Asn Ser Gln Gly Glu Leu
        35                  40                  45

Val Gly Phe Asp Ile Asp Leu Ala Lys Glu Leu Cys Lys Arg Ile Asn
50                  55                  60

Thr Gln Cys Thr Phe Val Glu Asn Pro Leu Asp Ala Leu Ile Pro Ser
65                  70                  75                  80

Leu Lys Ala Lys Lys Ile Asp Ala Ile Met Ser Ser Leu Ser Ile Thr
                85                  90                  95

Glu Lys Arg Gln Gln Glu Ile Ala Phe Thr Asp Lys Leu Tyr Ala Ala
            100                 105                 110

Asp Ser Arg Leu Val Val Ala Lys Asn Ser Asp Ile Gln Pro Thr Val
        115                 120                 125

Glu Ser Leu Lys Gly Lys Arg Val Gly Val Leu Gln Gly Thr Thr Gln
130                 135                 140

Glu Thr Phe Gly Asn Glu His Trp Ala Pro Lys Gly Ile Glu Ile Val
145                 150                 155                 160

Ser Tyr Gln Gly Gln Asp Asn Ile Tyr Ser Asp Leu Thr Ala Gly Arg
                165                 170                 175

Ile Asp Ala Ala Phe Gln Asp Glu Val Ala Ala Ser Glu Gly Phe Leu
            180                 185                 190

Lys Gln Pro Val Gly Lys Asp Tyr Lys Phe Gly Gly Pro Ser Val Lys
        195                 200                 205

Asp Glu Lys Leu Phe Gly Val Gly Thr Gly Met Gly Leu Arg Lys Glu
210                 215                 220

Asp Asn Glu Leu Arg Glu Ala Leu Asn Lys Ala Phe Ala Glu Met Arg
225                 230                 235                 240

Ala Asp Gly Thr Tyr Glu Lys Leu Ala Lys Lys Tyr Phe Asp Phe Asp
                245                 250                 255

Val Tyr Gly Gly
            260

<210> SEQ ID NO 32
<211> LENGTH: 474
<212> TYPE: PRT
<213> ORGANISM: Shigella flexneri

<400> SEQUENCE: 32

Met Lys Lys Asn Thr Leu Ala Leu Ser Ala Leu Ala Leu Ser Leu Gly
1               5                   10                  15

Leu Ala Leu Ser Pro Leu Ser Ala Thr Ala Ala Glu Thr Ser Ser Ala
            20                  25                  30

Thr Thr Ala Gln Gln Met Pro Ser Leu Ala Pro Met Leu Glu Lys Val
        35                  40                  45

Met Pro Ser Val Val Ser Ile Asn Val Glu Gly Ser Thr Thr Val Asn
50                  55                  60

Thr Pro Arg Met Pro Arg Asn Phe Gln Gln Phe Phe Gly Asp Asp Ser
65                  70                  75                  80

Pro Phe Cys Gln Glu Gly Ser Pro Phe Gln Ser Ser Pro Phe Cys Gln
                85                  90                  95

Gly Gly Gln Gly Gly Asn Gly Gly Gln Gln Gln Lys Phe Met Ala
            100                 105                 110
Leu Gly Ser Gly Val Ile Ile Asp Ala Asp Lys Gly Tyr Val Val Thr
        115                 120                 125
Asn Asn His Val Val Asp Asn Ala Thr Val Ile Lys Val Gln Leu Ser
    130                 135                 140
Asp Gly Arg Lys Phe Asp Ala Lys Met Val Gly Lys Asp Pro Arg Ser
145                 150                 155                 160
Asp Ile Ala Leu Ile Gln Ile Gln Asn Pro Lys Lys Leu Thr Ala Ile
                165                 170                 175
Lys Met Ala Asp Ser Asp Ala Leu Arg Val Gly Asp Tyr Thr Val Ala
            180                 185                 190
Ile Gly Asn Pro Phe Gly Leu Gly Glu Thr Val Thr Ser Gly Ile Val
        195                 200                 205
Ser Ala Leu Gly Arg Ser Gly Leu Asn Ala Glu Asn Tyr Glu Asn Phe
    210                 215                 220
Ile Gln Thr Asp Ala Ala Ile Asn Arg Gly Asn Ser Gly Gly Ala Leu
225                 230                 235                 240
Val Asn Leu Asn Gly Glu Leu Ile Gly Ile Asn Thr Ala Ile Leu Ala
                245                 250                 255
Pro Asp Gly Gly Asn Ile Gly Ile Gly Phe Ala Ile Pro Ser Asn Met
            260                 265                 270
Val Lys Asn Leu Thr Ser Gln Met Val Glu Tyr Gly Asn Val Lys Arg
        275                 280                 285
Gly Glu Leu Gly Ile Met Gly Thr Glu Leu Asn Ser Glu Leu Ala Lys
    290                 295                 300
Ala Met Lys Val Asp Ala Gln Arg Gly Ala Phe Val Ser Gln Val Leu
305                 310                 315                 320
Pro Asn Ser Ser Ala Ala Lys Ala Gly Ile Lys Ala Gly Asp Val Ile
                325                 330                 335
Thr Ser Leu Asn Gly Lys Pro Ile Ser Ser Phe Ala Ala Leu Arg Ala
            340                 345                 350
Gln Val Gly Thr Met Pro Val Gly Ser Lys Leu Thr Leu Gly Leu Leu
        355                 360                 365
Arg Asp Gly Lys Gln Val Asn Val Asn Leu Glu Leu Gln Gln Ser Ser
    370                 375                 380
Gln Asn Gln Val Asp Ser Ser Ile Phe Asn Gly Ile Glu Gly Ala
385                 390                 395                 400
Glu Met Ser Asn Lys Gly Lys Asp Gln Gly Val Val Val Asn Val
                405                 410                 415
Lys Thr Gly Thr Pro Ala Ala Gln Ile Gly Leu Lys Lys Gly Asp Val
            420                 425                 430
Ile Ile Gly Ala Asn Gln Gln Ala Val Lys Asn Ile Ala Glu Leu Arg
        435                 440                 445
Lys Val Leu Asp Ser Lys Pro Ser Val Leu Ala Leu Asn Ile Gln Arg
    450                 455                 460
Gly Asp Ser Thr Ile Tyr Leu Leu Met Gln
465                 470

<210> SEQ ID NO 33
<211> LENGTH: 430
<212> TYPE: PRT
<213> ORGANISM: Shigella flexneri -continued

```
<400> SEQUENCE: 33

Met Lys Gln Ala Leu Arg Val Ala Phe Gly Phe Leu Ile Leu Trp Ala
1               5                   10                  15

Ser Val Leu His Ala Glu Val Arg Ile Val Ile Asp Ser Gly Val Asp
            20                  25                  30

Ser Gly Arg Pro Ile Gly Val Pro Phe Gln Trp Ala Gly Pro Gly
        35                  40                  45

Ala Ala Pro Glu Asp Ile Gly Gly Ile Val Ala Ala Asp Leu Arg Asn
    50                  55                  60

Ser Gly Lys Phe Asn Pro Leu Asp Arg Ala Arg Leu Pro Gln Gln Pro
65                  70                  75                  80

Gly Ser Ala Gln Glu Val Gln Pro Ala Ala Trp Ser Ala Leu Gly Ile
                85                  90                  95

Asp Ala Val Val Val Gly Gln Val Thr Pro Asn Pro Asp Gly Ser Tyr
            100                 105                 110

Asn Val Ala Tyr Gln Leu Val Asp Thr Gly Ala Pro Gly Thr Val
        115                 120                 125

Leu Ala Gln Asn Ser Tyr Lys Val Asn Lys Gln Trp Leu Arg Tyr Ala
    130                 135                 140

Gly His Thr Ala Ser Asp Glu Val Phe Glu Lys Leu Thr Gly Ile Lys
145                 150                 155                 160

Gly Ala Phe Arg Thr Arg Ile Ala Tyr Val Val Gln Thr Asn Gly Gly
                165                 170                 175

Gln Phe Pro Tyr Glu Leu Arg Val Ser Asp Tyr Asp Gly Tyr Asn Gln
            180                 185                 190

Phe Val Val His Arg Ser Pro Gln Pro Leu Met Ser Pro Ala Trp Ser
        195                 200                 205

Pro Asp Gly Ser Lys Leu Ala Tyr Val Thr Phe Glu Ser Gly Arg Ser
    210                 215                 220

Ala Leu Val Ile Gln Thr Leu Ala Asn Gly Ala Val Arg Gln Val Ala
225                 230                 235                 240

Ser Phe Pro Arg His Asn Gly Ala Pro Ala Phe Ser Pro Asp Gly Ser
                245                 250                 255

Lys Leu Ala Phe Ala Leu Ser Lys Thr Gly Ser Leu Asn Leu Tyr Val
            260                 265                 270

Met Asp Leu Ala Ser Gly Gln Ile Arg Gln Val Thr Asp Gly Arg Ser
        275                 280                 285

Asn Asn Thr Glu Pro Thr Trp Phe Pro Asp Ser Gln Asn Leu Ala Phe
    290                 295                 300

Thr Ser Asp Gln Ala Gly Arg Pro Gln Val Tyr Lys Val Asn Ile Asn
305                 310                 315                 320

Gly Gly Ala Pro Gln Arg Ile Thr Trp Glu Gly Ser Gln Asn Gln Asp
                325                 330                 335

Ala Asp Val Ser Ser Asp Gly Lys Phe Met Val Met Val Ser Ser Asn
            340                 345                 350

Gly Gly Gln Gln His Ile Ala Lys Gln Asp Leu Ala Thr Gly Gly Val
        355                 360                 365

Gln Val Leu Ser Ser Thr Phe Leu Asp Glu Thr Pro Ser Leu Ala Pro
    370                 375                 380

Asn Gly Thr Met Val Ile Tyr Ser Ser Gln Gly Met Gly Ser Val
385                 390                 395                 400
```

Leu Asn Leu Val Ser Thr Asp Gly Arg Phe Lys Ala Arg Leu Pro Ala
            405                 410                 415

Thr Asp Gly Gln Val Lys Phe Pro Ala Trp Ser Pro Tyr Leu
            420                 425                 430

<210> SEQ ID NO 34
<211> LENGTH: 257
<212> TYPE: PRT
<213> ORGANISM: Shigella flexneri

<400> SEQUENCE: 34

Met Ala Arg Lys Trp Leu Asn Leu Phe Ala Gly Ala Ala Leu Ser Phe
1               5                   10                  15

Ala Val Ala Gly Asn Ala Leu Ala Asp Glu Gly Lys Ile Thr Val Phe
            20                  25                  30

Ala Ala Ala Ser Leu Thr Asn Ala Met Gln Asp Ile Ala Thr Gln Tyr
        35                  40                  45

Lys Lys Glu Lys Gly Val Asp Val Val Ser Ser Phe Ala Ser Ser Ser
    50                  55                  60

Thr Leu Ala Arg Gln Ile Glu Ala Gly Ala Pro Ala Asp Leu Phe Ile
65                  70                  75                  80

Ser Ala Asp Gln Lys Trp Met Asp Tyr Ala Val Asp Lys Lys Ala Ile
                85                  90                  95

Asp Thr Ala Thr Arg Gln Thr Leu Leu Gly Asn Ser Leu Val Val Val
            100                 105                 110

Ala Pro Lys Ala Ser Glu Gln Lys Asp Phe Thr Ile Asp Ser Lys Thr
        115                 120                 125

Asn Trp Thr Ser Leu Leu Asn Gly Gly Arg Leu Ala Val Gly Asp Pro
130                 135                 140

Glu His Val Pro Ala Gly Ile Tyr Ala Lys Glu Ala Leu Gln Lys Leu
145                 150                 155                 160

Gly Ala Trp Asp Thr Leu Ser Pro Lys Leu Ala Pro Ala Glu Asp Val
                165                 170                 175

Arg Gly Ala Leu Ala Leu Val Glu Arg Asn Glu Ala Pro Leu Gly Ile
            180                 185                 190

Val Tyr Gly Ser Asp Ala Val Ala Ser Lys Gly Val Lys Val Val Ala
        195                 200                 205

Thr Phe Pro Glu Asp Ser His Lys Lys Val Glu Tyr Pro Val Ala Val
    210                 215                 220

Val Glu Gly His Asn Asn Ala Thr Val Lys Ala Phe Tyr Asp Tyr Leu
225                 230                 235                 240

Lys Gly Pro Gln Ala Ala Glu Ile Phe Lys Arg Tyr Gly Phe Thr Thr
                245                 250                 255

Lys

<210> SEQ ID NO 35
<211> LENGTH: 193
<212> TYPE: PRT
<213> ORGANISM: Shigella flexneri

<400> SEQUENCE: 35

Met Phe Lys Ser Thr Leu Ala Ala Met Ala Ala Val Phe Ala Leu Ser
1               5                   10                  15

Ala Leu Ser Ala Leu Ser Pro Ala Ala Met Ala Ala Lys Gly Asp Pro
            20                  25                  30

His Val Leu Thr Thr Ser Ala Gly Asn Ile Glu Leu Glu Leu Asp
        35                  40                  45

Lys Gln Lys Ala Pro Val Ser Val Gln Asn Phe Val Asp Tyr Val Asn
 50                  55                  60

Ser Gly Phe Tyr Asn Asn Thr Thr Phe His Arg Val Ile Pro Gly Phe
 65                  70                  75                  80

Met Ile Gln Gly Gly Gly Phe Thr Glu Gln Met Gln Gln Lys Lys Pro
                 85                  90                  95

Asn Pro Pro Ile Lys Asn Glu Ala Asp Asn Gly Leu Arg Asn Thr Arg
            100                 105                 110

Gly Thr Ile Ala Met Ala Arg Thr Ala Asp Lys Asp Ser Ala Thr Ser
        115                 120                 125

Gln Phe Phe Ile Asn Val Ala Asp Asn Ala Phe Leu Asp His Gly Gln
130                 135                 140

Arg Asp Phe Gly Tyr Ala Val Phe Gly Lys Val Val Lys Gly Met Asp
145                 150                 155                 160

Val Ala Asp Lys Ile Ser Gln Val Pro Thr His Asp Val Gly Pro Tyr
                165                 170                 175

Gln Asn Val Pro Ser Lys Pro Val Val Ile Leu Ser Ala Lys Val Leu
            180                 185                 190

Pro

<210> SEQ ID NO 36
<211> LENGTH: 428
<212> TYPE: PRT
<213> ORGANISM: Shigella flexneri

<400> SEQUENCE: 36

Met Lys Asn Trp Lys Thr Leu Leu Gly Ile Ala Met Ile Ala Asn
 1               5                  10                  15

Thr Ser Phe Ala Ala Pro Gln Val Val Asp Lys Val Ala Ala Val Val
             20                  25                  30

Asn Asn Gly Val Val Leu Glu Ser Asp Val Asp Gly Leu Met Gln Ser
        35                  40                  45

Val Lys Leu Asn Ala Ala Gln Ala Arg Gln Gln Leu Pro Asp Asp Ala
 50                  55                  60

Thr Leu Arg His Gln Ile Met Glu Arg Leu Ile Met Asp Gln Ile Ile
 65                  70                  75                  80

Leu Gln Met Gly Gln Lys Met Gly Val Lys Ile Ser Asp Glu Gln Leu
                 85                  90                  95

Asp Gln Ala Ile Ala Asn Ile Ala Lys Gln Asn Asn Met Thr Leu Asp
            100                 105                 110

Gln Met Arg Ser Arg Leu Ala Tyr Asp Gly Leu Asn Tyr Asn Thr Tyr
        115                 120                 125

Arg Asn Gln Ile Arg Lys Glu Met Ile Ile Ser Glu Val Arg Asn Asn
130                 135                 140

Glu Val Arg Arg Arg Ile Thr Ile Leu Pro Gln Glu Val Glu Ser Leu
145                 150                 155                 160

Ala Gln Gln Val Gly Asn Gln Asn Asp Ala Ser Thr Glu Leu Asn Leu
                165                 170                 175

Ser His Ile Leu Ile Pro Leu Pro Glu Asn Pro Thr Ser Asp Gln Val
            180                 185                 190

Asn Glu Ala Glu Ser Gln Ala Arg Ala Ile Val Asp Gln Ala Arg Asn
        195                 200                 205

Gly Ala Asp Phe Gly Lys Leu Ala Ile Ala His Ser Ala Asp Gln Gln
210                 215                 220

Ala Leu Asn Gly Gly Gln Met Gly Trp Gly Arg Ile Gln Glu Leu Pro
225                 230                 235                 240

Gly Ile Phe Ala Gln Ala Leu Ser Thr Ala Lys Lys Gly Asp Ile Val
            245                 250                 255

Gly Pro Ile Arg Ser Gly Val Gly Phe His Ile Leu Lys Val Asn Asp
            260                 265                 270

Leu Arg Gly Glu Ser Lys Asn Ile Ser Val Thr Glu Val His Ala Arg
        275                 280                 285

His Ile Leu Leu Lys Pro Ser Pro Ile Met Thr Asp Glu Gln Ala Arg
    290                 295                 300

Val Lys Leu Glu Gln Ile Ala Ala Asp Ile Lys Ser Gly Lys Thr Thr
305                 310                 315                 320

Phe Ala Ala Ala Lys Glu Phe Ser Gln Asp Pro Gly Ser Ala Asn
                325                 330                 335

Gln Gly Gly Asp Leu Gly Trp Ala Thr Pro Asp Ile Phe Asp Pro Ala
                340                 345                 350

Phe Arg Asp Ala Leu Thr Arg Leu Asn Lys Gly Gln Met Ser Ala Pro
        355                 360                 365

Val His Ser Ser Phe Gly Trp His Leu Ile Glu Leu Leu Asp Thr Arg
    370                 375                 380

Asn Val Asp Lys Thr Asp Ala Ala Gln Lys Asp Arg Ala Tyr Arg Met
385                 390                 395                 400

Leu Met Asn Arg Lys Phe Ser Glu Glu Ala Ala Ser Trp Met Gln Glu
                405                 410                 415

Gln Arg Ala Ser Ala Tyr Val Lys Ile Leu Ser Asn
        420                 425

<210> SEQ ID NO 37
<211> LENGTH: 543
<212> TYPE: PRT
<213> ORGANISM: Shigella flexneri

<400> SEQUENCE: 37

Met Thr Asn Ile Thr Lys Arg Ser Leu Val Ala Ala Gly Val Leu Ala
1               5                   10                  15

Ala Leu Met Ala Gly Asn Val Ala Leu Ala Ala Asp Val Pro Ala Gly
                20                  25                  30

Val Thr Leu Ala Glu Lys Gln Thr Leu Val Arg Asn Asn Gly Ser Glu
            35                  40                  45

Val Gln Ser Leu Asp Pro His Lys Ile Glu Gly Val Pro Glu Ser Asn
    50                  55                  60

Ile Ser Arg Asp Leu Phe Glu Gly Leu Leu Val Ser Asp Leu Asp Gly
65                  70                  75                  80

His Pro Ala Pro Gly Val Ala Glu Ser Trp Asp Asn Lys Asp Ala Lys
                85                  90                  95

Val Trp Thr Phe His Leu Arg Lys Asp Ala Lys Trp Ser Asp Gly Thr
            100                 105                 110

Pro Val Thr Ala Gln Asp Phe Val Tyr Ser Trp Gln Arg Ser Val Asp
        115                 120                 125

Pro Asn Thr Ala Ser Pro Tyr Ala Ser Tyr Leu Gln Tyr Gly His Ile
    130                 135                 140

Ala Gly Ile Asp Glu Ile Leu Glu Gly Lys Lys Pro Ile Thr Asp Leu
145                 150                 155                 160

Gly Val Lys Ala Ile Asp Asp His Thr Leu Glu Val Thr Leu Ser Glu
              165                 170                 175

Pro Val Pro Tyr Phe Tyr Lys Leu Leu Val His Pro Ser Thr Ser Pro
            180                 185                 190

Val Pro Lys Ala Ala Ile Glu Lys Phe Gly Glu Lys Trp Thr Gln Pro
            195                 200                 205

Gly Asn Ile Val Thr Asn Gly Ala Tyr Thr Leu Lys Asp Trp Val Val
            210                 215                 220

Asn Glu Arg Ile Val Leu Glu Arg Ser Pro Thr Tyr Trp Asn Asn Ala
225                 230                 235                 240

Lys Thr Val Ile Asn Gln Val Thr Tyr Leu Pro Ile Ala Ser Glu Val
                245                 250                 255

Thr Asp Val Asn Arg Tyr Arg Ser Gly Glu Ile Asp Met Thr Tyr Asn
            260                 265                 270

Asn Met Pro Ile Glu Leu Phe Gln Lys Leu Lys Lys Glu Ile Pro Asp
            275                 280                 285

Glu Val His Val Asp Pro Tyr Leu Cys Thr Tyr Tyr Glu Ile Asn
            290                 295                 300

Asn Gln Lys Pro Pro Phe Asn Asp Val Arg Val Arg Thr Ala Leu Lys
305                 310                 315                 320

Leu Gly Met Asp Arg Asp Ile Ile Val Asn Lys Val Lys Ala Gln Gly
                325                 330                 335

Asp Met Pro Ala Tyr Gly Tyr Thr Pro Pro Tyr Thr Asp Gly Ala Lys
            340                 345                 350

Leu Thr Gln Pro Glu Trp Phe Gly Trp Ser Gln Glu Lys Arg Asn Glu
            355                 360                 365

Glu Ala Lys Lys Leu Leu Ala Glu Ala Gly Tyr Thr Ala Asp Lys Pro
            370                 375                 380

Leu Thr Ile Asn Leu Arg Tyr Asn Thr Ser Asp Leu His Lys Lys Leu
385                 390                 395                 400

Ala Ile Ala Ala Ser Ser Leu Trp Lys Lys Asn Ile Gly Val Asn Val
                405                 410                 415

Lys Leu Val Asn Gln Glu Trp Lys Thr Phe Leu Asp Thr Arg His Gln
            420                 425                 430

Gly Thr Phe Asp Val Ala Arg Ala Gly Trp Cys Ala Asp Tyr Asn Glu
            435                 440                 445

Pro Thr Ser Phe Leu Asn Thr Met Leu Ser Asn Ser Met Asn Thr
            450                 455                 460

Ala His Tyr Lys Ser Pro Ala Phe Asp Ser Ile Met Ala Glu Thr Leu
465                 470                 475                 480

Lys Val Thr Asp Glu Ala Gln Arg Thr Ala Leu Tyr Thr Lys Ala Glu
                485                 490                 495

Gln Gln Leu Asp Lys Asp Ser Ala Ile Val Pro Val Tyr Tyr Val
            500                 505                 510

Asn Ala Arg Leu Val Lys Pro Trp Val Gly Gly Tyr Thr Gly Lys Asp
            515                 520                 525

Pro Leu Asp Asn Thr Tyr Thr Arg Asn Met Tyr Ile Val Lys His
            530                 535                 540

<210> SEQ ID NO 38
<211> LENGTH: 201
<212> TYPE: PRT
<213> ORGANISM: Shigella flexneri

```
<400> SEQUENCE: 38

Met Thr Met Thr Arg Leu Lys Ile Ser Lys Thr Leu Leu Ala Val Met
1               5                   10                  15

Leu Thr Ser Ala Val Ala Thr Gly Ser Ala Tyr Ala Glu Asn Asn Ala
            20                  25                  30

Gln Thr Thr Asn Glu Ser Ala Gly Gln Lys Val Asp Ser Ser Met Asn
        35                  40                  45

Lys Val Gly Asn Phe Met Asp Asp Ser Ala Ile Thr Ala Lys Val Lys
    50                  55                  60

Ala Ala Leu Val Asp His Asp Asn Ile Lys Ser Thr Asp Ile Ser Val
65                  70                  75                  80

Lys Thr Asp Gln Lys Val Val Thr Leu Ser Gly Phe Val Glu Ser Gln
                85                  90                  95

Ala Gln Ala Glu Glu Ala Val Lys Val Ala Lys Gly Val Glu Gly Val
            100                 105                 110

Thr Ser Val Ser Asp Lys Leu His Val Arg Asp Ala Lys Glu Gly Ser
        115                 120                 125

Val Lys Gly Tyr Ala Gly Asp Thr Ala Thr Thr Ser Glu Ile Lys Ala
    130                 135                 140

Lys Leu Leu Ala Asp Asp Ile Val Pro Ser Arg Lys Val Lys Val Glu
145                 150                 155                 160

Thr Thr Asp Gly Val Val Gln Leu Ser Gly Thr Val Asp Ser Gln Ala
                165                 170                 175

Gln Ser Asp Arg Ala Glu Ser Ile Ala Lys Ala Val Asp Gly Val Lys
            180                 185                 190

Ser Val Lys Asn Asp Leu Lys Thr Lys
    195                 200

<210> SEQ ID NO 39
<211> LENGTH: 243
<212> TYPE: PRT
<213> ORGANISM: Shigella sonnei

<400> SEQUENCE: 39

Met Lys Lys Leu Val Leu Ala Ala Leu Leu Ala Ser Phe Thr Phe Gly
1               5                   10                  15

Ala Ser Ala Ala Glu Lys Ile Asn Phe Gly Val Ser Ala Thr Tyr Pro
            20                  25                  30

Pro Phe Glu Ser Ile Gly Ala Asn Asn Glu Ile Val Gly Phe Asp Ile
        35                  40                  45

Asp Leu Ala Lys Ala Leu Cys Lys Gln Met Gln Ala Glu Cys Thr Phe
    50                  55                  60

Thr Asn His Ala Phe Asp Ser Leu Ile Pro Ser Leu Lys Phe Arg Lys
65                  70                  75                  80

Tyr Asp Ser Val Ile Ser Gly Met Asp Ile Thr Pro Glu Arg Ser Lys
                85                  90                  95

Gln Val Ser Phe Thr Thr Pro Tyr Tyr Glu Asn Ser Ala Val Val Ile
            100                 105                 110

Ala Lys Lys Asp Thr Tyr Lys Thr Phe Ala Asp Leu Lys Gly Lys Arg
        115                 120                 125

Ile Gly Met Glu Asn Gly Thr Thr His Gln Lys Tyr Ile Gln Asp Gln
    130                 135                 140

His Pro Glu Val Lys Thr Val Ser Tyr Asp Ser Tyr Gln Asn Ala Phe
145                 150                 155                 160
```

```
Ile Asp Leu Lys Asn Gly Arg Ile Asp Gly Val Phe Gly Asp Thr Ala
            165                 170                 175

Val Val Asn Glu Trp Leu Lys Thr Asn Pro Gln Leu Gly Val Ala Thr
        180                 185                 190

Glu Lys Val Thr Asp Pro Gln Tyr Phe Gly Thr Gly Leu Gly Ile Ala
        195                 200                 205

Val Arg Pro Asp Asn Lys Ala Leu Leu Glu Lys Leu Asn Asn Ala Leu
    210                 215                 220

Ala Ala Ile Lys Ala Asp Gly Thr Tyr Gln Lys Ile Asn Asp Gln Trp
225                 230                 235                 240

Phe Pro Gln

<210> SEQ ID NO 40
<211> LENGTH: 550
<212> TYPE: PRT
<213> ORGANISM: Shigella sonnei

<400> SEQUENCE: 40

Met Lys Leu Leu Gln Arg Gly Val Ala Leu Ala Leu Leu Thr Thr Phe
1               5                   10                  15

Thr Leu Ala Ser Glu Thr Ala Leu Ala Tyr Glu Gln Asp Lys Thr Tyr
            20                  25                  30

Lys Ile Thr Val Leu His Thr Asn Asp His His Gly His Phe Trp Arg
        35                  40                  45

Asn Glu Tyr Gly Glu Tyr Gly Leu Ala Ala Gln Lys Thr Leu Val Asp
    50                  55                  60

Gly Ile Arg Lys Glu Val Ala Ala Glu Gly Ser Val Leu Leu Leu
65                  70                  75                  80

Ser Gly Gly Asp Ile Asn Thr Gly Val Pro Glu Ser Asp Leu Gln Asp
            85                  90                  95

Ala Glu Pro Asp Phe Arg Gly Met Asn Leu Val Gly Tyr Asp Ala Met
            100                 105                 110

Ala Ile Gly Asn His Glu Phe Asp Asn Pro Leu Thr Val Leu Arg Gln
        115                 120                 125

Gln Glu Lys Trp Ala Lys Phe Pro Leu Leu Ser Ala Asn Ile Tyr Gln
    130                 135                 140

Lys Ser Thr Gly Glu Arg Leu Phe Lys Pro Trp Ala Leu Phe Lys Arg
145                 150                 155                 160

Gln Asp Leu Lys Ile Ala Val Ile Gly Leu Thr Thr Asp Asp Thr Ala
            165                 170                 175

Lys Ile Gly Asn Pro Glu Tyr Phe Thr Asp Ile Glu Phe Arg Lys Pro
        180                 185                 190

Ala Asp Glu Ala Lys Leu Val Ile Gln Glu Leu Gln Gln Thr Glu Lys
    195                 200                 205

Pro Asp Ile Ile Ile Ala Ala Thr His Met Gly His Tyr Asp Asn Gly
    210                 215                 220

Glu His Gly Ser Asn Ala Pro Gly Asp Val Glu Met Ala Arg Ala Leu
225                 230                 235                 240

Pro Ala Gly Ser Leu Ala Met Ile Val Gly Gly His Ser Gln Asp Pro
            245                 250                 255

Val Cys Met Ala Ala Glu Asn Lys Lys Gln Val Asp Tyr Val Pro Gly
            260                 265                 270

Thr Pro Cys Lys Pro Asp Gln Gln Asn Gly Ile Trp Ile Val Gln Ala
        275                 280                 285
```

His Glu Trp Gly Lys Tyr Val Gly Arg Ala Asp Phe Glu Phe Arg Asn
        290                 295                 300

Gly Glu Met Lys Met Val Asn Tyr Gln Leu Ile Pro Val Asn Leu Lys
305                 310                 315                 320

Lys Lys Val Thr Arg Glu Asp Gly Lys Ser Glu Arg Val Leu Tyr Thr
                325                 330                 335

Pro Glu Ile Ala Glu Asn Gln Gln Met Ile Ser Leu Leu Ser Pro Phe
            340                 345                 350

Gln Asn Lys Gly Lys Ala Gln Leu Glu Val Lys Ile Gly Glu Thr Asn
        355                 360                 365

Gly Arg Leu Glu Gly Asp Arg Asp Lys Val Arg Phe Val Gln Thr Asn
370                 375                 380

Met Gly Arg Leu Ile Leu Ala Ala Gln Met Asp Arg Thr Gly Ala Asp
385                 390                 395                 400

Phe Ala Val Met Ser Gly Gly Ile Arg Asp Ser Ile Glu Ala Gly
                405                 410                 415

Asp Ile Ser Tyr Lys Asn Val Leu Lys Val Gln Pro Phe Gly Asn Val
            420                 425                 430

Val Val Tyr Ala Asp Met Ile Gly Lys Glu Val Ile Asp Tyr Leu Thr
        435                 440                 445

Ala Val Ala Gln Met Lys Pro Asp Ser Gly Ala Tyr Pro Gln Phe Ala
450                 455                 460

Asn Val Ser Phe Val Ala Lys Asp Gly Lys Leu Asn Asp Leu Lys Ile
465                 470                 475                 480

Lys Gly Glu Pro Val Asp Pro Ala Lys Thr Tyr Arg Met Ala Thr Leu
                485                 490                 495

Asn Phe Asn Ala Thr Gly Gly Asp Gly Tyr Pro Arg Leu Asp Asn Lys
            500                 505                 510

Pro Gly Tyr Val Asn Thr Gly Phe Ile Asp Ala Glu Val Leu Lys Ala
        515                 520                 525

Tyr Ile Gln Lys Ser Ser Pro Leu Asp Val Ser Val Tyr Glu Pro Lys
530                 535                 540

Gly Glu Val Ser Trp Gln
545                 550

<210> SEQ ID NO 41
<211> LENGTH: 266
<212> TYPE: PRT
<213> ORGANISM: Shigella sonnei

<400> SEQUENCE: 41

Met Lys Leu Ala His Leu Gly Arg Gln Ala Leu Met Gly Val Met Ala
1               5                   10                  15

Val Ala Leu Val Ala Gly Met Ser Val Lys Ser Phe Ala Asp Glu Gly
            20                  25                  30

Leu Leu Asn Lys Val Lys Glu Arg Gly Thr Leu Leu Val Gly Leu Glu
        35                  40                  45

Gly Thr Tyr Pro Pro Phe Ser Phe Gln Gly Asp Asp Gly Lys Leu Thr
    50                  55                  60

Gly Phe Glu Val Glu Phe Ala Gln Gln Leu Ala Lys His Leu Gly Val
65                  70                  75                  80

Glu Ala Ser Leu Lys Pro Thr Lys Trp Asp Gly Met Leu Ala Ser Leu
                85                  90                  95

Asp Ser Lys Arg Ile Asp Val Val Ile Asn Gln Val Thr Ile Ser Asp
            100                 105                 110

Glu Arg Lys Lys Lys Tyr Asp Phe Ser Thr Pro Tyr Thr Ile Ser Gly
            115                 120                 125

Ile Gln Ala Leu Val Lys Lys Gly Asn Glu Gly Thr Ile Lys Thr Ala
        130                 135                 140

Asp Asp Leu Lys Gly Lys Lys Val Gly Val Gly Leu Gly Thr Asn Tyr
145                 150                 155                 160

Glu Glu Trp Leu Arg Gln Asn Val Gln Gly Val Asp Val Arg Thr Tyr
                165                 170                 175

Asp Asp Asp Pro Thr Lys Tyr Gln Asp Leu Arg Val Gly Arg Ile Asp
            180                 185                 190

Ala Ile Leu Val Asp Arg Leu Ala Ala Leu Asp Leu Val Lys Lys Thr
        195                 200                 205

Asn Asp Thr Leu Ala Val Thr Gly Glu Ala Phe Ser Arg Gln Glu Ser
210                 215                 220

Gly Val Ala Leu Arg Lys Gly Asn Glu Asp Leu Leu Lys Ala Val Asn
225                 230                 235                 240

Asp Ala Ile Ala Glu Met Gln Lys Asp Gly Thr Leu Gln Ala Leu Ser
                245                 250                 255

Glu Lys Trp Phe Gly Ala Asp Val Thr Lys
            260                 265

<210> SEQ ID NO 42
<211> LENGTH: 508
<212> TYPE: PRT
<213> ORGANISM: Shigella flexneri

<400> SEQUENCE: 42

Met Arg Trp Leu Ser Ala Ala Val Met Leu Thr Leu Tyr Thr Ser Ser
1               5                   10                  15

Ser Trp Ala Phe Ser Ile Asp Asp Val Ala Lys Gln Ala Gln Ser Leu
            20                  25                  30

Ala Gly Lys Gly Tyr Glu Ala Pro Lys Ser Asn Leu Pro Ser Val Phe
        35                  40                  45

Arg Asp Met Lys Tyr Ala Asp Tyr Gln Gln Ile Gln Phe Asn His Asp
50                  55                  60

Lys Ala Tyr Trp Asn Asn Leu Lys Thr Pro Phe Lys Leu Glu Phe Tyr
65                  70                  75                  80

His Gln Gly Met Tyr Phe Asp Thr Pro Val Lys Ile Asn Glu Val Thr
                85                  90                  95

Ala Thr Ala Val Lys Arg Ile Lys Tyr Ser Pro Asp Tyr Phe Thr Phe
            100                 105                 110

Gly Asp Val Gln His Asp Lys Asp Thr Val Lys Asp Leu Gly Phe Ala
        115                 120                 125

Gly Phe Lys Val Leu Tyr Pro Ile Asn Ser Lys Asp Lys Asn Asp Glu
130                 135                 140

Ile Val Ser Met Leu Gly Ala Ser Tyr Phe Arg Val Ile Gly Ala Gly
145                 150                 155                 160

Gln Val Tyr Gly Leu Ser Ala Arg Gly Leu Ala Ile Asp Thr Ala Leu
                165                 170                 175

Pro Ser Gly Glu Glu Phe Pro Arg Phe Lys Glu Phe Trp Ile Glu Arg
            180                 185                 190

Pro Lys Pro Thr Asp Lys Arg Leu Thr Ile Tyr Ala Leu Leu Asp Ser
        195                 200                 205

Pro Arg Ala Thr Gly Ala Tyr Lys Phe Val Val Met Pro Gly Arg Asp
210                 215                 220

```
Thr Val Val Asp Val Gln Ser Lys Ile Tyr Leu Arg Asp Lys Val Gly
225                 230                 235                 240

Lys Leu Gly Val Ala Pro Leu Thr Ser Met Phe Leu Phe Gly Pro Asn
            245                 250                 255

Gln Pro Ser Pro Ala Asn Asn Tyr Arg Pro Glu Leu His Asp Ser Asn
        260                 265                 270

Gly Leu Ser Ile His Ala Gly Asn Gly Glu Trp Ile Trp Arg Pro Leu
    275                 280                 285

Asn Asn Pro Lys His Leu Ala Val Ser Ser Phe Ser Met Glu Asn Pro
290                 295                 300

Arg Gly Phe Gly Leu Leu Gln Arg Gly Arg Asp Phe Ser Arg Phe Glu
305                 310                 315                 320

Asp Leu Asp Asp Arg Tyr Asp Leu Arg Pro Ser Ala Trp Val Thr Pro
                325                 330                 335

Lys Gly Glu Trp Gly Lys Gly Ser Val Glu Leu Val Glu Ile Pro Thr
            340                 345                 350

Asn Asp Glu Thr Asn Asp Asn Ile Val Ala Tyr Trp Thr Pro Asp Gln
        355                 360                 365

Leu Pro Glu Pro Gly Lys Glu Met Asn Phe Lys Tyr Thr Ile Thr Phe
    370                 375                 380

Ser Arg Asp Glu Asp Lys Leu His Ala Pro Asp Asn Ala Trp Val Gln
385                 390                 395                 400

Gln Thr Arg Arg Ser Thr Gly Asp Val Lys Gln Ser Asn Leu Ile Arg
                405                 410                 415

Gln Pro Asp Gly Thr Ile Ala Phe Val Val Asp Phe Thr Gly Ala Glu
            420                 425                 430

Met Lys Lys Leu Pro Glu Asp Thr Pro Val Thr Ala Gln Thr Ser Ile
        435                 440                 445

Gly Asp Asn Gly Glu Ile Val Glu Ser Thr Val Arg Tyr Asn Pro Val
    450                 455                 460

Thr Lys Gly Trp Arg Leu Val Met Arg Val Lys Val Lys Asp Ala Lys
465                 470                 475                 480

Lys Thr Thr Glu Met Arg Ala Ala Leu Val Asn Ala Asp Gln Thr Leu
                485                 490                 495

Ser Glu Thr Trp Ser Tyr Gln Leu Pro Ala Asn Glu
            500                 505
```

<210> SEQ ID NO 43
<211> LENGTH: 338
<212> TYPE: PRT
<213> ORGANISM: Shigella sonnei

<400> SEQUENCE: 43

```
Met Ala Val Asn Leu Leu Lys Lys Asn Ser Leu Ala Leu Val Ala Ser
1               5                   10                  15

Leu Leu Leu Ala Gly His Val Gln Ala Thr Glu Leu Leu Asn Ser Ser
            20                  25                  30

Tyr Asp Val Ser Arg Glu Leu Phe Ala Ala Leu Asn Pro Pro Phe Glu
        35                  40                  45

Gln Gln Trp Thr Lys Glu Asn Gly Gly Asp Lys Leu Thr Ile Lys Gln
    50                  55                  60

Ser His Ala Gly Ser Ser Lys Gln Ala Leu Ala Ile Leu Gln Gly Leu
65                  70                  75                  80

Lys Ala Asp Val Val Thr Tyr Asn Gln Val Thr Asp Val Gln Ile Leu
                85                  90                  95
```

His Asp Lys Gly Lys Leu Ile Pro Ala Asp Trp Gln Thr Arg Leu Pro
            100                 105                 110

Asn Asn Ser Ser Pro Phe Tyr Ser Thr Met Gly Phe Leu Val Arg Lys
        115                 120                 125

Gly Asn Pro Lys Asn Ile His Asp Trp Asn Asp Leu Val Arg Ser Asp
    130                 135                 140

Val Lys Leu Ile Phe Pro Asn Pro Lys Thr Ser Gly Asn Ala Arg Tyr
145                 150                 155                 160

Thr Tyr Leu Ala Ala Trp Gly Ala Ala Asp Lys Ala Asp Gly Gly Asp
                165                 170                 175

Lys Ala Lys Thr Glu Gln Phe Met Thr Gln Phe Leu Lys Asn Val Glu
            180                 185                 190

Val Phe Asp Thr Gly Gly Arg Gly Ala Thr Thr Phe Ala Glu Arg
        195                 200                 205

Gly Leu Gly Asp Val Leu Ile Ser Phe Glu Ser Glu Val Asn Asn Ile
    210                 215                 220

Arg Lys Gln Tyr Glu Ala Gln Gly Phe Glu Val Val Ile Pro Lys Thr
225                 230                 235                 240

Asn Ile Leu Ala Glu Phe Pro Val Ala Trp Val Asp Lys Asn Val Gln
                245                 250                 255

Ala Asn Gly Thr Glu Lys Ala Ala Lys Ala Tyr Leu Asn Trp Leu Tyr
            260                 265                 270

Ser Pro Gln Ala Gln Thr Ile Ile Thr Asp Tyr Tyr Arg Val Asn
        275                 280                 285

Asn Pro Glu Val Met Asp Lys Leu Lys Asp Lys Phe Pro Gln Thr Glu
    290                 295                 300

Leu Phe Arg Val Glu Asp Lys Phe Gly Ser Trp Pro Glu Val Met Lys
305                 310                 315                 320

Thr His Phe Thr Ser Gly Gly Glu Leu Asp Lys Leu Leu Ala Ala Gly
                325                 330                 335

Arg Asn

<210> SEQ ID NO 44
<211> LENGTH: 191
<212> TYPE: PRT
<213> ORGANISM: Shigella flexneri

<400> SEQUENCE: 44

Met Lys Ala Leu Ser Pro Ile Ala Val Leu Ile Ser Ala Leu Leu Leu
1               5                   10                  15

Gln Gly Cys Val Ala Ala Ala Val Val Gly Thr Ala Ala Val Gly Thr
            20                  25                  30

Lys Ala Ala Thr Asp Pro Arg Ser Val Gly Thr Gln Val Asp Asp Gly
        35                  40                  45

Thr Leu Glu Val Arg Val Asn Ser Ala Leu Ser Lys Asp Glu Gln Ile
    50                  55                  60

Lys Lys Glu Thr Arg Ile Asn Val Thr Ala Tyr Gln Gly Lys Val Leu
65                  70                  75                  80

Leu Val Gly Gln Ser Pro Asn Ala Glu Leu Ser Ala Arg Ala Lys Gln
                85                  90                  95

Ile Ala Met Gly Val Asp Gly Ala Asn Glu Val Tyr Asn Glu Ile Arg
            100                 105                 110

Gln Gly Gln Pro Ile Gly Leu Gly Glu Ala Ser Asn Asp Thr Trp Ile
        115                 120                 125

```
Thr Thr Lys Val Arg Ser Gln Leu Leu Thr Ser Asp Leu Val Lys Ser
130                 135                 140

Ser Asn Val Lys Val Thr Thr Glu Asn Gly Glu Val Phe Leu Met Gly
145                 150                 155                 160

Leu Val Thr Glu Arg Glu Ala Lys Ala Ala Ala Asp Ile Ala Ser Arg
                165                 170                 175

Val Ser Gly Val Lys Arg Val Thr Thr Ala Phe Thr Phe Ile Lys
            180                 185                 190
```

<210> SEQ ID NO 45
<211> LENGTH: 353
<212> TYPE: PRT
<213> ORGANISM: Shigella sonnei

<400> SEQUENCE: 45

```
Met His Leu Arg His Leu Phe Ser Ser Arg Leu Arg Gly Ser Leu Leu
1               5                   10                  15

Leu Gly Ser Leu Leu Val Ala Ser Ser Phe Ser Thr Gln Ala Ala Glu
            20                  25                  30

Glu Met Leu Arg Lys Ala Val Gly Lys Gly Ala Tyr Glu Met Ala Tyr
        35                  40                  45

Ser Gln Gln Glu Asn Ala Leu Trp Leu Ala Thr Ser Gln Ser Arg Lys
50                  55                  60

Leu Asp Lys Gly Gly Val Val Tyr Arg Leu Asp Pro Val Thr Leu Glu
65                  70                  75                  80

Val Thr Gln Ala Ile His Asn Asp Leu Lys Pro Phe Gly Val Thr Ile
                85                  90                  95

Asn Asn Thr Thr Gln Thr Leu Trp Phe Gly Asn Thr Val Asn Ser Ala
            100                 105                 110

Val Thr Ala Ile Asp Ala Lys Thr Gly Glu Val Lys Gly Arg Leu Val
        115                 120                 125

Leu Asp Asp Arg Lys Arg Thr Glu Val Arg Pro Leu Gln Pro Arg
130                 135                 140

Glu Leu Val Ala Asp Ala Thr Asn Thr Val Tyr Ile Ser Gly Ile
145                 150                 155                 160

Gly Lys Glu Ser Val Ile Trp Val Val Asp Gly Glu Asn Ile Lys Leu
                165                 170                 175

Lys Thr Ala Ile Gln Asn Thr Gly Lys Met Ser Thr Gly Leu Ala Leu
            180                 185                 190

Asp Ser Lys Gly Lys Arg Leu Tyr Thr Thr Asn Ala Asp Gly Glu Leu
        195                 200                 205

Ile Thr Ile Asp Thr Ala Asp Asn Lys Ile Leu Ser Arg Lys Lys Leu
210                 215                 220

Leu Asp Asp Gly Lys Glu His Phe Phe Ile Asn Ile Ser Leu Asp Thr
225                 230                 235                 240

Ala Arg Gln Arg Ala Phe Ile Thr Asp Ser Lys Ala Ala Glu Val Leu
                245                 250                 255

Val Val Asp Thr Arg Asn Gly Asn Ile Leu Ala Lys Val Ala Ala Pro
            260                 265                 270

Glu Ser Leu Ala Val Leu Phe Asn Pro Ala Arg Asn Glu Ala Tyr Val
        275                 280                 285

Thr His Arg Gln Ala Gly Lys Val Ser Val Ile Asp Ala Lys Ser Tyr
290                 295                 300

Lys Val Val Lys Thr Phe Asp Thr Pro Thr His Pro Asn Ser Leu Ala
305                 310                 315                 320
```

-continued

Leu Ser Ala Asp Gly Lys Thr Leu Tyr Val Ser Val Lys Gln Lys Ser
                    325                 330                 335

Thr Lys Gln Gln Glu Ala Thr Gln Pro Asp Val Ile Arg Ile Ala
                340                 345                 350

Leu

<210> SEQ ID NO 46
<211> LENGTH: 502
<212> TYPE: PRT
<213> ORGANISM: Shigella sonnei

<400> SEQUENCE: 46

Met Asn Lys Ser Leu Val Ala Val Gly Val Ile Val Ala Leu Gly Val
1               5                   10                  15

Val Trp Thr Gly Gly Ala Trp Tyr Thr Gly Lys Lys Ile Glu Thr His
                20                  25                  30

Leu Glu Asp Met Val Ala Gln Ala Asn Ala Gln Leu Lys Leu Thr Ala
            35                  40                  45

Pro Glu Ser Asn Leu Glu Val Ser Tyr Gln Asn Tyr His Arg Gly Val
        50                  55                  60

Phe Ser Ser Gln Leu Gln Leu Leu Val Lys Pro Ile Ala Gly Lys Glu
65                  70                  75                  80

Asn Pro Trp Ile Lys Ser Gly Gln Ser Val Ile Phe Asn Glu Ser Val
                85                  90                  95

Asp His Gly Pro Phe Pro Leu Ala Gln Leu Lys Lys Leu Asn Leu Ile
            100                 105                 110

Pro Ser Met Ala Ser Ile Gln Thr Thr Leu Val Asn Asn Glu Val Ser
        115                 120                 125

Lys Pro Leu Phe Asp Met Ala Lys Gly Glu Thr Pro Phe Glu Ile Asn
130                 135                 140

Ser Arg Ile Gly Tyr Ser Gly Asp Ser Ser Asp Ile Ser Leu Lys
145                 150                 155                 160

Pro Leu Asn Tyr Glu Gln Lys Asp Glu Lys Val Ala Phe Ser Gly Gly
                165                 170                 175

Glu Phe Gln Leu Asn Ala Asp Arg Asp Gly Lys Ala Ile Ser Leu Ser
            180                 185                 190

Gly Glu Ala Gln Ser Gly Arg Ile Asp Ala Val Asn Glu Tyr Asn Gln
        195                 200                 205

Lys Val Gln Leu Thr Phe Asn Asn Leu Lys Thr Asp Gly Ser Ser Thr
    210                 215                 220

Leu Ala Ser Phe Gly Glu Arg Val Gly Asn Gln Lys Leu Ser Leu Glu
225                 230                 235                 240

Lys Met Thr Ile Ser Val Glu Gly Lys Glu Leu Ala Leu Leu Glu Gly
                245                 250                 255

Met Glu Ile Ser Gly Lys Ser Asp Leu Val Asn Asp Gly Lys Thr Ile
            260                 265                 270

Asn Ser Gln Leu Asp Tyr Ser Leu Asn Ser Leu Lys Val Gln Asn Gln
        275                 280                 285

Asp Leu Gly Ser Gly Lys Leu Thr Leu Lys Val Gly Gln Ile Asp Gly
    290                 295                 300

Glu Ala Trp His Gln Phe Ser Gln Gln Tyr Asn Ala Gln Thr Gln Ala
305                 310                 315                 320

Leu Leu Ala Gln Pro Glu Ile Ala Asn Asn Pro Glu Leu Tyr Gln Glu
                325                 330                 335

-continued

```
Lys Val Thr Glu Ala Phe Phe Ser Ala Leu Pro Leu Met Leu Lys Gly
                340                 345                 350

Asp Pro Val Ile Thr Ile Ala Pro Leu Ser Trp Lys Asn Ser Gln Gly
            355                 360                 365

Glu Ser Ala Leu Asn Leu Ser Leu Phe Leu Lys Asp Pro Ala Thr Thr
        370                 375                 380

Lys Glu Ala Pro Gln Thr Leu Ala Gln Glu Val Asp Arg Ser Val Lys
385                 390                 395                 400

Ser Leu Asp Ala Lys Leu Thr Ile Pro Val Asp Met Ala Thr Glu Phe
                405                 410                 415

Met Thr Gln Val Ala Lys Leu Glu Gly Tyr Gln Glu Asp Gln Ala Lys
            420                 425                 430

Lys Leu Ala Lys Gln Gln Val Glu Gly Ala Ser Ala Met Gly Gln Met
        435                 440                 445

Phe Arg Leu Thr Thr Leu Gln Asp Asn Thr Ile Thr Thr Ser Leu Gln
    450                 455                 460

Tyr Thr Asn Gly Gln Ile Thr Leu Asn Gly Gln Lys Met Pro Leu Glu
465                 470                 475                 480

Asp Phe Val Gly Met Phe Ala Met Pro Ala Leu Asn Val Pro Ala Val
                485                 490                 495

Pro Ala Ile Pro Gln Gln
                500
```

<210> SEQ ID NO 47
<211> LENGTH: 269
<212> TYPE: PRT
<213> ORGANISM: Shigella flexneri

<400> SEQUENCE: 47

```
Met Glu Lys Lys Ile Gly Phe Ile Gly Cys Gly Asn Met Gly Lys Ala
1               5                   10                  15

Ile Leu Gly Gly Leu Ile Ala Ser Gly Gln Val Leu Pro Gly Gln Ile
            20                  25                  30

Trp Val Tyr Thr Pro Ser Pro Asp Lys Val Ala Ala Leu His Asp Gln
        35                  40                  45

Phe Gly Ile Asn Ala Ala Glu Ser Ala Gln Glu Val Ala Gln Ile Ala
    50                  55                  60

Asp Ile Ile Phe Ala Ala Val Lys Pro Gly Ile Met Ile Lys Val Leu
65                  70                  75                  80

Ser Glu Ile Thr Ser Ser Leu Asn Lys Asp Ser Leu Val Val Ser Ile
                85                  90                  95

Ala Ala Gly Val Thr Leu Asp Gln Leu Ala Arg Ala Leu Gly His Asp
            100                 105                 110

Arg Lys Ile Ile Arg Ala Met Pro Asn Thr Pro Ala Leu Val Asn Ala
        115                 120                 125

Gly Met Thr Ser Val Thr Pro Asn Ala Leu Val Thr Pro Glu Asp Thr
    130                 135                 140

Ala Asp Val Leu Asn Ile Phe Arg Cys Phe Gly Glu Ala Glu Val Ile
145                 150                 155                 160

Ala Glu Pro Met Ile His Pro Val Val Gly Val Ser Gly Ser Ser Pro
                165                 170                 175

Ala Tyr Val Phe Met Phe Ile Glu Ala Met Ala Asp Ala Ala Val Leu
            180                 185                 190

Gly Gly Met Pro Arg Ala Gln Ala Tyr Lys Phe Ala Ala Gln Ala Val
        195                 200                 205
```

```
Met Gly Ser Ala Lys Met Val Leu Glu Thr Gly Glu His Pro Gly Ala
    210                 215                 220
Leu Lys Asp Met Val Cys Ser Pro Gly Thr Thr Ile Glu Ala Val
225                 230                 235                 240
Arg Val Leu Glu Glu Lys Gly Phe Arg Ala Ala Val Ile Glu Ala Met
                245                 250                 255
Thr Lys Cys Met Glu Lys Ser Glu Lys Leu Ser Lys Ser
                260                 265

<210> SEQ ID NO 48
<211> LENGTH: 307
<212> TYPE: PRT
<213> ORGANISM: Shigella flexneri

<400> SEQUENCE: 48

Met Arg Ser Arg Phe Ser Ala Phe Tyr Pro Lys Ala Asn Tyr Gly Leu
1               5                   10                  15
Gln Gly Ser Gln Pro Ser Asp Val Arg Ala His Asn Arg Ala Ala Asn
                20                  25                  30
Gly Ala Cys Asp Glu Tyr Lys Gln Leu Lys Val Leu Ser Met Gly Arg
            35                  40                  45
Gln Lys Ala Val Ile Lys Ala Arg Glu Ala Lys Arg Val Leu Arg
    50                  55                  60
Arg Asp Ser Arg Ser His Lys Gln Arg Glu Glu Glu Ser Val Thr Ser
65                  70                  75                  80
Leu Val Gln Met Ser Gly Val Glu Ala Ile Gly Met Ala Arg Asp Ser
                85                  90                  95
Arg Asp Thr Ser Pro Ile Leu Ala Arg Asn Glu Ala Gln Leu His Tyr
            100                 105                 110
Leu Gln Ala Ile Glu Ser Lys Gln Leu Ile Phe Ala Thr Gly Glu Ala
        115                 120                 125
Gly Cys Gly Lys Thr Trp Ile Ser Ala Ala Lys Ala Ala Glu Ala Leu
    130                 135                 140
Ile His Lys Asp Val Asp Arg Ile Ile Val Thr Arg Pro Val Leu Gln
145                 150                 155                 160
Ala Asp Glu Asp Leu Gly Phe Leu Pro Gly Asp Ile Ala Glu Lys Phe
                165                 170                 175
Ala Pro Tyr Phe Arg Pro Val Tyr Asp Leu Leu Val Arg Arg Leu Gly
            180                 185                 190
Ala Ser Phe Met Gln Tyr Cys Leu Arg Pro Glu Ile Gly Lys Val Glu
        195                 200                 205
Thr Ala Pro Phe Ala Tyr Met Arg Gly Arg Thr Phe Glu Asn Ala Val
    210                 215                 220
Val Ile Leu Asp Glu Ala Gln Asn Val Thr Ala Ala Gln Met Lys Met
225                 230                 235                 240
Phe Leu Thr Arg Leu Gly Glu Asn Val Thr Val Ile Val Asn Gly Asp
                245                 250                 255
Ile Thr Gln Cys Asp Leu Pro Arg Gly Val Cys Ser Gly Leu Ser Asp
            260                 265                 270
Ala Leu Glu Arg Phe Glu Asp Glu Met Val Gly Ile Val Arg Phe
        275                 280                 285
Gly Lys Glu Asp Cys Val Arg Ser Ala Leu Cys Gln Arg Thr Leu His
    290                 295                 300
Ala Tyr Ser
305
```

<210> SEQ ID NO 49
<211> LENGTH: 235
<212> TYPE: PRT
<213> ORGANISM: Shigella flexneri

<400> SEQUENCE: 49

Met Gly Ile Ser Gly Met Ala Ala Gln Ala Asn Glu Leu Pro Asp Gly
1               5                   10                  15

Pro His Ile Val Thr Ser Gly Thr Ala Ser Val Asp Ala Val Pro Asp
                20                  25                  30

Ile Ala Thr Leu Ala Ile Glu Val Asn Val Ala Ala Lys Asp Ala Ala
            35                  40                  45

Thr Ala Lys Lys Gln Ala Asp Glu Arg Val Ala Gln Tyr Ile Ser Phe
50                  55                  60

Leu Glu Leu Asn Gln Ile Ala Lys Lys Asp Ile Ser Ser Ala Asn Leu
65                  70                  75                  80

Arg Thr Gln Pro Asp Tyr Asp Tyr Gln Asp Gly Lys Ser Ile Leu Lys
                85                  90                  95

Gly Tyr Arg Ala Val Arg Thr Val Glu Val Thr Leu Arg Gln Leu Asp
                100                 105                 110

Lys Leu Asn Ser Leu Leu Asp Gly Ala Leu Lys Ala Gly Leu Asn Glu
            115                 120                 125

Ile Arg Ser Val Ser Leu Gly Val Ala Gln Pro Asp Ala Tyr Lys Asp
130                 135                 140

Lys Ala Arg Lys Ala Ala Ile Asp Asn Ala Ile His Gln Ala Gln Glu
145                 150                 155                 160

Leu Ala Asn Gly Phe His Arg Lys Leu Gly Pro Val Tyr Ser Val Arg
                165                 170                 175

Tyr His Val Ser Asn Tyr Gln Pro Ser Pro Met Val Arg Met Met Lys
                180                 185                 190

Ala Asp Ala Ala Pro Val Ser Ala Gln Glu Thr Tyr Glu Gln Ala Ala
            195                 200                 205

Ile Gln Phe Asp Asp Gln Val Asp Val Val Phe Gln Leu Glu Pro Val
210                 215                 220

Asp Gln Gln Pro Ala Lys Thr Pro Ala Ala Gln
225                 230                 235

<210> SEQ ID NO 50
<211> LENGTH: 314
<212> TYPE: PRT
<213> ORGANISM: Shigella sonnei

<400> SEQUENCE: 50

Met Lys Leu Lys Asn Thr Leu Leu Ala Ser Ala Leu Leu Ser Ala Thr
1               5                   10                  15

Ala Phe Ser Val Asn Ala Ala Thr Glu Leu Thr Pro Glu Gln Ala Ala
                20                  25                  30

Ala Val Lys Pro Phe Asp Arg Val Val Thr Gly Arg Phe Asn Ala
            35                  40                  45

Ile Gly Glu Ala Val Lys Ala Val Ser Arg Arg Ala Asp Lys Glu Gly
50                  55                  60

Ala Ala Ser Phe Tyr Val Val Asp Thr Ser Asp Phe Gly Asn Ser Gly
65                  70                  75                  80

Asn Trp Arg Val Val Ala Asp Leu Tyr Lys Ala Asp Ala Glu Lys Ala
                85                  90                  95

Glu Glu Thr Ser Asn Arg Val Ile Asn Gly Val Glu Leu Pro Lys
            100                 105                 110

Asp Gln Ala Val Leu Ile Glu Pro Phe Asp Thr Val Val Gln Gly
        115                 120                 125

Phe Tyr Arg Ser Gln Pro Glu Val Asn Asp Ala Ile Thr Lys Ala Ala
    130                 135                 140

Lys Ala Lys Gly Ala Tyr Ser Phe Tyr Ile Val Arg Gln Ile Asp Ala
145                 150                 155                 160

Asn Gln Gly Gly Asn Gln Arg Ile Thr Ala Phe Ile Tyr Lys Lys Asp
                165                 170                 175

Ala Lys Lys Arg Ile Val Gln Ser Pro Asp Val Ile Pro Ala Asp Ser
            180                 185                 190

Glu Ala Gly Arg Ala Ala Leu Ala Ala Gly Glu Ala Ala Lys Lys
        195                 200                 205

Val Glu Ile Leu Gly Val Ala Thr Thr Ala Ser Pro Ser Ser Glu Val
    210                 215                 220

Gly Arg Phe Phe Glu Thr Gln Ser Ser Lys Gly Gly Arg Tyr Thr Val
225                 230                 235                 240

Met Leu Pro Asp Gly Thr Lys Val Glu Glu Leu Asn Lys Ala Thr Ala
                245                 250                 255

Ala Met Met Val Pro Phe Asp Ser Ile Lys Phe Ser Gly Asn Tyr Gly
            260                 265                 270

Asn Met Thr Glu Val Ser Tyr Gln Val Ala Lys Arg Ala Ala Lys Lys
        275                 280                 285

Gly Ala Lys Tyr Tyr His Ile Thr Arg Gln Trp Gln Glu Arg Gly Asn
    290                 295                 300

Asn Leu Thr Val Ser Ala Asp Leu Tyr Lys
305                 310

<210> SEQ ID NO 51
<211> LENGTH: 211
<212> TYPE: PRT
<213> ORGANISM: Shigella sonnei

<400> SEQUENCE: 51

Met Phe Lys Arg Leu Met Met Val Ala Leu Val Ile Ala Pro Leu
1               5                   10                  15

Ser Ala Ala Thr Ala Ala Asp Gln Thr Asn Pro Tyr Lys Leu Met Asp
            20                  25                  30

Glu Ala Ala Gln Lys Thr Phe Asp Arg Leu Lys Asn Glu Gln Pro Gln
        35                  40                  45

Ile Arg Ala Asn Pro Asp Tyr Leu Arg Thr Ile Val Asp Gln Glu Leu
50                  55                  60

Leu Pro Tyr Val Gln Val Lys Tyr Ala Gly Leu Val Leu Gly Gln
65                  70                  75                  80

Tyr Tyr Lys Ser Ala Thr Pro Ala Gln Arg Glu Ala Tyr Phe Ala Ala
                85                  90                  95

Phe Arg Glu Tyr Leu Lys Gln Ala Tyr Gly Gln Ala Leu Ala Met Tyr
            100                 105                 110

His Gly Gln Thr Tyr Gln Ile Ala Pro Glu Gln Pro Leu Gly Asp Lys
        115                 120                 125

Thr Ile Val Pro Ile Arg Val Thr Ile Asp Pro Asn Gly Arg Pro
130                 135                 140

Pro Val Arg Leu Asp Phe Gln Trp Arg Lys Asn Ser Gln Thr Gly Asn
145                 150                 155                 160

```
Trp Gln Ala Tyr Asp Met Ile Ala Glu Gly Val Ser Met Ile Thr Thr
                165                 170                 175

Lys Gln Asn Glu Trp Gly Thr Leu Leu Arg Thr Lys Gly Ile Asp Gly
            180                 185                 190

Leu Thr Ala Gln Leu Lys Ser Ile Ser Gln Gln Lys Ile Thr Leu Glu
        195                 200                 205

Glu Lys Lys
    210

<210> SEQ ID NO 52
<211> LENGTH: 548
<212> TYPE: PRT
<213> ORGANISM: Shigella flexneri

<400> SEQUENCE: 52

Met Ala Ala Lys Asp Val Lys Phe Gly Asn Asp Ala Arg Val Lys Met
1               5                   10                  15

Leu Arg Gly Val Asn Val Leu Ala Asp Ala Val Lys Val Thr Leu Gly
            20                  25                  30

Pro Lys Gly Arg Asn Val Val Leu Asp Lys Ser Phe Gly Ala Pro Thr
        35                  40                  45

Ile Thr Lys Asp Gly Val Ser Val Ala Arg Glu Ile Glu Leu Glu Asp
    50                  55                  60

Lys Phe Glu Asn Met Gly Ala Gln Met Val Lys Glu Val Ala Ser Lys
65                  70                  75                  80

Ala Asn Asp Ala Ala Gly Asp Gly Thr Thr Thr Ala Thr Val Leu Ala
                85                  90                  95

Gln Ala Ile Ile Thr Glu Gly Leu Lys Ala Val Ala Ala Gly Met Asn
            100                 105                 110

Pro Met Asp Leu Lys Arg Gly Ile Asp Lys Ala Val Thr Ala Ala Val
        115                 120                 125

Glu Glu Leu Lys Ala Leu Ser Val Pro Cys Ser Asp Ser Lys Ala Ile
    130                 135                 140

Ala Gln Val Gly Thr Ile Ser Ala Asn Ser Asp Glu Thr Val Gly Lys
145                 150                 155                 160

Leu Ile Ala Glu Ala Met Asp Lys Val Gly Lys Glu Gly Val Ile Thr
                165                 170                 175

Val Glu Asp Gly Thr Gly Leu Gln Asp Glu Leu Asp Val Val Glu Gly
            180                 185                 190

Met Gln Phe Asp Arg Gly Tyr Leu Ser Pro Tyr Phe Ile Asn Lys Pro
        195                 200                 205

Glu Thr Gly Ala Val Glu Leu Glu Ser Pro Phe Ile Leu Leu Ala Asp
    210                 215                 220

Lys Lys Ile Ser Asn Ile Arg Glu Met Leu Pro Val Leu Glu Ala Val
225                 230                 235                 240

Ala Lys Ala Gly Lys Pro Leu Leu Ile Ile Ala Glu Asp Val Glu Gly
                245                 250                 255

Glu Ala Leu Ala Thr Leu Val Val Asn Thr Met Arg Gly Ile Val Lys
            260                 265                 270

Val Ala Ala Val Lys Ala Pro Gly Phe Gly Asp Arg Arg Lys Ala Met
        275                 280                 285

Leu Gln Asp Ile Ala Thr Leu Thr Gly Gly Thr Val Ile Ser Glu Glu
    290                 295                 300

Ile Gly Met Glu Leu Glu Lys Ala Thr Leu Glu Asp Leu Gly Gln Ala
305                 310                 315                 320
```

```
Lys Arg Val Val Ile Asn Lys Asp Thr Thr Thr Ile Ile Asp Gly Val
                325                 330                 335

Gly Glu Glu Ala Ala Ile Gln Gly Arg Val Ala Gln Ile Arg Gln Gln
            340                 345                 350

Ile Glu Glu Ala Thr Ser Asp Tyr Asp Arg Glu Lys Leu Gln Glu Arg
            355                 360                 365

Val Ala Lys Leu Ala Gly Gly Val Ala Val Ile Lys Val Gly Ala Ala
370                 375                 380

Thr Glu Val Glu Met Lys Glu Lys Lys Ala Arg Val Glu Asp Ala Leu
385                 390                 395                 400

His Ala Thr Arg Ala Ala Val Glu Glu Gly Val Val Ala Gly Gly Gly
                405                 410                 415

Val Ala Leu Ile Arg Val Ala Ser Lys Leu Ala Asp Leu Arg Gly Gln
                420                 425                 430

Asn Glu Asp Gln Asn Val Gly Ile Lys Val Ala Leu Arg Ala Met Glu
            435                 440                 445

Ala Pro Leu Arg Gln Ile Val Leu Asn Cys Gly Glu Glu Pro Ser Val
        450                 455                 460

Val Ala Asn Thr Val Lys Gly Asp Gly Asn Tyr Gly Tyr Asn Ala
465                 470                 475                 480

Ala Thr Glu Glu Tyr Gly Asn Met Ile Asp Met Gly Ile Leu Asp Pro
                485                 490                 495

Thr Lys Val Thr Arg Ser Ala Leu Gln Tyr Ala Ala Ser Val Ala Gly
            500                 505                 510

Leu Met Ile Thr Thr Glu Cys Met Val Thr Asp Leu Pro Lys Asn Asp
        515                 520                 525

Ala Ala Asp Leu Gly Ala Ala Gly Gly Met Gly Gly Met Gly Gly Met
    530                 535                 540

Gly Gly Met Met
545

<210> SEQ ID NO 53
<211> LENGTH: 474
<212> TYPE: PRT
<213> ORGANISM: Shigella flexneri

<400> SEQUENCE: 53

Met Ser Thr Glu Ile Lys Thr Gln Val Val Val Leu Gly Ala Gly Pro
1               5                   10                  15

Ala Gly Tyr Ser Ala Ala Phe Arg Cys Ala Asp Leu Gly Leu Glu Thr
            20                  25                  30

Val Ile Val Glu Arg Tyr Asn Thr Leu Gly Gly Val Cys Leu Asn Val
        35                  40                  45

Gly Cys Ile Pro Ser Lys Ala Leu Leu His Val Ala Lys Val Ile Glu
    50                  55                  60

Glu Ala Lys Ala Leu Ala Glu His Gly Ile Val Phe Gly Glu Pro Lys
65                  70                  75                  80

Thr Asp Ile Asp Lys Ile Arg Thr Trp Lys Glu Lys Val Ile Asn Gln
                85                  90                  95

Leu Thr Gly Gly Leu Ala Gly Met Ala Lys Gly Arg Lys Val Lys Val
            100                 105                 110

Val Asn Gly Leu Gly Lys Phe Thr Gly Ala Asn Thr Leu Glu Val Glu
        115                 120                 125

Gly Glu Asn Gly Lys Thr Val Ile Asn Phe Asp Asn Ala Ile Ile Ala
    130                 135                 140
```

Ala Gly Ser Arg Pro Ile Gln Leu Pro Phe Ile Pro His Glu Asp Pro
145                 150                 155                 160

Arg Ile Trp Asp Ser Thr Asp Ala Leu Glu Lys Glu Val Pro Glu
            165                 170                 175

Arg Leu Leu Val Met Gly Gly Ile Ile Gly Leu Glu Met Gly Thr
        180                 185                 190

Val Tyr His Ala Leu Gly Ser Gln Ile Asp Val Val Glu Met Phe Asp
    195                 200                 205

Gln Val Ile Pro Ala Ala Asp Lys Asp Ile Val Lys Val Phe Thr Lys
    210                 215                 220

Arg Ile Ser Lys Lys Phe Asn Leu Met Leu Glu Thr Lys Val Thr Ala
225                 230                 235                 240

Val Glu Ala Lys Glu Asp Gly Ile Tyr Val Thr Met Glu Gly Lys Lys
            245                 250                 255

Ala Pro Ala Glu Pro Gln Arg Tyr Asp Ala Val Leu Val Ala Ile Gly
            260                 265                 270

Arg Val Pro Asn Gly Lys Asn Leu Asp Ala Gly Lys Ala Gly Val Glu
            275                 280                 285

Val Asp Asp Arg Gly Phe Ile Arg Val Asp Lys Gln Leu Arg Thr Asn
290                 295                 300

Val Pro His Ile Phe Ala Ile Gly Asp Ile Val Gly Gln Pro Met Leu
305                 310                 315                 320

Ala His Lys Gly Val His Glu Gly His Val Ala Ala Glu Val Ile Ala
                325                 330                 335

Gly Lys Lys His Tyr Phe Asp Pro Lys Val Ile Pro Ser Ile Ala Tyr
            340                 345                 350

Thr Glu Pro Glu Val Ala Trp Val Gly Leu Thr Glu Lys Glu Ala Lys
            355                 360                 365

Glu Lys Gly Ile Ser Tyr Glu Thr Ala Thr Phe Pro Trp Ala Ala Ser
    370                 375                 380

Gly Arg Ala Ile Ala Ser Asp Cys Ala Asp Gly Met Thr Lys Leu Ile
385                 390                 395                 400

Phe Asp Lys Glu Ser His Arg Val Ile Gly Gly Ala Ile Val Gly Thr
                405                 410                 415

Asn Gly Gly Glu Leu Leu Gly Glu Ile Gly Leu Ala Ile Glu Met Gly
            420                 425                 430

Cys Asp Ala Glu Asp Ile Ala Leu Thr Ile His Ala His Pro Thr Leu
            435                 440                 445

His Glu Ser Val Gly Leu Ala Ala Glu Val Phe Glu Gly Ser Ile Thr
    450                 455                 460

Asp Leu Pro Asn Pro Lys Ala Lys Lys Lys
465                 470

<210> SEQ ID NO 54
<211> LENGTH: 112
<212> TYPE: PRT
<213> ORGANISM: Shigella flexneri

<400> SEQUENCE: 54

Met Asn Lys Asn Met Ala Gly Ile Leu Ser Ala Ala Val Leu Thr
1               5                   10                  15

Met Leu Ala Gly Cys Thr Ala Tyr Asp Arg Thr Lys Asp Gln Phe Val
        20                  25                  30

Gln Pro Val Val Lys Asp Val Lys Lys Gly Met Ser Arg Ala Gln Val
    35                  40                  45

```
Ala Gln Ile Ala Gly Lys Pro Ser Ser Glu Val Ser Met Ile His Ala
    50                  55                  60

Arg Gly Thr Cys Gln Thr Tyr Ile Leu Gly Gln Arg Asp Gly Lys Ala
65                  70                  75                  80

Glu Thr Tyr Phe Val Ala Leu Asp Asp Thr Gly His Val Ile Asn Ser
                    85                  90                  95

Gly Tyr Gln Thr Cys Ala Glu Tyr Asp Thr Asp Pro Gln Ala Ala Lys
                100                 105                 110
```

<210> SEQ ID NO 55
<211> LENGTH: 239
<212> TYPE: PRT
<213> ORGANISM: Shigella flexneri

<400> SEQUENCE: 55

```
Met Ala Thr Pro His Ile Asn Ala Glu Met Gly Asp Phe Ala Asp Val
1               5                   10                  15

Val Leu Met Pro Gly Asp Pro Leu Arg Ala Lys Tyr Ile Ala Glu Thr
                20                  25                  30

Phe Leu Glu Asp Ala Arg Glu Val Asn Asn Val Arg Gly Met Leu Gly
            35                  40                  45

Phe Thr Gly Thr Tyr Lys Gly Arg Lys Ile Ser Val Met Gly His Gly
    50                  55                  60

Met Gly Ile Pro Ser Cys Ser Ile Tyr Thr Lys Glu Leu Ile Thr Asp
65                  70                  75                  80

Phe Gly Val Lys Lys Ile Ile Arg Val Gly Ser Cys Gly Ala Val Leu
                85                  90                  95

Pro His Val Lys Leu Arg Asp Val Val Ile Gly Met Gly Ala Cys Thr
                100                 105                 110

Asp Ser Lys Val Asn Arg Ile Arg Phe Lys Asp His Asp Phe Ala Ala
            115                 120                 125

Ile Ala Asp Phe Asp Met Val Arg Asn Ala Val Asp Ala Ala Lys Ala
130                 135                 140

Leu Gly Val Asp Ala Arg Val Gly Asn Leu Phe Ser Ala Asp Leu Phe
145                 150                 155                 160

Tyr Ser Pro Asp Gly Glu Met Phe Asp Val Met Glu Lys Tyr Gly Ile
                165                 170                 175

Leu Gly Val Glu Met Glu Ala Ala Gly Ile Tyr Gly Val Ala Ala Glu
                180                 185                 190

Phe Gly Ala Lys Ala Leu Thr Ile Cys Thr Val Ser Asp His Ile Arg
            195                 200                 205

Thr His Glu Gln Thr Thr Ala Ala Glu Arg Gln Thr Thr Phe Asn Asp
    210                 215                 220

Met Ile Lys Ile Ala Leu Glu Ser Val Leu Leu Gly Asp Lys Glu
225                 230                 235
```

<210> SEQ ID NO 56
<211> LENGTH: 388
<212> TYPE: PRT
<213> ORGANISM: Shigella flexneri

<400> SEQUENCE: 56

```
Met Asn Leu His Glu Tyr Gln Ala Lys Gln Leu Phe Ala Arg Tyr Gly
1               5                   10                  15

Leu Pro Ala Pro Val Gly Tyr Ala Cys Thr Thr Pro Arg Glu Ala Glu
                20                  25                  30
```

```
Glu Ala Ala Ser Lys Ile Gly Ala Gly Pro Trp Val Val Lys Cys Gln
             35                  40                  45

Val His Ala Gly Gly Arg Gly Lys Ala Gly Gly Val Lys Val Val Asn
 50                  55                  60

Ser Lys Glu Asp Ile Arg Ala Phe Ala Glu Asn Trp Leu Gly Lys Arg
 65                  70                  75                  80

Leu Val Thr Tyr Gln Thr Asp Ala Asn Gly Gln Pro Val Asn Gln Ile
                 85                  90                  95

Leu Val Glu Ala Ala Thr Asp Ile Ala Lys Glu Leu Tyr Leu Gly Ala
             100                 105                 110

Val Val Asp Arg Ser Ser Arg Arg Val Val Phe Met Ala Ser Thr Glu
             115                 120                 125

Gly Gly Val Glu Ile Glu Lys Val Ala Glu Thr Pro His Leu Ile
130                 135                 140

His Lys Val Ala Leu Asp Pro Leu Thr Gly Pro Met Pro Tyr Gln Gly
145                 150                 155                 160

Arg Glu Leu Ala Phe Lys Leu Gly Leu Glu Gly Lys Leu Val Gln Gln
                165                 170                 175

Phe Thr Lys Ile Phe Met Gly Leu Ala Thr Ile Phe Leu Glu Arg Asp
            180                 185                 190

Leu Ala Leu Ile Glu Ile Asn Pro Leu Val Ile Thr Lys Gln Gly Asp
            195                 200                 205

Leu Ile Cys Leu Asp Gly Lys Leu Gly Ala Asp Gly Asn Ala Leu Phe
210                 215                 220

Arg Gln Pro Asp Leu Arg Glu Met Arg Asp Gln Ser Gln Glu Asp Pro
225                 230                 235                 240

Arg Glu Ala Gln Ala Ala Gln Trp Glu Leu Asn Tyr Val Ala Leu Asp
                245                 250                 255

Gly Asn Ile Gly Cys Met Val Asn Gly Ala Gly Leu Ala Met Gly Thr
            260                 265                 270

Met Asp Ile Val Lys Leu His Gly Gly Glu Pro Ala Asn Phe Leu Asp
            275                 280                 285

Val Gly Gly Gly Ala Thr Lys Glu Arg Val Thr Glu Ala Phe Lys Ile
290                 295                 300

Ile Leu Ser Asp Asp Lys Val Lys Ala Val Leu Val Asn Ile Phe Gly
305                 310                 315                 320

Gly Ile Val Arg Cys Asp Leu Ile Ala Asp Gly Ile Ile Gly Ala Val
                325                 330                 335

Ala Glu Val Gly Val Asn Val Pro Val Val Val Arg Leu Glu Gly Asn
            340                 345                 350

Asn Ala Glu Leu Gly Ala Lys Lys Leu Ala Asp Ser Gly Leu Asn Ile
            355                 360                 365

Ile Ala Ala Lys Gly Leu Thr Asp Ala Ala Gln Gln Val Val Ala Ala
370                 375                 380

Val Glu Gly Lys
385

<210> SEQ ID NO 57
<211> LENGTH: 169
<212> TYPE: PRT
<213> ORGANISM: Shigella flexneri
```

```
<400> SEQUENCE: 57

Met Gly Leu Phe Asp Lys Leu Lys Ser Leu Val Ser Asp Asp Lys Lys
1               5                   10                  15

Asp Thr Gly Thr Ile Glu Ile Ile Ala Pro Leu Ser Gly Glu Ile Val
            20                  25                  30

Asn Ile Glu Asp Val Pro Asp Val Phe Ala Glu Lys Ile Val Gly
        35                  40                  45

Asp Gly Ile Ala Ile Lys Pro Thr Gly Asn Lys Met Val Ala Pro Val
    50                  55                  60

Asp Gly Thr Ile Gly Lys Ile Phe Glu Thr Asn His Ala Phe Ser Ile
65                  70                  75                  80

Glu Ser Asp Ser Gly Val Glu Leu Phe Val His Phe Gly Ile Asp Thr
                85                  90                  95

Val Glu Leu Lys Gly Gly Phe Lys Arg Ile Ala Glu Glu Gly Gln
            100                 105                 110

Arg Val Lys Val Gly Asp Thr Val Ile Glu Phe Asp Leu Pro Leu Leu
        115                 120                 125

Glu Glu Lys Ala Lys Ser Thr Leu Thr Pro Val Val Ile Ser Asn Met
    130                 135                 140

Asp Glu Ile Lys Glu Leu Ile Lys Leu Ser Gly Ser Val Thr Val Gly
145                 150                 155                 160

Glu Thr Pro Val Ile Arg Ile Lys Lys
                165

<210> SEQ ID NO 58
<211> LENGTH: 638
<212> TYPE: PRT
<213> ORGANISM: Shigella flexneri

<400> SEQUENCE: 58

Met Gly Lys Ile Ile Gly Ile Asp Leu Gly Thr Thr Asn Ser Cys Val
1               5                   10                  15

Ala Ile Met Asp Gly Thr Ile Pro Arg Val Leu Glu Asn Ala Glu Gly
            20                  25                  30

Asp Arg Thr Thr Pro Ser Ile Ile Ala Tyr Thr Gln Asp Gly Glu Thr
        35                  40                  45

Leu Val Gly Gln Pro Ala Lys Arg Gln Ala Val Thr Asn Pro Gln Asn
    50                  55                  60

Thr Leu Phe Ala Ile Lys Arg Leu Ile Gly Arg Arg Phe Gln Asp Glu
65                  70                  75                  80

Glu Val Gln Arg Asp Val Ser Ile Met Pro Phe Lys Ile Ile Ala Ala
                85                  90                  95

Asp Asn Gly Asp Ala Trp Val Glu Val Lys Gly Gln Lys Met Ala Pro
            100                 105                 110

Pro Gln Ile Ser Ala Glu Val Leu Lys Lys Met Lys Lys Thr Ala Glu
        115                 120                 125

Asp Tyr Leu Gly Glu Pro Val Thr Glu Ala Val Ile Thr Val Pro Ala
    130                 135                 140

Tyr Phe Asn Asp Ala Gln Arg Gln Ala Thr Lys Asp Ala Gly Arg Ile
145                 150                 155                 160

Ala Gly Leu Glu Val Lys Arg Ile Ile Asn Glu Pro Thr Ala Ala Ala
                165                 170                 175

Leu Ala Tyr Gly Leu Asp Lys Gly Thr Gly Asn Arg Thr Ile Ala Val
            180                 185                 190
```

```
Tyr Asp Leu Gly Gly Gly Thr Phe Asp Ile Ser Ile Ile Glu Ile Asp
            195                 200                 205
Glu Val Asp Gly Glu Lys Thr Phe Glu Val Leu Ala Thr Asn Gly Asp
        210                 215                 220
Thr His Leu Gly Gly Glu Asp Phe Asp Ser Arg Leu Ile Asn Tyr Leu
225                 230                 235                 240
Val Glu Glu Phe Lys Lys Asp Gln Gly Ile Asp Leu Arg Asn Asp Pro
                245                 250                 255
Leu Ala Met Gln Arg Leu Lys Glu Ala Glu Lys Ala Lys Ile Glu
            260                 265                 270
Leu Ser Ser Ala Gln Gln Thr Asp Val Asn Leu Pro Tyr Ile Thr Ala
        275                 280                 285
Asp Ala Thr Gly Pro Lys His Met Asn Ile Lys Val Thr Arg Ala Lys
        290                 295                 300
Leu Glu Ser Leu Val Glu Asp Leu Val Asn Arg Ser Ile Glu Pro Leu
305                 310                 315                 320
Lys Val Ala Leu Gln Asp Ala Gly Leu Ser Val Ser Asp Ile Asp Asp
                325                 330                 335
Val Ile Leu Val Gly Gly Gln Thr Arg Met Pro Met Val Gln Lys Lys
            340                 345                 350
Val Ala Glu Phe Phe Gly Lys Glu Pro Arg Lys Asp Val Asn Pro Asp
        355                 360                 365
Glu Ala Val Ala Ile Gly Ala Ala Val Gln Gly Gly Val Leu Thr Gly
        370                 375                 380
Asp Val Lys Asp Val Leu Leu Leu Asp Val Thr Pro Leu Ser Leu Gly
385                 390                 395                 400
Ile Glu Thr Met Gly Gly Val Met Thr Thr Leu Ile Ala Lys Asn Thr
                405                 410                 415
Thr Ile Pro Thr Lys His Ser Gln Val Phe Ser Thr Ala Glu Asp Asn
            420                 425                 430
Gln Ser Ala Val Thr Ile His Val Leu Gln Gly Glu Arg Lys Arg Ala
        435                 440                 445
Ala Asp Asn Lys Ser Leu Gly Gln Phe Asn Leu Asp Gly Ile Asn Pro
450                 455                 460
Ala Pro Arg Gly Met Pro Gln Ile Glu Val Thr Phe Asp Ile Asp Ala
465                 470                 475                 480
Asp Gly Ile Leu His Val Ser Ala Lys Asp Lys Asn Ser Gly Lys Glu
                485                 490                 495
Gln Lys Ile Thr Ile Lys Ala Ser Ser Gly Leu Asn Glu Asp Glu Ile
            500                 505                 510
Gln Lys Met Val Arg Asp Ala Glu Ala Asn Ala Glu Ala Asp Arg Lys
        515                 520                 525
Phe Glu Glu Leu Val Gln Thr Arg Asn Gln Gly Asp His Leu Leu His
        530                 535                 540
Ser Thr Arg Lys Gln Val Glu Glu Ala Gly Asp Lys Leu Pro Ala Asp
545                 550                 555                 560
Asp Lys Thr Ala Ile Glu Ser Ala Leu Thr Ala Leu Glu Thr Ala Leu
                565                 570                 575
Lys Gly Glu Asp Lys Ala Ala Ile Glu Ala Lys Met Gln Glu Leu Ala
            580                 585                 590
Gln Val Ser Gln Lys Leu Met Glu Ile Ala Gln Gln His Ala Gln
        595                 600                 605
Gln Gln Thr Ala Gly Ala Asp Ala Ser Ala Asn Asn Ala Lys Asp Asp
```

```
                    610                 615                 620
Asp Val Val Asp Ala Glu Phe Glu Glu Val Lys Asp Lys Lys
625                 630                 635

<210> SEQ ID NO 59
<211> LENGTH: 190
<212> TYPE: PRT
<213> ORGANISM: Shigella sonnei

<400> SEQUENCE: 59

Met Lys Leu Val His Met Ala Ser Cys Leu Ala Val Ala Ile Ala Leu
1               5                   10                  15

Ala Ala Cys Ala Asp Lys Ser Ala Asp Ile Gln Thr Pro Ala Pro Ala
                20                  25                  30

Ala Asn Thr Ser Ile Ser Ala Thr Gln Gln Pro Ala Ile Gln Gln Pro
            35                  40                  45

Asn Val Ser Gly Thr Val Trp Ile Arg Gln Lys Val Ala Leu Pro Pro
        50                  55                  60

Asp Ala Val Leu Thr Val Thr Leu Ser Asp Ala Ser Leu Ala Asp Ala
65                  70                  75                  80

Pro Ser Lys Val Leu Ala Gln Lys Ala Val Arg Thr Glu Gly Lys Gln
                85                  90                  95

Ser Pro Phe Ser Phe Val Leu Pro Phe Asn Pro Ala Asp Val Gln Pro
            100                 105                 110

Asn Ala Arg Ile Leu Leu Ser Ala Ala Ile Thr Val Asn Asp Lys Leu
        115                 120                 125

Val Phe Ile Thr Asp Thr Val Gln Pro Val Ile Asn Lys Gly Gly Thr
130                 135                 140

Lys Ala Asp Leu Thr Leu Val Pro Met Gln Gln Thr Ala Val Pro Val
145                 150                 155                 160

Gln Ala Ser Gly Gly Ala Thr Thr Val Pro Ser Thr Ser Pro Thr
                165                 170                 175

Gln Val Asn Pro Ser Ser Ala Val Pro Ala Pro Thr Gln Tyr
            180                 185                 190

<210> SEQ ID NO 60
<211> LENGTH: 101
<212> TYPE: PRT
<213> ORGANISM: Shigella flexneri

<400> SEQUENCE: 60

Met Ser Lys Glu His Thr Thr Glu His Leu Arg Ala Glu Leu Lys Ser
1               5                   10                  15

Leu Ser Asp Thr Leu Glu Glu Val Leu Ser Ser Ser Gly Glu Lys Ser
                20                  25                  30

Lys Glu Glu Leu Ser Lys Ile Arg Ser Lys Ala Glu Gln Ala Leu Lys
            35                  40                  45

Gln Ser Arg Tyr Arg Leu Gly Glu Thr Gly Asp Ala Ile Ala Lys Gln
        50                  55                  60

Thr Arg Val Ala Ala Ala Arg Ala Asp Glu Tyr Val Arg Glu Asn Pro
65                  70                  75                  80

Trp Thr Gly Val Gly Ile Gly Ala Ala Ile Gly Val Val Leu Gly Val
                85                  90                  95

Leu Leu Ser Arg Arg
            100
```

<210> SEQ ID NO 61
<211> LENGTH: 330
<212> TYPE: PRT
<213> ORGANISM: Shigella dysenteriae

<400> SEQUENCE: 61

```
Met Arg Asn Ile Ile Lys Leu Ala Leu Val Gly Leu Leu Ser Val Ser
1               5                   10                  15

Thr Leu Ala Val Ala Ala Glu Ser Ser Pro Glu Ala Leu Arg Ile Gly
            20                  25                  30

Tyr Gln Lys Ser Asn Ile Ser Ser Val Leu Ala Lys Asn Tyr Gln Met
        35                  40                  45

Leu Glu Lys Arg Tyr Pro Gln Thr Lys Ile Ser Trp Gly Lys Phe Pro
    50                  55                  60

Ala Gly Pro Gln Met Leu Glu Ala Leu Asn Val Gly Ser Ile Asp Leu
65                  70                  75                  80

Gly Ser Thr Gly Asp Ile Pro Pro Ile Phe Ser Gln Ala Ala Gly Ala
                85                  90                  95

Asp Leu Leu Tyr Val Ser Val Glu Pro Pro Lys Pro Lys Ala Glu Val
            100                 105                 110

Ile Leu Val Ala Glu Asn Ser Pro Ile Lys Thr Val Ala Asp Leu Lys
        115                 120                 125

Gly His Lys Val Ala Phe Gln Lys Gly Ser Ser His Asn Leu Leu
    130                 135                 140

Leu Arg Ala Leu Arg Gln Ala Gly Leu Lys Phe Thr Asp Ile Gln Pro
145                 150                 155                 160

Thr Tyr Leu Thr Pro Ala Asp Ala Arg Ala Phe Gln Gln Gly Asn
                165                 170                 175

Val Asp Ala Trp Ala Ile Trp Asp Pro Tyr Tyr Ser Ala Ala Leu Leu
            180                 185                 190

Gln Gly Gly Val Arg Val Leu Lys Asp Gly Thr Asp Leu Asn Gln Thr
        195                 200                 205

Gly Ser Phe Tyr Leu Ala Ala Arg Pro Tyr Ala Glu Lys Asn Gly Ala
    210                 215                 220

Phe Ile Gln Gly Val Leu Ala Thr Phe Ser Glu Ala Asp Ala Leu Thr
225                 230                 235                 240

Arg Ser Gln Arg Glu Gln Ser Ile Ala Leu Leu Ala Lys Thr Met Gly
                245                 250                 255

Leu Pro Ala Pro Val Ile Ala Ser Tyr Leu Asp His Arg Pro Pro Thr
            260                 265                 270

Thr Ile Lys Pro Val Asn Ala Glu Val Ala Ala Leu Gln Gln Gln Thr
        275                 280                 285

Ala Asp Leu Phe Tyr Glu Asn Arg Leu Val Pro Lys Lys Val Asp Ile
    290                 295                 300

Asn Ala Ser Gly Ser Pro Leu Asn Trp Lys Glu Asn Asn Tyr Glu Ser
305                 310                 315                 320

Glu Tyr Val Leu Val Phe Thr Asp Pro Trp
                325                 330
```

<210> SEQ ID NO 62
<211> LENGTH: 678
<212> TYPE: PRT
<213> ORGANISM: Shigella sonnei

<400> SEQUENCE: 62

Met Val Pro Ser Thr Phe Ser Arg Leu Lys Ala Ala Arg Cys Leu Pro

-continued

```
1               5                   10                  15
Val Val Leu Ala Ala Leu Ile Phe Ala Gly Cys Gly Thr His Thr Pro
            20                  25                  30

Asp Gln Ser Thr Ala Tyr Met Gln Gly Thr Ala Gln Ala Asp Ser Ala
            35                  40                  45

Phe Tyr Leu Gln Gln Met Gln Gln Ser Ser Asp Asp Thr Arg Ile Asn
            50                  55                  60

Trp Gln Leu Leu Ala Ile Arg Ala Leu Val Lys Glu Gly Lys Thr Gly
 65                  70                  75                  80

Gln Ala Val Glu Leu Phe Asn Gln Leu Pro Gln Glu Leu Asn Asp Ser
                85                  90                  95

Gln Arg Arg Glu Lys Thr Leu Leu Ala Val Glu Ile Lys Leu Ala Gln
                100                 105                 110

Lys Asp Phe Ala Gly Ala Gln Asn Leu Leu Ala Lys Ile Thr Pro Ala
            115                 120                 125

Asp Leu Glu Gln Asn Gln Gln Ala Arg Tyr Trp Gln Ala Lys Ile Asp
            130                 135                 140

Ala Ser Gln Gly Arg Pro Ser Ile Asp Leu Leu Arg Ala Leu Ile Ala
145                 150                 155                 160

Gln Glu Pro Leu Leu Gly Ala Lys Glu Lys Lys Gln Asn Ile Asp Ala
                165                 170                 175

Thr Trp Gln Ala Leu Ser Ser Met Thr Gln Glu Gln Ala Asn Thr Leu
            180                 185                 190

Val Ile Asn Ala Asp Glu Asn Ile Leu Gln Gly Trp Leu Asp Leu Gln
            195                 200                 205

Arg Val Trp Phe Asp Asn Arg Asn Asp Pro Asp Met Met Lys Ala Gly
            210                 215                 220

Ile Ala Asp Trp Gln Lys Arg Tyr Pro Asn Asn Pro Gly Ala Lys Met
225                 230                 235                 240

Leu Pro Thr Gln Leu Val Asn Val Lys Ala Phe Lys Pro Ala Ser Thr
                245                 250                 255

Asn Lys Ile Ala Leu Leu Leu Pro Leu Asn Gly Gln Ala Ala Val Phe
            260                 265                 270

Gly Arg Thr Ile Gln Gln Gly Phe Glu Ala Ala Lys Asn Ile Gly Thr
            275                 280                 285

Gln Pro Val Ala Ala Gln Val Ala Ala Pro Ala Ala Asp Val Ala
            290                 295                 300

Glu Gln Pro Gln Pro Gln Thr Val Asp Gly Val Ala Ser Pro Ala Gln
305                 310                 315                 320

Ala Ser Val Ser Asp Leu Thr Gly Asp Gln Pro Ala Ala Gln Pro Val
                325                 330                 335

Pro Val Ser Ala Pro Ala Thr Ser Thr Ala Ala Val Ser Ala Pro Ala
            340                 345                 350

Asn Pro Ser Ala Glu Leu Lys Ile Tyr Asp Thr Ser Ser Gln Pro Leu
            355                 360                 365

Ser Gln Ile Leu Ser Gln Val Gln Gln Asp Gly Ala Ser Ile Val Val
            370                 375                 380

Gly Pro Leu Leu Lys Asn Asn Val Glu Glu Leu Leu Lys Ser Asn Thr
385                 390                 395                 400

Pro Leu Asn Val Leu Ala Leu Asn Gln Pro Glu Asn Ile Glu Asn Arg
                405                 410                 415

Val Asn Ile Cys Tyr Phe Ala Leu Ser Pro Glu Asp Glu Ala Arg Asp
            420                 425                 430
```

```
Ala Ala Arg His Ile Arg Asp Gln Gly Lys Gln Ala Pro Leu Val Leu
            435                 440                 445

Ile Pro Arg Ser Ser Leu Gly Asp Arg Val Ala Asn Ala Phe Ala Gln
450                 455                 460

Glu Trp Gln Lys Leu Gly Gly Thr Val Leu Gln Gln Lys Phe Gly
465                 470                 475                 480

Ser Thr Ser Glu Leu Arg Ala Gly Val Asn Gly Gly Ser Gly Ile Ala
                485                 490                 495

Leu Thr Gly Thr Pro Ile Thr Pro Arg Ala Thr Thr Asp Ser Gly Met
            500                 505                 510

Thr Thr Asn Asn Pro Thr Leu Gln Thr Thr Pro Thr Asp Gln Phe
            515                 520                 525

Thr Asn Asn Gly Gly Arg Val Asp Ala Val Tyr Ile Val Ala Thr Pro
            530                 535                 540

Gly Glu Ile Ala Phe Ile Lys Pro Met Ile Ala Met Arg Asn Gly Ser
545                 550                 555                 560

Gln Ser Gly Ala Met Leu Tyr Ala Ser Ser Arg Ser Ala Gln Gly Thr
                565                 570                 575

Ala Gly Pro Asp Phe Arg Leu Glu Met Glu Gly Leu Gln Tyr Ser Glu
            580                 585                 590

Ile Pro Met Leu Ala Gly Gly Asn Leu Pro Leu Met Gln Gln Ala Leu
            595                 600                 605

Ser Ala Val Asn Asn Asp Tyr Ser Leu Ala Arg Met Tyr Ala Met Gly
            610                 615                 620

Val Asp Ala Trp Ser Leu Ala Asn His Phe Ser Gln Met Arg Gln Val
625                 630                 635                 640

Gln Gly Phe Glu Ile Asn Gly Asn Thr Gly Ser Leu Thr Ala Asn Pro
                645                 650                 655

Asp Cys Val Ile Asn Arg Lys Leu Ser Trp Leu Gln Tyr Gln Gln Gly
            660                 665                 670

Gln Val Val Pro Val Ser
            675

<210> SEQ ID NO 63
<211> LENGTH: 392
<212> TYPE: PRT
<213> ORGANISM: Shigella flexneri

<400> SEQUENCE: 63

Met Gln Leu Arg Lys Leu Leu Pro Gly Leu Leu Ser Val Thr Leu
1               5                   10                  15

Leu Ser Gly Cys Ser Leu Phe Asn Ser Glu Glu Asp Val Val Lys Met
                20                  25                  30

Ser Pro Leu Pro Thr Val Glu Asn Gln Phe Thr Pro Thr Thr Ala Trp
            35                  40                  45

Ser Thr Ser Val Gly Ser Gly Ile Gly Asn Phe Tyr Ser Asn Leu His
        50                  55                  60

Pro Ala Leu Ala Asp Asn Val Val Tyr Ala Ala Asp Arg Ala Gly Leu
65                  70                  75                  80

Val Lys Ala Leu Asn Ala Asp Gly Lys Glu Ile Trp Ser Val Ser
                85                  90                  95

Leu Ala Glu Lys Asp Gly Trp Phe Ser Lys Glu Pro Ala Leu Leu Ser
                100                 105                 110

Gly Gly Val Thr Val Ser Gly Gly His Val Tyr Ile Gly Ser Glu Lys
```

```
                 115                 120                 125
Ala Gln Val Tyr Ala Leu Asn Thr Ser Asp Gly Thr Val Ala Trp Gln
130                 135                 140

Thr Lys Val Ala Gly Glu Ala Leu Ser Arg Pro Val Val Ser Asp Gly
145                 150                 155                 160

Leu Val Leu Ile His Thr Ser Asn Gly Gln Leu Gln Ala Leu Asn Glu
                165                 170                 175

Ala Asp Gly Ala Val Lys Trp Thr Val Asn Leu Asp Met Pro Ser Leu
            180                 185                 190

Ser Leu Arg Gly Glu Ser Ala Pro Ala Thr Ala Phe Gly Ala Ala Val
        195                 200                 205

Val Gly Gly Asp Asn Gly Arg Val Ser Ala Val Leu Met Glu Gln Gly
    210                 215                 220

Gln Met Ile Trp Gln Arg Ile Ser Gln Ala Thr Gly Ser Thr Glu
225                 230                 235                 240

Ile Asp Arg Leu Ser Asp Val Asp Thr Thr Pro Val Val Asn Gly
                245                 250                 255

Val Val Phe Ala Leu Ala Tyr Asn Gly Asn Leu Thr Ala Leu Asp Leu
            260                 265                 270

Arg Ser Gly Gln Ile Met Trp Lys Arg Glu Leu Gly Ser Val Asn Asp
        275                 280                 285

Phe Ile Val Asp Gly Asn Arg Ile Tyr Leu Val Asp Gln Asn Asp Arg
    290                 295                 300

Val Met Ala Leu Thr Ile Asp Gly Gly Val Thr Leu Trp Ala Gln Ser
305                 310                 315                 320

Asp Leu Leu His Arg Leu Leu Thr Ser Pro Val Leu Tyr Asn Gly Asn
                325                 330                 335

Leu Val Val Gly Asp Ser Glu Gly Tyr Leu His Trp Ile Asn Val Glu
            340                 345                 350

Asp Gly Arg Phe Val Ala Gln Gln Lys Val Asp Ser Ser Gly Phe Gln
        355                 360                 365

Thr Glu Pro Val Ala Ala Asp Gly Lys Leu Leu Ile Gln Ala Lys Asp
    370                 375                 380

Gly Thr Val Tyr Ser Ile Thr Arg
385                 390

<210> SEQ ID NO 64
<211> LENGTH: 306
<212> TYPE: PRT
<213> ORGANISM: Shigella flexneri

<400> SEQUENCE: 64

Met Asn Met Lys Leu Lys Thr Leu Phe Ala Ala Phe Ala Val Val
1               5                   10                  15

Gly Phe Cys Ser Thr Ala Ser Ala Val Thr Tyr Pro Leu Pro Thr Asp
                20                  25                  30

Gly Ser Arg Leu Val Gly Gln Asn Gln Val Ile Thr Ile Pro Glu Gly
            35                  40                  45

Asn Thr Gln Pro Leu Glu Tyr Phe Ala Ala Glu Tyr Gln Met Gly Leu
        50                  55                  60

Ser Asn Met Met Glu Ala Asn Pro Gly Val Asp Thr Phe Leu Pro Lys
65                  70                  75                  80

Gly Gly Thr Val Leu Asn Ile Pro Gln Gln Leu Ile Leu Pro Asp Thr
                85                  90                  95
```

Val His Glu Gly Ile Val Ile Asn Ser Ala Glu Met Arg Leu Tyr Tyr
                100                 105                 110

Tyr Pro Lys Gly Thr Asn Thr Val Ile Val Leu Pro Ile Gly Ile Gly
            115                 120                 125

Gln Leu Gly Lys Asp Thr Pro Ile Asn Trp Thr Thr Lys Val Glu His
        130                 135                 140

Lys Lys Ala Gly Pro Thr Trp Thr Pro Thr Ala Lys Met His Ala Glu
145                 150                 155                 160

Tyr Arg Ala Ala Gly Glu Pro Leu Pro Ala Val Val Pro Ala Gly Pro
                165                 170                 175

Asp Asn Pro Met Gly Leu Tyr Ala Leu Tyr Ile Gly Arg Leu Tyr Ala
            180                 185                 190

Ile His Gly Thr Asn Ala Asn Phe Gly Ile Gly Leu Arg Val Ser His
        195                 200                 205

Gly Cys Val Arg Leu Arg Asn Glu Asp Ile Lys Phe Leu Phe Glu Lys
    210                 215                 220

Val Pro Val Gly Thr Arg Val Gln Phe Ile Asp Glu Pro Val Lys Ala
225                 230                 235                 240

Thr Thr Glu Pro Asp Gly Ser Arg Tyr Ile Glu Val His Asn Pro Leu
                245                 250                 255

Ser Thr Thr Glu Ala Gln Phe Glu Gly Gln Glu Ile Val Pro Ile Thr
            260                 265                 270

Leu Thr Lys Ser Val Gln Thr Val Thr Gly Gln Pro Asp Val Asp Gln
        275                 280                 285

Val Val Leu Asp Glu Ala Ile Lys Asn Arg Ser Gly Met Pro Val Arg
290                 295                 300

Leu Asn
305

<210> SEQ ID NO 65
<211> LENGTH: 298
<212> TYPE: PRT
<213> ORGANISM: Shigella flexneri

<400> SEQUENCE: 65

Met Asn Val Thr Val Ala Tyr Gln Thr Ser Ala Glu Pro Ala Lys Val
1               5                   10                  15

Ala Gln Ala Asp Asn Thr Phe Ala Lys Glu Ser Gly Ala Ser Val Asp
            20                  25                  30

Trp Arg Lys Phe Asp Ser Gly Ala Ser Ile Val Arg Ala Leu Ala Ser
        35                  40                  45

Gly Asp Val Gln Ile Gly Asn Leu Gly Ser Ser Pro Leu Ala Val Ala
    50                  55                  60

Ala Ser Gln Gln Val Pro Ile Glu Val Phe Leu Ala Ser Lys Leu
65                  70                  75                  80

Gly Asn Ser Glu Ala Leu Val Val Lys Lys Thr Ile Ser Lys Pro Glu
                85                  90                  95

Asp Leu Ile Gly Lys Arg Ile Ala Val Pro Phe Ile Ser Thr Thr His
            100                 105                 110

Tyr Ser Leu Leu Ala Ala Leu Lys His Trp Gly Ile Lys Pro Gly Leu
        115                 120                 125

Val Glu Ile Val Asn Leu Gln Pro Pro Ala Ile Ile Ala Ala Trp Gln
    130                 135                 140

Arg Gly Asp Ile Asp Gly Ala Tyr Val Trp Ala Pro Ala Val Asn Ala
145                 150                 155                 160

-continued

Leu Glu Lys Asp Gly Lys Val Leu Thr Asp Ser Gln Val Gly Gln
                165                 170                 175

Trp Gly Ala Pro Thr Leu Asp Val Trp Val Arg Lys Asp Phe Ala
            180                 185                 190

Glu Lys His Pro Glu Val Val Lys Ala Phe Ala Lys Ser Ala Ile Asp
        195                 200                 205

Ala Gln Gln Pro Tyr Ile Ala Asn Pro Asp Ala Trp Leu Lys Gln Pro
    210                 215                 220

Glu Asn Ile Ser Lys Leu Ala Arg Leu Ser Gly Val Pro Glu Gly Asp
225                 230                 235                 240

Val Pro Gly Leu Val Lys Gly Asn Thr Tyr Leu Thr Pro Gln Gln Gln
                245                 250                 255

Thr Ala Glu Leu Thr Gly Pro Val Asn Lys Ala Ile Ile Asp Thr Ala
            260                 265                 270

Gln Phe Leu Lys Glu Gln Gly Lys Val Pro Ala Val Ala Asn Asp Tyr
        275                 280                 285

Ser Gln Tyr Val Thr Ser Arg Phe Val Gln
    290                 295

<210> SEQ ID NO 66
<211> LENGTH: 67
<212> TYPE: PRT
<213> ORGANISM: Shigella flexneri

<400> SEQUENCE: 66

Met Lys Asn Val Phe Lys Ala Leu Thr Val Leu Leu Thr Leu Phe Ser
1               5                   10                  15

Leu Thr Gly Cys Gly Leu Lys Gly Pro Leu Tyr Phe Pro Pro Ala Asp
                20                  25                  30

Lys Asn Ala Pro Pro Thr Lys Pro Val Glu Thr Gln Thr Gln Ser
            35                  40                  45

Thr Val Pro Asp Lys Asn Asp Arg Ala Thr Gly Asp Gly Pro Ser Gln
        50                  55                  60

Val Asn Tyr
65

<210> SEQ ID NO 67
<211> LENGTH: 251
<212> TYPE: PRT
<213> ORGANISM: Shigella flexneri

<400> SEQUENCE: 67

Met Lys Leu Arg Leu Ser Ala Leu Ala Leu Gly Thr Thr Leu Leu Val
1               5                   10                  15

Gly Cys Ala Ser Ser Gly Thr Asp Gln Gln Gly Arg Ser Asp Pro Leu
                20                  25                  30

Glu Gly Phe Asn Arg Thr Met Tyr Asn Phe Asn Phe Asn Val Leu Asp
            35                  40                  45

Pro Tyr Ile Val Arg Pro Val Ala Val Ala Trp Arg Asp Tyr Val Pro
        50                  55                  60

Gln Pro Ala Arg Asn Gly Leu Ser Asn Phe Thr Gly Asn Leu Glu Glu
65                  70                  75                  80

Pro Ala Val Met Val Asn Tyr Phe Leu Gln Gly Asp Pro Tyr Gln Gly
                85                  90                  95

Met Val His Phe Thr Arg Phe Phe Leu Asn Thr Ile Leu Gly Met Gly
            100                 105                 110

```
Gly Phe Ile Asp Val Ala Gly Met Ala Asn Pro Lys Leu Gln Arg Thr
            115                 120                 125

Glu Pro His Arg Phe Gly Ser Thr Leu Gly His Tyr Gly Val Gly Tyr
    130                 135                 140

Gly Pro Tyr Val Gln Leu Pro Phe Tyr Gly Ser Phe Thr Leu Arg Asp
145                 150                 155                 160

Asp Gly Gly Asp Met Ala Asp Ala Leu Tyr Pro Val Leu Ser Trp Leu
                165                 170                 175

Thr Trp Pro Met Ser Val Gly Lys Trp Thr Leu Glu Gly Ile Glu Thr
            180                 185                 190

Arg Ala Gln Leu Leu Asp Ser Asp Gly Leu Leu Arg Gln Ser Ser Asp
            195                 200                 205

Pro Tyr Ile Met Val Arg Glu Ala Tyr Phe Gln Arg His Asp Phe Ile
    210                 215                 220

Ala Asn Gly Gly Glu Leu Lys Pro Gln Glu Asn Pro Asn Ala Gln Ala
225                 230                 235                 240

Ile Gln Asp Asp Leu Lys Asp Ile Asp Ser Glu
                245                 250

<210> SEQ ID NO 68
<211> LENGTH: 249
<212> TYPE: PRT
<213> ORGANISM: Shigella flexneri

<400> SEQUENCE: 68

Met Lys Arg Gln Leu Phe Thr Leu Ser Ile Val Gly Val Phe Ser Leu
1               5                   10                  15

Asn Thr Phe Ala Ser Ile Pro Pro Gly Asn Asp Val Thr Thr Lys Pro
                20                  25                  30

Asp Leu Tyr Tyr Leu Thr Asn Asp Asn Ala Ile Asp Ser Leu Ala Leu
            35                  40                  45

Leu Pro Pro Pro Pro Gln Ile Gly Ser Ile Ala Phe Leu Asn Asp Gln
    50                  55                  60

Ala Met Tyr Glu Lys Gly Arg Leu Leu Arg Asn Thr Glu Arg Gly Lys
65                  70                  75                  80

Leu Ala Ala Glu Asp Ala Asn Leu Ser Ser Gly Gly Val Ala Asn Val
                85                  90                  95

Phe Ser Ala Ala Phe Gly Ser Pro Ile Thr Ala Lys Asp Ser Pro Glu
                100                 105                 110

Leu His Lys Leu Leu Thr Asn Met Ile Glu Asp Ala Gly Asp Leu Ala
            115                 120                 125

Thr Arg Ser Ala Lys Glu Tyr Tyr Met Arg Ile Arg Pro Phe Ala Phe
    130                 135                 140

Tyr Gly Val Ser Thr Cys Asn Thr Lys Glu Gln Asp Thr Leu Ser Arg
145                 150                 155                 160

Asn Gly Ser Tyr Pro Ser Gly His Thr Ser Ile Gly Trp Ala Thr Ala
                165                 170                 175

Leu Val Leu Ser Glu Ile Asn Pro Ala Arg Gln Asp Thr Ile Leu Lys
            180                 185                 190

Arg Gly Tyr Glu Leu Gly Asp Ser Arg Val Ile Cys Gly Tyr His Trp
    195                 200                 205

Gln Ser Asp Val Asp Ala Ala Arg Ile Val Gly Ser Ala Ile Val Ala
    210                 215                 220

Thr Leu His Ser Asn Pro Val Phe Gln Ala Gln Leu Gln Lys Ala Lys
```

```
                225                 230                 235                 240
Asp Glu Phe Ala Asn Asn Gln Lys Lys
                    245

<210> SEQ ID NO 69
<211> LENGTH: 566
<212> TYPE: PRT
<213> ORGANISM: Shigella flexneri

<400> SEQUENCE: 69

Met Lys Lys Phe Asn Ile Lys Ser Leu Thr Leu Leu Ile Val Leu Leu
1               5                   10                  15

Pro Leu Ile Val Asn Ala Asn Asn Ile Asp Ser His Leu Leu Glu Gln
            20                  25                  30

Asn Asp Ile Ala Lys Tyr Val Ala Gln Ser Asp Thr Val Gly Ser Phe
        35                  40                  45

Phe Glu Arg Phe Ser Ala Leu Leu Asn Tyr Pro Ile Val Val Ser Lys
    50                  55                  60

Gln Ala Ala Lys Lys Arg Ile Ser Gly Glu Phe Asp Leu Ser Asn Pro
65                  70                  75                  80

Glu Glu Met Leu Glu Lys Leu Thr Leu Leu Val Gly Leu Ile Trp Tyr
                85                  90                  95

Lys Asp Gly Asn Ala Leu Tyr Ile Tyr Asp Ser Gly Glu Leu Ile Ser
            100                 105                 110

Lys Val Ile Leu Leu Glu Asn Ile Ser Leu Asn Tyr Leu Ile Gln Tyr
        115                 120                 125

Leu Lys Asp Ala Asn Leu Tyr Asp His Arg Tyr Pro Ile Arg Gly Asn
    130                 135                 140

Ile Ser Asp Lys Thr Phe Tyr Ile Ser Gly Pro Pro Ala Leu Val Glu
145                 150                 155                 160

Leu Val Ala Asn Thr Ala Thr Leu Leu Asp Lys Gln Val Ser Ser Ile
                165                 170                 175

Gly Thr Asp Lys Val Asn Phe Gly Val Ile Lys Leu Lys Asn Thr Phe
            180                 185                 190

Val Ser Asp Arg Thr Tyr Asn Met Arg Gly Glu Asp Ile Val Ile Pro
        195                 200                 205

Gly Val Ala Thr Val Val Glu Arg Leu Leu Asn Asn Gly Lys Ala Leu
    210                 215                 220

Ser Asn Arg Gln Ala Gln Asn Asp Pro Met Pro Phe Asn Ile Thr
225                 230                 235                 240

Gln Lys Val Ser Glu Asp Ser Asn Asp Phe Ser Phe Ser Ser Val Thr
                245                 250                 255

Asn Ser Ser Ile Leu Glu Asp Val Ser Leu Ile Ala Tyr Pro Glu Thr
            260                 265                 270

Asn Ser Ile Leu Val Lys Gly Asn Asp Gln Gln Ile Gln Ile Ile Arg
        275                 280                 285

Asp Ile Ile Thr Gln Leu Asp Val Ala Lys Arg His Ile Glu Leu Ser
    290                 295                 300

Leu Trp Ile Ile Asp Ile Asp Lys Ser Glu Leu Asn Asn Leu Gly Val
305                 310                 315                 320

Asn Trp Gln Gly Thr Ala Ser Phe Gly Asp Ser Phe Gly Ala Ser Phe
                325                 330                 335

Asn Met Ser Ser Ser Ala Ser Ile Ser Thr Leu Asp Gly Asn Lys Phe
            340                 345                 350
```

```
Ile Ala Ser Val Met Ala Leu Asn Gln Lys Lys Ala Asn Val Val
            355                 360                 365

Ser Arg Pro Val Ile Leu Thr Gln Glu Asn Ile Pro Ala Ile Phe Asp
370                 375                 380

Asn Asn Arg Thr Phe Tyr Val Ser Leu Val Gly Glu Arg Asn Ser Ser
385                 390                 395                 400

Leu Glu His Val Thr Tyr Gly Thr Leu Ile Asn Val Ile Pro Arg Phe
                405                 410                 415

Ser Ser Arg Gly Gln Ile Glu Met Ser Leu Thr Ile Glu Asp Gly Thr
            420                 425                 430

Gly Asn Ser Gln Ser Asn Tyr Asn Tyr Asn Asn Glu Asn Thr Ser Val
            435                 440                 445

Leu Pro Glu Val Gly Arg Thr Lys Ile Ser Thr Ile Ala Arg Val Pro
450                 455                 460

Gln Gly Lys Ser Leu Leu Ile Gly Gly Tyr Thr His Glu Thr Asn Ser
465                 470                 475                 480

Asn Glu Ile Ile Ser Ile Pro Phe Leu Ser Ser Ile Pro Val Ile Gly
                485                 490                 495

Asn Val Phe Lys Tyr Lys Thr Ser Asn Ile Ser Asn Ile Val Arg Val
            500                 505                 510

Phe Leu Ile Gln Pro Arg Glu Ile Lys Glu Ser Ser Tyr Tyr Asn Thr
            515                 520                 525

Ala Glu Tyr Lys Ser Leu Ile Ser Glu Arg Glu Ile Gln Lys Thr Thr
            530                 535                 540

Gln Ile Ile Pro Ser Glu Thr Thr Leu Leu Glu Asp Glu Lys Ser Leu
545                 550                 555                 560

Val Ser Tyr Leu Asn Tyr
                565

<210> SEQ ID NO 70
<211> LENGTH: 222
<212> TYPE: PRT
<213> ORGANISM: Shigella flexneri

<400> SEQUENCE: 70

Met Gly Ile Phe Ser Arg Phe Ala Asp Ile Val Asn Ala Asn Ile Asn
1               5                   10                  15

Ala Leu Leu Glu Lys Ala Glu Asp Pro Gln Lys Leu Val Arg Leu Met
            20                  25                  30

Ile Gln Glu Met Glu Asp Thr Leu Val Glu Val Arg Ser Thr Ser Ala
        35                  40                  45

Arg Ala Leu Ala Glu Lys Lys Gln Leu Thr Arg Arg Ile Glu Gln Ala
    50                  55                  60

Ser Ala Arg Glu Val Glu Trp Gln Glu Lys Ala Glu Leu Ala Leu Leu
65                  70                  75                  80

Lys Glu Arg Glu Asp Leu Ala Arg Ala Ala Leu Ile Glu Lys Gln Lys
                85                  90                  95

Leu Thr Asp Leu Ile Lys Ser Leu Glu His Glu Val Thr Leu Val Asp
            100                 105                 110

Asp Thr Leu Ala Arg Met Lys Lys Glu Ile Gly Glu Leu Glu Asn Lys
        115                 120                 125

Leu Ser Glu Thr Arg Ala Arg Gln Gln Ala Leu Met Leu Arg His Gln
    130                 135                 140

Ala Ala Asn Ser Ser Arg Asp Val Arg Arg Gln Leu Asp Ser Gly Lys
145                 150                 155                 160
```

```
Leu Asp Glu Ala Met Ala Arg Phe Glu Ser Phe Arg Arg Ile Asp
            165                 170                 175

Gln Met Glu Ala Glu Ala Ser His Ser Phe Gly Lys Gln Lys Ser
            180                 185                 190

Leu Asp Asp Gln Phe Ala Glu Leu Lys Ala Asp Ala Ile Ser Glu
            195                 200                 205

Gln Leu Ala Gln Leu Lys Ala Lys Met Lys Gln Asp Asn Gln
            210                 215                 220
```

<210> SEQ ID NO 71
<211> LENGTH: 248
<212> TYPE: PRT
<213> ORGANISM: Shigella flexneri

<400> SEQUENCE: 71

```
Met Thr Lys Leu Lys Leu Leu Ala Leu Gly Val Leu Ile Ala Thr Ser
1               5                   10                  15

Ala Gly Val Ala His Ala Glu Gly Lys Phe Ser Leu Gly Ala Gly Val
            20                  25                  30

Gly Val Val Glu His Pro Tyr Lys Asp Tyr Asp Thr Asp Val Tyr Pro
        35                  40                  45

Val Pro Val Ile Asn Tyr Glu Gly Asp Asn Phe Trp Phe Arg Gly Leu
    50                  55                  60

Gly Gly Gly Tyr Tyr Leu Trp Asn Asp Ala Thr Asp Lys Leu Ser Ile
65                  70                  75                  80

Thr Ala Tyr Trp Ser Pro Leu Tyr Phe Lys Ala Lys Asp Ser Gly Asp
                85                  90                  95

His Gln Met Arg His Leu Asp Asp Arg Lys Ser Thr Met Met Ala Gly
            100                 105                 110

Leu Ser Tyr Ala His Phe Thr Gln Tyr Gly Tyr Leu Arg Thr Thr Leu
        115                 120                 125

Ala Gly Asp Thr Leu Asp Asn Ser Asn Gly Ile Val Trp Asp Met Ala
    130                 135                 140

Trp Leu Tyr Arg Tyr Thr Asn Gly Gly Leu Thr Val Thr Pro Gly Ile
145                 150                 155                 160

Gly Val Gln Trp Asn Ser Glu Asn Gln Asn Glu Tyr Tyr Gly Val
                165                 170                 175

Ser Arg Lys Glu Ser Ala Arg Ser Gly Leu Arg Gly Tyr Asn Pro Asn
            180                 185                 190

Asp Ser Trp Ser Pro Tyr Leu Glu Leu Ser Ala Ser Tyr Asn Phe Leu
        195                 200                 205

Gly Asp Trp Ser Val Tyr Gly Thr Ala Arg Tyr Thr Arg Leu Ser Asp
    210                 215                 220

Glu Val Thr Asp Ser Pro Met Val Asp Lys Ser Trp Thr Gly Leu Ile
225                 230                 235                 240

Ser Thr Gly Ile Thr Tyr Lys Phe
                245
```

<210> SEQ ID NO 72
<211> LENGTH: 285
<212> TYPE: PRT
<213> ORGANISM: Shigella flexneri

<400> SEQUENCE: 72

```
Met Phe Thr Asn Asn Gly Ser Thr Leu Gln Thr Asp Ile Thr Thr Phe
1               5                   10                  15
```

Gly Val Asn Met Lys Leu Ala His Leu Gly Arg Gln Ala Leu Met Gly
            20                  25                  30

Val Met Ala Val Ala Leu Val Ala Gly Met Ser Val Lys Ser Phe Ala
                35                  40                  45

Asp Glu Gly Leu Leu Asn Lys Val Lys Glu Ser Gly Thr Leu Leu Val
 50                  55                  60

Gly Leu Glu Gly Thr Tyr Pro Pro Phe Ser Phe Gln Gly Asp Asp Gly
65                  70                  75                  80

Lys Leu Thr Gly Phe Glu Val Glu Phe Ala Gln Gln Leu Ala Lys His
                85                  90                  95

Leu Gly Val Glu Ala Ser Leu Lys Pro Thr Lys Trp Asp Gly Met Leu
            100                 105                 110

Ala Ser Leu Asp Ser Lys Arg Ile Asp Val Val Ile Asn Gln Val Thr
        115                 120                 125

Ile Ser Asp Glu Arg Lys Lys Lys Tyr Asp Phe Ser Thr Pro Tyr Thr
130                 135                 140

Ile Ser Gly Ile Gln Ala Leu Val Lys Lys Gly Asn Glu Gly Thr Ile
145                 150                 155                 160

Lys Thr Ala Ala Asp Leu Lys Gly Lys Val Gly Val Gly Leu Gly
                165                 170                 175

Thr Asn Tyr Glu Glu Trp Leu Arg Gln Asn Val Gln Gly Val Asp Val
            180                 185                 190

Arg Thr Tyr Asp Asp Pro Thr Lys Tyr Gln Asp Leu Arg Val Gly
                195                 200                 205

Arg Ile Asp Ala Ile Leu Val Asp Arg Leu Ala Ala Leu Asp Leu Val
            210                 215                 220

Lys Lys Thr Asn Asp Thr Leu Ala Val Thr Gly Glu Ala Phe Ser Arg
225                 230                 235                 240

Gln Glu Ser Gly Val Ala Leu Arg Lys Gly Asn Glu Asp Leu Leu Lys
                245                 250                 255

Ala Val Asn Asp Ala Ile Ala Glu Met Gln Lys Asp Gly Thr Leu Gln
            260                 265                 270

Ala Leu Ser Glu Lys Trp Phe Gly Ala Asp Val Thr Lys
            275                 280                 285

<210> SEQ ID NO 73
<211> LENGTH: 245
<212> TYPE: PRT
<213> ORGANISM: Shigella flexneri

<400> SEQUENCE: 73

Met Thr Arg Met Lys Tyr Leu Val Ala Ala Thr Leu Ser Leu Phe
1               5                   10                  15

Leu Ala Gly Cys Ser Gly Ser Lys Glu Glu Val Pro Asp Asn Pro
                20                  25                  30

Asn Glu Ile Tyr Ala Thr Ala Gln Gln Lys Leu Gln Asp Gly Asn Trp
            35                  40                  45

Arg Gln Ala Ile Thr Gln Leu Glu Ala Leu Asp Asn Arg Tyr Pro Phe
 50                  55                  60

Gly Pro Tyr Ser Gln Gln Val Gln Leu Asp Ile Tyr Ala Tyr Tyr
65                  70                  75                  80

Lys Asn Ala Asp Leu Pro Leu Ala Gln Ala Ile Asp Arg Phe Ile
                85                  90                  95

Arg Leu Asn Pro Thr His Pro Asn Ile Asp Tyr Val Met Tyr Met Arg

```
            100                 105                 110
Gly Leu Thr Asn Met Ala Leu Asp Asp Ser Ala Leu Gln Gly Phe Phe
        115                 120                 125

Gly Val Asp Arg Ser Asp Arg Asp Pro Gln His Ala Arg Ala Ala Phe
    130                 135                 140

Ser Asp Phe Ser Lys Leu Val Arg Gly Tyr Pro Asn Ser Gln Tyr Thr
145                 150                 155                 160

Thr Asp Ala Thr Lys Arg Leu Val Phe Leu Lys Asp Arg Leu Ala Lys
                165                 170                 175

Tyr Glu Tyr Ser Val Ala Glu Tyr Tyr Thr Glu Arg Gly Ala Trp Val
            180                 185                 190

Ala Val Val Asn Arg Ile Glu Gly Met Leu Arg Asp Tyr Pro Asp Thr
        195                 200                 205

Gln Ala Thr Arg Asp Ala Leu Pro Leu Met Glu Asn Ala Tyr Arg Gln
    210                 215                 220

Met Gln Met Asn Ala Gln Ala Glu Lys Val Ala Lys Ile Ile Ala Ala
225                 230                 235                 240

Asn Ser Ser Asn Thr
                245

<210> SEQ ID NO 74
<211> LENGTH: 1285
<212> TYPE: PRT
<213> ORGANISM: Shigella flexneri

<400> SEQUENCE: 74

Met Asn Lys Ile Tyr Ser Leu Lys Tyr Ser His Ile Thr Gly Gly Leu
1               5                   10                  15

Val Ala Val Ser Glu Leu Thr Arg Lys Val Ser Val Gly Thr Ser Arg
            20                  25                  30

Lys Lys Val Ile Leu Gly Ile Ile Leu Ser Ser Ile Tyr Gly Ser Tyr
        35                  40                  45

Gly Glu Thr Ala Phe Ala Ala Met Leu Asp Ile Asn Asn Ile Trp Thr
    50                  55                  60

Arg Asp Tyr Leu Asp Leu Ala Gln Asn Arg Gly Glu Phe Arg Pro Gly
65                  70                  75                  80

Ala Thr Asn Val Gln Leu Met Met Lys Asp Gly Lys Ile Phe His Phe
                85                  90                  95

Pro Glu Leu Pro Val Pro Asp Phe Ser Ala Val Ser Asn Lys Gly Ala
            100                 105                 110

Thr Thr Ser Ile Gly Gly Ala Tyr Ser Val Thr Ala Thr His Asn Gly
        115                 120                 125

Thr Gln His His Ala Ile Thr Thr Gln Ser Trp Asp Gln Thr Ala Tyr
    130                 135                 140

Lys Ala Ser Asn Arg Val Ser Ser Gly Asp Phe Ser Val His Arg Leu
145                 150                 155                 160

Asn Lys Phe Val Val Glu Thr Thr Gly Val Thr Glu Ser Ala Asp Phe
                165                 170                 175

Ser Leu Ser Pro Glu Asp Ala Met Lys Arg Tyr Gly Val Asn Tyr Asn
            180                 185                 190

Gly Lys Glu Gln Ile Ile Gly Phe Arg Ala Gly Ala Gly Thr Thr Ser
        195                 200                 205

Thr Ile Leu Asn Gly Lys Gln Tyr Leu Phe Gly Gln Asn Tyr Asn Pro
    210                 215                 220
```

```
Asp Leu Leu Ser Ala Ser Leu Phe Asn Leu Asp Trp Lys Asn Lys Ser
225                 230                 235                 240

Tyr Ile Tyr Thr Asn Arg Thr Pro Phe Lys Asn Ser Pro Ile Phe Gly
                245                 250                 255

Asp Ser Gly Ser Gly Ser Tyr Leu Tyr Asp Lys Glu Gln Gln Lys Trp
            260                 265                 270

Val Phe His Gly Val Thr Ser Thr Val Gly Phe Ile Ser Ser Thr Asn
        275                 280                 285

Ile Ala Trp Thr Asn Tyr Ser Leu Phe Asn Asn Ile Leu Val Asn Asn
    290                 295                 300

Leu Lys Lys Asn Phe Thr Asn Thr Met Gln Leu Asp Gly Lys Lys Gln
305                 310                 315                 320

Glu Leu Ser Ser Ile Ile Lys Asp Lys Asp Leu Ser Val Ser Gly Gly
                325                 330                 335

Gly Val Leu Thr Leu Lys Gln Asp Thr Asp Leu Gly Ile Gly Gly Leu
            340                 345                 350

Ile Phe Asp Lys Asn Gln Thr Tyr Lys Val Tyr Gly Lys Asp Lys Ser
        355                 360                 365

Tyr Lys Gly Ala Gly Ile Asp Ile Asp Asn Asn Thr Thr Val Glu Trp
    370                 375                 380

Asn Val Lys Gly Val Ala Gly Asp Asn Leu His Lys Ile Gly Ser Gly
385                 390                 395                 400

Thr Leu Asp Val Lys Ile Ala Gln Gly Asn Asn Leu Lys Ile Gly Asn
                405                 410                 415

Gly Thr Val Ile Leu Ser Ala Glu Lys Ala Phe Asn Lys Ile Tyr Met
            420                 425                 430

Ala Gly Gly Lys Gly Thr Val Lys Ile Asn Ala Lys Asp Ala Leu Ser
        435                 440                 445

Glu Ser Gly Asn Gly Glu Ile Tyr Phe Thr Arg Asn Gly Gly Thr Leu
    450                 455                 460

Asp Leu Asn Gly Tyr Asp Gln Ser Phe Gln Lys Ile Ala Ala Thr Asp
465                 470                 475                 480

Ala Gly Thr Thr Val Thr Asn Ser Asn Val Lys Gln Ser Thr Leu Ser
                485                 490                 495

Leu Thr Asn Thr Asp Ala Tyr Met Tyr His Gly Asn Val Ser Gly Asn
            500                 505                 510

Ile Ser Ile Asn His Ile Ile Asn Thr Thr Gln Gln His Asn Asn Asn
        515                 520                 525

Ala Asn Leu Ile Phe Asp Gly Ser Val Asp Ile Lys Asn Asp Ile Ser
    530                 535                 540

Val Arg Asn Ala Gln Leu Thr Leu Gln Gly His Ala Thr Glu His Ala
545                 550                 555                 560

Ile Phe Lys Glu Gly Asn Asn Asn Cys Pro Ile Pro Phe Leu Cys Gln
                565                 570                 575

Lys Asp Tyr Ser Ala Ala Ile Lys Asp Gln Glu Ser Thr Val Asn Lys
            580                 585                 590

Arg Tyr Asn Thr Glu Tyr Lys Ser Asn Asn Gln Ile Ala Ser Phe Ser
        595                 600                 605

Gln Pro Asp Trp Glu Ser Arg Lys Phe Asn Phe Arg Lys Leu Asn Leu
    610                 615                 620

Glu Asn Ala Thr Leu Ser Ile Gly Arg Asp Ala Asn Val Lys Gly His
625                 630                 635                 640

Ile Glu Ala Lys Asn Ser Gln Ile Val Leu Gly Asn Lys Thr Ala Tyr
```

```
                 645                 650                 655
Ile Asp Met Phe Ser Gly Arg Asn Ile Thr Gly Glu Gly Phe Gly Phe
            660                 665                 670

Arg Gln Gln Leu Arg Ser Gly Asp Ser Ala Gly Glu Ser Ser Phe Asn
            675                 680                 685

Gly Ser Leu Ser Ala Gln Asn Ser Lys Ile Thr Val Gly Asp Lys Ser
            690                 695                 700

Thr Val Thr Met Thr Gly Ala Leu Ser Leu Ile Asn Thr Asp Leu Ile
705                 710                 715                 720

Ile Asn Lys Gly Ala Thr Val Thr Ala Gln Gly Lys Met Tyr Val Asp
                725                 730                 735

Lys Ala Ile Glu Leu Ala Gly Thr Leu Thr Leu Thr Gly Thr Pro Thr
            740                 745                 750

Glu Asn Asn Lys Tyr Ser Pro Ala Ile Tyr Met Ser Asp Gly Tyr Asn
            755                 760                 765

Met Thr Glu Asp Gly Ala Thr Leu Lys Ala Gln Asn Tyr Ala Trp Val
770                 775                 780

Asn Gly Asn Ile Lys Ser Asp Lys Lys Ala Ser Ile Leu Phe Gly Val
785                 790                 795                 800

Asp Gln Tyr Lys Glu Asp Asn Leu Asp Lys Thr Thr His Thr Pro Leu
            805                 810                 815

Ala Thr Gly Leu Leu Gly Gly Phe Asp Thr Ser Tyr Thr Gly Gly Ile
            820                 825                 830

Asp Ala Pro Ala Ala Ser Ala Ser Met Tyr Asn Thr Leu Trp Arg Val
            835                 840                 845

Asn Gly Gln Ser Ala Leu Gln Ser Leu Lys Thr Arg Asp Ser Leu Leu
            850                 855                 860

Leu Phe Ser Asn Ile Glu Asn Ser Gly Phe His Thr Val Thr Val Asn
865                 870                 875                 880

Thr Leu Asp Ala Thr Asn Thr Ala Val Ile Met Arg Ala Asp Leu Ser
            885                 890                 895

Gln Ser Val Asn Gln Ser Asp Lys Leu Ile Val Lys Asn Gln Leu Thr
            900                 905                 910

Gly Ser Asn Asn Ser Leu Ser Val Asp Ile Gln Lys Val Gly Asn Asn
            915                 920                 925

Asn Ser Gly Leu Asn Val Asp Leu Ile Thr Ala Pro Lys Gly Ser Asn
            930                 935                 940

Lys Glu Ile Phe Lys Ala Ser Thr Gln Ala Ile Gly Phe Ser Asn Ile
945                 950                 955                 960

Ser Pro Val Ile Ser Thr Lys Glu Asp Gln Glu His Thr Thr Trp Thr
            965                 970                 975

Leu Thr Gly Tyr Lys Val Ala Glu Asn Thr Ala Ser Ser Gly Ala Ala
            980                 985                 990

Lys Ser Tyr Met Ser Gly Asn Tyr Lys Ala Phe Leu Thr Glu Val Asn
            995                 1000                1005

Asn Leu Asn Lys Arg Met Gly Asp Leu Arg Asp Thr Asn Gly Glu Ala
            1010                1015                1020

Gly Ala Trp Ala Arg Ile Met Ser Gly Ala Gly Ser Ala Ser Gly Gly
1025                1030                1035                1040

Tyr Ser Asp Asn Tyr Thr His Val Gln Ile Gly Val Asp Lys Lys His
            1045                1050                1055

Glu Leu Asp Gly Leu Asp Leu Phe Thr Gly Leu Thr Met Thr Tyr Thr
            1060                1065                1070
```

-continued

```
Asp Ser His Ala Ser Ser Asn Ala Phe Ser Gly Lys Thr Lys Ser Val
        1075                1080                1085

Gly Ala Gly Leu Tyr Ala Ser Ala Ile Phe Asp Ser Gly Ala Tyr Ile
    1090                1095                1100

Asp Leu Ile Ser Lys Tyr Val His His Asp Asn Glu Tyr Ser Ala Thr
1105                1110                1115                1120

Phe Ala Gly Leu Gly Thr Lys Asp Tyr Ser Ser His Ser Leu Tyr Val
                1125                1130                1135

Gly Ala Glu Ala Gly Tyr Arg Tyr His Val Thr Glu Asp Ser Trp Ile
            1140                1145                1150

Glu Pro Gln Ala Glu Leu Val Tyr Gly Ala Val Ser Gly Lys Arg Phe
        1155                1160                1165

Asp Trp Gln Asp Arg Gly Met Ser Val Thr Met Lys Asp Lys Asp Phe
    1170                1175                1180

Asn Pro Leu Ile Gly Arg Thr Gly Val Asp Val Gly Lys Ser Phe Ser
1185                1190                1195                1200

Gly Lys Asp Trp Lys Val Thr Ala Arg Ala Gly Leu Gly Tyr Gln Phe
                1205                1210                1215

Asp Leu Phe Ala Asn Gly Glu Thr Val Leu Arg Asp Ala Ser Gly Glu
            1220                1225                1230

Lys Arg Ile Lys Gly Glu Lys Asp Gly Arg Ile Leu Met Asn Val Gly
        1235                1240                1245

Leu Asn Ala Glu Ile Arg Asp Asn Leu Arg Phe Gly Leu Glu Phe Glu
    1250                1255                1260

Lys Ser Ala Phe Gly Lys Tyr Asn Val Asp Asn Ala Ile Asn Ala Asn
1265                1270                1275                1280

Phe Arg Tyr Ser Phe
                1285

<210> SEQ ID NO 75
<211> LENGTH: 513
<212> TYPE: PRT
<213> ORGANISM: Shigella flexneri

<400> SEQUENCE: 75

Met Gln Leu Asn Ser Thr Glu Ile Ser Glu Leu Ile Lys Gln Arg Ile
1               5                   10                  15

Ala Gln Phe Asn Val Val Ser Glu Ala His Asn Glu Gly Thr Ile Val
                20                  25                  30

Ser Val Ser Asp Gly Val Ile Arg Ile His Gly Leu Ala Asp Cys Met
            35                  40                  45

Gln Gly Glu Met Ile Ser Leu Pro Gly Asn Arg Tyr Ala Ile Ala Leu
        50                  55                  60

Asn Leu Glu Arg Asp Ser Val Gly Ala Val Val Met Gly Pro Tyr Ala
65                  70                  75                  80

Asp Leu Ala Glu Gly Met Lys Val Lys Cys Thr Gly Arg Ile Leu Glu
                85                  90                  95

Val Pro Val Gly Arg Gly Leu Leu Gly Arg Val Val Asn Thr Leu Gly
            100                 105                 110

Ala Pro Ile Asp Gly Lys Gly Pro Leu Asp His Asp Gly Phe Ser Ala
        115                 120                 125

Val Glu Ala Ile Ala Pro Gly Val Ile Glu Arg Gln Ser Val Asp Gln
    130                 135                 140

Pro Val Gln Thr Gly Tyr Lys Ala Val Asp Ser Met Ile Pro Ile Gly
```

| | | | | 145 | | | | | 150 | | | | | 155 | | | | | 160 |

Arg Gly Gln Arg Glu Leu Ile Ile Gly Asp Arg Gln Thr Gly Lys Thr
165 170 175

Ala Leu Ala Ile Asp Ala Ile Ile Asn Gln Arg Asp Ser Gly Ile Lys
180 185 190

Cys Ile Tyr Val Ala Ile Gly Gln Lys Ala Ser Thr Ile Ser Asn Val
195 200 205

Val Arg Lys Leu Glu Glu His Gly Ala Leu Ala Asn Thr Ile Val Val
210 215 220

Val Ala Thr Ala Ser Glu Ser Ala Ala Leu Gln Tyr Leu Ala Pro Tyr
225 230 235 240

Ala Gly Cys Ala Met Gly Glu Tyr Phe Arg Asp Arg Gly Glu Asp Ala
245 250 255

Leu Ile Ile Tyr Asp Asp Leu Ser Lys Gln Ala Val Ala Tyr Arg Gln
260 265 270

Ile Ser Leu Leu Leu Arg Arg Pro Pro Gly Arg Glu Ala Phe Pro Gly
275 280 285

Asp Val Phe Tyr Leu His Ser Arg Leu Leu Glu Arg Ala Ala Arg Val
290 295 300

Asn Ala Glu Tyr Val Glu Ala Phe Thr Lys Gly Glu Val Lys Gly Lys
305 310 315 320

Thr Gly Ser Leu Thr Ala Leu Pro Ile Ile Glu Thr Gln Ala Gly Asp
325 330 335

Val Ser Ala Phe Val Pro Thr Asn Val Ile Ser Ile Thr Asp Gly Gln
340 345 350

Ile Phe Leu Glu Thr Asn Leu Phe Asn Ala Gly Ile Arg Pro Ala Val
355 360 365

Asn Pro Gly Ile Ser Val Ser Arg Val Gly Gly Ala Ala Gln Thr Lys
370 375 380

Ile Met Lys Lys Leu Ser Gly Gly Ile Arg Thr Ala Leu Ala Gln Tyr
385 390 395 400

Arg Glu Leu Ala Ala Phe Ser Gln Phe Ala Ser Asp Leu Asp Asp Ala
405 410 415

Thr Arg Lys Gln Leu Asp His Gly Gln Lys Val Thr Glu Leu Leu Lys
420 425 430

Gln Lys Gln Tyr Ala Pro Met Ser Val Ala Gln Ser Leu Val Leu
435 440 445

Phe Ala Ala Glu Arg Gly Tyr Leu Ala Asp Val Glu Leu Ser Lys Ile
450 455 460

Gly Ser Phe Glu Ala Ala Leu Leu Ala Tyr Val Asp Arg Asp His Ala
465 470 475 480

Pro Leu Met Gln Glu Ile Asn Gln Thr Gly Gly Tyr Asn Asp Glu Ile
485 490 495

Glu Gly Lys Leu Lys Gly Ile Leu Asp Ser Phe Lys Ala Thr Gln Ser
500 505 510

Trp

<210> SEQ ID NO 76
<211> LENGTH: 469
<212> TYPE: PRT
<213> ORGANISM: Shigella flexneri

<400> SEQUENCE: 76

Met Ser Ala Glu His Val Leu Thr Met Leu Asn Glu His Glu Val Lys

-continued

```
1               5                   10                  15
Phe Val Asp Leu Arg Phe Thr Asp Thr Lys Gly Lys Glu Gln His Val
                20                  25                  30

Thr Ile Pro Ala His Gln Val Asn Ala Glu Phe Phe Glu Glu Gly Lys
                35                  40                  45

Met Phe Asp Gly Ser Ser Ile Gly Gly Trp Lys Gly Ile Asn Glu Ser
                50                  55                  60

Asp Met Val Leu Met Pro Asp Ala Ser Thr Ala Val Ile Asp Pro Phe
65                  70                  75                  80

Phe Ala Asp Ser Thr Leu Ile Ile Arg Cys Asp Ile Leu Glu Pro Gly
                85                  90                  95

Thr Leu Gln Gly Tyr Asp Arg Asp Pro Arg Ser Ile Ala Lys Arg Ala
                100                 105                 110

Glu Asp Tyr Leu Arg Ser Thr Gly Ile Ala Asp Thr Val Leu Phe Gly
                115                 120                 125

Pro Glu Pro Glu Phe Phe Leu Phe Asp Asp Ile Arg Phe Gly Ser Ser
                130                 135                 140

Ile Ser Gly Ser His Val Ala Ile Asp Asp Ile Glu Gly Ala Trp Asn
145                 150                 155                 160

Ser Ser Thr Gln Tyr Glu Gly Gly Asn Lys Gly His Arg Pro Ala Val
                165                 170                 175

Lys Gly Gly Tyr Phe Pro Val Pro Pro Val Asp Ser Ala Gln Asp Ile
                180                 185                 190

Arg Ser Glu Met Cys Leu Val Met Glu Gln Met Gly Leu Val Val Glu
                195                 200                 205

Ala His His His Glu Val Ala Thr Ala Gly Gln Asn Glu Val Ala Thr
                210                 215                 220

Arg Phe Asn Thr Met Thr Lys Lys Ala Asp Glu Ile Gln Ile Tyr Lys
225                 230                 235                 240

Tyr Val Val His Asn Val Ala His Arg Phe Gly Lys Thr Ala Thr Phe
                245                 250                 255

Met Pro Lys Pro Met Phe Gly Asp Asn Gly Ser Gly Met His Cys His
                260                 265                 270

Met Ser Leu Ser Lys Asn Gly Val Asn Leu Phe Ala Gly Asp Lys Tyr
                275                 280                 285

Ala Gly Leu Ser Glu Gln Ala Leu Tyr Tyr Ile Gly Gly Val Ile Lys
                290                 295                 300

His Ala Lys Ala Ile Asn Ala Leu Ala Asn Pro Thr Thr Asn Ser Tyr
305                 310                 315                 320

Lys Arg Leu Val Pro Gly Tyr Glu Ala Pro Val Met Leu Ala Tyr Ser
                325                 330                 335

Ala Arg Asn Arg Ser Ala Ser Ile Arg Ile Pro Val Val Ser Ser Pro
                340                 345                 350

Lys Ala Arg Arg Ile Glu Val Arg Phe Pro Asp Pro Ala Ala Asn Pro
                355                 360                 365

Tyr Leu Cys Phe Ala Ala Leu Leu Met Ala Gly Leu Asp Gly Ile Lys
                370                 375                 380

Asn Lys Ile His Pro Gly Glu Ala Met Asp Lys Asn Leu Tyr Asp Leu
385                 390                 395                 400

Pro Pro Glu Glu Ala Lys Glu Ile Pro Gln Val Ala Gly Ser Leu Glu
                405                 410                 415

Glu Ala Leu Asn Glu Leu Asp Leu Asp Arg Glu Phe Leu Lys Ala Gly
                420                 425                 430
```

-continued

Gly Val Phe Thr Asp Glu Ala Ile Asp Ala Tyr Ile Ala Leu Arg Arg
        435                 440                 445

Glu Glu Asp Asp Arg Val Arg Met Thr Pro His Pro Val Glu Phe Glu
450                 455                 460

Leu Tyr Tyr Ser Val
465

<210> SEQ ID NO 77
<211> LENGTH: 626
<212> TYPE: PRT
<213> ORGANISM: Shigella flexneri

<400> SEQUENCE: 77

Met Ala Ile Glu Ile Lys Val Pro Asp Ile Gly Ala Asp Glu Val Glu
1               5                   10                  15

Ile Thr Glu Ile Leu Val Lys Val Gly Asp Lys Val Glu Ala Glu Gln
            20                  25                  30

Ser Leu Ile Thr Val Glu Gly Asp Lys Ala Ser Met Glu Val Pro Ser
        35                  40                  45

Pro Gln Ala Gly Ile Val Lys Glu Ile Lys Val Ser Val Gly Asp Lys
    50                  55                  60

Thr Gln Thr Gly Ala Leu Ile Met Ile Phe Asp Ser Ala Asp Gly Ala
65                  70                  75                  80

Ala Asp Ala Ala Pro Ala Gln Ala Glu Lys Lys Glu Ala Ala Pro
                85                  90                  95

Ala Ala Ala Pro Ala Ala Ala Ala Lys Asp Val Asn Val Pro Asp
            100                 105                 110

Ile Gly Ser Asp Glu Val Glu Val Thr Glu Ile Leu Val Lys Val Gly
        115                 120                 125

Asp Lys Val Glu Ala Glu Gln Ser Leu Ile Thr Val Glu Gly Asp Lys
    130                 135                 140

Ala Ser Met Glu Val Pro Ala Pro Phe Ala Gly Thr Val Lys Glu Ile
145                 150                 155                 160

Lys Val Asn Val Gly Asp Lys Val Ser Thr Gly Ser Leu Ile Met Val
                165                 170                 175

Phe Glu Val Ala Gly Glu Ala Gly Ala Ala Pro Ala Ala Lys Gln
            180                 185                 190

Glu Ala Thr Pro Ala Ala Thr Pro Ala Pro Ala Ala Gly Val Lys Glu
    195                 200                 205

Val Asn Val Pro Asp Ile Gly Gly Asp Glu Val Glu Val Thr Glu Val
210                 215                 220

Met Val Lys Val Gly Asp Lys Val Ala Ala Glu Gln Ser Leu Ile Thr
225                 230                 235                 240

Val Glu Gly Asp Lys Ala Ser Met Glu Val Pro Ala Pro Phe Ala Gly
                245                 250                 255

Val Val Lys Glu Leu Lys Val Asn Val Gly Asp Lys Val Lys Thr Gly
            260                 265                 270

Ser Leu Ile Met Ile Phe Glu Val Glu Gly Ala Ala Pro Ala Ala Ala
        275                 280                 285

Pro Ala Lys Gln Glu Ala Ala Pro Ala Pro Ala Lys Ala Glu
    290                 295                 300

Ala Pro Ala Ala Lys Ala Glu Gly Lys Ser Glu Phe Ala Glu Asn Asp
305                 310                 315                 320

Ala Tyr Val His Ala Thr Pro Leu Ile Arg Arg Leu Ala Arg Glu Phe

```
                325                 330                 335
Gly Val Asn Leu Ala Lys Val Lys Gly Thr Gly Arg Lys Gly Arg Ile
            340                 345                 350
Leu Arg Glu Asp Val Gln Ala Tyr Val Lys Glu Ala Ile Lys Arg Ala
            355                 360                 365
Glu Ala Ala Pro Ala Ala Thr Gly Gly Ile Pro Gly Met Leu Pro
370                 375                 380
Trp Pro Lys Val Asp Phe Ser Lys Phe Gly Glu Ile Glu Val Glu
385                 390                 395                 400
Leu Gly Arg Ile Gln Lys Ile Ser Gly Ala Asn Leu Ser Arg Asn Trp
                405                 410                 415
Val Met Ile Pro His Val Thr His Phe Asp Lys Thr Asp Ile Thr Glu
            420                 425                 430
Leu Glu Ala Phe Arg Lys Gln Gln Asn Glu Glu Ala Ala Lys Arg Lys
            435                 440                 445
Leu Asp Val Lys Ile Thr Pro Val Val Phe Ile Met Lys Ala Val Ala
            450                 455                 460
Ala Ala Leu Glu Gln Met Pro Arg Phe Asn Ser Ser Leu Ser Glu Asp
465                 470                 475                 480
Gly Gln Arg Leu Thr Leu Lys Lys Tyr Ile Asn Ile Gly Val Ala Val
                485                 490                 495
Asp Thr Pro Asn Gly Leu Val Val Pro Val Phe Lys Asp Val Asn Lys
            500                 505                 510
Lys Gly Ile Ile Glu Leu Ser Arg Glu Leu Met Thr Ile Ser Lys Lys
            515                 520                 525
Ala Arg Asp Gly Lys Leu Thr Ala Gly Glu Met Gln Gly Gly Cys Phe
530                 535                 540
Thr Ile Ser Ser Ile Gly Gly Leu Gly Thr Thr His Phe Ala Pro Ile
545                 550                 555                 560
Val Asn Ala Pro Glu Val Ala Ile Leu Gly Val Ser Lys Ser Ala Met
                565                 570                 575
Glu Pro Val Trp Asn Gly Lys Glu Phe Val Pro Arg Leu Met Leu Pro
            580                 585                 590
Ile Ser Leu Ser Phe Asp His Arg Val Ile Asp Gly Ala Asp Gly Ala
            595                 600                 605
Arg Phe Ile Thr Ile Ile Asn Asn Thr Leu Ser Asp Ile Arg Arg Leu
            610                 615                 620
Val Met
625

<210> SEQ ID NO 78
<211> LENGTH: 289
<212> TYPE: PRT
<213> ORGANISM: Shigella flexneri

<400> SEQUENCE: 78

Met Ser Ile Leu Ile Asp Lys Asn Thr Lys Val Ile Cys Gln Gly Phe
1               5                   10                  15
Thr Gly Ser Gln Gly Thr Phe His Ser Glu Gln Ala Ile Ala Tyr Gly
            20                  25                  30
Thr Lys Met Val Gly Gly Val Thr Pro Gly Lys Gly Gly Thr Thr His
        35                  40                  45
Leu Gly Leu Pro Val Phe Asn Thr Val Arg Glu Ala Val Ala Ala Thr
    50                  55                  60
```

-continued

Gly Ala Ser Ala Ser Val Ile Tyr Val Pro Ala Pro Phe Cys Lys Asp
65                  70                  75                  80

Ser Ile Leu Glu Ala Ile Asp Ala Gly Ile Lys Leu Ile Ile Thr Ile
                85                  90                  95

Thr Glu Gly Ile Pro Thr Leu Asp Met Leu Thr Val Lys Val Lys Leu
            100                 105                 110

Asp Glu Ala Gly Val Arg Met Ile Gly Pro Asn Cys Pro Gly Val Ile
            115                 120                 125

Thr Pro Gly Glu Cys Lys Ile Gly Ile Gln Pro Gly His Ile His Lys
        130                 135                 140

Pro Gly Lys Val Gly Ile Val Ser Arg Ser Gly Thr Leu Thr Tyr Glu
145                 150                 155                 160

Ala Val Lys Gln Thr Thr Asp Tyr Gly Phe Gly Gln Ser Thr Cys Val
                165                 170                 175

Gly Ile Gly Gly Asp Pro Ile Pro Gly Ser Asn Phe Ile Asp Ile Leu
            180                 185                 190

Glu Met Phe Glu Lys Asp Pro Gln Thr Glu Ala Ile Val Met Ile Gly
        195                 200                 205

Glu Ile Gly Gly Ser Ala Glu Glu Ala Ala Ala Tyr Ile Lys Glu
210                 215                 220

His Val Thr Lys Pro Val Val Gly Tyr Ile Ala Gly Val Thr Ala Pro
225                 230                 235                 240

Lys Gly Lys Arg Met Gly His Ala Gly Ala Ile Ile Ala Gly Gly Lys
                245                 250                 255

Gly Thr Ala Asp Glu Lys Phe Ala Ala Leu Glu Ala Ala Gly Val Lys
            260                 265                 270

Thr Val Arg Ser Leu Ala Asp Ile Gly Glu Ala Leu Lys Thr Val Leu
        275                 280                 285

Lys

<210> SEQ ID NO 79
<211> LENGTH: 405
<212> TYPE: PRT
<213> ORGANISM: Shigella flexneri

<400> SEQUENCE: 79

Met Ser Ser Val Asp Ile Leu Val Pro Asp Leu Pro Glu Ser Val Ala
1               5                   10                  15

Asp Ala Thr Val Ala Thr Trp His Lys Lys Pro Gly Asp Ala Val Val
            20                  25                  30

Arg Asp Glu Val Leu Val Glu Ile Glu Thr Asp Lys Val Val Leu Glu
        35                  40                  45

Val Pro Ala Ser Ala Asp Gly Ile Leu Asp Ala Val Leu Glu Asp Glu
    50                  55                  60

Gly Thr Thr Val Thr Ser Arg Gln Ile Leu Gly Arg Leu Arg Glu Gly
65                  70                  75                  80

Asn Ser Ala Gly Lys Glu Thr Ser Ala Lys Ser Glu Glu Lys Ala Ser
                85                  90                  95

Thr Pro Ala Gln Arg Gln Gln Ala Ser Leu Glu Glu Gln Asn Asn Asp
            100                 105                 110

Ala Leu Ser Pro Ala Ile Arg Arg Leu Leu Ala Glu His Asn Leu Asp
        115                 120                 125

Ala Ser Ala Ile Lys Gly Thr Gly Val Gly Gly Arg Leu Thr Arg Glu
    130                 135                 140

```
Asp Val Glu Lys His Leu Ala Lys Ala Pro Ala Lys Glu Ser Ala Pro
145                 150                 155                 160

Ala Ala Ala Ala Pro Ala Ala Gln Pro Ala Leu Ala Ala Arg Ser Glu
                165                 170                 175

Lys Arg Val Pro Met Thr Arg Leu Arg Lys Arg Val Ala Glu Arg Leu
                180                 185                 190

Leu Glu Ala Lys Asn Ser Thr Ala Met Leu Thr Thr Phe Asn Glu Val
            195                 200                 205

Asn Met Lys Pro Ile Met Asp Leu Arg Lys Gln Tyr Gly Glu Ala Phe
        210                 215                 220

Glu Lys Arg His Gly Ile Arg Leu Gly Phe Met Ser Phe Tyr Val Lys
225                 230                 235                 240

Ala Val Val Glu Ala Leu Lys Arg Tyr Pro Glu Val Asn Ala Ser Ile
                245                 250                 255

Asp Gly Asp Asp Val Val Tyr His Asn Tyr Phe Asp Val Ser Met Ala
            260                 265                 270

Val Ser Thr Pro Arg Gly Leu Val Thr Pro Val Leu Arg Asp Val Asp
        275                 280                 285

Thr Leu Gly Met Ala Asp Ile Glu Lys Lys Ile Lys Glu Leu Ala Val
290                 295                 300

Lys Gly Arg Asp Gly Lys Leu Thr Val Glu Asp Leu Thr Gly Gly Asn
305                 310                 315                 320

Phe Thr Ile Thr Asn Gly Gly Val Phe Gly Ser Leu Met Ser Thr Pro
                325                 330                 335

Ile Ile Asn Pro Pro Gln Ser Ala Ile Leu Gly Met His Ala Ile Lys
            340                 345                 350

Asp Arg Pro Met Ala Val Asn Gly Gln Val Glu Ile Leu Pro Met Met
            355                 360                 365

Tyr Leu Ala Leu Ser Tyr Asp His Arg Leu Ile Asp Gly Arg Glu Ser
370                 375                 380

Val Gly Phe Leu Val Thr Ile Lys Glu Leu Leu Glu Glu Pro Thr Arg
385                 390                 395                 400

Leu Leu Leu Asp Val
                405

<210> SEQ ID NO 80
<211> LENGTH: 427
<212> TYPE: PRT
<213> ORGANISM: Shigella flexneri

<400> SEQUENCE: 80

Met Ala Asp Thr Lys Ala Lys Leu Asn Leu Asn Gly Asp Thr Ala Val
1               5                   10                  15

Glu Leu Asp Val Leu Lys Gly Thr Leu Gly Gln Asp Val Ile Asp Ile
                20                  25                  30

Arg Thr Leu Gly Ser Lys Gly Val Phe Thr Phe Asp Pro Gly Phe Thr
            35                  40                  45

Ser Thr Ala Ser Cys Glu Ser Lys Ile Thr Phe Ile Asp Gly Asp Glu
        50                  55                  60

Gly Ile Leu Leu His Arg Gly Phe Pro Ile Asp Gln Leu Ala Thr Asp
65                  70                  75                  80

Ser Asn Tyr Leu Glu Val Cys Tyr Ile Leu Leu Asn Gly Glu Lys Pro
                85                  90                  95

Thr Gln Glu Gln Tyr Asp Glu Phe Lys Thr Thr Val Thr Arg His Thr
                100                 105                 110
```

Met Ile His Glu Gln Ile Thr Arg Leu Phe His Ala Phe Arg Arg Asp
          115                 120                 125

Ser His Pro Met Ala Val Met Cys Gly Ile Thr Gly Ala Leu Ala Ala
          130                 135                 140

Phe Tyr His Asp Ser Leu Asp Val Asn Asn Pro Arg His Arg Glu Ile
145                 150                 155                 160

Ala Ala Phe Arg Leu Leu Ser Lys Met Pro Thr Met Ala Ala Met Cys
              165                 170                 175

Tyr Lys Tyr Ser Ile Gly Gln Pro Phe Val Tyr Pro Arg Asn Asp Leu
              180                 185                 190

Ser Tyr Ala Gly Asn Phe Leu Asn Met Met Phe Ser Thr Pro Cys Glu
              195                 200                 205

Pro Tyr Glu Val Asn Pro Ile Leu Glu Arg Ala Met Asp Arg Ile Leu
              210                 215                 220

Ile Leu His Ala Asp His Glu Gln Asn Ala Ser Thr Ser Thr Val Arg
225                 230                 235                 240

Thr Ala Gly Ser Ser Gly Ala Asn Pro Phe Ala Cys Ile Ala Ala Gly
              245                 250                 255

Ile Ala Ser Leu Trp Gly Pro Ala His Gly Gly Ala Asn Glu Ala Ala
              260                 265                 270

Leu Lys Met Leu Glu Glu Ile Ser Ser Val Lys His Ile Pro Glu Phe
              275                 280                 285

Val Arg Arg Ala Lys Asp Lys Asn Asp Ser Phe Arg Leu Met Gly Phe
              290                 295                 300

Gly His Arg Val Tyr Lys Asn Tyr Asp Pro Arg Ala Thr Val Met Arg
305                 310                 315                 320

Glu Thr Cys His Glu Val Leu Lys Glu Leu Gly Thr Lys Asp Asp Leu
              325                 330                 335

Leu Glu Val Ala Met Glu Leu Glu Asn Ile Ala Leu Asn Asp Pro Tyr
              340                 345                 350

Phe Ile Glu Lys Lys Leu Tyr Pro Asn Val Asp Phe Tyr Ser Gly Ile
              355                 360                 365

Ile Leu Lys Ala Met Gly Ile Pro Ser Ser Met Phe Thr Val Ile Phe
              370                 375                 380

Ala Met Ala Arg Thr Val Gly Trp Ile Ala His Trp Ser Glu Met His
385                 390                 395                 400

Ser Tyr Gly Met Lys Ile Ala Arg Pro Arg Gln Leu Tyr Thr Gly Tyr
              405                 410                 415

Glu Lys Arg Asp Phe Lys Ser Asp Ile Lys Arg
              420                 425

<210> SEQ ID NO 81
<211> LENGTH: 403
<212> TYPE: PRT
<213> ORGANISM: Shigella flexneri

<400> SEQUENCE: 81

Met Asn Thr Ile Phe Ser Ala Arg Ile Met Lys Arg Leu Ala Leu Thr
1               5                   10                  15

Thr Ala Leu Cys Thr Ala Phe Ile Ser Ala Ala His Ala Asp Asp Leu
              20                  25                  30

Asn Ile Lys Thr Met Ile Pro Gly Val Pro Gln Ile Asp Ala Glu Ser
              35                  40                  45

Tyr Ile Leu Ile Asp Tyr Asn Ser Gly Lys Val Leu Ala Glu Gln Asn 50                  55                  60
Ala Asp Val Arg Arg Asp Pro Ala Ser Leu Thr Lys Met Met Thr Ser
 65                  70                  75                  80

Tyr Val Ile Gly Gln Ala Met Lys Ala Gly Lys Phe Lys Glu Thr Asp
                 85                  90                  95

Leu Val Thr Ile Gly Asn Asp Ala Trp Ala Thr Gly Asn Pro Val Phe
            100                 105                 110

Lys Gly Ser Ser Leu Met Phe Leu Lys Pro Gly Met Gln Val Pro Val
        115                 120                 125

Ser Gln Leu Ile Arg Gly Ile Asn Leu Gln Ser Gly Asn Asp Ala Cys
    130                 135                 140

Val Ala Met Ala Asp Phe Ala Ala Gly Ser Gln Asp Ala Phe Val Gly
145                 150                 155                 160

Leu Met Asn Ser Tyr Val Asn Ala Leu Gly Leu Lys Asn Thr His Phe
                165                 170                 175

Gln Thr Val His Gly Leu Asp Ala Asp Gly Gln Tyr Ser Ser Ala Arg
            180                 185                 190

Asp Met Ala Leu Ile Gly Gln Ala Leu Ile Arg Asp Val Pro Asn Glu
        195                 200                 205

Tyr Ser Ile Tyr Lys Glu Lys Glu Phe Thr Phe Asn Gly Ile Arg Gln
    210                 215                 220

Leu Asn Arg Asn Gly Leu Leu Trp Asp Asn Ser Leu Asn Val Asp Gly
225                 230                 235                 240

Ile Lys Thr Gly His Thr Asp Lys Ala Gly Tyr Asn Leu Val Ala Ser
                245                 250                 255

Ala Thr Glu Gly Gln Met Arg Leu Ile Ser Ala Val Met Gly Gly Arg
            260                 265                 270

Thr Phe Lys Gly Arg Glu Ala Glu Ser Lys Lys Leu Leu Thr Trp Gly
        275                 280                 285

Phe Arg Phe Phe Glu Thr Val Asn Pro Leu Lys Val Gly Lys Glu Phe
    290                 295                 300

Ala Ser Glu Pro Val Trp Phe Ser Asp Ser Asp Arg Ala Ser Leu Gly
305                 310                 315                 320

Val Asp Lys Asp Val Tyr Leu Thr Ile Pro Arg Gly Arg Met Lys Asp
                325                 330                 335

Leu Lys Ala Ser Tyr Val Leu Asn Ser Ser Glu Leu His Ala Pro Leu
            340                 345                 350

Gln Lys Asn Gln Val Val Gly Thr Ile Asn Phe Gln Leu Asp Gly Lys
        355                 360                 365

Thr Ile Glu Gln Arg Pro Leu Val Val Leu Gln Glu Ile Pro Glu Gly
    370                 375                 380

Asn Phe Phe Gly Lys Ile Ile Asp Tyr Ile Lys Leu Met Phe His His
385                 390                 395                 400

Trp Phe Gly

<210> SEQ ID NO 82
<211> LENGTH: 248
<212> TYPE: PRT
<213> ORGANISM: Shigella flexneri

<400> SEQUENCE: 82

Met Lys Ser Val Leu Lys Val Ser Leu Ala Ala Leu Thr Leu Ala Phe
 1               5                  10                  15

Ala Val Ser Ser His Ala Ala Asp Lys Lys Leu Val Val Ala Thr Asp

```
            20                  25                  30
Thr Ala Phe Val Pro Phe Glu Phe Lys Gln Gly Asp Lys Tyr Val Gly
         35                  40                  45

Phe Asp Val Asp Leu Trp Ala Ile Ala Lys Glu Leu Lys Leu Asp
 50                  55                  60

Tyr Glu Leu Lys Pro Met Asp Phe Ser Gly Ile Ile Pro Ala Leu Gln
 65                  70                  75                  80

Thr Lys Asn Val Asp Leu Ala Leu Ala Gly Ile Thr Ile Thr Asp Glu
                 85                  90                  95

Arg Lys Lys Ala Ile Asp Phe Ser Asp Gly Tyr Tyr Lys Ser Gly Leu
             100                 105                 110

Leu Val Met Val Lys Ala Asn Asn Asp Val Lys Ser Val Lys Asp
         115                 120                 125

Leu Asp Gly Lys Val Val Ala Val Lys Ser Gly Thr Gly Ser Val Asp
 130                 135                 140

Tyr Ala Lys Ala Asn Ile Lys Thr Lys Asp Leu Arg Gln Phe Pro Asn
145                 150                 155                 160

Ile Asp Asn Ala Tyr Met Glu Leu Gly Thr Asn Arg Ala Asp Ala Val
                165                 170                 175

Leu His Asp Thr Pro Asn Ile Leu Tyr Phe Ile Lys Thr Ala Gly Asn
             180                 185                 190

Gly Gln Phe Lys Ala Val Gly Asp Ser Leu Glu Ala Gln Gln Tyr Gly
         195                 200                 205

Ile Ala Phe Pro Lys Gly Ser Asp Glu Leu Arg Asp Lys Val Asn Gly
 210                 215                 220

Ala Leu Lys Thr Leu Arg Glu Asn Gly Thr Tyr Asn Glu Ile Tyr Lys
225                 230                 235                 240

Lys Trp Phe Ser Thr Glu Pro Lys
                245

<210> SEQ ID NO 83
<211> LENGTH: 413
<212> TYPE: PRT
<213> ORGANISM: Shigella flexneri

<400> SEQUENCE: 83

Met Asn Lys Thr Leu Ile Ala Ala Thr Val Ala Gly Ile Val Leu Leu
 1               5                  10                  15

Ala Ser Asn Ala Gln Ala Gln Thr Val Pro Glu Gly Tyr Gln Leu Gln
                 20                  25                  30

Gln Val Leu Met Met Ser Arg His Asn Leu Arg Ala Pro Leu Ala Asn
             35                  40                  45

Asn Gly Ser Val Leu Glu Gln Ser Thr Pro Asn Lys Trp Pro Glu Trp
         50                  55                  60

Asp Val Pro Gly Gly Gln Leu Thr Thr Lys Gly Gly Val Leu Glu Val
 65                  70                  75                  80

Tyr Met Gly His Tyr Met Arg Glu Trp Leu Ala Glu Gln Gly Ile Val
                 85                  90                  95

Lys Ser Gly Glu Cys Pro Pro Asp Thr Val Tyr Ala Tyr Ala Asn
             100                 105                 110

Ser Leu Gln Arg Thr Val Ala Thr Ala Gln Phe Phe Ile Thr Gly Ala
         115                 120                 125

Phe Pro Gly Cys Asp Ile Pro Val His His Gln Glu Lys Met Gly Thr
 130                 135                 140
```

```
Met Asp Pro Thr Phe Asn Pro Met Ile Thr Asp Asp Ser Ala Ala Phe
145                 150                 155                 160

Ser Glu Gln Ala Val Ala Ala Met Glu Lys Glu Leu Ser Lys Leu Gln
                165                 170                 175

Leu Thr Asp Ser Tyr Gln Leu Leu Glu Lys Ile Val Asn Tyr Lys Asp
            180                 185                 190

Ser Pro Ala Cys Lys Glu Lys Gln Gln Cys Ser Leu Val Asp Gly Lys
        195                 200                 205

Asn Thr Phe Ser Ala Lys Tyr Gln Gln Glu Pro Gly Val Ser Gly Pro
    210                 215                 220

Leu Lys Val Gly Asn Ser Leu Val Asp Ala Phe Thr Leu Gln Tyr Tyr
225                 230                 235                 240

Glu Gly Phe Pro Met Asp Gln Val Ala Trp Gly Glu Ile Lys Ser Asp
                245                 250                 255

Gln Gln Trp Lys Val Leu Ser Lys Leu Lys Asn Gly Tyr Gln Asp Ser
                260                 265                 270

Leu Phe Thr Ser Pro Glu Val Ala Arg Asn Val Ala Lys Pro Leu Val
            275                 280                 285

Ser Tyr Ile Asp Lys Ala Leu Val Thr Asp Arg Ala Ser Ala Pro Lys
    290                 295                 300

Ile Thr Val Leu Val Gly His Asp Ser Asn Ile Ala Ser Leu Leu Thr
305                 310                 315                 320

Ala Leu Asp Phe Lys Pro Tyr Gln Leu His Asp Gln Asn Glu Arg Thr
                325                 330                 335

Pro Ile Gly Gly Lys Ile Val Phe Gln Arg Trp His Asp Ser Lys Ala
                340                 345                 350

Asn Arg Asp Leu Met Lys Ile Glu Tyr Val Tyr Gln Ser Ala Glu Gln
                355                 360                 365

Leu Arg Asn Ala Asp Ala Leu Thr Leu Gln Ala Pro Ala Gln Arg Val
            370                 375                 380

Thr Leu Glu Leu Ser Gly Cys Pro Ile Asp Ala Asn Gly Phe Cys Pro
385                 390                 395                 400

Met Asp Lys Phe Asp Ser Val Leu Asn Glu Ala Val Lys
                405                 410

<210> SEQ ID NO 84
<211> LENGTH: 891
<212> TYPE: PRT
<213> ORGANISM: Shigella flexneri

<400> SEQUENCE: 84

Met Ala Val Thr Asn Val Ala Glu Leu Asn Ala Leu Val Glu Arg Val
1               5                   10                  15

Lys Lys Ala Gln Arg Glu Tyr Ala Ser Phe Thr Gln Glu Gln Val Asp
                20                  25                  30

Lys Ile Phe Arg Ala Ala Ala Leu Ala Ala Ala Asp Ala Arg Ile Pro
            35                  40                  45

Leu Ala Lys Met Ala Val Ala Glu Ser Gly Met Gly Ile Val Glu Asp
        50                  55                  60

Lys Val Ile Lys Asn His Phe Ala Ser Glu Tyr Ile Tyr Asn Ala Tyr
65                  70                  75                  80

Lys Asp Glu Lys Thr Cys Gly Val Leu Ser Glu Asp Asp Thr Phe Gly
                85                  90                  95

Thr Ile Thr Ile Ala Glu Pro Ile Gly Ile Ile Cys Gly Ile Val Pro
            100                 105                 110
```

```
Thr Thr Asn Pro Thr Ser Thr Ala Ile Phe Lys Ser Leu Ile Ser Leu
        115                 120                 125

Lys Thr Arg Asn Ala Ile Ile Phe Ser Pro His Pro Arg Ala Lys Asp
130                 135                 140

Ala Thr Asn Lys Ala Ala Asp Ile Val Leu Gln Ala Ala Ile Ala Ala
145                 150                 155                 160

Gly Ala Pro Lys Asp Leu Ile Gly Trp Ile Asp Gln Pro Ser Val Glu
                165                 170                 175

Leu Ser Asn Ala Leu Met His His Pro Asp Ile Asn Leu Ile Leu Ala
                180                 185                 190

Thr Gly Gly Pro Gly Met Val Lys Ala Ala Tyr Ser Ser Gly Lys Pro
                195                 200                 205

Ala Ile Gly Val Gly Ala Gly Asn Thr Pro Val Val Ile Asp Glu Thr
                210                 215                 220

Ala Asp Ile Lys Arg Ala Val Ala Ser Val Leu Met Ser Lys Thr Phe
225                 230                 235                 240

Asp Asn Gly Val Ile Cys Ala Ser Glu Gln Ser Val Val Val Val Asp
                245                 250                 255

Ser Val Tyr Asp Ala Val Arg Glu Arg Phe Ala Thr His Gly Gly Tyr
                260                 265                 270

Leu Leu Gln Gly Lys Glu Leu Lys Ala Val Gln Asp Val Ile Leu Lys
                275                 280                 285

Asn Gly Ala Leu Asn Ala Ala Ile Val Gly Gln Pro Ala Tyr Lys Ile
                290                 295                 300

Ala Glu Leu Ala Gly Phe Ser Val Pro Glu Asn Thr Lys Ile Leu Ile
305                 310                 315                 320

Gly Glu Val Thr Val Val Asp Glu Ser Glu Pro Phe Ala His Glu Lys
                325                 330                 335

Leu Ser Pro Thr Leu Ala Met Tyr Arg Ala Lys Asp Phe Glu Asp Ala
                340                 345                 350

Val Glu Lys Ala Glu Lys Leu Val Ala Met Gly Gly Ile Gly His Thr
                355                 360                 365

Ser Cys Leu Tyr Thr Asp Gln Asp Asn Gln Pro Ala Arg Val Ser Tyr
                370                 375                 380

Phe Gly Gln Lys Met Lys Thr Ala Arg Ile Leu Ile Asn Thr Pro Ala
385                 390                 395                 400

Ser Gln Gly Gly Ile Gly Asp Leu Tyr Asn Phe Lys Leu Ala Pro Ser
                405                 410                 415

Leu Thr Leu Gly Cys Gly Ser Trp Gly Gly Asn Ser Ile Ser Glu Asn
                420                 425                 430

Val Gly Pro Lys His Leu Ile Asn Lys Lys Thr Val Ala Lys Arg Ala
                435                 440                 445

Glu Asn Met Leu Trp His Lys Leu Pro Lys Ser Ile Tyr Phe Arg Arg
450                 455                 460

Gly Ser Leu Pro Ile Ala Leu Asp Glu Val Ile Thr Asp Gly His Lys
465                 470                 475                 480

Arg Ala Leu Ile Val Thr Asp Arg Phe Leu Phe Asn Asn Gly Tyr Ala
                485                 490                 495

Asp Gln Ile Thr Ser Val Leu Lys Ala Ala Gly Val Glu Thr Glu Val
                500                 505                 510

Phe Phe Glu Val Glu Ala Asp Pro Thr Leu Ser Ile Val Arg Lys Gly
                515                 520                 525
```

-continued

```
Ala Glu Leu Ala Asn Ser Phe Lys Pro Asp Val Ile Ile Ala Leu Gly
        530                 535                 540

Gly Gly Ser Pro Met Asp Ala Ala Lys Ile Met Trp Val Met Tyr Glu
545                 550                 555                 560

His Pro Glu Thr His Phe Glu Glu Leu Ala Leu Arg Phe Met Asp Ile
                565                 570                 575

Arg Lys Arg Ile Tyr Lys Phe Pro Lys Met Gly Val Lys Ala Lys Met
                580                 585                 590

Ile Ala Val Thr Thr Thr Ser Gly Thr Gly Ser Glu Val Thr Pro Phe
                595                 600                 605

Ala Val Val Thr Asp Asp Ala Thr Gly Gln Lys Tyr Pro Leu Ala Asp
            610                 615                 620

Tyr Ala Leu Thr Pro Asp Met Ala Ile Val Asp Ala Asn Leu Val Met
625                 630                 635                 640

Asp Met Pro Lys Ser Leu Cys Ala Phe Gly Gly Leu Asp Ala Val Thr
                645                 650                 655

His Ala Met Glu Ala Tyr Val Ser Val Leu Ala Ser Glu Phe Ser Asp
                660                 665                 670

Gly Gln Ala Leu Gln Ala Leu Lys Leu Leu Lys Glu Tyr Leu Pro Ala
            675                 680                 685

Ser Tyr His Glu Gly Ser Lys Asn Pro Val Ala Arg Glu Arg Val His
690                 695                 700

Ser Ala Ala Thr Ile Ala Gly Ile Ala Phe Ala Asn Ala Phe Leu Gly
705                 710                 715                 720

Val Cys His Ser Met Ala His Lys Leu Gly Ser Gln Phe His Ile Pro
                725                 730                 735

His Gly Leu Ala Asn Ala Leu Leu Ile Cys Asn Val Ile Arg Tyr Asn
            740                 745                 750

Ala Asn Asp Asn Pro Thr Lys Gln Thr Ala Phe Ser Gln Tyr Asp Arg
            755                 760                 765

Pro Gln Ala Arg Arg Arg Tyr Ala Glu Ile Ala Asp His Leu Gly Leu
        770                 775                 780

Ser Ala Pro Gly Asp Arg Thr Ala Ala Lys Ile Glu Lys Leu Leu Ala
785                 790                 795                 800

Trp Leu Glu Thr Leu Lys Ala Glu Leu Gly Ile Pro Lys Ser Ile Arg
                805                 810                 815

Glu Ala Gly Val Gln Glu Ala Asp Phe Leu Ala Asn Val Asp Lys Leu
                820                 825                 830

Ser Glu Asp Ala Phe Asp Gln Cys Thr Gly Ala Asn Pro Arg Tyr
            835                 840                 845

Pro Leu Ile Ser Glu Leu Lys Gln Ile Leu Leu Asp Thr Tyr Tyr Gly
850                 855                 860

Arg Asp Tyr Val Glu Asp Glu Thr Ala Ala Lys Lys Glu Ala Ala Pro
865                 870                 875                 880

Ala Lys Ala Glu Lys Lys Ala Lys Lys Ser Ala
                885                 890

<210> SEQ ID NO 85
<211> LENGTH: 551
<212> TYPE: PRT
<213> ORGANISM: Shigella flexneri

<400> SEQUENCE: 85

Met Asp Arg Arg Arg Phe Ile Lys Gly Ser Met Ala Met Ala Ala Val
1               5                  10                  15
```

```
Cys Gly Thr Ser Gly Ile Ala Ser Leu Phe Ser Gln Ala Ala Phe Ala
            20                  25                  30

Ala Asp Ser Asp Ile Ala Asp Gly Gln Thr Gln Arg Phe Asp Phe Ser
        35                  40                  45

Ile Leu Gln Ser Met Ala His Asp Leu Ala Gln Thr Ala Trp Arg Gly
50                  55                  60

Ala Pro Arg Pro Leu Pro Asp Thr Leu Ala Thr Met Thr Pro Gln Ala
65                  70                  75                  80

Tyr Asn Ser Ile Gln Tyr Asp Ala Glu Lys Ser Leu Trp His Asn Val
                85                  90                  95

Glu Asn Arg Gln Leu Asp Ala Gln Phe Phe His Met Gly Met Gly Phe
            100                 105                 110

Arg Arg Arg Val Arg Met Phe Ser Val Asp Pro Ala Thr His Leu Ala
        115                 120                 125

Arg Glu Ile His Phe Arg Pro Glu Leu Phe Lys Tyr Asn Asp Ala Gly
    130                 135                 140

Val Asp Thr Lys Gln Leu Glu Gly Gln Ser Asp Leu Gly Phe Ala Gly
145                 150                 155                 160

Phe Arg Val Phe Lys Ala Pro Glu Leu Ala Arg Arg Asp Val Val Ser
                165                 170                 175

Phe Leu Gly Ala Ser Tyr Phe Arg Ala Val Asp Asp Thr Tyr Gln Tyr
            180                 185                 190

Gly Leu Ser Ala Arg Gly Leu Ala Ile Asp Thr Tyr Thr Asp Ser Lys
        195                 200                 205

Glu Glu Phe Pro Asp Phe Thr Ala Phe Trp Phe Asp Thr Val Lys Pro
    210                 215                 220

Gly Ala Thr Thr Phe Thr Val Tyr Ala Leu Leu Asp Ser Ala Ser Ile
225                 230                 235                 240

Thr Gly Ala Tyr Lys Phe Thr Ile His Cys Glu Lys Ser Gln Val Ile
                245                 250                 255

Met Asp Val Glu Asn His Leu Tyr Ala Arg Lys Asp Ile Lys Gln Leu
            260                 265                 270

Gly Ile Ser Pro Met Thr Ser Met Phe Ser Cys Gly Thr Asn Glu Arg
        275                 280                 285

Arg Met Cys Asp Thr Ile His Pro Gln Ile His Asp Ser Asp Arg Leu
    290                 295                 300

Ser Met Trp Arg Gly Asn Gly Glu Trp Ile Cys Arg Pro Leu Asn Asn
305                 310                 315                 320

Pro Gln Lys Leu Gln Phe Asn Ala Tyr Thr Asp Asn Asn Pro Lys Gly
                325                 330                 335

Phe Gly Leu Leu Gln Leu Asp Arg Asp Phe Ser His Tyr Gln Asp Ile
            340                 345                 350

Met Gly Trp Tyr Asn Lys Arg Pro Ser Leu Trp Val Glu Pro Arg Asn
        355                 360                 365

Lys Trp Gly Lys Gly Thr Ile Gly Leu Met Glu Ile Pro Thr Thr Gly
    370                 375                 380

Glu Thr Leu Asp Asn Ile Val Cys Phe Trp Gln Pro Glu Lys Ala Val
385                 390                 395                 400

Lys Ala Gly Asp Glu Phe Ala Phe Gln Tyr Arg Leu Tyr Trp Ser Ala
                405                 410                 415

Gln Pro Pro Val His Cys Pro Leu Ala Arg Val Met Ala Thr Arg Thr
            420                 425                 430
```

```
Gly Met Gly Gly Phe Pro Glu Gly Trp Ala Pro Gly Glu His Tyr Pro
        435                 440                 445

Glu Lys Trp Ala Arg Arg Phe Ala Val Asp Phe Val Gly Gly Asp Leu
    450                 455                 460

Lys Ala Ala Pro Lys Gly Ile Glu Pro Val Ile Thr Leu Ser Ser
465                 470                 475                 480

Gly Glu Ala Lys Gln Ile Glu Ile Leu Tyr Ile Glu Pro Ile Asp Gly
                485                 490                 495

Tyr Arg Ile Gln Phe Asp Trp Tyr Pro Thr Ser Asp Ser Thr Asp Pro
                500                 505                 510

Val Asp Met Arg Met Tyr Leu Arg Cys Gln Gly Asp Ala Ile Ser Glu
                515                 520                 525

Thr Trp Leu Tyr Gln Tyr Phe Pro Pro Ala Pro Asp Lys Arg Gln Tyr
            530                 535                 540

Val Asp Asp Arg Val Met Ser
545                 550

<210> SEQ ID NO 86
<211> LENGTH: 331
<212> TYPE: PRT
<213> ORGANISM: Shigella flexneri

<400> SEQUENCE: 86

Met Thr Ile Lys Val Gly Ile Asn Gly Phe Gly Arg Ile Gly Arg Ile
1               5                   10                  15

Val Phe Arg Ala Ala Gln Lys Arg Ser Asp Ile Glu Ile Val Ala Ile
            20                  25                  30

Asn Asp Leu Leu Asp Ala Asp Tyr Met Ala Tyr Met Leu Lys Tyr Asp
        35                  40                  45

Ser Thr His Gly Arg Phe Asp Gly Thr Val Glu Val Lys Asp Gly His
    50                  55                  60

Leu Ile Val Asn Gly Lys Lys Ile Arg Val Thr Ala Glu Arg Asp Pro
65                  70                  75                  80

Ala Asn Leu Lys Trp Asp Glu Val Gly Val Asp Val Val Ala Glu Ala
                85                  90                  95

Thr Gly Leu Phe Leu Thr Asp Glu Thr Ala Arg Lys His Ile Thr Ala
            100                 105                 110

Gly Ala Lys Lys Val Val Met Thr Gly Pro Ser Lys Asp Asn Thr Pro
        115                 120                 125

Met Phe Val Lys Gly Ala Asn Phe Asp Lys Tyr Ala Gly Gln Asp Ile
    130                 135                 140

Val Ser Asn Ala Ser Cys Thr Thr Asn Cys Leu Ala Pro Leu Ala Lys
145                 150                 155                 160

Val Ile Asn Asp Asn Phe Gly Ile Ile Glu Gly Leu Met Thr Thr Val
                165                 170                 175

His Ala Thr Thr Ala Thr Gln Lys Thr Val Asp Gly Pro Ser His Lys
            180                 185                 190

Asp Trp Arg Gly Gly Arg Gly Ala Ser Gln Asn Ile Ile Pro Ser Ser
        195                 200                 205

Thr Gly Ala Ala Lys Ala Val Gly Lys Val Leu Pro Glu Leu Asn Gly
    210                 215                 220

Lys Leu Thr Gly Met Ala Phe Arg Val Pro Thr Pro Asn Val Ser Val
225                 230                 235                 240

Val Asp Leu Thr Val Arg Leu Glu Lys Ala Ala Thr Tyr Glu Gln Ile
                245                 250                 255
```

```
Lys Ala Ala Val Lys Ala Ala Glu Gly Glu Met Lys Gly Val Leu
            260                 265                 270

Gly Tyr Thr Glu Asp Asp Val Ser Thr Asp Phe Asn Gly Glu Val
            275                 280                 285

Cys Thr Ser Val Phe Asp Ala Lys Ala Gly Ile Ala Leu Asn Asp Asn
            290                 295                 300

Phe Val Lys Leu Val Ser Trp Tyr Asp Asn Glu Thr Gly Tyr Ser Asn
305                 310                 315                 320

Lys Val Leu Asp Leu Ile Ala His Ile Ser Lys
            325                 330

<210> SEQ ID NO 87
<211> LENGTH: 404
<212> TYPE: PRT
<213> ORGANISM: Shigella flexneri

<400> SEQUENCE: 87

Met Lys Ile Val Lys Ala Glu Val Phe Val Thr Cys Pro Gly Arg Asn
1               5                   10                  15

Phe Val Thr Leu Lys Ile Thr Thr Glu Asp Gly Ile Thr Gly Leu Gly
            20                  25                  30

Asp Ala Thr Leu Asn Gly Arg Glu Leu Ser Val Ala Ser Tyr Leu Gln
        35                  40                  45

Asp His Leu Cys Pro Arg Leu Ile Gly Arg Asp Ala His Arg Ile Glu
    50                  55                  60

Asp Ile Trp Gln Phe Phe Tyr Lys Gly Ala Tyr Trp Arg Arg Gly Pro
65                  70                  75                  80

Val Thr Met Ser Ala Ile Ser Ala Val Asp Met Ala Leu Trp Asp Ile
                85                  90                  95

Lys Ala Lys Ala Ala Asn Met Pro Leu Tyr Gln Leu Leu Gly Gly Ala
            100                 105                 110

Ser Arg Glu Gly Val Met Val Tyr Cys His Thr Thr Gly His Ser Ile
        115                 120                 125

Asp Glu Ala Leu Asp Asp Tyr Ala Arg His Gln Glu Leu Gly Phe Lys
    130                 135                 140

Ala Ile Arg Val Gln Cys Gly Ile Pro Gly Met Lys Thr Thr Tyr Gly
145                 150                 155                 160

Met Ser Lys Gly Lys Gly Leu Ala Tyr Glu Pro Ala Thr Lys Gly Gln
                165                 170                 175

Trp Pro Glu Glu Gln Leu Trp Ser Thr Glu Lys Tyr Leu Asp Phe Met
            180                 185                 190

Pro Lys Leu Phe Asp Ala Val Arg Asn Lys Phe Gly Phe Asn Glu His
        195                 200                 205

Leu Leu His Asp Met His His Arg Leu Thr Pro Ile Glu Ala Ala Arg
    210                 215                 220

Phe Gly Lys Ser Ile Glu Asp Tyr Arg Met Phe Trp Met Glu Asp Pro
225                 230                 235                 240

Thr Pro Ala Glu Asn Gln Glu Cys Phe Arg Leu Ile Arg Gln His Thr
                245                 250                 255

Val Thr Pro Ile Ala Val Gly Glu Val Phe Asn Ser Ile Trp Asp Cys
            260                 265                 270

Lys Gln Leu Ile Glu Glu Gln Leu Ile Asp Tyr Ile Arg Thr Thr Leu
        275                 280                 285

Thr His Ala Gly Gly Ile Thr Gly Met Arg Arg Ile Ala Asp Phe Ala
```

```
            290                 295                 300
Ser Leu Tyr Gln Val Arg Thr Gly Ser His Gly Pro Ser Asp Leu Ser
305                 310                 315                 320

Pro Val Cys Met Ala Ala Leu His Phe Asp Leu Trp Val Pro Asn
                325                 330                 335

Phe Gly Val Gln Glu Tyr Met Gly Tyr Ser Glu Gln Met Leu Glu Val
                340                 345                 350

Phe Pro His Asn Trp Thr Phe Asp Asn Gly Tyr Met His Pro Gly Asp
                355                 360                 365

Lys Pro Gly Leu Gly Ile Glu Phe Asp Glu Lys Leu Ala Ala Lys Tyr
            370                 375                 380

Pro Tyr Glu Pro Ala Tyr Leu Pro Val Ala Arg Leu Glu Asp Gly Thr
385                 390                 395                 400

Leu Trp Asn Arg

<210> SEQ ID NO 88
<211> LENGTH: 406
<212> TYPE: PRT
<213> ORGANISM: Shigella flexneri

<400> SEQUENCE: 88

Met Thr Phe Ser Val Asp Lys Val Arg Ala Asp Phe Pro Val Leu Ser
1               5                   10                  15

Arg Glu Val Asn Gly Leu Pro Leu Ala Tyr Leu Asp Ser Ala Ala Ser
                20                  25                  30

Ala Gln Lys Pro Ser Gln Val Ile Asp Ala Glu Ala Glu Phe Tyr Arg
            35                  40                  45

His Gly Tyr Ala Ala Val His Arg Gly Ile His Thr Leu Ser Ala Gln
        50                  55                  60

Ala Thr Glu Lys Met Glu Asn Val Arg Lys Arg Ala Ser Leu Phe Ile
65                  70                  75                  80

Asn Ala Arg Ser Ala Glu Glu Leu Val Phe Val Arg Gly Thr Thr Glu
                85                  90                  95

Gly Ile Asn Leu Val Ala Asn Ser Trp Gly Asn Ser Asn Val Arg Ala
            100                 105                 110

Gly Asp Asn Ile Ile Ile Ser Gln Met Glu His His Ala Asn Ile Val
        115                 120                 125

Pro Trp Gln Met Leu Cys Ala Arg Val Gly Ala Glu Leu Arg Val Ile
130                 135                 140

Pro Leu Asn Pro Asp Gly Thr Leu Gln Leu Glu Thr Leu Pro Thr Leu
145                 150                 155                 160

Phe Asp Glu Lys Thr Arg Leu Leu Ala Ile Thr His Val Ser Asn Val
                165                 170                 175

Leu Gly Thr Glu Asn Pro Leu Ala Glu Met Ile Thr Leu Ala His Gln
            180                 185                 190

His Gly Ala Lys Val Leu Val Asp Gly Ala Gln Ala Val Met His His
        195                 200                 205

Pro Val Asp Val Gln Ala Leu Asp Cys Asp Phe Tyr Val Phe Ser Gly
    210                 215                 220

His Lys Leu Tyr Gly Pro Thr Gly Ile Gly Ile Leu Tyr Val Lys Glu
225                 230                 235                 240

Ala Leu Leu Gln Glu Met Pro Pro Trp Glu Gly Gly Gly Ser Met Ile
                245                 250                 255

Ala Thr Val Ser Leu Ser Glu Gly Thr Thr Trp Thr Lys Ala Pro Trp
```

```
            260                 265                 270
Arg Phe Glu Ala Gly Thr Pro Asn Thr Gly Gly Ile Ile Gly Leu Gly
            275                 280                 285

Ala Ala Leu Glu Tyr Val Ser Ala Leu Gly Leu Asn Ser Ile Ala Glu
            290                 295                 300

Tyr Glu Gln Asn Leu Met His Tyr Ala Leu Ser Gln Leu Glu Ser Val
305                 310                 315                 320

Pro Asp Leu Thr Leu Tyr Gly Gln Gln Asn Arg Leu Gly Val Ile Ala
                325                 330                 335

Phe Asn Leu Gly Lys His His Ala Tyr Asp Val Gly Ser Phe Leu Asp
                340                 345                 350

Asn Tyr Gly Ile Ala Val Arg Thr Gly His His Cys Ala Met Pro Leu
                355                 360                 365

Met Ala Tyr Tyr Asn Val Pro Ala Met Cys Arg Ala Ser Leu Ala Met
            370                 375                 380

Tyr Asn Thr His Glu Glu Val Glu Arg Leu Val Thr Gly Leu Gln Arg
385                 390                 395                 400

Ile His Arg Leu Leu Gly
                405

<210> SEQ ID NO 89
<211> LENGTH: 491
<212> TYPE: PRT
<213> ORGANISM: Shigella flexneri

<400> SEQUENCE: 89

Met Ala Val Thr Gln Thr Ala Gln Ala Cys Asp Leu Val Ile Phe Gly
1               5                   10                  15

Ala Lys Gly Asp Leu Ala Arg Arg Lys Leu Leu Pro Ser Leu Tyr Gln
            20                  25                  30

Leu Glu Lys Val Gly Gln Leu Asn Pro Asp Thr Arg Ile Ile Gly Val
        35                  40                  45

Gly Arg Ala Asp Trp Asp Lys Ala Ala Tyr Thr Lys Val Val Arg Glu
    50                  55                  60

Ala Leu Glu Thr Phe Met Lys Glu Thr Ile Asp Glu Gly Leu Trp Asp
65                  70                  75                  80

Thr Leu Ser Ala Arg Leu Asp Phe Cys Asn Leu Asp Val Asn Asp Thr
                85                  90                  95

Ala Ala Phe Asn Arg Leu Gly Ala Met Leu Asp Gln Lys Asn Arg Ile
            100                 105                 110

Thr Ile Asn Tyr Phe Ala Met Pro Pro Ser Thr Phe Gly Ala Ile Cys
        115                 120                 125

Lys Gly Leu Gly Glu Ala Lys Leu Asn Ala Lys Pro Ala Arg Val Val
    130                 135                 140

Met Glu Lys Pro Leu Gly Thr Ser Leu Ala Thr Ser Gln Glu Ile Asn
145                 150                 155                 160

Asp Gln Val Gly Glu Tyr Phe Glu Glu Cys Gln Val Tyr Arg Ile Asp
                165                 170                 175

His Tyr Leu Gly Lys Glu Thr Val Leu Asn Leu Leu Ala Leu Arg Phe
            180                 185                 190

Ala Asn Ser Leu Phe Val Asn Asn Trp Asp Asn Arg Thr Ile Asp His
        195                 200                 205

Val Glu Ile Thr Val Ala Glu Glu Val Gly Ile Glu Gly Arg Trp Gly
    210                 215                 220
```

Tyr Phe Asp Lys Ala Gly Gln Met Arg Asp Met Ile Gln Asn His Leu
225                 230                 235                 240

Leu Gln Ile Leu Cys Met Ile Ala Met Ser Pro Pro Ser Asp Leu Ser
            245                 250                 255

Ala Asp Ser Ile Arg Asp Glu Lys Val Lys Val Leu Lys Ser Leu Arg
        260                 265                 270

Arg Ile Asp Arg Ser Asn Val Arg Glu Lys Thr Val Arg Gly Gln Tyr
    275                 280                 285

Thr Ala Gly Phe Ala Gln Gly Lys Lys Val Pro Gly Tyr Leu Glu Glu
        290                 295                 300

Glu Gly Ala Asn Lys Ser Ser Asn Thr Glu Thr Phe Val Ala Ile Arg
305                 310                 315                 320

Val Asp Ile Asp Asn Trp Arg Trp Ala Gly Val Pro Phe Tyr Leu Arg
                325                 330                 335

Thr Gly Lys Arg Leu Pro Thr Lys Cys Ser Glu Val Val Tyr Phe
            340                 345                 350

Lys Thr Pro Glu Leu Asn Leu Phe Lys Glu Ser Trp Gln Asp Leu Pro
        355                 360                 365

Gln Asn Lys Leu Thr Ile Arg Leu Gln Pro Asp Glu Gly Val Asp Ile
    370                 375                 380

Gln Val Leu Asn Lys Val Pro Gly Leu Asp His Lys His Asn Leu Gln
385                 390                 395                 400

Ile Thr Lys Leu Asp Leu Ser Tyr Ser Glu Thr Phe Asn Gln Thr His
                405                 410                 415

Leu Ala Asp Ala Tyr Glu Arg Leu Leu Leu Glu Thr Met Arg Gly Ile
            420                 425                 430

Gln Ala Leu Phe Val Arg Arg Asp Glu Val Glu Ala Trp Lys Trp
        435                 440                 445

Val Asp Ser Ile Thr Glu Ala Trp Ala Met Asp Asn Asp Ala Pro Lys
    450                 455                 460

Pro Tyr Gln Ala Gly Thr Trp Gly Pro Val Ala Ser Val Ala Met Ile
465                 470                 475                 480

Thr Arg Asp Gly Arg Ser Trp Asn Glu Phe Glu
                485                 490

<210> SEQ ID NO 90
<211> LENGTH: 590
<212> TYPE: PRT
<213> ORGANISM: Shigella flexneri

<400> SEQUENCE: 90

Met Arg Thr Glu Tyr Cys Gly Gln Leu Arg Leu Ser His Val Gly Gln
1               5                   10                  15

Gln Val Thr Leu Cys Gly Trp Val Asn Arg Arg Arg Asp Leu Gly Ser
            20                  25                  30

Leu Ile Phe Ile Asp Met Arg Asp Arg Glu Gly Ile Val Gln Val Phe
        35                  40                  45

Phe Asp Pro Asp Arg Ala Asp Ala Leu Lys Leu Ala Ser Glu Leu Arg
    50                  55                  60

Asn Glu Phe Cys Ile Gln Val Thr Gly Thr Val Arg Ala Arg Asp Glu
65                  70                  75                  80

Lys Asn Ile Asn Arg Asp Met Ala Thr Gly Glu Ile Glu Val Leu Ala
                85                  90                  95

Ser Ser Leu Thr Ile Ile Asn Arg Ala Asp Val Leu Pro Leu Asp Ser
            100                 105                 110

```
Asn His Val Asn Thr Glu Glu Ala Arg Leu Lys Tyr Arg Tyr Leu Asp
        115                 120                 125

Leu Arg Arg Pro Glu Met Ala Gln Arg Leu Lys Thr Arg Ala Lys Ile
130                 135                 140

Thr Ser Leu Val Arg Arg Phe Met Asp Asp His Gly Phe Leu Asp Ile
145                 150                 155                 160

Glu Thr Pro Met Leu Thr Lys Ala Thr Pro Glu Gly Ala Arg Asp Tyr
                165                 170                 175

Leu Val Pro Ser Arg Val His Lys Gly Lys Phe Tyr Ala Leu Pro Gln
                180                 185                 190

Ser Pro Gln Leu Phe Lys Gln Leu Leu Met Met Ser Gly Phe Asp Arg
                195                 200                 205

Tyr Tyr Gln Ile Val Lys Cys Phe Arg Asp Glu Asp Leu Arg Ala Asp
        210                 215                 220

Arg Gln Pro Glu Phe Thr Gln Ile Asp Val Glu Thr Ser Phe Met Thr
225                 230                 235                 240

Ala Pro Gln Val Arg Glu Val Met Glu Ala Leu Val Arg His Leu Trp
                245                 250                 255

Leu Glu Val Lys Gly Val Asp Leu Gly Asp Phe Pro Val Met Thr Phe
                260                 265                 270

Ala Glu Ala Glu Arg Arg Tyr Gly Ser Asp Lys Pro Asp Leu Arg Asn
        275                 280                 285

Pro Met Glu Leu Thr Asp Val Ala Asp Leu Leu Lys Ser Val Glu Phe
        290                 295                 300

Ala Val Phe Ala Gly Pro Ala Asn Asp Pro Lys Gly Arg Val Ala Ala
305                 310                 315                 320

Leu Arg Val Pro Gly Gly Ala Ser Leu Thr Arg Lys Gln Ile Asp Glu
                325                 330                 335

Tyr Gly Asn Phe Val Lys Ile Tyr Gly Ala Lys Gly Leu Ala Tyr Ile
                340                 345                 350

Lys Val Asn Glu Arg Ala Lys Gly Leu Glu Gly Ile Asn Ser Pro Val
        355                 360                 365

Ala Lys Phe Leu Asn Ala Glu Ile Ile Glu Ala Ile Leu Asp Arg Thr
        370                 375                 380

Ala Ala Gln Asp Gly Asp Met Ile Phe Phe Gly Ala Asp Asn Lys Lys
385                 390                 395                 400

Ile Val Ala Asp Gly Met Gly Ala Leu Leu Leu Lys Val Gly Lys Asp
                405                 410                 415

Leu Gly Leu Thr Asp Glu Ser Lys Trp Ala Pro Leu Trp Val Ile Asp
                420                 425                 430

Phe Pro Met Leu Gly Asp Asp Gly Glu Gly Gly Leu Thr Ala Met His
        435                 440                 445

His Pro Phe Thr Ser Pro Lys Asp Met Thr Ala Ala Glu Leu Lys Ala
        450                 455                 460

Ala Pro Glu Asn Ala Val Ala Asn Ala Tyr Asp Met Val Ile Asn Gly
465                 470                 475                 480

Tyr Glu Val Gly Gly Gly Ser Val Arg Ile His Asn Gly Asp Met Gln
                485                 490                 495

Gln Thr Val Phe Gly Ile Leu Gly Ile Asn Glu Glu Glu Gln Arg Glu
                500                 505                 510

Lys Phe Gly Phe Leu Leu Asp Ala Leu Lys Tyr Gly Thr Pro Pro His
        515                 520                 525
```

```
Ala Gly Leu Ala Phe Gly Leu Asp Arg Leu Thr Met Leu Leu Thr Gly
        530                 535                 540

Thr Asp Asn Ile Arg Asp Val Ile Ala Phe Pro Lys Thr Thr Ala Ala
545                 550                 555                 560

Ala Cys Leu Met Thr Glu Ala Pro Ser Phe Ala Asn Pro Thr Ala Leu
                565                 570                 575

Ala Glu Leu Ser Ile Gln Val Val Lys Lys Ala Glu Asn Asn
        580                 585                 590

<210> SEQ ID NO 91
<211> LENGTH: 296
<212> TYPE: PRT
<213> ORGANISM: Shigella flexneri

<400> SEQUENCE: 91

Met Leu Leu Gly Cys Leu Ala Leu Thr Cys Ser Ile Ala Phe Gln Ala
1               5                   10                  15

Ser Ala Thr Glu Lys Phe Lys Val Ile Thr Thr Phe Thr Ile Ile Ala
            20                  25                  30

Asp Met Ala Lys Asn Val Ala Gly Asp Ala Ala Glu Val Ser Ser Ile
        35                  40                  45

Thr Lys Pro Gly Ala Glu Ile His Glu Tyr Gln Pro Thr Pro Gly Asp
    50                  55                  60

Ile Lys Arg Ala Gln Gly Ala Gln Leu Ile Leu Ala Asn Gly Met Asn
65                  70                  75                  80

Leu Glu Leu Trp Phe Gln Arg Phe Tyr Gln His Leu Asn Gly Val Pro
                85                  90                  95

Glu Val Ile Val Ser Ser Gly Val Thr Pro Val Gly Ile Thr Glu Gly
            100                 105                 110

Pro Tyr Glu Gly Lys Pro Asn Pro His Ala Trp Met Ser Pro Asp Asn
        115                 120                 125

Ala Leu Ile Tyr Val Asp Asn Ile Arg Asp Ala Leu Ile Lys Tyr Asp
    130                 135                 140

Pro Ala Asn Ala Gln Thr Tyr Gln Arg Asn Ala Asp Thr Tyr Lys Ala
145                 150                 155                 160

Lys Ile Thr Gln Thr Leu Ala Pro Leu Arg Lys Gln Ile Thr Glu Leu
                165                 170                 175

Pro Glu Asn Gln Arg Trp Met Val Thr Ser Glu Gly Ala Phe Ser Tyr
            180                 185                 190

Leu Ala Arg Asp Leu Gly Leu Lys Glu Leu Tyr Leu Trp Pro Ile Asn
        195                 200                 205

Ala Asp Gln Gln Gly Thr Pro Gln Gln Val Arg Lys Val Val Asp Ile
    210                 215                 220

Val Lys Lys Asn His Ile Pro Ala Val Phe Ser Glu Ser Thr Ile Ser
225                 230                 235                 240

Asp Lys Pro Ala Arg Gln Val Ala Arg Glu Thr Gly Ala His Tyr Gly
                245                 250                 255

Gly Val Leu Tyr Val Asp Ser Leu Ser Thr Glu Asn Gly Pro Val Pro
            260                 265                 270

Thr Tyr Ile Asp Leu Leu Lys Val Thr Thr Ser Thr Leu Val Gln Gly
        275                 280                 285

Ile Lys Ala Gly Lys Arg Glu Lys
    290                 295

<210> SEQ ID NO 92
```

```
<211> LENGTH: 131
<212> TYPE: PRT
<213> ORGANISM: Shigella flexneri

<400> SEQUENCE: 92

Met Leu Ala Leu Thr Asn Ser Gly Cys Leu Asn Glu Ser Asp Ser His
1               5                   10                  15

Ile Ile Arg Gly Ile Lys Met Glu Thr Thr Lys Pro Ser Phe Gln Asp
                20                  25                  30

Val Leu Glu Phe Val Arg Leu Phe Arg Arg Lys Asn Lys Leu Gln Arg
            35                  40                  45

Glu Ile Gln Asp Val Glu Lys Lys Ile Arg Asp Asn Gln Lys Arg Val
    50                  55                  60

Leu Leu Leu Asp Asn Leu Ser Asp Tyr Ile Lys Pro Gly Met Ser Val
65                  70                  75                  80

Glu Ala Ile Gln Gly Ile Ile Ala Ser Met Lys Gly Asp Tyr Glu Asp
                85                  90                  95

Arg Val Asp Asp Tyr Ile Ile Lys Asn Ala Glu Leu Ser Lys Glu Arg
            100                 105                 110

Arg Asp Ile Ser Lys Lys Leu Lys Ala Met Gly Glu Met Lys Asn Gly
        115                 120                 125

Glu Ala Lys
    130

<210> SEQ ID NO 93
<211> LENGTH: 355
<212> TYPE: PRT
<213> ORGANISM: Shigella flexneri

<400> SEQUENCE: 93

Met Ser Gln Lys Tyr Leu Phe Ile Asp Arg Asp Gly Thr Leu Ile Ser
1               5                   10                  15

Glu Pro Pro Ser Asp Phe Gln Val Asp Arg Phe Asp Lys Leu Ala Phe
                20                  25                  30

Glu Pro Gly Val Ile Pro Glu Leu Leu Lys Leu Gln Lys Ala Gly Tyr
            35                  40                  45

Lys Leu Val Met Ile Thr Asn Gln Asp Gly Leu Gly Thr Gln Ser Phe
    50                  55                  60

Pro Gln Ala Asp Phe Asp Gly Pro His Asn Leu Met Met Gln Ile Phe
65                  70                  75                  80

Thr Ser Gln Gly Val Gln Phe Asp Glu Val Leu Ile Cys Pro His Leu
                85                  90                  95

Pro Ala Asp Glu Cys Asp Cys Arg Lys Pro Lys Val Lys Leu Val Glu
            100                 105                 110

Gly Tyr Leu Ala Glu Gln Ala Met Asp Arg Ala Asn Ser Tyr Val Ile
        115                 120                 125

Gly Asp Arg Ala Thr Asp Ile Gln Leu Ala Glu Asn Met Gly Ile Asn
    130                 135                 140

Gly Leu Arg Tyr Asp Arg Glu Thr Leu Asn Trp Pro Met Ile Gly Glu
145                 150                 155                 160

Gln Leu Thr Lys Arg Asp Arg Tyr Ala His Val Val Arg Asn Thr Lys
                165                 170                 175

Glu Thr Gln Ile Asp Val Gln Val Trp Leu Asp Arg Glu Gly Gly Ser
            180                 185                 190

Lys Ile Asn Thr Gly Val Gly Phe Phe Asp His Met Leu Asp Gln Ile
        195                 200                 205
```

```
Ala Thr His Gly Gly Phe Arg Met Glu Ile Asn Val Lys Gly Asp Leu
    210                 215                 220

Tyr Ile Asp Asp His His Thr Val Glu Asp Thr Gly Leu Ala Leu Gly
225                 230                 235                 240

Glu Ala Leu Lys Ile Ala Leu Gly Asp Lys Arg Gly Ile Cys Arg Phe
                245                 250                 255

Gly Phe Val Leu Pro Met Asp Glu Cys Leu Ala Arg Cys Ala Leu Asp
                260                 265                 270

Ile Ser Gly Arg Pro His Leu Glu Tyr Lys Ala Glu Phe Thr Tyr Gln
            275                 280                 285

Arg Val Gly Asp Leu Ser Thr Glu Met Ile Glu His Phe Phe Arg Ser
        290                 295                 300

Leu Ser Tyr Thr Met Gly Val Thr Leu His Leu Lys Thr Lys Gly Lys
305                 310                 315                 320

Asn Asp His His Arg Val Glu Ser Leu Phe Lys Ala Phe Gly Arg Thr
                325                 330                 335

Leu Arg Gln Ala Ile Arg Val Glu Gly Asp Thr Leu Pro Ser Ser Lys
                340                 345                 350

Gly Val Leu
        355

<210> SEQ ID NO 94
<211> LENGTH: 332
<212> TYPE: PRT
<213> ORGANISM: Shigella flexneri

<400> SEQUENCE: 94

Met Asn Lys Lys Val Leu Thr Leu Ser Ala Val Met Ala Ser Met Leu
1               5                   10                  15

Phe Gly Ala Ala Ala His Ala Ala Asp Thr Arg Ile Gly Val Thr Ile
                20                  25                  30

Tyr Lys Tyr Asp Asp Asn Phe Met Ser Val Val Arg Lys Ala Ile Glu
            35                  40                  45

Gln Asp Ala Lys Ala Ala Pro Asp Val Gln Leu Leu Met Asn Asp Ser
50                  55                  60

Gln Asn Asp Gln Ser Lys Gln Asn Asp Gln Ile Asp Val Leu Leu Ala
65                  70                  75                  80

Lys Gly Val Lys Ala Leu Ala Ile Asn Leu Val Asp Pro Ala Ala Ala
                85                  90                  95

Gly Thr Val Ile Glu Lys Ala Arg Gly Gln Asn Val Pro Val Val Phe
                100                 105                 110

Phe Asn Lys Glu Pro Ser Arg Lys Ala Leu Asp Ser Tyr Asp Lys Ala
            115                 120                 125

Tyr Tyr Val Gly Thr Asp Ser Lys Glu Ser Gly Ile Ile Gln Gly Asp
130                 135                 140

Leu Ile Ala Lys His Trp Ala Asn Gln Gly Trp Asp Leu Asn Lys
145                 150                 155                 160

Asp Gly Gln Ile Gln Phe Val Leu Leu Lys Gly Glu Pro Gly His Pro
                165                 170                 175

Asp Ala Glu Ala Arg Thr Thr Tyr Val Ile Lys Glu Leu Asn Asp Lys
                180                 185                 190

Gly Ile Lys Thr Glu Gln Leu Gln Leu Asp Thr Ala Met Trp Asp Thr
            195                 200                 205

Ala Gln Ala Lys Asp Lys Met Asp Ala Trp Leu Ser Gly Pro Asn Ala
```

```
              210                 215                 220
Asn Lys Ile Glu Val Val Ile Ala Asn Asn Asp Ala Met Ala Met Gly
225                 230                 235                 240

Ala Val Glu Ala Leu Lys Ala His Asn Lys Ser Ser Ile Pro Val Phe
                245                 250                 255

Gly Val Asp Ala Leu Pro Glu Ala Leu Ala Leu Val Lys Ser Gly Ala
                260                 265                 270

Leu Ala Gly Thr Val Leu Asn Asp Ala Asn Asn Gln Ala Lys Ala Thr
                275                 280                 285

Phe Asp Leu Ala Lys Asn Leu Ala Asp Gly Lys Gly Ala Ala Asp Gly
                290                 295                 300

Thr Asn Trp Lys Ile Asp Asn Lys Val Val Arg Val Pro Tyr Val Gly
305                 310                 315                 320

Val Asp Lys Asp Asn Leu Ala Glu Phe Ser Lys Lys
                325                 330

<210> SEQ ID NO 95
<211> LENGTH: 432
<212> TYPE: PRT
<213> ORGANISM: Shigella flexneri

<400> SEQUENCE: 95

Met Ser Lys Ile Val Lys Ile Ile Gly Arg Glu Ile Ile Asp Ser Arg
1               5                   10                  15

Gly Asn Pro Thr Val Glu Ala Glu Val His Leu Glu Gly Gly Phe Val
                20                  25                  30

Gly Met Ala Ala Ala Pro Ser Gly Ala Ser Thr Gly Ser Arg Glu Ala
                35                  40                  45

Leu Glu Leu Arg Asp Gly Asp Lys Ser Arg Phe Leu Gly Lys Gly Val
            50                  55                  60

Thr Lys Ala Val Ala Ala Val Asn Gly Pro Ile Ala Gln Ala Leu Ile
65              70                  75                  80

Gly Lys Asp Ala Lys Asp Gln Ala Gly Ile Asp Lys Ile Met Ile Asp
                85                  90                  95

Leu Asp Gly Thr Glu Asn Lys Ser Lys Phe Gly Ala Asn Ala Ile Leu
                100                 105                 110

Ala Val Ser Leu Ala Asn Ala Lys Ala Ala Ala Ala Lys Gly Met Pro
                115                 120                 125

Pro Leu Tyr Glu His Ile Ala Glu Leu Asn Gly Thr Pro Gly Lys Tyr
            130                 135                 140

Ser Met Pro Val Pro Met Met Asn Ile Ile Asn Gly Gly Glu His Ala
145                 150                 155                 160

Asp Asn Asn Val Asp Ile Gln Glu Phe Met Ile Gln Pro Val Gly Ala
                165                 170                 175

Lys Thr Val Lys Glu Ala Ile Arg Met Gly Ser Glu Val Phe His His
                180                 185                 190

Leu Ala Lys Val Leu Lys Ala Lys Gly Met Asn Thr Ala Val Gly Asp
            195                 200                 205

Glu Gly Gly Tyr Ala Pro Asn Leu Gly Ser Asn Ala Glu Ala Leu Ala
            210                 215                 220

Val Ile Ala Glu Ala Val Lys Ala Ala Gly Tyr Glu Leu Gly Lys Asp
225                 230                 235                 240

Ile Thr Leu Ala Met Asp Cys Ala Ala Ser Glu Phe Tyr Lys Asp Gly
                245                 250                 255
```

```
Lys Tyr Val Leu Ala Gly Glu Gly Asn Lys Ala Phe Thr Ser Glu Glu
                260                 265                 270

Phe Thr His Phe Leu Glu Glu Leu Thr Lys Gln Tyr Pro Ile Val Ser
            275                 280                 285

Ile Glu Asp Gly Leu Asp Glu Ser Asp Trp Asp Gly Phe Ala Tyr Gln
        290                 295                 300

Thr Lys Val Leu Gly Asp Lys Ile Gln Leu Val Gly Asp Asp Leu Phe
305                 310                 315                 320

Val Thr Asn Thr Lys Ile Leu Lys Glu Gly Ile Glu Lys Gly Ile Ala
                325                 330                 335

Asn Ser Ile Leu Ile Lys Phe Asn Gln Ile Gly Ser Leu Thr Glu Thr
            340                 345                 350

Leu Ala Ala Ile Lys Met Ala Lys Asp Ala Gly Tyr Thr Ala Val Ile
        355                 360                 365

Ser His Arg Ser Gly Glu Thr Glu Asp Ala Thr Ile Ala Asp Leu Ala
370                 375                 380

Val Gly Thr Ala Ala Gly Gln Ile Lys Thr Gly Ser Met Ser Arg Ser
385                 390                 395                 400

Asp Arg Val Ala Lys Tyr Asn Gln Leu Ile Arg Ile Glu Glu Ala Leu
                405                 410                 415

Gly Glu Lys Ala Pro Tyr Asn Gly Arg Lys Glu Ile Lys Gly Gln Ala
            420                 425                 430

<210> SEQ ID NO 96
<211> LENGTH: 663
<212> TYPE: PRT
<213> ORGANISM: Shigella flexneri

<400> SEQUENCE: 96

Met Ser Ser Arg Lys Glu Leu Ala Asn Ala Ile Arg Ala Leu Ser Met
1               5                   10                  15

Asp Ala Val Gln Lys Ala Lys Ser Gly His Pro Gly Ala Pro Met Gly
                20                  25                  30

Met Ala Asp Ile Ala Glu Val Leu Trp Arg Asp Phe Leu Lys His Asn
            35                  40                  45

Pro Gln Asn Pro Ser Trp Ala Asp Arg Asp Arg Phe Val Leu Ser Asn
        50                  55                  60

Gly His Gly Ser Met Leu Ile Tyr Ser Leu Leu His Leu Thr Gly Tyr
65                  70                  75                  80

Asp Leu Pro Met Glu Glu Leu Lys Asn Phe Arg Gln Leu His Ser Lys
                85                  90                  95

Thr Pro Gly His Pro Glu Val Gly Tyr Thr Ala Gly Val Glu Thr Thr
            100                 105                 110

Thr Gly Pro Leu Gly Gln Gly Ile Ala Asn Ala Val Gly Met Ala Ile
        115                 120                 125

Ala Glu Lys Thr Leu Ala Ala Gln Phe Asn Arg Pro Gly His Asp Ile
130                 135                 140

Val Asp His Tyr Thr Tyr Ala Phe Met Gly Asp Gly Cys Met Met Glu
145                 150                 155                 160

Gly Ile Ser His Glu Val Cys Ser Leu Ala Gly Thr Leu Lys Leu Gly
                165                 170                 175

Lys Leu Ile Ala Phe Tyr Asp Asp Asn Gly Ile Ser Ile Asp Gly His
            180                 185                 190

Val Glu Gly Trp Phe Thr Asp Asp Thr Ala Met Arg Phe Glu Ala Tyr
        195                 200                 205
```

```
Gly Trp His Val Ile Arg Asp Ile Asp Gly His Asp Ala Ala Ser Ile
            210                 215                 220

Lys Arg Ala Val Glu Glu Ala Arg Ala Val Thr Asp Lys Pro Ser Leu
225                 230                 235                 240

Leu Met Cys Lys Thr Ile Ile Gly Phe Gly Ser Pro Asn Lys Ala Gly
                245                 250                 255

Thr His Asp Ser His Gly Ala Pro Leu Gly Asp Ala Glu Ile Ala Leu
            260                 265                 270

Thr Arg Glu Gln Leu Gly Trp Lys Tyr Ala Pro Phe Glu Ile Pro Ser
        275                 280                 285

Glu Ile Tyr Ala Gln Trp Asp Ala Lys Glu Ala Gly Ala Lys
        290                 295                 300

Ser Ala Trp Asn Glu Lys Phe Ala Ala Tyr Ala Lys Ala Tyr Pro Gln
305                 310                 315                 320

Glu Ala Ala Glu Phe Thr Arg Arg Met Lys Gly Glu Met Pro Ser Asp
                325                 330                 335

Phe Asp Ala Lys Ala Lys Glu Phe Ile Ala Lys Leu Gln Ala Asn Pro
                340                 345                 350

Ala Lys Ile Ala Ser Arg Lys Ala Ser Gln Asn Ala Ile Glu Ala Phe
                355                 360                 365

Gly Pro Leu Leu Pro Glu Phe Leu Gly Gly Ser Ala Asp Leu Ala Pro
370                 375                 380

Ser Asn Leu Thr Leu Trp Ser Gly Ser Lys Ala Ile Asn Glu Asp Ala
385                 390                 395                 400

Ala Gly Asn Tyr Ile His Tyr Gly Val Arg Glu Phe Gly Met Thr Ala
                405                 410                 415

Ile Ala Asn Gly Ile Ser Leu His Gly Gly Phe Leu Pro Tyr Thr Ser
                420                 425                 430

Thr Phe Leu Met Phe Val Glu Tyr Ala Arg Asn Ala Val Arg Met Ala
                435                 440                 445

Ala Leu Met Lys Gln Arg Gln Val Met Val Tyr Thr His Asp Ser Ile
450                 455                 460

Gly Leu Gly Glu Asp Gly Pro Thr His Gln Pro Val Glu Gln Val Ala
465                 470                 475                 480

Ser Leu Arg Val Thr Pro Asn Met Ser Thr Trp Arg Pro Cys Asp Gln
                485                 490                 495

Val Glu Ser Ala Val Ala Trp Lys Tyr Gly Val Glu Arg Gln Asp Gly
                500                 505                 510

Pro Thr Ala Leu Ile Leu Ser Arg Gln Asn Leu Ala Gln Gln Glu Arg
                515                 520                 525

Thr Glu Glu Gln Leu Ala Asn Ile Ala Arg Gly Gly Tyr Val Leu Lys
        530                 535                 540

Asp Cys Ala Gly Gln Pro Glu Leu Ile Phe Ile Ala Thr Gly Ser Glu
545                 550                 555                 560

Val Glu Leu Ala Val Ala Ala Tyr Glu Lys Leu Thr Ala Glu Gly Val
                565                 570                 575

Lys Ala Arg Val Val Ser Met Pro Ser Thr Asp Ala Phe Asp Lys Gln
                580                 585                 590

Asp Ala Ala Tyr Arg Glu Ser Val Leu Pro Lys Ala Val Thr Ala Arg
            595                 600                 605

Val Ala Val Glu Ala Gly Ile Ala Asp Tyr Trp Tyr Lys Tyr Val Gly
610                 615                 620
```

```
Leu Asn Gly Ala Ile Val Gly Met Thr Thr Phe Gly Glu Ser Ala Pro
625                 630                 635                 640

Ala Glu Leu Leu Phe Glu Glu Phe Gly Phe Thr Val Asp Asn Val Val
            645                 650                 655

Ala Lys Ala Lys Ala Leu Leu
            660

<210> SEQ ID NO 97
<211> LENGTH: 348
<212> TYPE: PRT
<213> ORGANISM: Shigella flexneri

<400> SEQUENCE: 97

Met Glu Phe Phe Lys Lys Thr Ala Leu Ala Ala Leu Val Met Gly Phe
1               5                   10                  15

Ser Gly Ala Ala Leu Ala Leu Pro Asn Ile Thr Ile Leu Ala Thr Gly
            20                  25                  30

Gly Thr Ile Ala Gly Gly Gly Asp Ser Ala Thr Lys Ser Asn Tyr Thr
        35                  40                  45

Ala Gly Lys Val Gly Val Glu Asn Leu Val Asn Ala Val Pro Gln Leu
    50                  55                  60

Lys Asp Ile Ala Asn Val Lys Gly Glu Gln Val Val Asn Ile Gly Ser
65                  70                  75                  80

Gln Asp Met Asn Asp Asn Val Trp Leu Thr Leu Ala Lys Lys Ile Asn
                85                  90                  95

Ala Asp Cys Asp Lys Thr Asp Gly Phe Val Ile Thr His Gly Thr Asp
            100                 105                 110

Thr Met Glu Glu Thr Ala Tyr Phe Leu Asp Leu Thr Val Lys Cys Asp
        115                 120                 125

Lys Pro Val Val Met Val Gly Ala Met Arg Pro Ser Thr Ser Met Ser
    130                 135                 140

Ala Asp Gly Pro Phe Asn Leu Tyr Asn Ala Val Val Thr Ala Ala Asp
145                 150                 155                 160

Lys Ala Ser Ala Asn Arg Gly Val Leu Val Val Met Asn Asp Thr Val
                165                 170                 175

Leu Asp Gly Arg Asp Val Thr Lys Thr Asn Thr Thr Asp Val Ala Thr
            180                 185                 190

Phe Lys Ser Val Asn Tyr Gly Pro Leu Gly Tyr Ile His Asn Gly Lys
        195                 200                 205

Ile Asp Tyr Gln Arg Thr Pro Ala Arg Lys His Thr Ser Asp Thr Pro
    210                 215                 220

Phe Asp Val Ser Lys Leu Asn Glu Leu Pro Lys Val Gly Ile Val Tyr
225                 230                 235                 240

Asn Tyr Ala Asn Ala Ser Asp Leu Pro Ala Lys Ala Leu Val Asp Ala
                245                 250                 255

Gly Tyr Asp Gly Ile Val Ser Ala Gly Val Gly Asn Gly Asn Leu Tyr
            260                 265                 270

Lys Ser Val Phe Asp Thr Leu Ala Thr Ala Ala Lys Asn Gly Thr Ala
        275                 280                 285

Val Val Arg Ser Ser Arg Val Pro Thr Gly Ala Thr Thr Gln Asp Ala
    290                 295                 300

Glu Val Asp Asp Ala Lys Tyr Gly Phe Val Ala Ser Gly Thr Leu Asn
305                 310                 315                 320

Pro Gln Lys Ala Arg Val Leu Leu Gln Leu Ala Leu Thr Gln Thr Lys
                325                 330                 335
```

```
Asp Pro Gln Gln Ile Gln Gln Ile Phe Asn Gln Tyr
            340                 345
```

<210> SEQ ID NO 98
<211> LENGTH: 1171
<212> TYPE: PRT
<213> ORGANISM: Shigella flexneri

<400> SEQUENCE: 98

```
Met Asp Glu Asn Ala Leu Gly Phe Ala Ser Tyr Trp Arg Asn Ser Leu
1               5                   10                  15

Ala Asp Ala Glu Ser Gly Lys Gly Ser Phe Lys Arg Lys Asp Ala Gln
            20                  25                  30

Asn Phe Thr His Trp His Gly Ile Ala Ala Gly Arg Leu Asp Glu Ala
        35                  40                  45

Ile Val Ser Lys Phe Phe Glu Gly Glu Lys Asp Asp Val Glu Thr Val
50                  55                  60

Asp Val Ile Leu Arg Pro Lys Val Tyr Phe Arg Leu Leu Gln His Gly
65                  70                  75                  80

Lys Asp Arg Ser Ala Gly Ala Pro Asp Ile Val Thr Pro Ile Val Thr
                85                  90                  95

Pro Ala Leu Leu Ser Arg Glu Gly Phe Leu Tyr Pro Thr Pro Ala Thr
            100                 105                 110

Ser Ile Pro Arg Asp Leu Leu Glu Pro Leu Pro Lys Gly Ala Phe Ser
        115                 120                 125

Ile Gly Glu Ile Gly Gln Tyr Asp Lys Tyr Lys Thr Thr His Thr Thr
130                 135                 140

Phe Ser Ile Asn Phe Asp Asp Ser Val Asp Lys Thr Ala Glu Thr Asp
145                 150                 155                 160

Glu Glu Arg Glu Ala Arg Tyr Ala Ala Leu Gln Gln Glu Trp Arg Gln
                165                 170                 175

Tyr Leu Tyr Asp Ser Glu Arg Leu Leu Lys Ser Val Ala Gly Asp Trp
            180                 185                 190

Ile Glu Lys Pro Glu Gln Tyr Glu Leu Ala Glu His Gly Tyr Ile Val
        195                 200                 205

Lys Thr Ala Gln Ser Gly Gly Ala Ser Ser His Ile Leu Ser Leu Tyr
210                 215                 220

Asp His Leu Leu Val Cys Asn Lys Asp Val Pro Leu Phe Asn Arg Phe
225                 230                 235                 240

Ala Ser Arg Glu Val His Ala Ala Glu Ser Leu Leu Ala Pro Gly Ala
                245                 250                 255

Lys Phe Ser Asp Arg Leu Gly His Ser Gly Asp Lys Phe Pro Leu Ala
            260                 265                 270

Lys Ala Gln Arg Asp Ala Leu Ser His Phe Leu Asp Ala Arg His Gly
        275                 280                 285

Asp Ile Leu Ala Val Asn Gly Pro Pro Gly Thr Gly Lys Thr Thr Leu
290                 295                 300

Val Leu Ser Ile Ile Ala Thr Gln Trp Ala Arg Ala Ala Leu Glu Lys
305                 310                 315                 320

Ser Glu Pro Pro Val Ile Ala Thr Ser Thr Asn Asn Gln Ala Val
                325                 330                 335

Thr Asn Ile Ile Glu Ala Phe Gly Lys Asp Phe Ser Gln Gly Ser Gly
            340                 345                 350

Ala Met Ala Gly Arg Trp Leu Pro Glu Leu Lys Ser Phe Gly Ala Tyr
```

-continued

```
               355                 360                 365
Phe Pro Ser Ser Arg Lys Ala Glu Ala Ala Lys Lys Tyr Gln Thr
370                 375                 380
Glu Asp Phe Phe Asn Gln Val Glu Ser Lys Glu Tyr Val Glu Asp Ala
385                 390                 395                 400
Leu Leu Phe Tyr Leu Glu Lys Ala Lys Ala Phe Pro Gly Lys Glu
                405                 410                 415
Cys Ser Ser Pro Glu Lys Val Ile Glu Leu Leu His Gly Gln Leu Ala
                420                 425                 430
Ala Lys Ser Glu Gln Leu Ile Arg Leu Asn Ala Thr Trp Gln Thr Leu
                435                 440                 445
Ser Gln Ile Arg Ala Ala Arg Glu Leu Ile Ala Asn Asp Ile Glu Gln
                450                 455                 460
Tyr Leu Asp Asn Leu Asn Lys Leu Leu Ser Gly Gln Glu Gln Lys Val
465                 470                 475                 480
Thr Leu Leu Lys Ser Ala Lys Thr Glu Trp Lys Lys Tyr Arg Ala Gly
                485                 490                 495
Glu Ser Leu Ile Tyr Ser Leu Phe Ser Trp Leu Pro Ala Val Arg Asn
                500                 505                 510
Lys Arg Gln Tyr Gln Ile Gln Leu Phe Leu Glu Asp Lys Leu Gly Ala
                515                 520                 525
Leu Ile Ala Gly Asn Gln Trp Ser Asp Pro Glu Thr Ile Glu Arg Asn
                530                 535                 540
Ile Asp Gly Leu Leu Asn Ser Ala Glu Arg Glu Gln Thr Thr Tyr Arg
545                 550                 555                 560
Gln Gln Ile Asp Ser Ala His Glu Ile Val Leu Lys Glu Gln Gln Ala
                565                 570                 575
Val Gln Glu Trp Gln Arg Leu Ala Phe Asp Leu Gly Tyr Glu Gly Asp
                580                 585                 590
Glu Glu Leu Ser Phe Ser Gln Ala Asp Glu Leu Ala Asp Thr Gln Ile
                595                 600                 605
Arg Phe Pro Ala Phe Leu Leu Thr Thr His Tyr Trp Glu Gly Arg Trp
                610                 615                 620
Leu Met Asp Met Ala Ser Ile Asp Asp Leu Gln Asp Glu Lys Lys Lys
625                 630                 635                 640
Lys Gly Ala Lys Gly Val Thr Ala Arg Trp Gln Arg Arg Met Lys Leu
                645                 650                 655
Thr Pro Cys Val Val Met Thr Cys Tyr Met Leu Pro Gly Asn Met Gln
                660                 665                 670
Ile Ser Glu His Lys Gly Gln Arg Lys Phe Glu Lys Ser Tyr Leu Tyr
                675                 680                 685
Asp Phe Ala Asp Leu Leu Ile Val Asp Glu Ala Gly Gln Val Leu Pro
                690                 695                 700
Glu Val Ala Ala Ser Phe Ala Leu Ala Lys Lys Ala Leu Val Ile
705                 710                 715                 720
Gly Asp Thr Glu Gln Ile Pro Pro Ile Trp Ser Ile Ala Pro Ala Ile
                725                 730                 735
Asp Val Gly Asn Met Leu Ala Glu Lys Ile Leu Ser Gly Ser Thr Gln
                740                 745                 750
Glu Glu Ile Thr Glu Lys Tyr Thr Ala Ile Ala Asp Leu Gly Lys Ser
                755                 760                 765
Ala Ala Ser Gly Ser Val Met Lys Ile Ala Gln Phe Ala Ser Arg Tyr
                770                 775                 780
```

Gln Tyr Asp Pro Glu Leu Ala Arg Gly Met Tyr Leu Tyr Glu His Arg
785                 790                 795                 800

Arg Cys Tyr Asp Asn Ile Ile Gly Tyr Cys Asn Thr Leu Cys Tyr His
            805                 810                 815

Gly Lys Leu Leu Pro Lys Arg Gly Arg Glu Glu Ser Asn Leu Met Pro
            820                 825                 830

Ala Met Gly Tyr Leu His Ile Asp Gly Lys Gly Glu Leu Ala Ser Ser
            835                 840                 845

Gly Ser Arg Tyr Asn Leu Leu Glu Ala Glu Thr Ile Ala Val Trp Leu
            850                 855                 860

Ala Glu Asn Gln Gln Asn Ile Glu Ala His Tyr Gly Lys Ser Leu His
865                 870                 875                 880

Glu Val Val Gly Ile Val Thr Pro Phe Ser Ala Gln Val Ser Thr Ile
                885                 890                 895

Lys Gln Val Leu Gly Lys Gln Asp Ile Ser Thr Gly Thr Asn Glu Lys
                900                 905                 910

Ser Leu Thr Val Gly Thr Val His Ser Leu Gln Gly Ala Glu Arg Ala
            915                 920                 925

Ile Val Ile Phe Ser Pro Val Tyr Ser Lys His Glu Asp Gly Gly Phe
            930                 935                 940

Ile Asp Ser Asp Asn Ser Met Leu Asn Val Ala Val Ser Arg Ala Lys
945                 950                 955                 960

Asp Ser Phe Leu Val Phe Gly Asp Met Asp Leu Phe Glu Val Gln Pro
                965                 970                 975

Ala Ser Ser Pro Arg Gly Leu Leu Ala Lys Tyr Leu Phe Glu Ser Glu
            980                 985                 990

Lys Asn Ala Leu Ser Phe Asp Tyr Lys Glu Arg Lys Asp Leu Lys Thr
            995                 1000                1005

Ala Gly Thr Lys Ile Tyr Thr Leu His Gly Val Glu Gln His Asp Asn
    1010                1015                1020

Phe Leu Asn Gln Thr Phe Glu Asn Thr Ser Lys His Ile Thr Ile Ile
1025                1030                1035                1040

Ser Pro Trp Leu Thr Trp Gln Arg Leu Glu Gln Thr Gly Phe Leu Asp
            1045                1050                1055

Ser Met Ile Ala Ala Cys Ser Arg Gly Ile Asn Val Thr Ile Val Thr
            1060                1065                1070

Asp Arg Ser Tyr Asn Thr Glu His Asn Asp Phe Glu Lys Arg Lys Glu
        1075                1080                1085

Lys Gln Gln Asn Phe Lys Ala Ala Leu Glu Lys Leu Asn Ala Leu Gly
    1090                1095                1100

Ile Ala Thr Lys Leu Val Asn Arg Val His Ser Lys Ile Val Ile Gly
1105                1110                1115                1120

Asp Asp Gly Leu Leu Cys Val Gly Ser Phe Asn Trp Phe Ser Ala Thr
            1125                1130                1135

Arg Glu Ala Arg Tyr Glu Arg Tyr Asp Thr Ser Met Val Tyr Cys Gly
        1140                1145                1150

Asp Asn Leu Lys Gly Glu Ile Glu Ala Ile Tyr Asn Ser Leu Glu Arg
        1155                1160                1165

Arg Gln Val
    1170

<210> SEQ ID NO 99
<211> LENGTH: 294

<212> TYPE: PRT
<213> ORGANISM: Shigella flexneri

<400> SEQUENCE: 99

Met Lys Pro Phe Leu Arg Trp Cys Phe Val Ala Thr Ala Leu Thr Leu
1               5                   10                  15

Ala Gly Cys Ser Asn Thr Ser Trp Arg Lys Ser Glu Val Leu Ala Val
            20                  25                  30

Pro Leu Gln Pro Thr Leu Gln Gln Glu Val Ile Leu Ala Arg Met Glu
        35                  40                  45

Gln Ile Leu Ala Ser Arg Ala Leu Thr Asp Asp Glu Arg Ala Gln Leu
    50                  55                  60

Leu Tyr Glu Arg Gly Val Leu Tyr Asp Ser Leu Gly Leu Arg Ala Leu
65                  70                  75                  80

Ala Arg Asn Asp Phe Ser Gln Ala Leu Ala Ile Arg Pro Asp Met Pro
                85                  90                  95

Glu Val Phe Asn Tyr Leu Gly Ile Tyr Leu Thr Gln Ala Gly Asn Phe
            100                 105                 110

Asp Ala Ala Tyr Glu Ala Phe Asp Ser Val Leu Glu Leu Asp Pro Thr
        115                 120                 125

Tyr Asn Tyr Ala His Leu Asn Arg Gly Ile Ala Leu Tyr Tyr Gly Gly
    130                 135                 140

Arg Asp Lys Leu Ala Gln Asp Leu Leu Ala Phe Tyr Gln Asp Asp
145                 150                 155                 160

Pro Asn Asp Pro Phe Arg Ser Leu Trp Leu Tyr Leu Ala Glu Gln Lys
                165                 170                 175

Leu Asp Glu Lys Gln Ala Lys Glu Val Leu Lys Gln His Phe Glu Lys
            180                 185                 190

Ser Asp Lys Glu Gln Trp Gly Trp Asn Ile Val Glu Phe Tyr Leu Gly
        195                 200                 205

Asn Ile Ser Glu Gln Thr Leu Met Glu Arg Leu Lys Ala Asp Ala Thr
    210                 215                 220

Asp Asn Thr Ser Leu Ala Glu His Leu Ser Glu Thr Asn Phe Tyr Leu
225                 230                 235                 240

Gly Lys Tyr Tyr Leu Ser Leu Gly Asp Leu Asp Ser Ala Thr Ala Leu
                245                 250                 255

Phe Lys Leu Ala Val Ala Asn Asn Val His Asn Phe Val Glu His Arg
            260                 265                 270

Tyr Ala Leu Leu Glu Leu Ser Leu Leu Gly Gln Asp Gln Asp Asp Leu
        275                 280                 285

Ala Glu Ser Asp Gln Gln
    290

<210> SEQ ID NO 100
<211> LENGTH: 1407
<212> TYPE: PRT
<213> ORGANISM: Shigella flexneri

<400> SEQUENCE: 100

Met Lys Asp Leu Leu Lys Phe Leu Lys Ala Gln Thr Lys Thr Glu Glu
1               5                   10                  15

Phe Asp Ala Ile Lys Ile Ala Leu Ala Ser Pro Asp Met Ile Arg Ser
            20                  25                  30

Trp Ser Phe Gly Glu Val Lys Lys Pro Glu Thr Ile Asn Tyr Arg Thr
        35                  40                  45

```
Phe Lys Pro Glu Arg Asp Gly Leu Phe Cys Ala Arg Ile Phe Gly Pro
    50                  55                  60

Val Lys Asp Tyr Glu Cys Leu Cys Gly Lys Tyr Lys Arg Leu Lys His
65                  70                  75                  80

Arg Gly Val Ile Cys Glu Lys Cys Gly Val Glu Val Thr Gln Thr Lys
                85                  90                  95

Val Arg Arg Glu Arg Met Gly His Ile Glu Leu Ala Ser Pro Thr Ala
            100                 105                 110

His Ile Trp Phe Leu Lys Ser Leu Pro Ser Arg Ile Gly Leu Leu Leu
        115                 120                 125

Asp Met Pro Leu Arg Asp Ile Glu Arg Val Leu Tyr Phe Glu Ser Tyr
    130                 135                 140

Val Val Ile Glu Gly Gly Met Thr Asn Leu Glu Arg Gln Gln Ile Leu
145                 150                 155                 160

Thr Glu Glu Gln Tyr Leu Asp Ala Leu Glu Glu Phe Gly Asp Glu Phe
                165                 170                 175

Asp Ala Lys Met Gly Ala Glu Ala Ile Gln Ala Leu Leu Lys Ser Met
            180                 185                 190

Asp Leu Glu Gln Glu Cys Glu Gln Leu Arg Glu Glu Leu Asn Glu Thr
        195                 200                 205

Asn Ser Glu Thr Lys Arg Lys Leu Thr Lys Arg Ile Lys Leu Leu
    210                 215                 220

Glu Ala Phe Val Gln Ser Gly Asn Lys Pro Glu Trp Met Ile Leu Thr
225                 230                 235                 240

Val Leu Pro Val Leu Pro Pro Asp Leu Arg Pro Leu Val Pro Leu Asp
                245                 250                 255

Gly Gly Arg Phe Ala Thr Ser Asp Leu Asn Asp Leu Tyr Arg Arg Val
            260                 265                 270

Ile Asn Arg Asn Asn Arg Leu Lys Arg Leu Leu Asp Leu Ala Ala Pro
        275                 280                 285

Asp Ile Ile Val Arg Asn Glu Lys Arg Met Leu Gln Glu Ala Val Asp
    290                 295                 300

Ala Leu Leu Asp Asn Gly Arg Arg Gly Arg Ala Ile Thr Gly Ser Asn
305                 310                 315                 320

Lys Arg Pro Leu Lys Ser Leu Ala Asp Met Ile Lys Gly Lys Gln Gly
                325                 330                 335

Arg Phe Arg Gln Asn Leu Leu Gly Lys Arg Val Asp Tyr Ser Gly Arg
            340                 345                 350

Ser Val Ile Thr Val Gly Pro Tyr Leu Arg Leu His Gln Cys Gly Leu
        355                 360                 365

Pro Lys Lys Met Ala Leu Glu Leu Phe Lys Pro Phe Ile Tyr Gly Lys
    370                 375                 380

Leu Glu Leu Arg Gly Leu Ala Thr Thr Ile Lys Ala Ala Lys Lys Met
385                 390                 395                 400

Val Glu Arg Glu Glu Ala Val Val Trp Asp Ile Leu Asp Glu Val Ile
                405                 410                 415

Arg Glu His Pro Val Leu Leu Asn Arg Ala Pro Thr Leu His Arg Leu
            420                 425                 430

Gly Ile Gln Ala Phe Glu Pro Val Leu Ile Glu Gly Lys Ala Ile Gln
        435                 440                 445

Leu His Pro Leu Val Cys Ala Ala Tyr Asn Ala Asp Phe Asp Gly Asp
    450                 455                 460

Gln Met Ala Val His Val Pro Leu Thr Leu Glu Ala Gln Leu Glu Ala
```

```
               465                 470                 475                 480
          Arg Ala Leu Met Met Ser Thr Asn Asn Ile Leu Ser Pro Ala Asn Gly
                          485                 490                 495

Glu Pro Ile Ile Val Pro Ser Gln Asp Val Val Leu Gly Leu Tyr Tyr
                          500                 505                 510

Met Thr Arg Asp Cys Val Asn Ala Lys Gly Glu Gly Met Val Leu Thr
                          515                 520                 525

Gly Pro Lys Glu Ala Glu Arg Leu Tyr Arg Ser Gly Leu Ala Ser Leu
                          530                 535                 540

His Ala Arg Val Lys Val Arg Ile Thr Glu Tyr Glu Lys Asp Ala Asn
          545                 550                 555                 560

Gly Glu Leu Val Ala Lys Thr Ser Leu Lys Asp Thr Val Gly Arg
                          565                 570                 575

Ala Ile Leu Trp Met Ile Val Pro Lys Gly Leu Pro Tyr Ser Ile Val
                          580                 585                 590

Asn Gln Ala Leu Gly Lys Lys Ala Ile Ser Lys Met Leu Asn Thr Cys
                          595                 600                 605

Tyr Arg Ile Leu Gly Leu Lys Pro Thr Val Ile Phe Ala Asp Gln Ile
          610                 615                 620

Met Tyr Thr Gly Phe Ala Tyr Ala Ala Arg Ser Gly Ala Ser Val Gly
          625                 630                 635                 640

Ile Asp Asp Met Val Ile Pro Glu Lys Lys His Glu Ile Ile Ser Glu
                          645                 650                 655

Ala Glu Ala Glu Val Ala Glu Ile Gln Glu Gln Phe Gln Ser Gly Leu
                          660                 665                 670

Val Thr Ala Gly Glu Arg Tyr Asn Lys Val Ile Asp Ile Trp Ala Ala
                          675                 680                 685

Ala Asn Asp Arg Val Ser Lys Ala Met Met Asp Asn Leu Gln Thr Glu
                          690                 695                 700

Thr Val Ile Asn Arg Asp Gly Gln Glu Glu Lys Gln Val Ser Phe Asn
          705                 710                 715                 720

Ser Ile Tyr Met Met Ala Asp Ser Gly Ala Arg Gly Ser Ala Ala Gln
                          725                 730                 735

Ile Arg Gln Leu Ala Gly Met Arg Gly Leu Met Ala Lys Pro Asp Gly
                          740                 745                 750

Ser Ile Ile Glu Thr Pro Ile Thr Ala Asn Phe Arg Glu Gly Leu Asn
                          755                 760                 765

Val Leu Gln Tyr Phe Ile Ser Thr His Gly Ala Arg Lys Gly Leu Ala
                          770                 775                 780

Asp Thr Ala Leu Lys Thr Ala Asn Ser Gly Tyr Leu Thr Arg Arg Leu
          785                 790                 795                 800

Val Asp Val Ala Gln Asp Leu Val Val Thr Glu Asp Cys Gly Thr
                          805                 810                 815

His Glu Gly Ile Met Met Thr Pro Val Ile Glu Gly Gly Asp Val Lys
                          820                 825                 830

Glu Pro Leu Arg Asp Arg Val Leu Gly Arg Val Thr Ala Glu Asp Val
                          835                 840                 845

Leu Lys Pro Gly Thr Ala Asp Ile Leu Val Pro Arg Asn Thr Leu Leu
                          850                 855                 860

His Glu Gln Trp Cys Asp Leu Leu Glu Glu Asn Ser Val Asp Ala Val
          865                 870                 875                 880

Lys Val Arg Ser Val Val Ser Cys Asp Thr Asp Phe Gly Val Cys Ala
                          885                 890                 895
```

His Cys Tyr Gly Arg Asp Leu Ala Arg Gly His Ile Ile Asn Lys Gly
                900                 905                 910

Glu Ala Ile Gly Val Ile Ala Ala Gln Ser Ile Gly Glu Pro Gly Thr
            915                 920                 925

Gln Leu Thr Met Arg Thr Phe His Ile Gly Gly Ala Ala Ser Arg Ala
930                 935                 940

Ala Ala Glu Ser Ser Ile Gln Val Lys Asn Lys Gly Ser Ile Lys Leu
945                 950                 955                 960

Ser Asn Val Lys Ser Val Val Asn Ser Ser Gly Lys Leu Val Ile Thr
                965                 970                 975

Ser Arg Asn Thr Glu Leu Lys Leu Ile Asp Glu Phe Gly Arg Thr Lys
            980                 985                 990

Glu Ser Tyr Lys Val Pro Tyr Gly Ala Val Leu Ala Lys Gly Asp Gly
        995                 1000                1005

Glu Gln Val Ala Gly Gly Glu Thr Val Ala Asn Trp Asp Pro His Thr
    1010                1015                1020

Met Pro Val Ile Thr Glu Val Ser Gly Phe Val Arg Phe Thr Asp Met
1025                1030                1035                1040

Ile Asp Gly Gln Thr Ile Thr Arg Gln Thr Asp Glu Leu Thr Gly Leu
                1045                1050                1055

Ser Ser Leu Val Val Leu Asp Ser Ala Glu Arg Thr Ala Gly Gly Lys
                1060                1065                1070

Asp Leu Arg Pro Ala Leu Lys Ile Val Asp Ala Gln Gly Asn Asp Val
            1075                1080                1085

Leu Ile Pro Gly Thr Asp Met Pro Ala Gln Tyr Phe Leu Pro Gly Lys
            1090                1095                1100

Ala Ile Val Gln Leu Glu Asp Gly Val Gln Ile Ser Ser Gly Asp Thr
1105                1110                1115                1120

Leu Ala Arg Ile Pro Gln Glu Ser Gly Gly Thr Lys Asp Ile Thr Gly
                1125                1130                1135

Gly Leu Pro Arg Val Ala Asp Leu Phe Glu Ala Arg Arg Pro Lys Glu
                1140                1145                1150

Pro Ala Ile Leu Ala Glu Ile Ser Gly Ile Val Ser Phe Gly Lys Glu
            1155                1160                1165

Thr Lys Gly Lys Arg Arg Leu Val Ile Thr Pro Val Asp Gly Ser Asp
            1170                1175                1180

Pro Tyr Glu Glu Met Ile Pro Lys Trp Arg Gln Leu Asn Val Phe Glu
1185                1190                1195                1200

Gly Glu Arg Val Glu Arg Gly Asp Val Ile Ser Asp Gly Pro Glu Ala
                1205                1210                1215

Pro His Asp Ile Leu Arg Leu Arg Gly Val His Ala Val Thr Arg Tyr
            1220                1225                1230

Ile Val Asn Glu Val Gln Asp Val Tyr Arg Leu Gln Gly Val Lys Ile
            1235                1240                1245

Asn Asp Lys His Ile Glu Val Ile Val Arg Gln Met Leu Arg Lys Ala
            1250                1255                1260

Thr Ile Val Asn Ala Gly Ser Ser Asp Phe Leu Glu Gly Glu Gln Val
1265                1270                1275                1280

Glu Tyr Ser Arg Val Lys Ile Ala Asn Arg Glu Leu Glu Ala Asn Gly
                1285                1290                1295

Lys Val Gly Ala Thr Tyr Ser Arg Asp Leu Leu Gly Ile Thr Lys Ala
                1300                1305                1310

```
Ser Leu Ala Thr Glu Ser Phe Ile Ser Ala Ala Ser Phe Gln Glu Thr
            1315                1320                1325

Thr Arg Val Leu Thr Glu Ala Ala Val Ala Gly Lys Arg Asp Glu Leu
        1330                1335                1340

Arg Gly Leu Lys Glu Asn Val Ile Val Gly Arg Leu Ile Pro Ala Gly
1345                1350                1355                1360

Thr Gly Tyr Ala Tyr His Gln Asp Arg Met Arg Arg Ala Ala Gly
                1365                1370                1375

Glu Ala Pro Ala Ala Pro Gln Val Thr Ala Glu Asp Ala Ser Ala Ser
            1380                1385                1390

Leu Ala Glu Leu Leu Asn Ala Gly Leu Gly Gly Ser Asp Asn Glu
            1395                1400                1405

<210> SEQ ID NO 101
<211> LENGTH: 1342
<212> TYPE: PRT
<213> ORGANISM: Shigella flexneri

<400> SEQUENCE: 101

Met Val Tyr Ser Tyr Thr Glu Lys Lys Arg Ile Arg Lys Asp Phe Gly
1               5                   10                  15

Lys Arg Pro Gln Val Leu Asp Val Pro Tyr Leu Leu Ser Ile Gln Leu
                20                  25                  30

Asp Ser Phe Gln Lys Phe Ile Glu Gln Asp Pro Glu Gly Gln Tyr Gly
            35                  40                  45

Leu Glu Ala Ala Phe Arg Ser Val Phe Pro Ile Gln Ser Tyr Ser Gly
        50                  55                  60

Asn Ser Glu Leu Gln Tyr Val Ser Tyr Arg Leu Gly Glu Pro Val Phe
65                  70                  75                  80

Asp Val Gln Glu Cys Gln Ile Arg Gly Val Thr Tyr Ser Ala Pro Leu
                85                  90                  95

Arg Val Lys Leu Arg Leu Val Ile Tyr Glu Arg Glu Ala Pro Glu Gly
                100                 105                 110

Thr Val Lys Asp Ile Lys Glu Gln Glu Val Tyr Met Gly Glu Ile Pro
            115                 120                 125

Leu Met Thr Asp Asn Gly Thr Phe Val Ile Asn Gly Thr Glu Arg Val
        130                 135                 140

Ile Val Ser Gln Leu His Arg Ser Pro Gly Val Phe Phe Asp Ser Asp
145                 150                 155                 160

Lys Gly Lys Thr His Ser Ser Gly Lys Val Leu Tyr Asn Ala Arg Ile
                165                 170                 175

Ile Pro Tyr Arg Gly Ser Trp Leu Asp Phe Glu Phe Asp Pro Lys Asp
                180                 185                 190

Asn Leu Phe Val Arg Ile Asp Arg Arg Lys Leu Pro Ala Thr Ile
            195                 200                 205

Ile Leu Arg Ala Leu Asn Tyr Thr Thr Glu Gln Ile Leu Asp Leu Phe
        210                 215                 220

Phe Glu Lys Val Ile Phe Glu Ile Arg Asp Asn Lys Leu Gln Met Glu
225                 230                 235                 240

Leu Val Pro Glu Arg Leu Arg Gly Glu Thr Ala Ser Phe Asp Ile Glu
                245                 250                 255

Ala Asn Gly Lys Val Tyr Val Glu Lys Gly Arg Arg Ile Thr Ala Arg
                260                 265                 270

His Ile Arg Gln Leu Glu Lys Asp Asp Val Lys Leu Ile Glu Val Pro
            275                 280                 285
```

```
Val Glu Tyr Ile Ala Gly Lys Val Ala Lys Asp Tyr Ile Asp Glu
    290                 295                 300

Ser Thr Gly Glu Leu Ile Cys Ala Ala Asn Met Glu Leu Ser Leu Asp
305                 310                 315                 320

Leu Leu Ala Lys Leu Ser Gln Ser Gly His Lys Arg Ile Glu Thr Leu
                325                 330                 335

Phe Thr Asn Asp Leu Asp His Gly Pro Tyr Ile Ser Glu Thr Leu Arg
            340                 345                 350

Val Asp Pro Thr Asn Asp Arg Leu Ser Ala Leu Val Glu Ile Tyr Arg
        355                 360                 365

Met Met Arg Pro Gly Glu Pro Pro Thr Arg Glu Ala Ala Glu Ser Leu
    370                 375                 380

Phe Glu Asn Leu Phe Phe Ser Glu Asp Arg Tyr Asp Leu Ser Ala Val
385                 390                 395                 400

Gly Arg Met Lys Phe Asn Arg Ser Leu Leu Arg Glu Glu Ile Glu Gly
                405                 410                 415

Ser Gly Ile Leu Ser Lys Asp Asp Ile Asp Val Met Lys Lys Leu
            420                 425                 430

Ile Asp Ile Arg Asn Gly Lys Gly Glu Val Asp Ile Asp His Leu
        435                 440                 445

Gly Asn Arg Arg Ile Arg Ser Val Gly Glu Met Ala Glu Asn Gln Phe
    450                 455                 460

Arg Val Gly Leu Val Arg Val Glu Arg Ala Val Lys Glu Arg Leu Ser
465                 470                 475                 480

Leu Gly Asp Leu Asp Thr Leu Met Pro Gln Asp Met Ile Asn Ala Lys
                485                 490                 495

Pro Ile Ser Ala Ala Val Lys Glu Phe Phe Gly Ser Ser Gln Leu Ser
            500                 505                 510

Gln Phe Met Asp Gln Asn Asn Pro Leu Ser Glu Ile Thr His Lys Arg
        515                 520                 525

Arg Ile Ser Ala Leu Gly Pro Gly Gly Leu Thr Arg Glu Arg Ala Gly
    530                 535                 540

Phe Glu Val Arg Asp Val His Pro Thr His Tyr Gly Arg Val Cys Pro
545                 550                 555                 560

Ile Glu Thr Pro Glu Gly Pro Asn Ile Gly Leu Ile Asn Ser Leu Ser
                565                 570                 575

Val Tyr Ala Gln Thr Asn Glu Tyr Gly Phe Leu Glu Thr Pro Tyr Arg
            580                 585                 590

Lys Val Thr Asp Gly Val Val Thr Asp Glu Ile His Tyr Leu Ser Ala
        595                 600                 605

Ile Glu Glu Gly Asn Tyr Val Ile Ala Gln Ala Asn Ser Asn Leu Asp
    610                 615                 620

Glu Glu Gly His Phe Val Glu Asp Leu Val Thr Cys Arg Ser Lys Gly
625                 630                 635                 640

Glu Ser Ser Leu Phe Ser Arg Asp Gln Val Asp Tyr Met Asp Val Ser
                645                 650                 655

Thr Gln Gln Val Val Ser Val Gly Ala Ser Leu Ile Pro Phe Leu Glu
            660                 665                 670

His Asp Asp Ala Asn Arg Ala Leu Met Gly Ala Asn Met Gln Arg Gln
        675                 680                 685

Ala Val Pro Thr Leu Arg Ala Asp Lys Pro Leu Val Gly Thr Gly Met
    690                 695                 700
```

```
Glu Arg Ala Val Ala Val Asp Ser Gly Val Thr Ala Val Ala Lys Arg
705                 710                 715                 720

Gly Gly Val Val Gln Tyr Val Asp Ala Ser Arg Ile Val Ile Lys Val
            725                 730                 735

Asn Glu Asp Glu Met Tyr Pro Gly Glu Ala Gly Ile Asp Ile Tyr Asn
        740                 745                 750

Leu Thr Lys Tyr Thr Arg Ser Asn Gln Asn Thr Cys Ile Asn Gln Met
        755                 760                 765

Pro Cys Val Ser Leu Gly Glu Pro Val Glu Arg Gly Asp Val Leu Ala
    770                 775                 780

Asp Gly Pro Ser Thr Asp Leu Gly Glu Leu Ala Leu Gly Gln Asn Met
785                 790                 795                 800

Arg Val Ala Phe Met Pro Trp Asn Gly Tyr Asn Phe Glu Asp Ser Ile
                805                 810                 815

Leu Val Ser Glu Arg Val Val Gln Glu Asp Arg Phe Thr Thr Ile His
            820                 825                 830

Ile Gln Glu Leu Ala Cys Val Ser Arg Asp Thr Lys Leu Gly Pro Glu
        835                 840                 845

Glu Ile Thr Ala Asp Ile Pro Asn Val Gly Glu Ala Ala Leu Ser Lys
    850                 855                 860

Leu Asp Glu Ser Gly Ile Val Tyr Ile Gly Ala Glu Val Thr Gly Gly
865                 870                 875                 880

Asp Ile Leu Val Gly Lys Val Thr Pro Lys Gly Glu Thr Gln Leu Thr
                885                 890                 895

Pro Glu Glu Lys Leu Leu Arg Ala Ile Phe Gly Glu Lys Ala Ser Asp
            900                 905                 910

Val Lys Asp Ser Ser Leu Arg Val Pro Asn Gly Val Ser Gly Thr Val
        915                 920                 925

Ile Asp Val Gln Val Phe Thr Arg Asp Gly Val Glu Lys Asp Lys Arg
    930                 935                 940

Ala Leu Glu Ile Glu Glu Met Gln Leu Lys Gln Ala Lys Lys Asp Leu
945                 950                 955                 960

Ser Glu Glu Leu Gln Ile Leu Glu Ala Gly Leu Phe Ser Arg Ile Arg
                965                 970                 975

Ala Val Leu Val Ala Gly Gly Val Glu Ala Glu Lys Leu Asp Lys Leu
            980                 985                 990

Pro Arg Asp Arg Trp Leu Glu Leu Gly Leu Thr Asp Glu Glu Lys Gln
        995                 1000                1005

Asn Gln Leu Glu Gln Leu Ala Glu Gln Tyr Asp Glu Leu Lys His Glu
    1010                1015                1020

Phe Glu Lys Lys Leu Glu Ala Lys Arg Arg Lys Ile Thr Gln Gly Asp
1025                1030                1035                1040

Asp Leu Ala Pro Gly Val Leu Lys Ile Val Lys Val Tyr Leu Ala Val
                1045                1050                1055

Lys Arg Arg Ile Gln Pro Gly Asp Lys Met Ala Gly Arg His Gly Asn
            1060                1065                1070

Lys Gly Val Ile Ser Lys Ile Asn Pro Ile Glu Asp Met Pro Tyr Asp
        1075                1080                1085

Glu Asn Gly Thr Pro Val Asp Ile Val Leu Asn Pro Leu Gly Val Pro
    1090                1095                1100

Ser Arg Met Asn Ile Gly Gln Ile Leu Glu Thr His Leu Gly Met Ala
1105                1110                1115                1120

Ala Lys Gly Ile Gly Asp Lys Ile Asn Ala Met Leu Lys Gln Gln Gln
```

```
                    1125                1130                1135
        Glu Val Ala Lys Leu Arg Glu Phe Ile Gln Arg Ala Tyr Asp Leu Gly
                        1140                1145                1150

Ala Asp Val Arg Gln Lys Val Asp Leu Ser Thr Phe Ser Asp Glu Glu
                        1155                1160                1165

Val Met Arg Leu Ala Glu Asn Leu Arg Lys Gly Met Pro Ile Ala Thr
                        1170                1175                1180

Pro Val Phe Asp Gly Ala Lys Glu Ala Glu Ile Lys Glu Leu Leu Lys
        1185                1190                1195                1200

Leu Gly Asp Leu Pro Thr Ser Gly Gln Ile Arg Leu Tyr Asp Gly Arg
                        1205                1210                1215

Thr Gly Glu Gln Phe Glu Arg Pro Val Thr Val Gly Tyr Met Tyr Met
                        1220                1225                1230

Leu Lys Leu Asn His Leu Val Asp Asp Lys Met His Ala Arg Ser Thr
                        1235                1240                1245

Gly Ser Tyr Ser Leu Val Thr Gln Gln Pro Leu Gly Gly Lys Ala Gln
                        1250                1255                1260

Phe Gly Gly Gln Arg Phe Gly Glu Met Glu Val Trp Ala Leu Glu Ala
        1265                1270                1275                1280

Tyr Gly Ala Ala Tyr Thr Leu Gln Glu Met Leu Thr Val Lys Ser Asp
                        1285                1290                1295

Asp Val Asn Gly Arg Thr Lys Met Tyr Lys Asn Ile Val Asp Gly Asn
                        1300                1305                1310

His Gln Met Glu Pro Gly Met Pro Glu Ser Phe Asn Val Leu Leu Lys
                        1315                1320                1325

Glu Ile Arg Ser Leu Gly Ile Asn Ile Glu Leu Glu Asp Glu
                        1330                1335                1340

<210> SEQ ID NO 102
<211> LENGTH: 253
<212> TYPE: PRT
<213> ORGANISM: Shigella flexneri

<400> SEQUENCE: 102

Met Ser Lys Ser Asp Val Phe His Leu Gly Leu Thr Lys Asn Asp Leu
1               5                   10                  15

Gln Gly Ala Thr Leu Ala Ile Val Pro Gly Asp Pro Asp Arg Val Glu
            20                  25                  30

Lys Ile Ala Ala Leu Met Asp Lys Pro Val Lys Leu Ala Ser His Arg
        35                  40                  45

Glu Phe Thr Thr Trp Arg Ala Glu Leu Asp Gly Lys Pro Val Ile Val
    50                  55                  60

Cys Ser Thr Gly Ile Gly Gly Pro Ser Thr Ser Ile Ala Val Glu Glu
65                  70                  75                  80

Leu Ala Gln Leu Gly Ile Arg Thr Phe Leu Arg Ile Gly Thr Thr Gly
                85                  90                  95

Ala Ile Gln Pro His Ile Asn Val Gly Asp Val Leu Val Thr Thr Ala
            100                 105                 110

Ser Val Arg Leu Asp Gly Ala Ser Leu His Phe Ala Pro Leu Glu Phe
        115                 120                 125

Pro Ala Val Ala Asp Phe Glu Cys Thr Thr Ala Leu Val Glu Ala Ala
    130                 135                 140

Lys Ser Ile Gly Ala Thr Thr His Val Gly Val Thr Val Ser Ser Asp
145                 150                 155                 160
```

```
Thr Phe Tyr Pro Gly Gln Glu Arg Tyr Asp Thr Tyr Ser Gly Arg Val
                165                 170                 175

Val Arg His Phe Lys Gly Ser Met Glu Glu Trp Gln Ala Met Gly Val
        180                 185                 190

Met Asn Tyr Glu Met Glu Ser Ala Thr Leu Leu Thr Met Cys Ala Ser
            195                 200                 205

Gln Gly Leu Arg Ala Gly Met Val Ala Gly Val Ile Val Asn Arg Thr
        210                 215                 220

Gln Gln Glu Ile Pro Asn Ala Glu Thr Met Lys Gln Thr Glu Ser His
225                 230                 235                 240

Ala Val Lys Ile Val Val Glu Ala Ala Arg Arg Leu Leu
                245                 250
```

<210> SEQ ID NO 103
<211> LENGTH: 289
<212> TYPE: PRT
<213> ORGANISM: Shigella flexneri

<400> SEQUENCE: 103

```
Met Arg Thr Leu Gln Gly Trp Leu Leu Pro Val Phe Met Leu Pro Met
1               5                   10                  15

Ala Val Tyr Ala Gln Glu Ala Thr Val Lys Glu Val His Asp Ala Pro
            20                  25                  30

Ala Val Arg Gly Ser Ile Ile Ala Asn Met Leu Gln Glu His Asp Asn
        35                  40                  45

Pro Phe Thr Leu Tyr Pro Tyr Asp Thr Asn Tyr Leu Ile Tyr Thr Gln
    50                  55                  60

Thr Ser Asp Leu Asn Lys Glu Ala Ile Ala Ser Tyr Asp Trp Ala Glu
65                  70                  75                  80

Asn Ala Arg Lys Asp Glu Val Lys Phe Gln Leu Ser Leu Ala Phe Pro
                85                  90                  95

Leu Trp Arg Gly Ile Leu Gly Pro Asn Ser Val Leu Gly Ala Ser Tyr
            100                 105                 110

Thr Gln Lys Ser Trp Trp Gln Leu Ser Asn Ser Glu Glu Ser Ser Pro
        115                 120                 125

Phe Arg Glu Thr Asn Tyr Glu Pro Gln Leu Phe Leu Gly Phe Ala Thr
    130                 135                 140

Asp Tyr Arg Phe Ala Gly Trp Thr Leu Arg Asp Val Glu Met Gly Tyr
145                 150                 155                 160

Asn His Asp Ser Asn Gly Arg Ser Asp Pro Thr Ser Arg Ser Trp Asn
                165                 170                 175

Arg Leu Tyr Thr Arg Leu Met Ala Glu Asn Gly Asn Trp Leu Val Glu
            180                 185                 190

Val Lys Pro Trp Tyr Val Val Gly Asn Thr Asp Asn Pro Asp Ile
        195                 200                 205

Thr Lys Tyr Met Gly Tyr Tyr Gln Leu Lys Ile Gly Tyr His Leu Gly
    210                 215                 220

Asp Ala Val Leu Ser Ala Lys Gly Gln Tyr Asn Trp Asn Thr Gly Tyr
225                 230                 235                 240

Gly Gly Ala Glu Leu Gly Leu Ser Tyr Pro Ile Thr Lys His Val Arg
                245                 250                 255

Leu Tyr Thr Gln Val Tyr Ser Gly Tyr Gly Glu Ser Leu Ile Asp Tyr
            260                 265                 270

Asn Phe Asn Gln Thr Arg Val Gly Val Gly Val Met Leu Asn Asp Leu
        275                 280                 285
```

Phe

<210> SEQ ID NO 104
<211> LENGTH: 460
<212> TYPE: PRT
<213> ORGANISM: Shigella flexneri

<400> SEQUENCE: 104

```
Met Ala Thr Gly Lys Ile Val Gln Val Ile Gly Ala Val Val Asp Val
1               5                   10                  15

Glu Phe Pro Gln Asp Ala Val Pro Arg Val Tyr Asp Ala Leu Glu Val
            20                  25                  30

Gln Asn Gly Asn Glu Arg Leu Val Leu Glu Val Gln Gln Gln Leu Gly
        35                  40                  45

Gly Gly Ile Val Arg Thr Ile Ala Met Gly Ser Ser Asp Gly Leu Arg
    50                  55                  60

Arg Gly Leu Asp Val Lys Asp Leu Glu His Pro Ile Glu Val Pro Val
65                  70                  75                  80

Gly Lys Ala Thr Leu Gly Arg Ile Met Asn Val Leu Gly Glu Pro Val
                85                  90                  95

Asp Met Lys Gly Glu Ile Gly Glu Glu Arg Trp Ala Ile His Arg
            100                 105                 110

Ala Ala Pro Ser Tyr Glu Glu Leu Ser Asn Ser Gln Glu Leu Leu Glu
        115                 120                 125

Thr Gly Ile Lys Val Ile Asp Leu Met Cys Pro Phe Ala Lys Gly Gly
    130                 135                 140

Lys Val Gly Leu Phe Gly Gly Ala Gly Val Gly Lys Thr Val Asn Met
145                 150                 155                 160

Met Glu Leu Ile Arg Asn Ile Ala Ile Glu His Ser Gly Tyr Ser Val
                165                 170                 175

Phe Ala Gly Val Gly Glu Arg Thr Arg Glu Gly Asn Asp Phe Tyr His
            180                 185                 190

Glu Met Thr Asp Ser Asn Val Ile Asp Lys Val Ser Leu Val Tyr Gly
        195                 200                 205

Gln Met Asn Glu Pro Pro Gly Asn Arg Leu Arg Val Ala Leu Thr Gly
    210                 215                 220

Leu Thr Met Ala Glu Lys Phe Arg Asp Glu Gly Arg Asp Val Leu Leu
225                 230                 235                 240

Phe Val Asp Asn Ile Tyr Arg Tyr Thr Leu Ala Gly Thr Glu Val Ser
                245                 250                 255

Ala Leu Leu Gly Arg Met Pro Ser Ala Val Gly Tyr Gln Pro Thr Leu
            260                 265                 270

Ala Glu Glu Met Gly Val Leu Gln Glu Arg Ile Thr Ser Thr Lys Thr
        275                 280                 285

Gly Ser Ile Thr Ser Val Gln Ala Val Tyr Val Pro Ala Asp Asp Leu
    290                 295                 300

Thr Asp Pro Ser Pro Ala Thr Thr Phe Ala His Leu Asp Ala Thr Val
305                 310                 315                 320

Val Leu Ser Arg Gln Ile Ala Ser Leu Gly Ile Tyr Pro Ala Val Asp
                325                 330                 335

Pro Leu Asp Ser Thr Ser Arg Gln Leu Asp Pro Leu Val Val Gly Gln
            340                 345                 350

Glu His Tyr Asp Thr Ala Arg Gly Val Gln Ser Ile Leu Gln Arg Tyr
        355                 360                 365
```

```
Gln Glu Leu Lys Asp Ile Ile Ala Ile Leu Gly Met Asp Glu Leu Ser
        370                 375                 380

Glu Glu Asp Lys Leu Val Val Ala Arg Ala Arg Lys Ile Gln Arg Phe
385                 390                 395                 400

Leu Ser Gln Pro Phe Phe Val Ala Glu Val Phe Thr Gly Ser Pro Gly
                405                 410                 415

Lys Tyr Val Ser Leu Lys Asp Thr Ile Arg Gly Phe Lys Gly Ile Met
                420                 425                 430

Glu Gly Glu Tyr Asp His Leu Pro Glu Gln Ala Phe Tyr Met Val Gly
                435                 440                 445

Ser Ile Glu Glu Ala Val Glu Lys Ala Lys Lys Leu
450                 455                 460

<210> SEQ ID NO 105
<211> LENGTH: 731
<212> TYPE: PRT
<213> ORGANISM: Shigella flexneri

<400> SEQUENCE: 105

Met Arg Lys Lys Tyr Met Pro Arg Ala Leu Gly Pro Leu Leu Leu Val
1               5                   10                  15

Val Leu Ser Pro Ala Val Ala Gln Gln Asn Asp Asp Asn Glu Ile Ile
                20                  25                  30

Val Ser Ala Ser Arg Ser Asn Arg Thr Val Ala Glu Met Ala Gln Thr
            35                  40                  45

Thr Trp Val Ile Glu Asn Ala Glu Leu Glu Gln Gln Ile Gln Gly Gly
        50                  55                  60

Lys Glu Leu Lys Asp Ala Leu Ala Gln Leu Ile Pro Gly Leu Asp Val
65                  70                  75                  80

Ser Ser Gln Ser Arg Thr Asn Tyr Gly Met Asn Met Arg Gly Arg Pro
                85                  90                  95

Leu Val Val Leu Ile Asp Gly Val Arg Leu Asn Ser Ser Arg Ser Asp
                100                 105                 110

Ser Arg Gln Leu Asp Ser Val Asp Pro Phe Asn Ile Asp His Ile Glu
            115                 120                 125

Val Ile Ser Gly Ala Thr Ala Leu Tyr Gly Gly Ser Thr Gly Gly
        130                 135                 140

Leu Ile Asn Ile Val Thr Lys Lys Gly Gln Pro Glu Thr Met Met Glu
145                 150                 155                 160

Phe Glu Ala Gly Thr Lys Ser Gly Phe Asn Ser Ser Lys Asp His Asp
                165                 170                 175

Glu Arg Ile Ala Gly Ala Val Ser Gly Gly Asn Asp His Ile Ser Gly
            180                 185                 190

Arg Leu Ser Val Ala Tyr Gln Lys Phe Gly Gly Trp Phe Asp Gly Asn
        195                 200                 205

Gly Asp Ala Thr Leu Leu Asp Asn Thr Gln Thr Gly Leu Gln His Ser
    210                 215                 220

Asn Arg Leu Asp Ile Met Gly Thr Gly Thr Leu Asn Ile Asp Glu Ser
225                 230                 235                 240

Arg Gln Leu Gln Leu Ile Thr Gln Tyr Tyr Lys Ser Gln Gly Asp Asp
                245                 250                 255

Asn Tyr Gly Leu Asn Leu Gly Lys Gly Phe Ser Ala Ile Ser Gly Ser
            260                 265                 270

Ser Thr Pro Tyr Val Ser Lys Gly Leu Asn Ser Asp Arg Ile Pro Gly
```

```
                275                 280                 285
Thr Glu Arg His Leu Ile Ser Leu Gln Tyr Ser Asp Ser Asp Phe Leu
290                 295                 300
Gly Gln Glu Leu Val Gly Gln Val Tyr Tyr Arg Asp Glu Ser Leu Arg
305                 310                 315                 320
Tyr Tyr Pro Phe Pro Thr Val Asn Ala Asn Lys Gln Ala Thr Ala Phe
                325                 330                 335
Ser Ser Ser Gln Gln Asp Thr Asp Gln Tyr Gly Met Lys Leu Thr Leu
            340                 345                 350
Asn Ser Gln Leu Met Asp Gly Trp Gln Ile Thr Trp Gly Leu Asp Ala
                355                 360                 365
Glu His Glu Arg Phe Thr Ser Asn Gln Met Phe Phe Asp Leu Ala Gln
370                 375                 380
Ala Ser Ala Ser Gly Gly Leu Asn Asn His Lys Ile Tyr Thr Thr Gly
385                 390                 395                 400
Arg Tyr Pro Ser Tyr Asp Ile Thr Asn Leu Ala Ala Phe Leu Gln Ser
                405                 410                 415
Ser Tyr Asp Ile Asn Asp Ile Phe Thr Val Ser Gly Gly Val Arg Tyr
            420                 425                 430
Gln Tyr Thr Glu Asn Arg Val Asp Asp Phe Ile Asp Tyr Thr Gln Gln
            435                 440                 445
Gln Lys Ile Ala Thr Gly Lys Ala Ile Ser Ala Asp Ala Ile Pro Gly
450                 455                 460
Gly Ser Val Asp Tyr Asp Asn Phe Leu Phe Asn Ala Gly Leu Leu Met
465                 470                 475                 480
His Ile Thr Glu Arg Gln Gln Ala Trp Phe Asn Phe Ser Gln Gly Val
                485                 490                 495
Ala Leu Pro Asp Pro Gly Lys Tyr Tyr Gly Arg Gly Ile Tyr Gly Ala
                500                 505                 510
Ala Val Asn Gly His Leu Pro Leu Thr Lys Ser Val Asn Val Ser Asp
            515                 520                 525
Ser Lys Leu Glu Gly Val Lys Val Asp Ser Tyr Glu Leu Gly Trp Arg
            530                 535                 540
Phe Ile Gly Asp Asn Leu Arg Thr Gln Ile Ala Ala Tyr Tyr Ser Leu
545                 550                 555                 560
Ser Asn Lys Ser Val Glu Arg Asn Lys Asp Leu Thr Ile Ser Val Lys
                565                 570                 575
Asp Asp Arg Arg Arg Ile Tyr Gly Val Glu Gly Ala Val Asp Tyr Leu
            580                 585                 590
Ile Pro Asp Thr Asp Trp Ser Thr Gly Val Asn Phe Asn Val Leu Lys
            595                 600                 605
Thr Glu Ser Lys Val Asn Gly Gln Trp Gln Lys Tyr Asp Val Lys Glu
            610                 615                 620
Ser Ser Pro Ser Lys Ala Thr Ala Tyr Ile Asn Trp Ala Pro Glu Pro
625                 630                 635                 640
Trp Ser Leu Arg Val Gln Ser Thr Thr Ser Phe Asp Val Ser Asp Ala
                645                 650                 655
Glu Gly Asn Asp Ile Asn Gly Tyr Thr Thr Val Asp Phe Ile Ser Ser
                660                 665                 670
Trp Gln Leu Pro Val Gly Thr Leu Ser Phe Ser Val Glu Asn Leu Phe
            675                 680                 685
Asp Arg Asp Tyr Thr Thr Val Trp Gly Gln Arg Ala Pro Leu Tyr Tyr
            690                 695                 700
```

```
Ser Pro Gly Tyr Gly Pro Ala Ser Leu Tyr Asp Tyr Lys Gly Arg Gly
705                 710                 715                 720

Arg Thr Phe Gly Leu Asn Tyr Ser Val Leu Phe
                725                 730
```

<210> SEQ ID NO 106
<211> LENGTH: 396
<212> TYPE: PRT
<213> ORGANISM: Shigella flexneri

<400> SEQUENCE: 106

```
Met Ile Ile Ser Ala Ala Ser Asp Tyr Arg Ala Ala Gln Arg Ile
1               5                   10                  15

Leu Pro Pro Phe Leu Phe His Tyr Met Asp Gly Gly Ala Tyr Ser Glu
                20                  25                  30

Tyr Thr Leu Arg Arg Asn Val Glu Asp Leu Ser Glu Val Ala Leu Arg
                35                  40                  45

Gln Arg Ile Leu Lys Asn Met Ser Asp Leu Ser Leu Glu Thr Thr Leu
    50                  55                  60

Phe Asn Glu Lys Leu Ser Met Pro Val Ala Leu Ala Pro Val Gly Leu
65                  70                  75                  80

Cys Gly Met Tyr Ala Arg Arg Gly Glu Val Gln Ala Ala Lys Ala Ala
                85                  90                  95

Asp Ala His Gly Ile Pro Phe Thr Leu Ser Thr Val Ser Val Cys Pro
                100                 105                 110

Ile Glu Glu Val Ala Pro Ala Ile Lys Arg Pro Met Trp Phe Gln Leu
                115                 120                 125

Tyr Val Leu Arg Asp Arg Gly Phe Met Arg Asn Ala Leu Glu Arg Ala
                130                 135                 140

Lys Ala Ala Gly Cys Ser Thr Leu Val Phe Thr Val Asp Met Pro Thr
145                 150                 155                 160

Pro Gly Ala Arg Tyr Arg Asp Ala His Ser Gly Met Ser Gly Pro Asn
                165                 170                 175

Ala Ala Met Arg Arg Tyr Leu Gln Ala Val Thr His Pro Gln Trp Ala
                180                 185                 190

Trp Asp Val Gly Leu Asn Gly Arg Pro His Asp Leu Gly Asn Ile Ser
                195                 200                 205

Ala Tyr Leu Gly Lys Pro Thr Gly Leu Glu Asp Tyr Ile Gly Trp Leu
                210                 215                 220

Gly Asn Asn Phe Asp Pro Ser Ile Ser Trp Lys Asp Leu Glu Trp Ile
225                 230                 235                 240

Arg Asp Phe Trp Asp Gly Pro Met Val Ile Lys Gly Ile Leu Asp Pro
                245                 250                 255

Glu Asp Ala Arg Asp Ala Val Arg Phe Gly Ala Asp Gly Ile Val Val
                260                 265                 270

Ser Asn His Gly Gly Arg Gln Leu Asp Gly Val Leu Ser Ser Ala Arg
                275                 280                 285

Ala Leu Pro Ala Ile Ala Asp Ala Val Lys Gly Asp Ile Ala Ile Leu
                290                 295                 300

Ala Asp Ser Gly Ile Arg Asn Gly Leu Asp Val Val Arg Met Ile Ala
305                 310                 315                 320

Leu Gly Ala Asp Thr Val Leu Leu Gly Arg Ala Phe Leu Tyr Ala Leu
                325                 330                 335

Ala Thr Ala Gly Gln Ala Gly Val Ala Asn Leu Leu Asn Leu Ile Glu
```

```
                340                 345                 350
Lys Glu Met Lys Val Ala Met Thr Leu Thr Gly Ala Lys Ser Ile Ser
                355                 360                 365
Glu Ile Thr Gln Asp Ser Leu Val Gln Gly Leu Gly Lys Glu Leu Pro
            370                 375                 380
Thr Ala Leu Ala Pro Met Ala Lys Gly Asn Ala Ala
385                 390                 395

<210> SEQ ID NO 107
<211> LENGTH: 524
<212> TYPE: PRT
<213> ORGANISM: Shigella flexneri

<400> SEQUENCE: 107

Met Leu Ser Thr Leu Arg Arg Thr Leu Phe Ala Leu Leu Ala Cys Ala
1               5                   10                  15
Ser Phe Ile Val His Ala Ala Pro Asp Glu Ile Thr Thr Ala Trp
                20                  25                  30
Pro Val Asn Val Gly Pro Leu Asn Pro His Leu Tyr Thr Pro Asn Gln
            35                  40                  45
Met Phe Ala Gln Ser Met Val Tyr Glu Pro Leu Val Lys Tyr Gln Ala
        50                  55                  60
Asp Gly Ser Val Ile Pro Trp Leu Ala Lys Ser Trp Thr His Ser Glu
65                  70                  75                  80
Asp Gly Lys Thr Trp Thr Phe Thr Leu Arg Asp Asp Val Lys Phe Ser
                85                  90                  95
Asn Gly Glu Pro Phe Asp Ala Glu Ala Ala Glu Asn Phe Arg Ala
                100                 105                 110
Val Leu Asp Asn Arg Gln Arg His Ala Trp Leu Glu Leu Ala Asn Gln
            115                 120                 125
Ile Val Asp Val Lys Ala Leu Asn Lys Thr Glu Leu Gln Ile Thr Leu
        130                 135                 140
Lys Ser Ala Tyr Tyr Pro Phe Leu Gln Glu Leu Ala Leu Pro Arg Pro
145                 150                 155                 160
Phe Arg Phe Ile Ala Pro Ser Gln Phe Lys Asn His Glu Thr Met Asn
                165                 170                 175
Gly Ile Lys Ala Pro Ile Gly Thr Gly Pro Trp Ile Leu Gln Glu Ser
            180                 185                 190
Lys Leu Asn Gln Tyr Asp Val Phe Val Arg Asn Glu Asn Tyr Trp Gly
        195                 200                 205
Glu Lys Pro Ala Ile Lys Lys Ile Thr Phe Asn Val Ile Pro Asp Pro
210                 215                 220
Thr Thr Arg Ala Val Ala Phe Glu Thr Gly Asp Ile Asp Leu Leu Tyr
225                 230                 235                 240
Gly Asn Glu Gly Leu Leu Pro Leu Asp Thr Phe Ala Arg Phe Ser Gln
                245                 250                 255
Asn Pro Ala Tyr His Thr Gln Leu Ser Gln Pro Ile Glu Thr Val Met
            260                 265                 270
Leu Ala Leu Asn Thr Ala Lys Ala Pro Thr Asn Glu Leu Ala Val Arg
        275                 280                 285
Glu Ala Leu Asn Tyr Ala Val Asn Lys Lys Ser Leu Ile Asp Asn Ala
    290                 295                 300
Leu Tyr Gly Thr Gln Gln Val Ala Asp Thr Leu Phe Ala Pro Ser Val
305                 310                 315                 320
```

Pro Tyr Ala Asn Leu Gly Leu Lys Pro Arg Gln Tyr Asp Pro Gln Lys
            325                 330                 335

Ala Lys Glu Leu Leu Glu Lys Ala Gly Trp Thr Leu Pro Ala Gly Lys
        340                 345                 350

Asp Ile Arg Glu Lys Asn Gly Gln Pro Leu Arg Ile Glu Leu Ser Phe
            355                 360                 365

Ile Gly Thr Asp Ala Leu Ser Lys Ser Met Ala Glu Ile Gln Ala
370                 375                 380

Asp Met Arg Gln Ile Gly Ala Asp Val Ser Leu Ile Gly Glu Glu
385                 390                 395                 400

Ser Ser Ile Tyr Ala Arg Gln Arg Asp Gly Arg Phe Gly Met Ile Phe
            405                 410                 415

His Arg Thr Trp Gly Ala Pro Tyr Asp Pro His Ala Phe Leu Ser Ser
            420                 425                 430

Met Arg Val Pro Ser His Ala Asp Phe Gln Ala Gln Gln Gly Leu Ala
        435                 440                 445

Asp Lys Pro Leu Ile Asp Lys Glu Ile Gly Glu Val Leu Ala Thr His
        450                 455                 460

Asp Glu Thr Gln Arg Gln Ala Leu Tyr Arg Asp Ile Leu Thr Arg Leu
465                 470                 475                 480

His Asp Glu Ala Val Tyr Leu Pro Ile Ser Tyr Ile Ser Met Met Val
                485                 490                 495

Val Ser Lys Pro Glu Leu Gly Asn Ile Pro Tyr Ala Pro Ile Ala Thr
        500                 505                 510

Glu Ile Pro Phe Glu Gln Ile Lys Pro Val Lys Pro
        515                 520

<210> SEQ ID NO 108
<211> LENGTH: 492
<212> TYPE: PRT
<213> ORGANISM: Shigella flexneri

<400> SEQUENCE: 108

Met Ala Ala Ser Met Val Leu Val Ser Arg Ala Asp Ala Ala Gly Arg
1               5                   10                  15

Gly Leu Ser Val Leu Met Leu Glu Ala Gln Asp Leu Ala Cys Ala Thr
                20                  25                  30

Ser Ser Ala Ser Ser Lys Leu Ile His Gly Gly Leu Arg Tyr Leu Glu
            35                  40                  45

His Tyr Glu Phe Arg Leu Val Ser Glu Ala Leu Ala Glu Arg Glu Val
        50                  55                  60

Leu Leu Lys Met Ala Pro His Ile Ala Phe Pro Met Arg Phe Arg Leu
65                  70                  75                  80

Pro His Arg Pro His Leu Arg Pro Ala Trp Met Ile Arg Ile Gly Leu
                85                  90                  95

Phe Met Tyr Asp His Leu Gly Lys Arg Thr Ser Leu Pro Gly Ser Thr
            100                 105                 110

Gly Leu Arg Phe Gly Ala Asn Ser Val Leu Lys Pro Glu Ile Lys Arg
        115                 120                 125

Gly Phe Glu Tyr Ser Asp Cys Trp Val Asp Ala Arg Leu Val Leu
    130                 135                 140

Ala Asn Ala Gln Met Val Val Arg Lys Gly Gly Glu Val Leu Thr Arg
145                 150                 155                 160

Thr Arg Ala Thr Ser Ala Arg Arg Glu Asn Gly Leu Trp Ile Val Glu
                165                 170                 175

```
Ala Glu Asp Ile Asp Thr Gly Lys Lys Tyr Ser Trp Gln Ala Arg Gly
            180                 185                 190

Leu Val Asn Ala Thr Gly Pro Trp Val Lys Gln Phe Phe Asp Glu Gly
            195                 200                 205

Met His Leu Pro Ser Pro Tyr Gly Ile Arg Leu Ile Lys Gly Ser His
            210                 215                 220

Ile Val Val Pro Arg Val His Thr Gln Lys Gln Ala Tyr Ile Leu Gln
225                 230                 235                 240

Asn Glu Asp Lys Arg Ile Val Phe Val Ile Pro Trp Met Asp Glu Phe
                245                 250                 255

Ser Ile Ile Gly Thr Thr Asp Val Glu Tyr Lys Gly Asp Pro Lys Ala
            260                 265                 270

Val Lys Ile Glu Glu Ser Glu Ile Asn Tyr Leu Leu Lys Val Tyr Asn
            275                 280                 285

Ala His Phe Lys Lys Gln Leu Ser Arg Asp Asp Ile Val Trp Thr Tyr
            290                 295                 300

Ser Gly Val Arg Pro Leu Cys Asp Asp Glu Ser Asp Ser Pro Gln Ala
305                 310                 315                 320

Ile Thr Arg Asp Tyr Thr Leu Asp Ile His Asp Glu Asn Gly Lys Ala
                325                 330                 335

Pro Leu Leu Ser Val Phe Gly Gly Lys Leu Thr Thr Tyr Arg Lys Leu
            340                 345                 350

Ala Glu His Ala Leu Glu Lys Leu Thr Pro Tyr Tyr Gln Gly Ile Gly
            355                 360                 365

Pro Ala Trp Thr Lys Glu Ser Val Leu Pro Gly Gly Ala Ile Glu Gly
            370                 375                 380

Asp Arg Asp Asp Tyr Ala Ala Arg Leu Arg Arg Tyr Pro Phe Leu
385                 390                 395                 400

Thr Glu Ser Leu Ala Arg His Tyr Thr Arg Thr Tyr Gly Ser Asn Ser
                405                 410                 415

Glu Leu Leu Leu Gly Asn Ala Gly Thr Val Ser Asp Leu Gly Glu Asp
            420                 425                 430

Phe Gly His Glu Phe Tyr Glu Ala Glu Leu Lys Tyr Leu Val Asp His
            435                 440                 445

Glu Trp Val Arg Arg Thr Asp Asp Ala Leu Trp Arg Arg Thr Lys Gln
            450                 455                 460

Gly Met Trp Leu Asn Ala Asp Gln Gln Ser Arg Val Ser Gln Trp Leu
465                 470                 475                 480

Val Glu Tyr Thr Gln Gln Lys Leu Ser Leu Ala Ser
                485                 490

<210> SEQ ID NO 109
<211> LENGTH: 329
<212> TYPE: PRT
<213> ORGANISM: Shigella flexneri

<400> SEQUENCE: 109

Met Gln Gly Ser Val Thr Glu Phe Leu Lys Pro Arg Leu Val Asp Ile
1               5                   10                  15

Glu Gln Val Ser Ser Thr His Ala Lys Val Thr Leu Glu Pro Leu Glu
                20                  25                  30

Arg Gly Phe Gly His Thr Leu Gly Asn Ala Leu Arg Arg Ile Leu Leu
            35                  40                  45

Ser Ser Met Pro Gly Cys Ala Val Thr Glu Val Glu Ile Asp Gly Val
```

```
            50                  55                  60
Leu His Glu Tyr Ser Thr Lys Glu Gly Val Gln Glu Asp Ile Leu Glu
 65                  70                  75                  80

Ile Leu Leu Asn Leu Lys Gly Leu Ala Val Arg Val Gln Gly Lys Asp
                 85                  90                  95

Glu Val Ile Leu Thr Leu Asn Lys Ser Gly Ile Gly Pro Val Thr Ala
            100                 105                 110

Ala Asp Ile Thr His Asp Gly Asp Val Glu Ile Val Lys Pro Gln His
        115                 120                 125

Val Ile Cys His Leu Thr Asp Glu Asn Ala Ser Ile Ser Met Arg Ile
    130                 135                 140

Lys Val Gln Arg Gly Arg Gly Tyr Val Pro Ala Ser Thr Arg Ile His
145                 150                 155                 160

Ser Glu Glu Asp Glu Arg Pro Ile Gly Arg Leu Leu Val Asp Ala Cys
                165                 170                 175

Tyr Ser Pro Val Glu Arg Ile Ala Tyr Asn Val Glu Ala Ala Arg Val
            180                 185                 190

Glu Gln Arg Thr Asp Leu Asp Lys Leu Val Ile Glu Met Glu Thr Asn
        195                 200                 205

Gly Thr Ile Asp Pro Glu Glu Ala Ile Arg Arg Ala Thr Ile Leu
    210                 215                 220

Ala Glu Gln Leu Glu Ala Phe Val Asp Leu Arg Asp Val Arg Gln Pro
225                 230                 235                 240

Glu Val Lys Glu Glu Lys Pro Glu Phe Asp Pro Ile Leu Leu Arg Pro
                245                 250                 255

Val Asp Asp Leu Glu Leu Thr Val Arg Ser Ala Asn Cys Leu Lys Ala
            260                 265                 270

Glu Ala Ile His Tyr Ile Gly Asp Leu Val Gln Arg Thr Glu Val Glu
        275                 280                 285

Leu Leu Lys Thr Pro Asn Leu Gly Lys Lys Ser Leu Thr Glu Ile Lys
    290                 295                 300

Asp Val Leu Ala Ser Arg Gly Leu Ser Leu Gly Met Arg Leu Glu Asn
305                 310                 315                 320

Trp Pro Pro Ala Ser Ile Ala Asp Glu
                325

<210> SEQ ID NO 110
<211> LENGTH: 102
<212> TYPE: PRT
<213> ORGANISM: Shigella flexneri

<400> SEQUENCE: 110

Met Ala Lys Gly Gln Ser Leu Gln Asp Pro Phe Leu Asn Ala Leu Arg
 1               5                  10                  15

Arg Glu Arg Val Pro Val Ser Ile Tyr Leu Val Asn Gly Ile Lys Leu
                20                  25                  30

Gln Gly Gln Ile Glu Ser Phe Asp Gln Phe Val Ile Leu Leu Lys Asn
            35                  40                  45

Thr Val Ser Gln Met Val Tyr Lys His Ala Ile Ser Thr Val Val Pro
        50                  55                  60

Ser Arg Pro Val Ser His His Ser Asn Asn Ala Gly Gly Gly Thr Ser
 65                  70                  75                  80

Ser Asn Tyr His His Gly Ser Ser Ala Gln Asn Thr Ser Ala Gln Gln
                 85                  90                  95
```

```
Asp Ser Glu Glu Thr Glu
            100

<210> SEQ ID NO 111
<211> LENGTH: 379
<212> TYPE: PRT
<213> ORGANISM: Shigella flexneri

<400> SEQUENCE: 111

Met Lys Lys Asn Ile Phe Lys Phe Ser Val Leu Thr Leu Ala Val Leu
1               5                   10                  15

Ser Leu Thr Ala Cys Thr Leu Val Pro Gly Gln Asn Leu Ser Thr Ser
            20                  25                  30

Asn Lys Asp Val Ile Glu Leu Pro Asp Asn Gln Tyr Asp Leu Asp Lys
        35                  40                  45

Met Val Asn Ile Tyr Pro Val Thr Pro Gly Leu Ile Asp Gln Leu Arg
    50                  55                  60

Ala Lys Pro Ile Met Ser Gln Ala Asn Pro Glu Leu Glu Gln Gln Ile
65                  70                  75                  80

Ala Asn Tyr Glu Tyr Arg Ile Gly Ile Gly Asp Val Leu Met Val Thr
                85                  90                  95

Val Trp Asp His Pro Glu Leu Thr Thr Pro Ala Gly Gln Tyr Arg Ser
            100                 105                 110

Ala Ser Asp Thr Gly Asn Trp Val Asn Ala Asp Gly Ala Ile Phe Tyr
        115                 120                 125

Pro Tyr Ile Gly Arg Leu Lys Val Ala Gly Lys Thr Leu Thr Gln Val
    130                 135                 140

Arg Asn Glu Ile Thr Ala Arg Leu Asp Ser Val Ile Glu Ser Pro Gln
145                 150                 155                 160

Val Asp Val Ser Val Ala Ala Phe Arg Ser Gln Lys Ala Tyr Val Thr
                165                 170                 175

Gly Glu Val Ser Lys Ser Gly Gln Gln Pro Ile Thr Asn Ile Pro Leu
            180                 185                 190

Thr Ile Met Asp Ala Ile Asn Ala Ala Gly Gly Leu Thr Ala Asp Ala
        195                 200                 205

Asp Trp Arg Asn Val Val Leu Thr Gln Asn Gly Val Lys Thr Lys Val
    210                 215                 220

Asn Leu Tyr Ala Leu Met Gln Arg Gly Asp Leu Arg Gln Asn Lys Leu
225                 230                 235                 240

Leu His Pro Gly Asp Ile Leu Phe Ile Pro Arg Asn Asp Asp Leu Lys
                245                 250                 255

Val Phe Val Met Gly Glu Val Gly Lys Gln Ser Thr Leu Lys Met Asp
            260                 265                 270

Arg Ser Gly Met Thr Leu Ala Glu Ala Leu Gly Asn Ala Glu Gly Met
        275                 280                 285

Asn Gln Asp Val Ala Asp Ala Thr Gly Ile Phe Val Ile Arg Ala Thr
    290                 295                 300

Gln Asn Lys Gln Asn Gly Lys Ile Ala Asn Ile Tyr Gln Leu Asn Ala
305                 310                 315                 320

Lys Asp Ala Ser Ala Met Ile Leu Gly Thr Glu Phe Gln Leu Glu Pro
                325                 330                 335

Tyr Asp Ile Val Tyr Val Thr Thr Ala Pro Leu Ala Arg Trp Asn Arg
            340                 345                 350

Val Ile Ser Leu Leu Val Pro Thr Ile Ser Gly Val His Asp Leu Thr
        355                 360                 365
```

Glu Thr Ser Arg Trp Ile Gln Thr Trp Pro Asn
    370                 375

<210> SEQ ID NO 112
<211> LENGTH: 445
<212> TYPE: PRT
<213> ORGANISM: Shigella flexneri

<400> SEQUENCE: 112

Met Ile Thr Leu Arg Lys Leu Pro Leu Ala Val Ala Val Ala Ala Gly
1               5                   10                  15

Val Met Ser Ala Gln Ala Met Ala Val Asp Phe His Gly Tyr Ala Arg
            20                  25                  30

Ser Gly Ile Gly Trp Thr Gly Ser Gly Gly Glu Gln Gln Cys Phe Gln
        35                  40                  45

Thr Thr Gly Ala Gln Ser Lys Tyr Arg Leu Gly Asn Glu Cys Glu Thr
    50                  55                  60

Tyr Ala Glu Leu Lys Leu Gly Gln Glu Val Trp Lys Glu Gly Asp Lys
65                  70                  75                  80

Ser Phe Tyr Phe Asp Thr Asn Val Ala Tyr Ser Val Ala Gln Gln Asn
                85                  90                  95

Asp Trp Glu Ala Thr Asp Pro Ala Phe Arg Glu Ala Asn Val Gln Gly
            100                 105                 110

Lys Asn Leu Ile Glu Trp Leu Pro Gly Ser Thr Ile Trp Ala Gly Lys
        115                 120                 125

Arg Phe Tyr Gln Arg His Asp Val His Met Ile Asp Phe Tyr Tyr Trp
    130                 135                 140

Asp Ile Ser Gly Pro Gly Ala Gly Leu Glu Asn Ile Asp Val Gly Phe
145                 150                 155                 160

Gly Lys Leu Ser Leu Ala Ala Thr Arg Ser Ser Glu Ala Gly Gly Ser
                165                 170                 175

Ser Ser Phe Ala Ser Asn Asn Ile Tyr Asp Tyr Thr Asn Glu Thr Ala
            180                 185                 190

Asn Asp Val Phe Asp Val Arg Leu Ala Gln Met Glu Ile Asn Pro Gly
        195                 200                 205

Gly Thr Leu Glu Leu Gly Val Asp Tyr Gly Arg Ala Asn Leu Arg Asp
    210                 215                 220

Asn Tyr Arg Leu Val Asp Gly Ala Ser Lys Asp Gly Trp Leu Phe Thr
225                 230                 235                 240

Ala Glu His Thr Gln Ser Val Leu Lys Gly Phe Asn Lys Phe Val Val
                245                 250                 255

Gln Tyr Ala Thr Asp Ser Met Thr Ser Gln Gly Lys Gly Leu Ser Gln
            260                 265                 270

Gly Ser Gly Val Ala Phe Asp Asn Glu Lys Phe Ala Tyr Asn Ile Asn
        275                 280                 285

Asn Asn Gly His Met Leu Arg Ile Leu Asp His Gly Ala Ile Ser Met
    290                 295                 300

Gly Asp Asn Trp Asp Met Met Tyr Val Gly Met Tyr Gln Asp Ile Asn
305                 310                 315                 320

Trp Asp Asn Asp Asn Gly Thr Lys Trp Trp Thr Val Gly Ile Arg Pro
                325                 330                 335

Met Tyr Lys Trp Thr Pro Ile Met Ser Thr Val Met Glu Ile Gly Tyr
            340                 345                 350

Asp Asn Val Glu Ser Gln Arg Thr Gly Asp Lys Asn Asn Gln Tyr Lys

|  |  |  |  | 355 |  |  |  |  | 360 |  |  |  |  | 365 |  |

Ile Thr Leu Ala Gln Gln Trp Gln Ala Gly Asp Ser Ile Trp Ser Arg
    370                 375                 380

Pro Ala Ile Arg Val Phe Ala Thr Tyr Ala Lys Trp Asp Glu Lys Trp
385                 390                 395                 400

Gly Tyr Asp Tyr Asn Gly Asp Ser Lys Val Asn Pro Asn Tyr Gly Lys
                405                 410                 415

Ala Val Pro Ala Asp Phe Asn Gly Gly Ser Phe Gly Arg Gly Asp Ser
            420                 425                 430

Asp Glu Trp Thr Phe Gly Ala Gln Met Glu Ile Trp Trp
            435                 440                 445

<210> SEQ ID NO 113
<211> LENGTH: 1262
<212> TYPE: PRT
<213> ORGANISM: Shigella flexneri

<400> SEQUENCE: 113

Met Ala Asp Phe Ser Ser Ala Thr Ile Thr Thr Gly Ser Leu Pro Pro
1               5                   10                  15

Gly Asp His Thr Leu Tyr Ser Pro Gln Tyr Val Val Thr Ala Lys His
            20                  25                  30

Val Ser Gly Ser Asp Thr Met Ser Phe Gly Tyr Ala Lys Asn Thr Tyr
        35                  40                  45

Thr Ala Val Gly Thr Asn Asn Asn Ser Gly Leu Asp Ile Lys Thr Arg
    50                  55                  60

Arg Leu Ser Lys Leu Val Thr Glu Val Ala Pro Ala Glu Val Ser Asp
65                  70                  75                  80

Ile Gly Ala Val Ser Gly Ala Tyr Gln Ala Gly Gly Arg Phe Thr Glu
                85                  90                  95

Phe Tyr Arg Leu Gly Gly Gly Met Gln Tyr Val Lys Asp Lys Asn Gly
            100                 105                 110

Asn Arg Thr Gln Val Tyr Thr Asn Gly Gly Phe Leu Val Gly Gly Thr
        115                 120                 125

Val Ser Ala Leu Asn Ser Tyr Asn Asn Gly Gln Met Ile Thr Ala Gln
    130                 135                 140

Thr Gly Asp Ile Phe Asn Pro Ala Asn Gly Pro Leu Ala Asn Tyr Leu
145                 150                 155                 160

Asn Met Gly Asp Ser Gly Ser Pro Leu Phe Ala Tyr Asp Ser Leu Gln
                165                 170                 175

Lys Lys Trp Val Leu Ile Gly Val Leu Ser Ser Gly Thr Asn Tyr Gly
            180                 185                 190

Asn Asn Trp Val Val Thr Thr Gln Asp Phe Leu Gly Gln Gln Pro Gln
        195                 200                 205

Asn Asp Phe Asp Lys Thr Ile Ala Tyr Thr Ser Gly Glu Gly Val Leu
    210                 215                 220

Gln Trp Lys Tyr Asp Ala Ala Asn Gly Thr Gly Thr Leu Thr Gln Gly
225                 230                 235                 240

Asn Thr Thr Trp Asp Met His Gly Lys Lys Gly Asn Asp Leu Asn Ala
                245                 250                 255

Gly Lys Asn Leu Leu Phe Thr Gly Asn Asn Gly Glu Val Val Leu Gln
            260                 265                 270

Asn Ser Val Asn Gln Gly Ala Gly Tyr Leu Gln Phe Ala Gly Asp Tyr
        275                 280                 285

```
Arg Val Ser Ala Leu Asn Gly Gln Thr Trp Met Gly Gly Ile Ile
    290                 295                 300
Thr Asp Lys Gly Thr His Val Leu Trp Gln Val Asn Gly Val Ala Gly
305                 310                 315                 320
Asp Asn Leu His Lys Thr Gly Glu Gly Thr Leu Thr Val Asn Gly Thr
                    325                 330                 335
Gly Val Asn Ala Gly Gly Leu Lys Val Gly Asp Gly Thr Val Ile Leu
                340                 345                 350
Asn Gln Gln Ala Asp Ala Asp Gly Lys Val Gln Ala Phe Ser Ser Val
                355                 360                 365
Gly Ile Ala Ser Gly Arg Pro Thr Val Val Leu Ser Asp Ser Gln Gln
370                 375                 380
Val Asn Pro Asp Asn Ile Ser Trp Gly Tyr Arg Gly Arg Leu Glu
385                 390                 395                 400
Leu Asn Gly Asn Asn Leu Thr Phe Thr Arg Leu Gln Ala Ala Asp Tyr
                    405                 410                 415
Gly Ala Ile Ile Thr Asn Asn Ser Glu Lys Lys Ser Thr Val Thr Leu
                420                 425                 430
Asp Leu Gln Thr Leu Lys Ala Ser Asp Ile Asn Val Pro Val Asn Thr
                435                 440                 445
Val Ser Ile Phe Gly Gly Arg Gly Ala Pro Gly Asp Leu Tyr Tyr Asp
450                 455                 460
Ser Ser Thr Lys Gln Tyr Phe Ile Leu Lys Ala Ser Ser Tyr Ser Pro
465                 470                 475                 480
Phe Phe Ser Asp Leu Asn Asn Ser Ser Val Trp Gln Asn Val Gly Lys
                    485                 490                 495
Asp His Asn Lys Ala Ile Asp Thr Val Lys Gln Gln Lys Ile Glu Ala
                500                 505                 510
Ser Ser Gln Pro Tyr Met Tyr His Gly Gln Leu Asn Gly Asn Met Asp
            515                 520                 525
Val Asn Ile Pro Gln Leu Ser Gly Lys Asp Val Leu Ala Leu Asp Gly
            530                 535                 540
Ser Val Asn Leu Pro Glu Gly Ser Ile Thr Lys Lys Ser Gly Thr Leu
545                 550                 555                 560
Ile Phe Gln Gly His Pro Val Ile His Ala Gly Thr Thr Ser Ser
                565                 570                 575
Ser Gln Ser Asp Trp Glu Thr Arg Gln Phe Thr Leu Glu Lys Leu Lys
            580                 585                 590
Leu Asp Ala Ala Thr Phe His Leu Ser Arg Asn Gly Lys Met Gln Gly
            595                 600                 605
Asp Ile Asn Ala Thr Asn Gly Ser Thr Val Ile Leu Gly Ser Ser Arg
            610                 615                 620
Val Phe Thr Asp Arg Ser Asp Gly Thr Gly Asn Ala Val Ser Ser Val
625                 630                 635                 640
Glu Gly Ser Ala Thr Ala Thr Val Gly Asp Gln Ser Asp Tyr Ser
                645                 650                 655
Gly Asn Val Thr Leu Glu Asn Lys Ser Ser Leu Gln Ile Met Glu Arg
                660                 665                 670
Phe Thr Gly Gly Ile Glu Ala Tyr Asp Ser Val Ser Val Thr Ser
                675                 680                 685
Gln Asn Ala Val Phe Asp Arg Val Gly Ser Phe Val Asn Ser Ser Leu
            690                 695                 700
Thr Leu Gly Lys Gly Ala Lys Leu Thr Ala Gln Ser Gly Ile Phe Ser
```

-continued

```
      705                 710                 715                 720
Thr Gly Ala Val Asp Val Lys Glu Asn Ala Ser Leu Thr Leu Thr Gly
                    725                 730                 735
Met Pro Ser Ala Gln Lys Gln Gly Tyr Tyr Ser Pro Val Ile Ser Thr
                740                 745                 750
Thr Glu Gly Ile Asn Leu Glu Asp Asn Ala Ser Phe Ser Val Lys Asn
            755                 760                 765
Met Gly Tyr Leu Ser Ser Asp Ile His Ala Gly Thr Thr Ala Ala Thr
        770                 775                 780
Ile Asn Leu Gly Asp Ser Asp Ala Asp Ala Gly Lys Thr Asp Ser Pro
785                 790                 795                 800
Leu Phe Ser Ser Leu Met Lys Gly Tyr Asn Ala Val Leu Arg Gly Ser
                805                 810                 815
Ile Thr Gly Ala Gln Ser Thr Val Asn Met Ile Asn Ala Leu Trp Tyr
                820                 825                 830
Ser Asp Gly Lys Ser Glu Ala Gly Ala Leu Lys Ala Lys Gly Ser Arg
            835                 840                 845
Ile Glu Leu Gly Asp Gly Lys His Phe Ala Thr Leu Gln Val Lys Glu
        850                 855                 860
Leu Ser Ala Asp Asn Thr Thr Phe Leu Met His Thr Asn Asn Ser Arg
865                 870                 875                 880
Ala Asp Gln Leu Asn Val Thr Asp Lys Leu Ser Gly Ser Asn Asn Ser
                885                 890                 895
Val Leu Val Asp Phe Leu Asn Lys Pro Ala Ser Glu Met Ser Val Thr
                900                 905                 910
Leu Ile Thr Ala Pro Lys Gly Ser Asp Glu Lys Thr Phe Thr Ala Gly
            915                 920                 925
Thr Gln Gln Ile Gly Phe Ser Asn Val Thr Pro Val Ile Ser Thr Glu
        930                 935                 940
Lys Thr Asp Asp Ala Thr Lys Trp Val Leu Thr Gly Tyr Gln Thr Thr
945                 950                 955                 960
Ala Asp Ala Gly Ala Ser Lys Ala Ala Lys Asp Phe Met Ala Ser Gly
                965                 970                 975
Tyr Lys Ser Phe Leu Thr Glu Val Asn Asn Leu Asn Lys Arg Met Gly
                980                 985                 990
Asp Leu Arg Asp Thr Gln Gly Asp Ala Gly Val Trp Ala Arg Ile Met
            995                 1000                1005
Asn Gly Thr Gly Ser Ala Asp Gly Asp Tyr Ser Asp Asn Tyr Thr His
        1010                1015                1020
Val Gln Ile Gly Val Asp Arg Lys His Glu Leu Asp Gly Val Asp Leu
1025                1030                1035                1040
Phe Thr Gly Ala Leu Leu Thr Tyr Thr Asp Ser Asn Ala Ser Ser His
                1045                1050                1055
Ala Phe Ser Gly Lys Asn Lys Ser Val Gly Gly Gly Leu Tyr Ala Ser
                1060                1065                1070
Ala Leu Phe Asn Ser Gly Ala Tyr Phe Asp Leu Ile Gly Lys Tyr Leu
            1075                1080                1085
His His Asp Asn Gln His Thr Ala Asn Phe Ala Ser Leu Gly Thr Lys
        1090                1095                1100
Asp Tyr Ser Ser His Ser Trp Tyr Ala Gly Ala Glu Val Gly Tyr Arg
1105                1110                1115                1120
Tyr His Leu Thr Lys Glu Ser Trp Val Glu Pro Gln Ile Glu Leu Val
                1125                1130                1135
```

Tyr Gly Ser Val Ser Gly Lys Ala Phe Ser Trp Glu Asp Arg Gly Met
            1140                1145                1150

Ala Leu Ser Met Lys Asp Lys Asp Tyr Asn Pro Leu Ile Gly Arg Thr
            1155                1160                1165

Gly Val Asp Val Gly Arg Ala Phe Ser Gly Asp Trp Lys Ile Thr
    1170                1175                1180

Ala Arg Ala Gly Leu Gly Tyr Gln Phe Asp Leu Leu Ala Asn Gly Glu
1185                1190                1195                1200

Thr Val Leu Gln Asp Ala Ser Gly Glu Lys Arg Phe Glu Gly Glu Lys
            1205                1210                1215

Asp Ser Arg Met Leu Met Thr Val Gly Met Asn Ala Glu Ile Lys Asp
            1220                1225                1230

Asn Met Arg Leu Gly Leu Glu Leu Glu Lys Ser Ala Phe Gly Lys Tyr
            1235                1240                1245

Asn Val Asp Asn Ala Ile Asn Ala Asn Phe Arg Tyr Val Phe
    1250                1255                1260

<210> SEQ ID NO 114
<211> LENGTH: 887
<212> TYPE: PRT
<213> ORGANISM: Shigella sonnei

<400> SEQUENCE: 114

Met Ser Glu Arg Phe Pro Asn Asp Val Asp Pro Ile Glu Thr Arg Asp
1               5                   10                  15

Trp Leu Gln Ala Ile Glu Ser Val Ile Arg Glu Glu Gly Val Glu Arg
            20                  25                  30

Ala Gln Tyr Leu Ile Asp Gln Leu Leu Ala Glu Ala Arg Lys Gly Gly
        35                  40                  45

Val Asn Val Ala Ala Gly Thr Gly Ile Ser Asn Tyr Ile Asn Thr Ile
    50                  55                  60

Pro Val Glu Glu Gln Pro Glu Tyr Pro Gly Asn Leu Glu Leu Glu Arg
65                  70                  75                  80

Arg Ile Arg Ser Ala Ile Arg Trp Asn Ala Ile Met Thr Val Leu Arg
                85                  90                  95

Ala Ser Lys Lys Asp Leu Glu Leu Gly Gly His Met Ala Ser Phe Gln
            100                 105                 110

Ser Ser Ala Thr Ile Tyr Asp Val Cys Phe Asn His Phe Phe Arg Ala
        115                 120                 125

Arg Asn Glu Gln Asp Gly Gly Asp Leu Val Tyr Phe Gln Gly His Ile
    130                 135                 140

Ser Pro Gly Val Tyr Ala Arg Ala Phe Leu Glu Gly Arg Leu Thr Gln
145                 150                 155                 160

Glu Gln Leu Asp Asn Phe Arg Gln Glu Val His Gly Asn Gly Leu Ser
                165                 170                 175

Ser Tyr Pro His Pro Lys Leu Met Pro Glu Phe Trp Gln Phe Pro Thr
            180                 185                 190

Val Ser Met Gly Leu Gly Pro Ile Gly Ala Ile Tyr Gln Ala Lys Phe
        195                 200                 205

Leu Lys Tyr Leu Glu His Arg Gly Leu Lys Asp Thr Ser Lys Gln Thr
    210                 215                 220

Val Tyr Ala Phe Leu Gly Asp Gly Glu Met Asp Glu Pro Glu Ser Lys
225                 230                 235                 240

Gly Ala Ile Thr Ile Ala Thr Arg Glu Lys Leu Asp Asn Leu Val Phe

-continued

```
            245                 250                 255
Val Ile Asn Cys Asn Leu Gln Arg Leu Asp Gly Pro Val Thr Gly Asn
            260                 265                 270

Gly Lys Ile Ile Asn Glu Leu Glu Gly Ile Phe Glu Gly Ala Gly Trp
            275                 280                 285

Asn Val Ile Lys Val Met Trp Gly Ser Arg Trp Asp Glu Leu Leu Arg
            290                 295                 300

Lys Asp Thr Ser Gly Lys Leu Ile Gln Leu Met Asn Glu Thr Val Asp
305                 310                 315                 320

Gly Asp Tyr Gln Thr Phe Lys Ser Lys Asp Gly Ala Tyr Val Arg Glu
                    325                 330                 335

His Phe Phe Gly Lys Tyr Pro Glu Thr Ala Ala Leu Val Ala Asp Trp
                    340                 345                 350

Thr Asp Glu Gln Ile Trp Ala Leu Asn Arg Gly His Asp Pro Lys
                    355                 360                 365

Lys Ile Tyr Ala Ala Phe Lys Lys Ala Gln Glu Thr Lys Gly Lys Ala
                    370                 375                 380

Thr Val Ile Leu Ala His Thr Ile Lys Gly Tyr Gly Met Gly Asp Ala
385                 390                 395                 400

Ala Glu Gly Lys Asn Ile Ala His Gln Val Lys Lys Met Asn Met Asp
                    405                 410                 415

Gly Val Arg His Ile Arg Asp Arg Phe Asn Val Pro Val Ser Asp Ala
                    420                 425                 430

Asp Ile Glu Lys Leu Pro Tyr Ile Thr Phe Pro Glu Gly Ser Glu Glu
                    435                 440                 445

His Thr Tyr Leu His Ala Gln Arg Gln Lys Leu His Gly Tyr Leu Pro
                    450                 455                 460

Ser Arg Gln Pro Asn Phe Thr Glu Lys Leu Glu Leu Pro Ser Leu Gln
465                 470                 475                 480

Asp Phe Gly Ala Leu Leu Glu Glu Gln Ser Lys Glu Ile Ser Thr Thr
                    485                 490                 495

Ile Ala Phe Val Arg Ala Leu Asn Val Met Leu Lys Asn Lys Ser Ile
                    500                 505                 510

Lys Asp Arg Leu Val Pro Ile Ile Ala Asp Glu Ala Arg Thr Phe Gly
                    515                 520                 525

Met Glu Gly Leu Phe Arg Gln Ile Gly Ile Tyr Ser Pro Asn Gly Gln
                    530                 535                 540

Gln Tyr Ile Pro Gln Asp Arg Glu Gln Val Ala Tyr Tyr Lys Glu Asp
545                 550                 555                 560

Glu Lys Gly Gln Ile Leu Gln Glu Gly Ile Asn Glu Leu Gly Ala Gly
                    565                 570                 575

Cys Ser Trp Leu Ala Ala Ala Thr Ser Tyr Ser Thr Asn Asn Leu Pro
                    580                 585                 590

Met Ile Pro Phe Tyr Ile Tyr Tyr Ser Met Phe Gly Phe Gln Arg Ile
                    595                 600                 605

Gly Asp Leu Cys Trp Ala Ala Gly Asp Gln Gln Ala Arg Gly Phe Leu
                    610                 615                 620

Ile Gly Gly Thr Ser Gly Arg Thr Thr Leu Asn Gly Glu Gly Leu Gln
625                 630                 635                 640

His Glu Asp Gly His Ser His Ile Gln Ser Leu Thr Ile Pro Asn Cys
                    645                 650                 655

Ile Ser Tyr Asp Pro Ala Tyr Ala Tyr Glu Val Ala Val Ile Met His
                    660                 665                 670
```

```
Asp Gly Leu Glu Arg Met Tyr Gly Glu Lys Gln Glu Asn Val Tyr Tyr
            675                 680                 685

Tyr Ile Thr Thr Leu Asn Glu Asn Tyr His Met Pro Ala Met Pro Glu
        690                 695                 700

Gly Ala Glu Glu Gly Ile Arg Lys Gly Ile Tyr Lys Leu Glu Thr Ile
705                 710                 715                 720

Glu Gly Ser Lys Gly Lys Val Gln Leu Leu Gly Ser Gly Ser Ile Leu
                725                 730                 735

Arg His Val Arg Glu Ala Ala Glu Ile Leu Ala Lys Asp Tyr Gly Val
                740                 745                 750

Gly Ser Asp Val Tyr Ser Val Thr Ser Phe Thr Glu Leu Ala Arg Asp
            755                 760                 765

Gly Gln Asp Cys Glu Arg Trp Asn Met Leu His Pro Leu Glu Thr Pro
            770                 775                 780

Arg Val Pro Tyr Ile Ala Gln Val Met Asn Asp Ala Pro Ala Val Ala
785                 790                 795                 800

Ser Thr Asp Tyr Met Lys Leu Phe Ala Glu Gln Val Arg Thr Tyr Val
                805                 810                 815

Pro Ala Asp Asp Tyr Arg Val Leu Gly Thr Asp Gly Phe Gly Arg Ser
            820                 825                 830

Asp Ser Arg Glu Asn Leu Arg His His Phe Glu Val Asp Ala Ser Tyr
835                 840                 845

Val Val Val Ala Ala Leu Gly Glu Leu Ala Lys Arg Gly Glu Ile Asp
            850                 855                 860

Lys Lys Val Val Ala Asp Ala Ile Ala Lys Phe Asn Ile Asp Ala Asp
865                 870                 875                 880

Lys Val Asn Pro Arg Leu Ala
                885

<210> SEQ ID NO 115
<211> LENGTH: 729
<212> TYPE: PRT
<213> ORGANISM: Shigella sonnei

<400> SEQUENCE: 115

Met Ala Arg Ser Lys Thr Ala Gln Pro Lys His Ser Leu Arg Lys Ile
1               5                   10                  15

Ala Val Val Val Ala Thr Ala Val Ser Gly Met Ser Val Tyr Ala Gln
                20                  25                  30

Ala Ala Val Glu Pro Lys Glu Asp Thr Ile Thr Val Thr Ala Ala Pro
            35                  40                  45

Ala Pro Gln Glu Ser Ala Trp Gly Pro Ala Ala Thr Ile Ala Ala Lys
        50                  55                  60

His Ser Ala Thr Ala Thr Lys Thr Asp Thr Pro Ile Glu Lys Thr Pro
65                  70                  75                  80

Gln Ser Ile Ser Val Val Thr Asn Glu Glu Met Gln Met Arg Gln Phe
                85                  90                  95

Gln Ser Val Lys Glu Ala Leu Gly Tyr Thr Pro Gly Val Thr Val Ser
                100                 105                 110

Ser Arg Gly Ala Ser Asn Thr Tyr Asp Phe Val Ile Ile Arg Gly Phe
            115                 120                 125

Ser Ser Val Gly Leu Asn Gln Asn Asn Tyr Leu Asp Gly Leu Lys Leu
        130                 135                 140

Gln Gly Asn Phe Tyr Asn Asp Ala Val Ile Asp Pro Tyr Met Leu Glu
```

```
            145                 150                 155                 160
Arg Val Glu Leu Met Arg Gly Pro Thr Ser Val Leu Tyr Gly Lys Ser
                    165                 170                 175

Asn Pro Gly Gly Ile Ile Ser Met Val Ser Lys Arg Pro Thr Thr Glu
                    180                 185                 190

Pro Leu Lys Glu Ile Gln Phe Lys Met Gly Thr Asp Asn Leu Phe Gln
                    195                 200                 205

Thr Gly Phe Asp Phe Ser Asp Ala Leu Asp Asn Gly Glu Phe Ser
    210                 215                 220

Tyr Arg Leu Thr Gly Leu Ala Arg Ser Thr Asn Glu Gln Gln Lys Asn
225                 230                 235                 240

Ser Glu Ser Gln Arg Tyr Thr Ile Ala Pro Ser Phe Ser Trp Arg Pro
                245                 250                 255

Asp Asp Lys Thr Asn Phe Thr Phe Leu Ser Tyr Phe Gln Asn Glu Pro
                260                 265                 270

Glu Thr Gly Tyr Tyr Gly Trp Leu Pro Lys Glu Gly Thr Val Glu Pro
                275                 280                 285

Leu Pro Asn Gly Lys Arg Leu Pro Thr Asp Phe Asn Glu Gly Ala Ser
    290                 295                 300

Asn Asn Thr Tyr Ser Arg Asn Gln Lys Met Val Gly Tyr Ser Phe Glu
305                 310                 315                 320

His Gly Phe Asn Asp Thr Phe Thr Val Arg Gln Asn Leu Arg Phe Ser
                325                 330                 335

Glu Met Lys Thr Ser Gln Lys Ser Val Tyr Gly Thr Ile Ala Gly
                340                 345                 350

Asp Gly His Thr Leu Asn Arg Gly Thr Val Val Asp Asn Glu Arg Leu
                355                 360                 365

Gln Asn Phe Ser Val Asp Thr Gln Leu Glu Ser Lys Phe Ala Thr Gly
    370                 375                 380

Asp Val Glu His Thr Leu Leu Thr Gly Val Asp Phe Met Arg Met Arg
385                 390                 395                 400

Asn Asp Ile Asn Ala Ser Phe Gly Ser Ala Pro Ser Ile Asp Leu Tyr
                405                 410                 415

Asn Lys Tyr His Pro Glu Tyr Phe Ala Phe Gly Ser Ala Glu Pro Tyr
                420                 425                 430

Gln Met Asn Glu Ser Lys Gln Thr Gly Ile Tyr Val Gln Asp Gln Ala
                435                 440                 445

Glu Trp Asn Lys Trp Val Phe Thr Leu Gly Gly Arg Tyr Asp Trp Ser
    450                 455                 460

Lys Gln Ala Thr Thr Val Arg Glu Asn Ser Tyr Thr Pro Thr Glu Gly
465                 470                 475                 480

Tyr Ile Glu Arg Asn Asp His Gln Phe Thr Trp Arg Gly Gly Val Asn
                485                 490                 495

Tyr Leu Phe Asp Asn Gly Ile Ser Pro Tyr Phe Ser Tyr Ser Gln Ser
                500                 505                 510

Phe Glu Pro Ser Ala Phe Asp Leu Trp Ser Asn Pro Arg Ile Ser Tyr
                515                 520                 525

Lys Pro Ser Lys Gly Glu Gln Tyr Glu Ala Gly Val Lys Tyr Val Pro
    530                 535                 540

Asn Asp Met Pro Val Val Val Thr Gly Ala Val Tyr Gln Leu Thr Lys
545                 550                 555                 560

Thr Asn Asn Leu Thr Ala Asp Pro Thr Asn Pro Leu Ala Gln Val Pro
                565                 570                 575
```

```
Ala Gly Glu Ile Arg Ala Arg Gly Val Glu Leu Ala Lys Ala Ala
            580                 585                 590

Leu Asn Ala Asn Ile Asn Leu Thr Ala Ser Tyr Thr Tyr Asp Ala
            595                 600                 605

Glu Tyr Thr Lys Asp Thr Asn Leu Lys Gly Lys Thr Pro Glu Gln Val
610                 615                 620

Pro Glu His Met Ala Ser Leu Trp Gly Asp Tyr Thr Phe Asn Glu Gly
625                 630                 635                 640

Pro Leu Ser Gly Leu Thr Leu Gly Thr Gly Arg Phe Ile Gly Ser
            645                 650                 655

Ser Tyr Gly Asp Pro Ala Asn Thr Phe Lys Val Gly Ser Thr Ala Val
            660                 665                 670

Met Asp Ala Val Val Lys Tyr Asp Leu Ala Arg Phe Gly Met Ala Gly
            675                 680                 685

Ser Ser Leu Ala Val Asn Val Asn Asn Leu Leu Asp Arg Glu Tyr Val
            690                 695                 700

Ala Ser Cys Phe Gln Thr Tyr Gly Cys Phe Trp Gly Ala Glu Arg Gln
705                 710                 715                 720

Val Val Ala Thr Ala Thr Phe Arg Phe
                725

<210> SEQ ID NO 116
<211> LENGTH: 746
<212> TYPE: PRT
<213> ORGANISM: Shigella sonnei

<400> SEQUENCE: 116

Met Asn Lys Lys Ile His Ser Leu Ala Leu Leu Val Asn Leu Gly Ile
1               5                   10                  15

Tyr Gly Val Ala Gln Ala Gln Glu Pro Thr Asp Thr Pro Val Ser His
                20                  25                  30

Asp Asp Thr Ile Val Val Thr Ala Ala Glu Gln Asn Leu Gln Ala Pro
            35                  40                  45

Gly Val Ser Thr Ile Thr Ala Asp Glu Ile Arg Lys Asn Pro Val Ala
        50                  55                  60

Arg Asp Val Ser Glu Ile Ile Arg Thr Met Pro Gly Val Asn Leu Thr
65                  70                  75                  80

Gly Asn Ser Thr Ser Gly Gln Arg Gly Asn Asn Arg Gln Ile Asp Ile
                85                  90                  95

Arg Gly Met Gly Pro Glu Asn Thr Leu Ile Leu Ile Asp Gly Lys Pro
            100                 105                 110

Val Ser Ser Arg Asn Ser Val Arg Gln Gly Trp Arg Gly Glu Arg Asp
        115                 120                 125

Thr Arg Gly Asp Thr Ser Trp Val Pro Pro Glu Met Ile Glu Arg Ile
130                 135                 140

Glu Val Leu Arg Gly Pro Ala Ala Ala Arg Tyr Gly Asn Gly Ala Ala
145                 150                 155                 160

Gly Gly Val Val Asn Ile Ile Thr Lys Lys Gly Ser Gly Glu Trp His
                165                 170                 175

Gly Ser Trp Asp Ala Tyr Phe Asn Ala Pro Glu His Lys Glu Glu Gly
            180                 185                 190

Ala Thr Lys Arg Thr Asn Phe Ser Leu Thr Gly Pro Leu Gly Asp Glu
        195                 200                 205

Phe Ser Phe Arg Leu Tyr Gly Asn Leu Asp Lys Thr Gln Ala Asp Ala
```

```
              210                 215                 220
Trp Asp Ile Asn Gln Gly His Gln Ser Ala Arg Ala Gly Thr Tyr Ala
225                 230                 235                 240

Thr Thr Leu Pro Ala Gly Arg Glu Gly Val Ile Asn Lys Asp Ile Asn
                245                 250                 255

Gly Val Val Arg Trp Asp Phe Ala Pro Leu Gln Ser Leu Glu Leu Glu
                260                 265                 270

Ala Gly Tyr Ser Arg Gln Gly Asn Leu Tyr Ala Gly Asp Thr Gln Asn
                275                 280                 285

Thr Asn Ser Asp Ser Tyr Thr Arg Ser Lys Tyr Gly Asp Glu Thr Asn
                290                 295                 300

Arg Leu Tyr Arg Gln Asn Tyr Ser Leu Thr Trp Asn Gly Gly Trp Asp
305                 310                 315                 320

Asn Gly Val Thr Thr Ser Asn Trp Val Gln Tyr Glu His Thr Arg Asn
                325                 330                 335

Ser Arg Ile Pro Glu Gly Leu Ala Gly Gly Thr Glu Gly Lys Phe Asn
                340                 345                 350

Glu Lys Ala Thr Gln Asp Phe Val Asp Ile Asp Leu Asp Asp Val Met
                355                 360                 365

Leu His Ser Glu Val Asn Leu Pro Ile Asp Phe Leu Val Asn Gln Thr
                370                 375                 380

Leu Thr Leu Gly Thr Glu Trp Asn Gln Gln Arg Met Lys Asp Leu Ser
385                 390                 395                 400

Ser Asn Thr Gln Ala Leu Thr Gly Ala Asn Thr Gly Gly Ala Ile Asp
                405                 410                 415

Gly Val Ser Ala Thr Asp Arg Ser Pro Tyr Ser Lys Ala Glu Ile Phe
                420                 425                 430

Ser Leu Phe Ala Glu Asn Asn Met Glu Leu Thr Asp Ser Thr Ile Val
                435                 440                 445

Thr Pro Gly Leu Arg Phe Asp His His Ser Ile Val Gly Asn Asn Trp
                450                 455                 460

Ser Pro Ala Leu Asn Ile Ser Gln Gly Leu Gly Asp Asp Phe Thr Leu
465                 470                 475                 480

Lys Met Gly Ile Ala Arg Ala Tyr Lys Ala Pro Ser Leu Tyr Gln Thr
                485                 490                 495

Asn Pro Asn Tyr Ile Leu Tyr Ser Lys Gly Gln Gly Cys Tyr Ala Ser
                500                 505                 510

Ala Gly Gly Cys Tyr Gln Gln Gly Asn Asp Asp Leu Lys Ala Glu Thr
                515                 520                 525

Ser Ile Asn Lys Glu Ile Gly Leu Glu Phe Lys Arg Asp Gly Trp Leu
530                 535                 540

Ala Gly Val Thr Trp Phe Arg Asn Asp Tyr Arg Asn Lys Ile Glu Ala
545                 550                 555                 560

Gly Tyr Val Ala Val Gly Gln Asn Ala Val Gly Thr Asp Leu Tyr Gln
                565                 570                 575

Trp Asp Asn Val Pro Lys Ala Val Val Glu Gly Leu Glu Gly Ser Leu
                580                 585                 590

Asn Val Pro Val Ser Glu Met Val Met Trp Thr Asn Asn Ile Thr Tyr
                595                 600                 605

Met Leu Lys Ser Glu Asn Lys Thr Thr Gly Asp Arg Leu Ser Ile Ile
                610                 615                 620

Pro Glu Tyr Thr Leu Asn Ser Thr Leu Ser Trp Gln Ala Arg Glu Asp
625                 630                 635                 640
```

```
Leu Ser Met Gln Thr Thr Phe Thr Trp Tyr Gly Lys Gln Pro Lys
                645                 650                 655

Lys Tyr Asn Tyr Lys Gly Gln Pro Ala Val Gly Pro Glu Thr Lys Glu
                660                 665                 670

Ile Ser Pro Tyr Ser Ile Val Gly Leu Ser Ala Thr Trp Asp Val Thr
                675                 680                 685

Lys Asn Val Ser Leu Thr Gly Gly Val Asp Asn Leu Phe Asp Lys Arg
            690                 695                 700

Leu Trp Arg Ala Gly Asn Ala Gln Thr Thr Gly Asp Leu Ala Gly Ala
705                 710                 715                 720

Asn Tyr Ile Ala Gly Ala Gly Ala Tyr Thr Tyr Asn Glu Pro Gly Arg
                725                 730                 735

Thr Trp Tyr Met Ser Val Asn Thr His Phe
                740                 745

<210> SEQ ID NO 117
<211> LENGTH: 682
<212> TYPE: PRT
<213> ORGANISM: Shigella sonnei

<400> SEQUENCE: 117

Met Asn Met Phe Phe Arg Leu Thr Ala Leu Ala Gly Leu Leu Ala Ile
1               5                   10                  15

Ala Gly Gln Thr Phe Ala Val Glu Asp Ile Thr Arg Ala Asp Gln Ile
                20                  25                  30

Pro Val Leu Lys Glu Thr Gln His Ala Thr Val Ser Glu Arg Val
            35                  40                  45

Thr Ser Arg Phe Thr Arg Ser His Tyr Arg Gln Phe Asp Leu Asp Gln
    50                  55                  60

Ala Phe Ser Ala Lys Ile Phe Asp Arg Tyr Leu Asn Leu Leu Asp Tyr
65                  70                  75                  80

Ser His Asn Val Leu Leu Ala Ser Asp Val Glu Gln Phe Ala Lys Lys
                85                  90                  95

Lys Thr Glu Leu Gly Asp Glu Leu Arg Ser Gly Lys Leu Asp Val Phe
            100                 105                 110

Tyr Asp Leu Tyr Asn Leu Ala Gln Lys Arg Phe Glu Arg Tyr Gln
        115                 120                 125

Tyr Ala Leu Ser Val Leu Glu Lys Pro Met Asp Phe Thr Gly Asn Asp
    130                 135                 140

Thr Tyr Asn Leu Asp Arg Ser Lys Ala Pro Trp Pro Lys Asn Glu Ala
145                 150                 155                 160

Glu Leu Asn Ala Leu Trp Asp Ser Lys Val Lys Phe Asp Glu Leu Ser
                165                 170                 175

Leu Lys Leu Ala Gly Lys Thr Asp Lys Glu Ile Arg Glu Thr Leu Thr
            180                 185                 190

Arg Arg Tyr Lys Phe Ala Ile Arg Arg Leu Ala Gln Thr Asn Ser Glu
        195                 200                 205

Asp Val Phe Ser Leu Ala Met Thr Ala Phe Ala Arg Glu Ile Asp Pro
    210                 215                 220

His Thr Asn Tyr Leu Ser Pro Arg Asn Thr Glu Gln Phe Asn Thr Glu
225                 230                 235                 240

Met Ser Leu Ser Leu Glu Gly Ile Gly Ala Val Leu Gln Met Asp Asp
                245                 250                 255

Asp Tyr Thr Val Ile Asn Ser Met Val Ala Gly Gly Pro Ala Ala Lys
```

```
                260                 265                 270
Ser Lys Ala Ile Ser Val Gly Asp Lys Ile Val Gly Val Gly Gln Thr
            275                 280                 285

Gly Lys Pro Met Val Asp Val Ile Gly Trp Arg Leu Asp Asp Val Val
            290                 295                 300

Ala Leu Ile Lys Gly Pro Lys Gly Ser Lys Val Arg Leu Glu Ile Leu
305                 310                 315                 320

Pro Ala Gly Lys Gly Thr Lys Thr Arg Thr Val Thr Leu Thr Arg Glu
                325                 330                 335

Arg Ile Arg Leu Glu Asp Arg Ala Val Lys Met Ser Val Lys Thr Val
            340                 345                 350

Gly Lys Glu Lys Val Gly Val Leu Asp Ile Pro Gly Phe Tyr Val Gly
            355                 360                 365

Leu Thr Asp Asp Val Lys Val Gln Leu Gln Lys Leu Glu Lys Gln Asn
            370                 375                 380

Val Ser Ser Val Ile Ile Asp Leu Arg Ser Asn Gly Gly Gly Ala Leu
385                 390                 395                 400

Thr Glu Ala Val Ser Leu Ser Gly Leu Phe Ile Pro Ala Gly Pro Ile
                405                 410                 415

Val Gln Val Arg Asp Asn Asn Gly Lys Val Arg Glu Asp Ser Asp Thr
            420                 425                 430

Asp Gly Gln Val Phe Tyr Lys Gly Pro Leu Val Val Leu Val Asp Arg
            435                 440                 445

Phe Ser Ala Ser Ala Ser Glu Ile Phe Ala Ala Met Gln Asp Tyr
450                 455                 460

Gly Arg Ala Leu Val Val Gly Glu Pro Thr Phe Gly Lys Gly Thr Val
465                 470                 475                 480

Gln Gln Tyr Arg Ser Leu Asn Arg Ile Tyr Asp Gln Met Leu Arg Pro
                485                 490                 495

Glu Trp Pro Ala Leu Gly Ser Val Gln Tyr Thr Ile Gln Lys Phe Tyr
            500                 505                 510

Arg Val Asn Gly Gly Ser Thr Gln Arg Lys Gly Val Thr Pro Asp Ile
            515                 520                 525

Ile Met Pro Thr Gly Asn Glu Glu Thr Glu Thr Gly Glu Lys Phe Glu
            530                 535                 540

Asp Asn Ala Leu Pro Trp Asp Ser Ile Asp Ala Ala Thr Tyr Val Lys
545                 550                 555                 560

Ser Gly Asp Leu Thr Ala Phe Gly Pro Glu Leu Leu Lys Glu His Asn
                565                 570                 575

Ala Arg Ile Ala Lys Asp Pro Glu Phe Gln Asn Ile Met Lys Asp Ile
            580                 585                 590

Ala Arg Phe Asn Ala Met Arg Asp Lys Arg Asn Ile Val Ser Leu Asn
            595                 600                 605

Tyr Ala Val Arg Glu Lys Glu Asn Asn Glu Asp Asp Ala Thr Arg Leu
610                 615                 620

Ala Arg Leu Asn Glu Arg Phe Lys Arg Glu Gly Lys Pro Glu Leu Lys
625                 630                 635                 640

Lys Leu Asp Asp Leu Pro Lys Asp Tyr Gln Glu Pro Asp Pro Tyr Leu
                645                 650                 655

Asp Glu Thr Val Asn Ile Ala Leu Asp Leu Ala Lys Leu Glu Lys Ala
            660                 665                 670

Arg Pro Ala Glu Gln Pro Ala Pro Val Lys
            675                 680
```

<210> SEQ ID NO 118
<211> LENGTH: 212
<212> TYPE: PRT
<213> ORGANISM: Shigella sonnei

<400> SEQUENCE: 118

```
Met Lys Lys Leu Thr Val Ala Ala Leu Ala Val Thr Thr Leu Leu Ser
1               5                   10                  15

Gly Ser Ala Phe Ala His Glu Ala Gly Phe Phe Met Arg Ala Gly
            20                  25                  30

Ser Ala Thr Val Arg Pro Thr Glu Gly Ala Gly Gly Thr Leu Gly Ser
        35                  40                  45

Leu Gly Gly Phe Ser Val Thr Asn Asn Thr Gln Leu Gly Leu Thr Phe
    50                  55                  60

Thr Tyr Met Ala Thr Asp Asn Ile Gly Val Glu Leu Leu Ala Ala Thr
65                  70                  75                  80

Pro Phe Arg His Lys Ile Gly Thr Arg Ala Thr Gly Asp Ile Ala Thr
                85                  90                  95

Val His His Leu Pro Pro Thr Leu Met Ala Gln Trp Tyr Phe Gly Asp
            100                 105                 110

Ala Gly Ser Lys Phe Arg Pro Tyr Val Gly Ala Gly Ile Asn Tyr Thr
        115                 120                 125

Thr Phe Phe Asp Asn Gly Phe Asn Asp His Gly Lys Glu Ala Gly Leu
    130                 135                 140

Ser Asp Leu Ser Leu Lys Asp Tyr Trp Gly Ala Ala Gly Gln Val Gly
145                 150                 155                 160

Val Asp Tyr Leu Ile Asn Arg Asp Trp Leu Val Asn Met Ser Val Trp
                165                 170                 175

Tyr Met Asp Ile Asp Thr Thr Ala Lys Tyr Lys Ser Gly Val Thr Thr
            180                 185                 190

Val Lys Asp Ser Val Arg Leu Asp Pro Trp Val Phe Met Phe Ser Ala
        195                 200                 205

Gly Tyr Arg Phe
    210
```

<210> SEQ ID NO 119
<211> LENGTH: 315
<212> TYPE: PRT
<213> ORGANISM: Shigella sonnei

<400> SEQUENCE: 119

```
Met Pro Asp Met Lys Leu Phe Ala Gly Asn Ala Thr Pro Glu Leu Ala
1               5                   10                  15

Gln Arg Ile Ala Asn Arg Leu Tyr Thr Ser Leu Gly Asp Ala Ala Val
            20                  25                  30

Gly Arg Phe Ser Asp Gly Glu Val Ser Val Gln Ile Asn Glu Asn Val
        35                  40                  45

Arg Gly Gly Asp Ile Phe Ile Ile Gln Ser Thr Cys Ala Pro Thr Asn
    50                  55                  60

Asp Asn Leu Met Glu Leu Val Val Met Val Asp Ala Leu Arg Arg Ala
65                  70                  75                  80

Ser Ala Gly Arg Ile Thr Ala Val Ile Pro Tyr Phe Gly Tyr Ala Arg
                85                  90                  95

Gln Asp Arg Arg Val Arg Ser Ala Arg Val Pro Ile Thr Ala Lys Val
            100                 105                 110
```

```
Val Ala Asp Phe Leu Ser Ser Val Gly Val Asp Arg Val Leu Thr Val
            115                 120                 125

Asp Leu His Ala Glu Gln Ile Gln Gly Phe Phe Asp Val Pro Val Asp
130                 135                 140

Asn Val Phe Gly Ser Pro Ile Leu Leu Glu Asp Met Leu Gln Leu Asn
145                 150                 155                 160

Leu Asp Asn Pro Ile Val Val Ser Pro Asp Ile Gly Gly Val Val Arg
                165                 170                 175

Ala Arg Ala Ile Ala Lys Leu Leu Asn Asp Thr Asp Met Ala Ile Ile
            180                 185                 190

Asp Lys Arg Arg Pro Arg Ala Asn Val Ser Gln Val Met His Ile Ile
        195                 200                 205

Gly Asp Val Ala Gly Arg Asp Cys Val Leu Val Asp Asp Met Ile Asp
210                 215                 220

Thr Gly Gly Thr Leu Cys Lys Ala Ala Glu Ala Leu Lys Glu Arg Gly
225                 230                 235                 240

Ala Lys Arg Val Phe Ala Tyr Ala Thr His Pro Ile Phe Ser Gly Asn
                245                 250                 255

Ala Ala Asn Asn Leu Arg Asn Ser Val Ile Asp Glu Val Val Val Cys
            260                 265                 270

Asp Thr Ile Pro Leu Ser Asp Glu Ile Lys Ser Leu Pro Asn Val Arg
        275                 280                 285

Thr Leu Thr Leu Ser Gly Met Leu Ala Glu Ala Ile Arg Arg Ile Ser
290                 295                 300

Asn Glu Glu Ser Ile Ser Ala Met Phe Glu His
305                 310                 315

<210> SEQ ID NO 120
<211> LENGTH: 663
<212> TYPE: PRT
<213> ORGANISM: Shigella sonnei

<400> SEQUENCE: 120

Met Phe Arg Leu Asn Pro Phe Val Arg Val Gly Leu Cys Leu Ser Ala
1               5                   10                  15

Ile Ser Cys Val Trp Pro Val Leu Ala Val Asp Asp Asp Gly Glu Thr
            20                  25                  30

Met Val Val Thr Ala Ser Ser Val Glu Gln Asn Leu Lys Asp Ala Pro
        35                  40                  45

Ala Ser Ile Ser Val Ile Thr Gln Glu Asp Leu Gln Arg Lys Pro Val
50                  55                  60

Gln Asn Leu Lys Asp Val Leu Lys Glu Val Pro Gly Val Gln Leu Thr
65                  70                  75                  80

Asn Glu Gly Asp Asn Arg Lys Gly Val Ser Ile Arg Gly Leu Asp Ser
                85                  90                  95

Ser Tyr Thr Leu Ile Leu Val Asp Gly Lys Arg Val Asn Ser Arg Asn
            100                 105                 110

Ala Val Phe Arg His Asn Asp Phe Asp Leu Asn Trp Ile Pro Val Asp
        115                 120                 125

Ser Ile Glu Arg Ile Glu Val Val Arg Gly Pro Met Ser Ser Leu Tyr
130                 135                 140

Gly Ser Asp Ala Leu Gly Gly Val Val Asn Ile Ile Thr Lys Lys Ile
145                 150                 155                 160

Gly Gln Lys Trp Ser Gly Thr Val Thr Val Asp Thr Thr Ile Gln Glu
```

```
                165                 170                 175
His Arg Asp Arg Gly Asp Thr Tyr Asn Gly Gln Phe Phe Thr Ser Gly
            180                 185                 190

Pro Leu Ile Asp Gly Val Leu Gly Met Lys Ala Tyr Gly Ser Leu Ala
            195                 200                 205

Lys Arg Glu Lys Asp Asp Pro Gln Asn Ser Thr Thr Thr Asp Thr Gly
210                 215                 220

Glu Thr Pro Arg Ile Glu Gly Phe Ser Ser Arg Asp Gly Asn Val Glu
225                 230                 235                 240

Phe Ala Trp Thr Pro Asn Gln Asn His Asp Phe Thr Ala Gly Tyr Gly
            245                 250                 255

Phe Asp Arg Gln Asp Arg Asp Ser Asp Ser Leu Asp Lys Asn Arg Leu
            260                 265                 270

Glu Arg Gln Asn Tyr Ser Val Ser His Asn Gly Arg Trp Asp Tyr Gly
            275                 280                 285

Thr Ser Glu Leu Lys Tyr Tyr Gly Glu Lys Val Glu Asn Lys Asn Pro
        290                 295                 300

Gly Asn Ser Ser Pro Ile Thr Ser Glu Ser Asn Thr Val Asp Gly Lys
305                 310                 315                 320

Tyr Thr Leu Pro Leu Thr Ala Ile Asn Gln Phe Leu Thr Val Gly Gly
            325                 330                 335

Glu Trp Arg His Asp Lys Leu Ser Asp Ala Val Asn Leu Thr Gly Gly
            340                 345                 350

Thr Ser Ser Lys Thr Ser Ala Ser Gln Tyr Ala Leu Phe Val Glu Asp
            355                 360                 365

Glu Trp Arg Ile Phe Glu Pro Leu Ala Leu Thr Thr Gly Val Arg Met
        370                 375                 380

Asp Asp His Glu Thr Tyr Gly Glu His Trp Ser Pro Arg Ala Tyr Leu
385                 390                 395                 400

Val Tyr Asn Ala Thr Asp Thr Val Thr Val Lys Gly Gly Trp Ala Thr
            405                 410                 415

Ala Phe Lys Ala Pro Ser Leu Leu Gln Leu Ser Pro Asp Trp Thr Ser
            420                 425                 430

Asn Ser Cys Arg Gly Ala Cys Lys Ile Val Gly Ser Pro Asp Leu Lys
            435                 440                 445

Pro Glu Thr Ser Glu Ser Trp Glu Leu Gly Leu Tyr Tyr Met Gly Glu
        450                 455                 460

Glu Gly Trp Leu Glu Gly Val Glu Ser Ser Val Thr Val Phe Arg Asn
465                 470                 475                 480

Asp Val Lys Asp Arg Ile Ser Ile Ser Arg Thr Ser Asp Val Asn Ala
            485                 490                 495

Ala Pro Gly Tyr Gln Asn Phe Val Gly Phe Glu Thr Gly Ala Asn Gly
            500                 505                 510

Arg Arg Ile Pro Val Phe Ser Tyr Tyr Asn Val Asn Lys Ala Arg Ile
            515                 520                 525

Gln Gly Val Glu Thr Glu Leu Lys Ile Pro Phe Asn Asp Glu Trp Lys
        530                 535                 540

Leu Ser Ile Asn Tyr Thr Tyr Asn Asp Gly Arg Asp Val Ser Asn Gly
545                 550                 555                 560

Glu Asn Lys Pro Leu Ser Asp Leu Pro Phe His Thr Ala Asn Gly Thr
            565                 570                 575

Leu Asp Trp Lys Pro Leu Ala Leu Glu Asp Trp Ser Phe Tyr Val Ser
            580                 585                 590
```

```
Gly His Tyr Thr Gly Gln Lys Arg Ala Asp Ser Ala Thr Ala Lys Thr
            595                 600                 605

Pro Gly Gly Tyr Thr Ile Trp Asn Thr Gly Ala Ala Trp Gln Val Thr
            610                 615                 620

Lys Asp Val Lys Leu Arg Ala Gly Val Leu Asn Leu Gly Asp Lys Asp
625                 630                 635                 640

Leu Ser Arg Asp Asp Tyr Ser Tyr Asn Glu Asp Gly Arg Arg Tyr Phe
            645                 650                 655

Met Ala Val Asp Tyr Arg Phe
            660

<210> SEQ ID NO 121
<211> LENGTH: 358
<212> TYPE: PRT
<213> ORGANISM: Shigella sonnei

<400> SEQUENCE: 121

Met Lys Leu Lys Leu Lys Asn Leu Ser Met Ala Ile Met Met Ser Thr
1               5                   10                  15

Ile Val Met Gly Ser Ser Ala Met Ala Ala Asp Ser Asn Glu Lys Ile
            20                  25                  30

Val Ile Ala His Arg Gly Ala Ser Gly Tyr Leu Pro Glu His Thr Leu
            35                  40                  45

Pro Ala Lys Ala Met Ala Tyr Ala Gln Gly Ala Asp Tyr Leu Glu Gln
        50                  55                  60

Asp Leu Val Met Thr Lys Asp His Leu Val Val Leu His Asp His
65                  70                  75                  80

Tyr Leu Asp Arg Val Thr Asp Val Ala Asp Arg Phe Pro Asp Arg Ala
                85                  90                  95

Arg Lys Asp Gly Arg Tyr Tyr Ala Ile Asp Phe Thr Leu Asp Glu Ile
            100                 105                 110

Lys Ser Leu Lys Phe Thr Glu Gly Phe Asp Ile Glu Asn Gly Lys Lys
        115                 120                 125

Val Gln Thr Tyr Pro Gly Arg Phe Pro Met Gly Lys Ser Asp Phe Arg
130                 135                 140

Gly His Thr Phe Glu Glu Ile Glu Phe Val Gln Gly Leu Asn His
145                 150                 155                 160

Ser Thr Gly Lys Asn Ile Gly Ile Tyr Pro Glu Ile Lys Ala Pro Trp
                165                 170                 175

Phe His His Gln Glu Gly Lys Asp Ile Ala Ala Lys Thr Leu Glu Val
            180                 185                 190

Leu Lys Lys Tyr Gly Tyr Thr Gly Lys Asp Asp Lys Val Tyr Leu Gln
        195                 200                 205

Cys Phe Asp Ala Asp Glu Leu Lys Arg Ile Lys Asn Glu Leu Glu Pro
210                 215                 220

Lys Met Gly Met Asp Leu Asn Leu Val Gln Leu Ile Ala Tyr Thr Asp
225                 230                 235                 240

Trp Asn Glu Thr Gln Gln Lys Gln Pro Asp Gly Ser Trp Val Asn Tyr
                245                 250                 255

Ser Tyr Asp Trp Met Phe Lys Pro Gly Ala Met Lys Gln Val Ala Glu
            260                 265                 270

Tyr Ala Asp Gly Ile Gly Pro Asp Tyr His Met Leu Ile Glu Glu Thr
        275                 280                 285

Ser Gln Pro Gly Asn Ile Lys Leu Thr Gly Met Val Gln Asp Ala Gln
```

```
                290                 295                 300
Gln Asn Lys Leu Val Val His Pro Tyr Thr Val Arg Ser Asp Lys Leu
305                 310                 315                 320

Pro Glu Tyr Thr Thr Asp Val Asn Gln Leu Tyr Asp Ala Leu Tyr Asn
                325                 330                 335

Lys Ala Gly Val Asn Gly Leu Phe Thr Asp Phe Pro Asp Lys Ala Val
            340                 345                 350

Lys Phe Leu Asn Lys Glu
        355

<210> SEQ ID NO 122
<211> LENGTH: 316
<212> TYPE: PRT
<213> ORGANISM: Shigella sonnei

<400> SEQUENCE: 122

Met Asn Glu Leu Asp Gly Ile Lys Gln Phe Thr Thr Val Ala Asp
1               5                   10                  15

Ser Gly Asp Ile Glu Ser Ile Arg His Tyr His Pro Gln Asp Ala Thr
            20                  25                  30

Thr Asn Pro Ser Leu Leu Leu Lys Ala Ala Gly Leu Ser Gln Tyr Glu
        35                  40                  45

His Leu Ile Asp Asp Ala Ile Ala Trp Gly Lys Lys Asn Gly Lys Thr
    50                  55                  60

Gln Glu Gln Gln Val Val Ala Ala Cys Asp Lys Leu Ala Val Asn Phe
65                  70                  75                  80

Gly Ala Glu Ile Leu Lys Ile Val Pro Gly Arg Val Ser Thr Glu Val
                85                  90                  95

Asp Ala Arg Leu Ser Phe Asp Lys Glu Lys Ser Ile Glu Lys Ala Arg
            100                 105                 110

His Leu Val Asp Leu Tyr Gln Gln Gln Gly Val Glu Lys Ser Arg Ile
        115                 120                 125

Leu Ile Lys Leu Ala Ser Thr Trp Glu Gly Ile Arg Ala Ala Glu Glu
130                 135                 140

Leu Glu Lys Glu Gly Ile Asn Cys Asn Leu Thr Leu Leu Phe Ser Phe
145                 150                 155                 160

Ala Gln Ala Arg Ala Cys Ala Glu Ala Gly Val Phe Leu Ile Ser Pro
                165                 170                 175

Phe Val Gly Arg Ile Tyr Asp Trp Tyr Gln Ala Arg Lys Pro Met Asp
            180                 185                 190

Pro Tyr Val Val Glu Glu Asp Pro Gly Val Lys Ser Val Arg Asn Ile
        195                 200                 205

Tyr Asp Tyr Tyr Lys Gln His His Tyr Glu Thr Ile Val Met Gly Ala
    210                 215                 220

Ser Phe Arg Arg Thr Glu Gln Ile Leu Ala Leu Thr Gly Cys Asp Arg
225                 230                 235                 240

Leu Thr Ile Ala Pro Asn Leu Leu Lys Glu Leu Gln Glu Lys Val Ser
                245                 250                 255

Pro Val Val Arg Lys Leu Ile Pro Pro Ser Gln Thr Phe Pro Arg Pro
            260                 265                 270

Ala Pro Met Ser Glu Ala Glu Phe Arg Trp Glu His Asn Gln Tyr Ala
        275                 280                 285

Met Ala Val Glu Lys Leu Ser Glu Gly Ile Arg Leu Phe Ala Val Asp
    290                 295                 300
```

```
Gln Arg Lys Leu Glu Asp Leu Leu Ala Ala Lys Leu
305                 310                 315
```

<210> SEQ ID NO 123
<211> LENGTH: 455
<212> TYPE: PRT
<213> ORGANISM: Shigella sonnei

<400> SEQUENCE: 123

```
Met Lys Lys Gln Pro Gln Leu Leu Ser Ala Leu Ala Leu Ser Val Gly
1               5                   10                  15

Leu Thr Leu Ser Ala Ser Phe Gln Ala Val Ala Ser Ile Pro Gly Gln
            20                  25                  30

Val Ala Asp Gln Ala Pro Leu Pro Ser Leu Ala Pro Met Leu Glu Lys
        35                  40                  45

Val Leu Pro Ala Val Val Ser Val Arg Val Glu Gly Thr Ala Ser Gln
50                  55                  60

Gly Gln Lys Ile Pro Glu Glu Phe Lys Lys Phe Phe Gly Asp Asp Leu
65                  70                  75                  80

Pro Glu Gln Pro Ala Gln Pro Phe Glu Gly Leu Gly Ser Gly Val Ile
                85                  90                  95

Ile Asn Ala Ser Lys Gly Tyr Val Leu Thr Asn Asn His Val Ile Asn
            100                 105                 110

Gln Ala Gln Lys Ile Ser Ile Gln Leu Asn Asp Gly Arg Glu Phe Asp
        115                 120                 125

Ala Lys Leu Ile Gly Ser Asp Asp Gln Ser Asp Ile Ala Leu Leu Gln
130                 135                 140

Ile Gln Asn Pro Ser Lys Leu Thr Gln Ile Ala Ile Ala Asp Ser Asp
145                 150                 155                 160

Lys Leu Arg Val Gly Asp Phe Ala Val Ala Val Gly Asn Pro Phe Gly
                165                 170                 175

Leu Gly Gln Thr Ala Thr Ser Gly Ile Val Ser Ala Leu Gly Arg Ser
            180                 185                 190

Gly Leu Asn Leu Glu Gly Leu Glu Asn Phe Ile Gln Thr Asp Ala Ser
        195                 200                 205

Ile Asn Arg Gly Asn Ser Gly Gly Ala Leu Leu Asn Leu Asn Gly Glu
210                 215                 220

Leu Ile Gly Ile Asn Thr Ala Ile Leu Ala Pro Gly Gly Gly Ser Val
225                 230                 235                 240

Gly Ile Gly Phe Ala Ile Pro Ser Asn Met Ala Arg Thr Leu Ala Gln
                245                 250                 255

Gln Leu Ile Asp Phe Gly Glu Ile Lys Arg Gly Leu Leu Gly Ile Lys
            260                 265                 270

Gly Thr Glu Met Ser Ala Asp Ile Ala Lys Ala Phe Asn Leu Asp Val
        275                 280                 285

Gln Arg Gly Ala Phe Val Ser Glu Val Leu Pro Gly Ser Gly Ser Ala
290                 295                 300

Lys Ala Gly Val Lys Ala Gly Asp Ile Ile Thr Ser Leu Asn Gly Lys
305                 310                 315                 320

Pro Leu Asn Ser Phe Ala Glu Leu Arg Ser Arg Ile Ala Thr Thr Glu
                325                 330                 335

Pro Gly Thr Lys Val Lys Leu Gly Leu Leu Arg Asn Gly Lys Pro Leu
            340                 345                 350

Glu Val Glu Val Thr Leu Asp Thr Ser Thr Ser Ser Ser Ala Ser Ala
        355                 360                 365
```

Glu Met Ile Ala Pro Ala Leu Glu Gly Ala Thr Leu Ser Asp Gly Gln
    370                 375                 380

Leu Lys Asp Gly Gly Lys Gly Ile Lys Ile Asp Glu Val Val Lys Gly
385                 390                 395                 400

Ser Pro Ala Ala Gln Ala Gly Leu Gln Lys Asp Asp Val Ile Ile Gly
                405                 410                 415

Val Asn Arg Asp Arg Val Asn Ser Ile Ala Glu Met Arg Lys Val Leu
            420                 425                 430

Ala Ala Lys Ser Ala Ile Ile Ala Leu Gln Ile Val Arg Gly Asn Glu
                435                 440                 445

Ser Ile Tyr Leu Leu Met Arg
    450                 455

<210> SEQ ID NO 124
<211> LENGTH: 396
<212> TYPE: PRT
<213> ORGANISM: Shigella sonnei

<400> SEQUENCE: 124

Met Lys Ile Lys Thr Gly Ala Arg Ile Leu Ala Leu Ser Ala Leu Thr
1               5                   10                  15

Thr Met Met Phe Ser Ala Ser Ala Leu Ala Lys Ile Glu Glu Gly Lys
            20                  25                  30

Leu Val Ile Trp Ile Asn Gly Asp Lys Gly Tyr Asn Gly Leu Ala Glu
        35                  40                  45

Val Gly Lys Lys Phe Glu Lys Asp Thr Gly Ile Lys Val Thr Val Glu
    50                  55                  60

His Pro Asp Lys Leu Glu Glu Lys Phe Pro Gln Val Ala Ala Thr Gly
65                  70                  75                  80

Asp Gly Pro Asp Ile Ile Phe Trp Ala His Asp Arg Phe Gly Gly Tyr
                85                  90                  95

Ala Gln Ser Gly Leu Leu Ala Glu Ile Thr Pro Asp Lys Ala Phe Gln
            100                 105                 110

Asp Lys Leu Tyr Pro Phe Thr Trp Asp Ala Val Arg Tyr Asn Gly Lys
        115                 120                 125

Leu Ile Ala Tyr Pro Ile Ala Val Glu Ala Leu Ser Leu Ile Tyr Asn
    130                 135                 140

Lys Asp Leu Leu Pro Asn Pro Pro Lys Thr Trp Glu Glu Ile Pro Ala
145                 150                 155                 160

Leu Asp Lys Glu Leu Lys Ala Lys Gly Lys Ser Ala Leu Met Phe Asn
                165                 170                 175

Leu Gln Glu Pro Tyr Phe Thr Trp Pro Leu Ile Ala Ala Asp Gly Gly
            180                 185                 190

Tyr Ala Phe Lys Tyr Glu Asn Gly Lys Tyr Asp Ile Lys Asp Val Ala
        195                 200                 205

Val Asp Asn Ala Gly Ala Lys Ala Gly Leu Thr Phe Leu Val Asp Leu
    210                 215                 220

Ile Lys Asn Lys His Met Asn Ala Asp Thr Asp Tyr Ser Ile Ala Glu
225                 230                 235                 240

Ala Ala Phe Asn Lys Gly Glu Thr Ala Met Thr Ile Asn Gly Pro Trp
                245                 250                 255

Ala Trp Ser Asn Ile Asp Thr Ser Lys Val Asn Tyr Gly Val Thr Val
            260                 265                 270

Leu Pro Thr Phe Lys Gly Gln Pro Ser Lys Pro Phe Val Gly Val Leu 275                 280                 285
Ser Ala Gly Ile Asn Ala Ala Ser Pro Asn Lys Glu Leu Ala Lys Glu
    290                 295                 300

Phe Leu Glu Asn Tyr Leu Leu Thr Asp Glu Gly Leu Glu Ala Val Asn
305                 310                 315                 320

Lys Asp Lys Pro Leu Gly Ala Val Ala Leu Lys Ser Tyr Glu Glu Glu
                325                 330                 335

Leu Ala Lys Asp Pro Arg Ile Ala Ala Thr Met Glu Asn Ala Gln Lys
            340                 345                 350

Gly Glu Ile Met Pro Asn Ile Pro Gln Met Ser Ala Phe Trp Tyr Ala
        355                 360                 365

Val Arg Thr Ala Val Ile Asn Ala Ala Ser Gly Arg Gln Thr Val Asp
    370                 375                 380

Glu Ala Leu Lys Asp Ala Gln Thr Arg Ile Thr Lys
385                 390                 395

<210> SEQ ID NO 125
<211> LENGTH: 290
<212> TYPE: PRT
<213> ORGANISM: Shigella boydii

<400> SEQUENCE: 125

Met Ile Gly Val Thr Asp Gln Lys Gly Glu Lys Ile Leu Leu Asp Thr
1               5                   10                  15

Thr Gly Pro Ile Ala Arg Thr Asn Thr Ser Tyr Asp Gly Thr Lys Arg
            20                  25                  30

Arg Asn Pro Asn Asn Val Val Asp Leu Lys Asn Arg Lys Tyr Gln Cys
        35                  40                  45

Glu Gln Val Asn Tyr Asp Thr Phe Ile Ser Tyr Pro Gln Leu Asp Ala
    50                  55                  60

Trp Ser Ala His Pro Asp Phe Gln Ser Arg Ile Ser Ala Gln Ile Ala
65                  70                  75                  80

Arg Gln Val Ala Leu Asp Arg Ile Met Ile Gly Phe Asn Gly Thr Ser
                85                  90                  95

His Ala Asp Glu Ser Asn Phe Ser Thr Asn Lys Leu Leu Gln Asp Val
            100                 105                 110

Asn Val Gly Trp Leu Glu His Ile Arg Thr Asp Ala Ser Glu Arg Val
        115                 120                 125

Met Asn Asp Val Thr Leu Thr Ser Arg Asn Met Asp Asn Thr Val Ala
    130                 135                 140

His Ala Gly Lys Tyr Ala Asn Ala Asp Ala Leu Val Gln Asp Ala Arg
145                 150                 155                 160

Ser Ser Leu Leu Asp Glu Trp His Lys Glu Ala Asp Leu Val Val
                165                 170                 175

Ile Met Gly Arg Asn Leu Phe Asn Ser Leu Arg Leu Pro Val Leu Asn
            180                 185                 190

Ser Ile Ser Gly Gln Asn Pro Asn Ala Glu Leu Leu Ala Gly Gln Leu
        195                 200                 205

Ile Leu Ser Ser Arg Thr Ile Gly Gly Leu Gly Val Phe Leu Ala Pro
    210                 215                 220

Phe Phe Pro Asp Ala Thr Met Leu Ile Thr Ser Phe Asn Asn Leu Ser
225                 230                 235                 240

Ile Tyr Trp Gln Lys Gly Ser Met Arg Arg Leu Met Lys Asp Glu Pro
                245                 250                 255

Glu Tyr Asn Arg Ile Ala Thr Tyr Gln Ser Ile Asn Asp Tyr Val
            260                 265                 270

Val Glu Asp Tyr Gly Lys Cys Ala Met Val Thr Gly Leu Lys Phe Ala
            275                 280                 285

Asp Ser
    290

<210> SEQ ID NO 126
<211> LENGTH: 375
<212> TYPE: PRT
<213> ORGANISM: Shigella boydii

<400> SEQUENCE: 126

Met Thr Ile Asn Phe Cys Arg Asn Ala Leu Gln Leu Ser Val Ala Ala
1               5                   10                  15

Leu Phe Ser Ser Ala Phe Met Ala Asn Ala Ala Asp Val Pro Gln Val
            20                  25                  30

Lys Val Thr Val Thr Asp Lys Gln Cys Glu Pro Met Thr Ile Thr Val
            35                  40                  45

Asn Ala Gly Lys Thr Gln Phe Ile Ile Gln Asn His Ser Gln Lys Ala
        50                  55                  60

Leu Glu Trp Glu Ile Leu Lys Gly Val Met Val Glu Glu Arg Glu
65              70                  75                  80

Asn Ile Ala Pro Gly Phe Ser Gln Lys Met Thr Ala Asn Leu Gln Pro
                85                  90                  95

Gly Glu Tyr Asp Met Thr Cys Gly Leu Leu Thr Asn Pro Lys Gly Lys
            100                 105                 110

Leu Ile Val Lys Gly Glu Ala Thr Ala Asp Ala Ala Gln Ser Asp Ala
            115                 120                 125

Leu Leu Ser Leu Gly Gly Ala Ile Thr Ala Tyr Lys Ala Tyr Val Met
        130                 135                 140

Ala Glu Thr Thr Gln Leu Val Thr Asp Thr Lys Ala Phe Thr Asp Ala
145                 150                 155                 160

Ile Lys Ala Gly Asp Ile Glu Lys Ala Lys Ala Leu Tyr Ala Pro Thr
                165                 170                 175

Arg Gln His Tyr Glu Arg Ile Glu Pro Ile Ala Glu Leu Phe Ser Asp
            180                 185                 190

Leu Asp Gly Ser Ile Asp Ala Arg Glu Asp Tyr Glu Gln Lys Ala
            195                 200                 205

Ala Asp Pro Lys Phe Thr Gly Phe His Arg Leu Glu Lys Ala Leu Phe
        210                 215                 220

Gly Asp Asn Thr Thr Lys Gly Met Asp Gln Tyr Ala Glu Gln Leu Tyr
225                 230                 235                 240

Thr Asp Val Val Asp Leu Gln Lys Arg Ile Ser Glu Leu Ala Phe Pro
                245                 250                 255

Pro Ser Lys Val Val Gly Gly Ala Ala Gly Leu Ile Glu Val Ala
            260                 265                 270

Ala Ser Lys Ile Ser Gly Glu Glu Asp Arg Tyr Ser His Thr Asp Leu
        275                 280                 285

Trp Asp Phe Gln Ala Asn Val Glu Gly Ser Gln Lys Ile Val Asp Leu
        290                 295                 300

Leu Arg Pro Gln Leu Gln Lys Ala Asn Pro Glu Leu Leu Ala Lys Val
305                 310                 315                 320

Asp Ala Asn Phe Lys Lys Val Asp Thr Ile Leu Ala Lys Tyr Arg Thr
                325                 330                 335

Lys Asp Gly Phe Glu Thr Tyr Asp Lys Leu Thr Asp Ala Asp Arg Asn
            340                 345                 350

Ala Leu Lys Gly Pro Ile Thr Ala Gln Ala Glu Asp Leu Ala Gln Leu
            355                 360                 365

Arg Gly Val Leu Gly Leu Asp
            370             375

<210> SEQ ID NO 127
<211> LENGTH: 236
<212> TYPE: PRT
<213> ORGANISM: Shigella boydii

<400> SEQUENCE: 127

Met Lys Lys Gly Phe Met Leu Phe Thr Leu Leu Ala Ala Phe Ser Gly
1               5                   10                  15

Phe Ala Gln Ala Asp Asp Ala Ala Ile Gln Gln Thr Leu Ala Lys Met
            20                  25                  30

Gly Ile Lys Ser Ser Asp Ile Gln Pro Ala Pro Val Ala Gly Met Lys
            35                  40                  45

Thr Val Leu Thr Asn Ser Gly Val Leu Tyr Ile Thr Asp Asp Gly Lys
50                  55                  60

His Ile Ile Gln Gly Pro Met Tyr Asp Val Ser Gly Ala Ala Pro Val
65                  70                  75                  80

Asn Val Thr Asn Lys Met Leu Leu Lys Gln Leu Asn Ala Leu Glu Lys
                85                  90                  95

Glu Met Ile Val Tyr Lys Ala Pro Gln Glu Lys His Val Ile Thr Val
            100                 105                 110

Phe Thr Asp Ile Thr Cys Gly Tyr Cys His Lys Leu His Glu Gln Met
            115                 120                 125

Ala Asp Tyr Asn Ala Leu Gly Ile Thr Val Arg Tyr Leu Ala Phe Pro
130                 135                 140

Arg Gln Gly Leu Glu Ser Gln Ala Glu Gln Met Lys Ala Ile Trp
145                 150                 155                 160

Cys Ala Lys Asp Lys Asn Lys Ala Phe Asp Asp Val Met Ala Gly Lys
                165                 170                 175

Ala Ala Thr Pro Ala Ser Cys Asp Ile Asp Ile Ala Asp His Tyr Ala
            180                 185                 190

Leu Gly Val Gln Leu Gly Val Ser Gly Thr Pro Ala Ile Val Leu Ser
            195                 200                 205

Asn Gly Thr Leu Val Pro Gly Tyr Gln Pro Pro Lys Glu Met Lys Glu
    210                 215                 220

Phe Leu Asp Glu His Gln Lys Met Thr Ser Gly Asn
225                 230                 235

<210> SEQ ID NO 128
<211> LENGTH: 128
<212> TYPE: PRT
<213> ORGANISM: Shigella dysenteriae

<400> SEQUENCE: 128

Met Ala Gln Gln Phe Tyr Asp Tyr Arg Ile Gln His Arg Ser Asn Asp
1               5                   10                  15

Ile Thr Ala Leu Arg Pro Tyr Leu Ser Asp Lys Leu Ala Thr Leu Leu
            20                  25                  30

Ser Asp Ala Ser Arg Asp Asn Ser His Arg Glu Leu Leu Ser Ser Asp
            35                  40                  45

```
Pro Phe Ser Ser Arg Thr Thr Leu Pro Asp Ser Ala His Val Ala Ser
    50                  55                  60

Ala Ser Thr Ile Pro Asn Arg Asp Ala Arg Asn Ile Pro Leu Arg Val
65                  70                  75                  80

Asp Leu Lys Gln Gly Asp Gln Gly Trp Gln Asp Glu Val Leu Met Ile
                85                  90                  95

Gln Glu Gly Gln Cys Trp Val Ile Asp Asp Val Arg Tyr Leu Gly Gly
                100                 105                 110

Ser Val His Ala Thr Ala Gly Thr Leu Arg Gln Ser Ile Glu Asn Arg
                115                 120                 125

<210> SEQ ID NO 129
<211> LENGTH: 192
<212> TYPE: PRT
<213> ORGANISM: Shigella flexneri

<400> SEQUENCE: 129

Met Lys Arg Leu Glu His Pro Met Lys Phe Lys Thr Asn Lys Leu Ser
1               5                   10                  15

Leu Asn Leu Val Leu Ala Ser Ser Leu Leu Ala Ala Ser Ile Pro Ala
                20                  25                  30

Phe Ala Val Thr Gly Asp Thr Asp Gln Pro Ile His Ile Glu Ser Asp
                35                  40                  45

Gln Gln Ser Leu Asp Met Gln Gly Asn Val Val Thr Phe Thr Gly Asn
            50                  55                  60

Val Ile Val Thr Gln Gly Thr Ile Lys Ile Asn Ala Asp Lys Val Val
65                  70                  75                  80

Val Thr Arg Pro Gly Gly Glu Gln Gly Lys Glu Val Ile Asp Gly Tyr
                85                  90                  95

Gly Lys Pro Ala Thr Phe Tyr Gln Met Gln Asp Asn Gly Lys Pro Val
                100                 105                 110

Glu Gly His Ala Ser Gln Met His Tyr Glu Leu Ala Lys Asp Phe Val
                115                 120                 125

Val Leu Thr Gly Asn Ala Tyr Leu Gln Gln Val Asp Ser Asn Ile Lys
            130                 135                 140

Gly Asp Lys Ile Thr Tyr Leu Val Lys Glu Gln Lys Met Gln Ala Phe
145                 150                 155                 160

Ser Asp Lys Gly Lys Arg Val Thr Thr Val Leu Val Pro Ser Gln Leu
                165                 170                 175

Gln Asp Lys Asn Asn Lys Gly Leu Thr Pro Ala Gln Lys Lys Gly Asn
                180                 185                 190

<210> SEQ ID NO 130
<211> LENGTH: 192
<212> TYPE: PRT
<213> ORGANISM: Shigella flexneri

<400> SEQUENCE: 130

Met Phe Lys Lys Ile Leu Phe Pro Leu Val Ala Leu Phe Met Leu Ala
1               5                   10                  15

Gly Cys Ala Lys Pro Pro Thr Thr Ile Glu Val Ser Pro Thr Ile Thr
                20                  25                  30

Leu Pro Gln Gln Asp Pro Ser Leu Met Gly Val Thr Val Ser Ile Asn
            35                  40                  45

Gly Ala Asp Gln Arg Thr Asp Gln Ala Leu Ala Lys Val Thr Arg Asp
50                  55                  60
```

Asn Gln Ile Val Thr Leu Thr Ala Ser Arg Ala Leu Arg Phe Leu Leu
65                  70                  75                  80

Gln Glu Val Leu Glu Lys Gln Met Thr Ala Arg Gly Tyr Met Val Gly
                85                  90                  95

Pro Asn Gly Pro Val Asn Leu Gln Ile Ile Val Ser Gln Leu Tyr Ala
            100                 105                 110

Asp Val Ser Gln Gly Asn Val Arg Tyr Asn Ile Ala Thr Lys Ala Asp
        115                 120                 125

Ile Ala Ile Ile Ala Thr Ala Gln Asn Gly Asn Lys Met Thr Lys Asn
130                 135                 140

Tyr Arg Ala Ser Tyr Asn Val Glu Gly Ala Phe Gln Ala Ser Asn Lys
145                 150                 155                 160

Asn Ile Ala Asp Ala Val Asn Ser Val Leu Thr Asp Thr Ile Ala Asp
                165                 170                 175

Met Ser Gln Asp Thr Ser Ile His Glu Phe Ile Lys Gln Asn Ala Arg
            180                 185                 190

<210> SEQ ID NO 131
<211> LENGTH: 495
<212> TYPE: PRT
<213> ORGANISM: Shigella boydii

<400> SEQUENCE: 131

Met Gln Met Lys Lys Leu Leu Pro Ile Leu Ile Gly Leu Ser Leu Ser
1               5                   10                  15

Gly Phe Ser Ser Leu Ser Gln Ala Glu Asn Leu Met Gln Val Tyr Gln
                20                  25                  30

Gln Ala Arg Leu Ser Asn Pro Glu Leu Arg Lys Ser Ala Ala Asp Arg
            35                  40                  45

Asp Ala Ala Phe Glu Lys Ile Asn Glu Ala Arg Ser Pro Leu Leu Pro
        50                  55                  60

Gln Leu Gly Leu Gly Ala Asp Tyr Thr Tyr Ser Asn Gly Tyr Arg Asp
65                  70                  75                  80

Ala Asn Gly Ile Asn Ser Asn Ala Thr Ser Ala Ser Leu Gln Leu Ala
                85                  90                  95

Gln Ser Ile Phe Asp Met Ser Lys Trp Arg Ala Leu Thr Leu Gln Glu
            100                 105                 110

Lys Ala Ala Gly Ile Gln Asp Val Thr Tyr Gln Thr Asp Gln Gln Thr
        115                 120                 125

Leu Ile Leu Asn Thr Ala Thr Ala Tyr Phe Asn Val Leu Asn Ala Ile
130                 135                 140

Asp Val Leu Ser Tyr Thr Gln Ala Gln Lys Glu Ala Ile Tyr Arg Gln
145                 150                 155                 160

Leu Asp Gln Thr Thr Gln Arg Phe Asn Val Gly Leu Val Ala Ile Thr
                165                 170                 175

Asp Val Gln Asn Ala Arg Ala Gln Tyr Asp Thr Val Leu Ala Asn Glu
            180                 185                 190

Val Thr Ala Arg Asn Asn Leu Asp Asn Ala Val Glu Gln Leu Arg Gln
        195                 200                 205

Ile Thr Gly Asn Tyr Tyr Pro Glu Leu Ala Ala Leu Asn Val Glu Asn
210                 215                 220

Phe Lys Thr Asp Lys Pro Gln Pro Val Asn Ala Leu Leu Lys Glu Ala
225                 230                 235                 240

Glu Lys Arg Asn Leu Ser Leu Leu Gln Ala Arg Leu Ser Gln Asp Leu 245                 250                 255
Ala Arg Glu Gln Ile Arg Gln Ala Gln Asp Gly His Leu Pro Thr Leu
                260                 265                 270

Asp Leu Thr Ala Ser Thr Gly Ile Ser Asp Thr Ser Tyr Ser Gly Ser
            275                 280                 285

Lys Thr Arg Gly Ala Ala Gly Thr Gln Tyr Asp Asp Ser Asn Met Gly
        290                 295                 300

Gln Asn Lys Val Gly Leu Ser Phe Ser Leu Pro Ile Tyr Gln Gly Gly
305                 310                 315                 320

Met Val Asn Ser Gln Val Lys Gln Ala Gln Tyr Asn Phe Val Gly Ala
                325                 330                 335

Ser Glu Gln Leu Glu Ser Ala His Arg Ser Ile Val Gln Thr Val Arg
            340                 345                 350

Ser Ser Phe Asn Asn Ile Asn Ala Ser Ile Ser Ser Ile Asn Ala Tyr
        355                 360                 365

Lys Gln Ala Val Val Ser Ala Gln Ser Ser Leu Asp Ala Met Glu Ala
370                 375                 380

Gly Tyr Ser Val Gly Thr Arg Thr Ile Val Asp Val Leu Asp Ala Thr
385                 390                 395                 400

Thr Thr Leu Tyr Asn Ala Lys Gln Glu Leu Ala Asn Ala Arg Tyr Asn
                405                 410                 415

Tyr Leu Ile Asn Gln Leu Asn Ile Lys Ser Ala Leu Gly Thr Leu Asn
            420                 425                 430

Glu Gln Asp Leu Leu Ala Leu Asn Asn Ala Leu Ser Lys Pro Val Ser
        435                 440                 445

Thr Asn Pro Glu Asn Val Ala Pro Gln Thr Pro Glu Gln Asn Ala Ile
    450                 455                 460

Ala Asp Gly Tyr Ala Pro Asp Ser Pro Ala Pro Val Val Gln Gln Thr
465                 470                 475                 480

Ser Ala Arg Thr Thr Thr Ser Asn Gly His Asn Pro Phe Arg Asn
                485                 490                 495

<210> SEQ ID NO 132
<211> LENGTH: 252
<212> TYPE: PRT
<213> ORGANISM: Shigella boydii

<400> SEQUENCE: 132

Met Lys Ile Arg Ala Leu Leu Val Ala Met Ser Val Ala Thr Val Leu
1               5                   10                  15

Thr Gly Cys Gln Asn Met Asp Ser Asn Gly Leu Leu Ser Ser Gly Ala
                20                  25                  30

Glu Ala Phe Gln Ala Tyr Ser Leu Ser Asp Ala Gln Val Lys Thr Leu
            35                  40                  45

Ser Asp Gln Ala Cys Gln Glu Met Asp Ser Lys Ala Thr Ile Ala Pro
        50                  55                  60

Ala Asn Ser Glu Tyr Ala Lys Arg Leu Thr Thr Ile Ala Asn Ala Leu
65                  70                  75                  80

Gly Asn Asn Ile Asn Gly Gln Pro Val Asn Tyr Lys Val Tyr Met Ala
                85                  90                  95

Lys Asp Val Asn Ala Phe Ala Met Ala Asn Gly Cys Ile Arg Val Tyr
            100                 105                 110

Ser Gly Leu Met Asp Met Met Thr Asp Asn Glu Val Glu Ala Val Ile
        115                 120                 125

-continued

```
Gly His Glu Met Gly His Val Ala Leu Gly His Val Lys Lys Gly Met
    130                 135                 140

Gln Val Ala Leu Gly Thr Asn Ala Val Arg Val Ala Ala Ala Ser Ala
145                 150                 155                 160

Gly Gly Ile Val Gly Ser Leu Ser Gln Ser Gln Leu Gly Asp Leu Gly
                165                 170                 175

Glu Lys Leu Val Asn Ser Gln Phe Ser Gln Arg Gln Glu Ala Glu Ala
            180                 185                 190

Asp Asp Tyr Ser Tyr Asp Leu Leu Arg Gln Arg Gly Ile Ser Pro Ala
        195                 200                 205

Gly Leu Ala Thr Ser Phe Glu Lys Leu Ala Lys Leu Glu Glu Gly Arg
    210                 215                 220

Gln Ser Ser Met Phe Asp Asp His Pro Ala Ser Ala Glu Arg Ala Gln
225                 230                 235                 240

His Ile Arg Asp Arg Met Ser Ala Asp Gly Ile Lys
                245                 250

<210> SEQ ID NO 133
<211> LENGTH: 188
<212> TYPE: PRT
<213> ORGANISM: Shigella boydii

<400> SEQUENCE: 133

Met Asn Met Thr Lys Gly Ala Leu Ile Leu Ser Leu Ser Phe Leu Leu
1               5                   10                  15

Ala Ala Cys Ser Ser Ile Pro Gln Asn Ile Lys Gly Asn Asn Gln Pro
            20                  25                  30

Asp Ile Gln Lys Ser Phe Val Ala Val His Asn Gln Pro Gly Leu Tyr
        35                  40                  45

Val Gly Gln Gln Ala Arg Phe Gly Gly Lys Val Ile Asn Val Ile Asn
    50                  55                  60

Gly Lys Thr Asp Thr Leu Leu Glu Ile Ala Val Leu Pro Leu Asp Ser
65                  70                  75                  80

Tyr Ala Lys Pro Asp Ile Glu Ala Asn Tyr Gln Gly Arg Leu Leu Ala
                85                  90                  95

Arg Gln Ser Gly Phe Leu Asp Pro Val Asn Tyr Arg Asn His Phe Val
            100                 105                 110

Thr Ile Leu Gly Thr Ile Gln Gly Glu Gln Pro Gly Phe Ile Asn Lys
        115                 120                 125

Val Pro Tyr Asn Phe Leu Glu Val Asn Met Gln Gly Ile Gln Val Trp
    130                 135                 140

His Leu Arg Glu Val Val Asn Thr Thr Tyr Asn Leu Trp Asp Tyr Gly
145                 150                 155                 160

Tyr Gly Ala Phe Trp Pro Glu Pro Gly Trp Gly Ala Pro Tyr Tyr Thr
                165                 170                 175

Asn Ala Val Ser Gln Val Thr Pro Glu Leu Val Lys
            180                 185

<210> SEQ ID NO 134
<211> LENGTH: 201
<212> TYPE: PRT
<213> ORGANISM: Shigella boydii

<400> SEQUENCE: 134

Met Thr Met Thr Arg Leu Lys Ile Ser Lys Thr Leu Arg Ala Val Met
1               5                   10                  15
```

Leu Thr Ser Ala Val Ala Thr Gly Ser Ala Tyr Ala Glu Asn Asn Ala
            20                  25                  30

Gln Thr Thr Asn Glu Ser Ala Gly Gln Lys Val Asp Ser Ser Met Asn
        35                  40                  45

Lys Val Gly Asn Phe Met Asp Asp Ser Ala Ile Thr Ala Lys Val Lys
 50                  55                  60

Ala Ala Leu Val Asp His Asp Asn Ile Lys Ser Thr Asp Ile Ser Val
65                  70                  75                  80

Lys Thr Glu Gln Lys Val Val Thr Leu Ser Gly Phe Val Glu Ser Gln
                85                  90                  95

Ala Gln Ala Glu Glu Ala Val Lys Val Ala Lys Gly Val Glu Gly Val
            100                 105                 110

Thr Ser Val Ser Asp Lys Leu His Val Arg Asp Ala Lys Glu Gly Ser
        115                 120                 125

Val Lys Gly Tyr Ala Gly Asp Thr Ala Thr Thr Ser Glu Ile Lys Ala
130                 135                 140

Lys Leu Leu Ala Asp Asp Ile Val Pro Ser Arg His Val Lys Val Glu
145                 150                 155                 160

Thr Thr Asp Gly Val Val Gln Leu Ser Gly Thr Val Asp Ser Gln Ala
                165                 170                 175

Gln Ser Asp Arg Ala Glu Ser Ile Ala Lys Ala Val Asp Gly Val Lys
            180                 185                 190

Ser Val Lys Asn Asp Leu Lys Thr Lys
        195                 200

<210> SEQ ID NO 135
<211> LENGTH: 765
<212> TYPE: PRT
<213> ORGANISM: Shigella boydii

<400> SEQUENCE: 135

Met Lys Trp Leu Cys Ser Val Gly Ile Ala Val Ser Leu Ala Leu Gln
1               5                   10                  15

Pro Ala Leu Ala Asp Asp Leu Phe Gly Asn His Pro Leu Thr Pro Glu
            20                  25                  30

Ala Arg Asp Ala Phe Val Thr Glu Leu Leu Lys Lys Met Thr Val Asp
        35                  40                  45

Glu Lys Ile Gly Gln Leu Arg Leu Ile Ser Val Gly Pro Asp Asn Pro
 50                  55                  60

Lys Glu Ala Ile Arg Glu Met Ile Lys Asp Gly Gln Val Gly Ala Ile
65                  70                  75                  80

Phe Asn Thr Val Thr Arg Gln Asp Ile Arg Ala Met Gln Asp Gln Val
                85                  90                  95

Met Glu Leu Ser Arg Leu Lys Ile Pro Leu Phe Ala Tyr Asp Val
            100                 105                 110

Leu His Gly Gln Arg Thr Val Phe Pro Ile Ser Leu Gly Leu Ala Ser
        115                 120                 125

Ser Phe Asn Leu Asp Ala Val Lys Thr Val Gly Arg Val Ser Ala Tyr
130                 135                 140

Glu Ala Ala Asp Asp Gly Leu Asn Met Thr Trp Ala Pro Met Val Asp
145                 150                 155                 160

Val Ser Arg Asp Pro Arg Trp Gly Arg Ala Ser Glu Gly Phe Gly Glu
                165                 170                 175

Asp Thr Tyr Leu Thr Ser Thr Met Gly Lys Thr Met Val Glu Ala Met
            180                 185                 190

-continued

```
Gln Gly Lys Ser Pro Ala Asp Arg Tyr Ser Val Met Thr Ser Val Lys
        195                 200                 205

His Phe Ala Ala Tyr Gly Ala Val Glu Gly Gly Lys Glu Tyr Asn Thr
    210                 215                 220

Val Asp Met Ser Pro Gln Arg Leu Phe Asn Asp Tyr Met Pro Pro Tyr
225                 230                 235                 240

Lys Ala Gly Leu Asp Ala Gly Ser Gly Ala Val Met Val Ala Leu Asn
                245                 250                 255

Ser Leu Asn Gly Thr Pro Ala Thr Ser Asp Ser Trp Leu Leu Lys Asp
            260                 265                 270

Val Leu Arg Asp Gln Trp Gly Phe Lys Gly Ile Thr Val Ser Asp His
        275                 280                 285

Gly Ala Ile Lys Glu Leu Ile Lys His Gly Thr Ala Ala Asp Pro Glu
    290                 295                 300

Asp Ala Val Arg Val Ala Leu Lys Ser Gly Ile Asn Met Ser Met Ser
305                 310                 315                 320

Asp Glu Tyr Tyr Ser Lys Tyr Leu Pro Gly Leu Ile Lys Ser Gly Lys
                325                 330                 335

Val Thr Met Ala Glu Leu Asp Asp Ala Ala Arg His Val Leu Asn Val
            340                 345                 350

Lys Tyr Asp Met Gly Leu Phe Asn Asp Pro Tyr Ser His Leu Gly Pro
        355                 360                 365

Lys Glu Ser Asp Pro Val Asp Thr Asn Ala Glu Ser Arg Leu His Arg
    370                 375                 380

Lys Glu Ala Arg Glu Val Ala Arg Glu Ser Leu Val Leu Leu Lys Asn
385                 390                 395                 400

Arg Leu Glu Thr Leu Pro Leu Lys Lys Ser Ala Thr Ile Ala Val Val
                405                 410                 415

Gly Pro Leu Ala Asp Ser Lys Arg Asp Val Met Gly Ser Trp Ser Ala
            420                 425                 430

Ala Gly Val Ala Asp Gln Ser Val Thr Val Leu Thr Gly Ile Lys Asn
        435                 440                 445

Ala Val Gly Glu Asn Gly Lys Val Leu Tyr Ala Lys Gly Ala Asn Val
    450                 455                 460

Thr Ser Asp Lys Gly Ile Ile Asp Phe Leu Asn Gln Tyr Glu Glu Ala
465                 470                 475                 480

Val Lys Val Asp Pro Arg Ser Pro Gln Glu Met Ile Asp Glu Ala Val
                485                 490                 495

Gln Thr Ala Lys Gln Ser Asp Val Val Ala Val Val Gly Glu Ala
            500                 505                 510

Gln Gly Met Ala His Glu Ala Ser Ser Arg Thr Asp Ile Thr Ile Pro
        515                 520                 525

Gln Ser Gln Arg Asp Leu Ile Ala Ala Leu Lys Ala Thr Gly Lys Pro
    530                 535                 540

Leu Val Leu Val Leu Met Asn Gly Arg Pro Leu Ala Leu Val Lys Glu
545                 550                 555                 560

Asp Gln Gln Ala Asp Ala Ile Leu Glu Thr Trp Phe Ala Gly Thr Glu
                565                 570                 575

Gly Gly Asn Ala Ile Ala Asp Val Leu Phe Gly Asp Tyr Asn Pro Ser
            580                 585                 590

Gly Lys Leu Pro Met Ser Phe Pro Arg Ser Val Gly Gln Ile Pro Val
        595                 600                 605
```

-continued

```
Tyr Tyr Ser His Leu Asn Thr Gly Arg Pro Tyr Asn Ala Asp Lys Pro
    610                 615                 620

Asn Lys Tyr Thr Ser Arg Tyr Phe Asp Glu Ala Asn Gly Ala Leu Tyr
625                 630                 635                 640

Pro Phe Gly Tyr Gly Leu Ser Tyr Thr Thr Phe Thr Val Ser Asp Val
                645                 650                 655

Lys Leu Ser Ala Pro Thr Met Lys Arg Asp Gly Lys Val Thr Ala Ser
            660                 665                 670

Val Gln Val Met Asn Thr Gly Lys Arg Glu Gly Ala Thr Val Val Gln
        675                 680                 685

Met Tyr Leu Gln Asp Val Thr Ala Ser Met Ser Arg Pro Val Lys Gln
690                 695                 700

Leu Lys Gly Phe Glu Lys Ile Thr Leu Lys Pro Gly Glu Thr Gln Thr
705                 710                 715                 720

Val Ser Phe Pro Ile Asp Ile Glu Ala Leu Lys Phe Trp Asn Gln Gln
                725                 730                 735

Met Lys Tyr Asp Ala Glu Pro Gly Lys Phe Asn Val Phe Ile Gly Thr
            740                 745                 750

Asp Ser Ala Arg Val Lys Lys Gly Glu Phe Glu Leu Leu
        755                 760                 765

<210> SEQ ID NO 136
<211> LENGTH: 503
<212> TYPE: PRT
<213> ORGANISM: Shigella flexneri

<400> SEQUENCE: 136

Met Glu Phe Ser Val Lys Ser Gly Ser Pro Glu Lys Gln Arg Ser Ala
1               5                   10                  15

Cys Ile Val Val Gly Val Phe Glu Pro Arg Arg Leu Ser Pro Ile Ala
                20                  25                  30

Glu Gln Leu Asp Lys Ile Ser Asp Gly Tyr Ile Ser Ala Leu Leu Arg
            35                  40                  45

Arg Gly Glu Leu Glu Gly Lys Pro Gly Gln Thr Leu Leu His His
    50                  55                  60

Val Pro Asn Val Leu Ser Glu Arg Ile Leu Ile Gly Cys Gly Lys
65                  70                  75                  80

Glu Arg Glu Leu Asp Glu Arg Gln Tyr Lys Gln Val Ile Gln Lys Thr
                85                  90                  95

Ile Asn Thr Leu Asn Asp Thr Gly Ser Met Glu Ala Val Cys Phe Leu
            100                 105                 110

Thr Glu Leu His Val Lys Gly Arg Asn Asn Tyr Trp Lys Val Arg Gln
        115                 120                 125

Ala Val Glu Thr Ala Lys Glu Thr Leu Tyr Ser Phe Asp Gln Leu Lys
    130                 135                 140

Thr Asn Lys Ser Glu Pro Arg Arg Pro Leu Arg Lys Met Val Phe Asn
145                 150                 155                 160

Val Pro Thr Arg Arg Glu Leu Thr Ser Gly Glu Arg Ala Ile Gln His
                165                 170                 175

Gly Gln Ala Ile Ala Ala Gly Ile Lys Ala Ala Lys Asp Leu Gly Asn
            180                 185                 190

Met Pro Pro Asn Ile Cys Asn Ala Ala Tyr Leu Ala Ser Gln Ala Arg
        195                 200                 205

Gln Leu Ala Asp Ser Tyr Ser Lys Asn Val Ile Thr Arg Val Ile Gly
    210                 215                 220
```

-continued

```
Glu Gln Gln Met Lys Glu Leu Gly Met His Ser Tyr Leu Ala Val Gly
225                 230                 235                 240

Gln Gly Ser Gln Asn Glu Ser Leu Met Ser Val Ile Glu Tyr Lys Gly
                245                 250                 255

Asn Ala Ser Glu Asp Ala Arg Pro Ile Val Leu Val Gly Lys Gly Leu
            260                 265                 270

Thr Phe Asp Ser Gly Gly Ile Ser Ile Lys Pro Ser Glu Gly Met Asp
        275                 280                 285

Glu Met Lys Tyr Asp Met Cys Gly Ala Ala Ala Val Tyr Gly Val Met
    290                 295                 300

Arg Met Val Ala Glu Leu Gln Leu Pro Ile Asn Val Ile Gly Val Leu
305                 310                 315                 320

Ala Gly Cys Glu Asn Met Pro Gly Gly Arg Ala Tyr Arg Pro Gly Asp
                325                 330                 335

Val Leu Thr Thr Met Ser Gly Gln Thr Val Glu Val Leu Asn Thr Asp
            340                 345                 350

Ala Glu Gly Arg Leu Val Leu Cys Asp Val Leu Thr Tyr Val Glu Arg
        355                 360                 365

Phe Glu Pro Glu Ala Val Ile Asp Val Ala Thr Leu Thr Gly Ala Cys
    370                 375                 380

Val Ile Ala Leu Gly His His Ile Thr Gly Leu Met Thr Asn His Asn
385                 390                 395                 400

Pro Leu Ala His Glu Leu Ile Ala Ala Ser Glu Gln Ser Gly Asp Arg
                405                 410                 415

Ala Trp Arg Leu Pro Leu Gly Asp Glu Tyr Gln Glu Gln Leu Glu Ser
            420                 425                 430

Asn Phe Ala Asp Met Ala Asn Ile Gly Gly Arg Pro Gly Gly Ala Ile
        435                 440                 445

Thr Ala Gly Cys Phe Leu Ser Arg Phe Thr Arg Lys Tyr Asn Trp Ala
    450                 455                 460

His Leu Asp Ile Ala Gly Thr Ala Trp Arg Ser Gly Lys Ala Lys Gly
465                 470                 475                 480

Ala Thr Gly Arg Pro Val Ala Leu Leu Ala Gln Phe Leu Leu Asn Arg
                485                 490                 495

Ala Gly Phe Asn Gly Glu Glu
            500
```

HYPERBLEBBING *SHIGELLA* STRAINS

This application incorporates by reference the contents of a 437 kb text file created on May 18, 2016 and named "15094077substitutesequencelisting.txt," which is the sequence listing for this application.

TECHNICAL FIELD

This invention is in the field of immunisation against *Shigella* species.

BACKGROUND ART

*Shigella* are Gram-negative non-motile facultative anaerobic bacilli that fall into four serogroups: *S. dysenteriae, S. flexneri, S. boydii* and *S. sonnei*. They cause shigellosis (bacillary dysentery).

The hallmark of clinical shigellosis is an acute rectocolitis associated with fever, nausea, anorexia, dehydration, mucopurulent and bloody diarrhea, and tenesmus. *Shigella*-caused dysentery is endemic and causes millions of illness episodes in developing countries. For example, there are estimated to be 165 million cases of *Shigella* diarrhea per year, 99% of which occur in developing countries and 69% of which occur in children under five years of age. The morbidity and mortality due to shigellosis are especially high among children in developing countries.

Existing approaches to *Shigella* vaccines were reviewed in ref 1 and have been based on live attenuated strains for oral immunisation, conjugated 0 saccharides for injection, proteosomes (meningococcal outer membrane vesicles with attached *Shigella* LPS) for intranasal use, invaplexes (subcellular extracts of *Shigella* including IpaB, IpaC and LPS) for intranasal use, and nuclear protein-ribosomal complexes prepared from msbB$^{-ve}$ strains with detoxified LPS.

Although some of these vaccines have been efficacious in field trials, none protects against multiple *Shigella* serotypes.

It is an object of the invention to provide further and improved components useful in preparing *Shigella* vaccines, and in particular vaccines which can protect against multiple serotypes.

DISCLOSURE OF THE INVENTION

*Shigella* spontaneously release outer membrane blebs during growth due to the turgour pressure of the cell envelope. As disclosed in reference 2, release of the blebs is highly dependent on the bacterial envelope structure. The inventors have used a mutant strain of *Shigella* in which the Tol-Pal system has been disrupted to disturb the envelope structure. During normal growth these mutant strains release into their culture medium large quantities of blebs which are rich in immunogenic outer membrane proteins, and these blebs can thus be used as immunogens.

Thus the invention provides a *Shigella* bacterium which expresses no more than 4 of TolA, TolB, TolQ, TolR and Pal proteins. Thus at least one protein from the natural five-protein Tol-Pal system is absent, resulting in a bacterium which, during growth in culture medium, releases greater quantities of outer membrane blebs into the medium than the same bacterium expressing all 5 Tol-Pal proteins. Preferably TolR is not expressed, but the other four proteins may be expressed.

The invention also provides a *Shigella* bacterium which does not express a TolR protein. The invention also provides a ΔtolR strain of *Shigella*, such as a ΔtolRΔgalU strain.

The invention also provides a *Shigella* bacterium which expresses TolA, TolB, TolQ, TolR and Pal proteins, wherein the TolA, TolQ, TolR and/or Pal protein (a) is located in the bacterium's inner or outer membrane, and (b) includes one or more amino acid sequence mutation(s) such that, compared to the same bacterium without said mutation(s), the bacterium releases greater quantities of outer membrane blebs when growing in culture medium.

The invention also provides a *Shigella* bacterium in which one or more components of its Tol-Pal system has a modification such that, during growth in culture medium, the bacterium releases greater quantities of outer membrane blebs into the medium than the same bacterium lacking the modification, and which does not express: (i) a native *Shigella* lipopolysaccharide and/or (ii) a *Shigella* enteric toxin.

The invention also provides a method of preparing a hyperblebbing *Shigella* bacterium, comprising a step of modifying gene(s) encoding one or more components of a starting bacterium's Tol-Pal system such that the modification causes the bacterium, when grown in culture medium, to release greater quantities of outer membrane blebs into the medium than the starting bacterium, and wherein the modification involves mutating one or more of the starting bacterium's tolA, tolB, tolQ, tolR and/or pal genes. The mutating step may delete the gene. The method may also involve modification of gene(s) encoding a protein required for synthesis of the bacterium's lipopolysaccharide or an enteric toxin.

The invention also provides a bleb isolated or obtainable from a bacterium of the invention. These blebs are useful as components of *Shigella* vaccines.

The invention also provides a process for preparing *Shigella* blebs, comprising a step of separating the blebs from a culture medium comprising bacteria of the invention which have been grown under conditions which permit the release of blebs into the medium by the bacteria. Blebs prepared by this process can be used as components of *Shigella* vaccines.

The invention also provides a culture medium comprising bacteria of the invention which have been grown under conditions which permit the release of blebs into the medium by the bacteria. Blebs may be purified from this culture medium.

The invention also provides a composition comprising blebs that, during culture of bacteria of the invention, are released into the culture medium. This composition does not comprise any living and/or whole bacteria. This composition and/or its components can be used for *Shigella* vaccine preparation.

The invention also provides a composition comprising blebs, wherein the blobs are present in the filtrate obtainable after filtration through a 0.22 μm filter of a culture medium in which a bacterium of the invention has been grown. This composition and/or its components can be used for *Shigella* vaccine preparation.

The invention also provides a *Shigella* bleb which includes one or more (i.e. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59 or 60) of: (a) a protein consisting of an amino acid sequence selected from SEQ ID NOs: 8 to 67; (b) a protein comprising an amino acid sequence having at least j % identity to one of SEQ ID NOs: 8 to 67, where j is 50 or more (e.g. 60, 65, 70, 75, 80, 85, 90, 91, 92, 93, 94, 95, 96, 97, 98, 99) and/or comprising a fragment of at least n consecutive amino acids of any one of SEQ ID NOs: 8 to 67, wherein n is 7 or more (e.g. 8, 10, 12, 14, 16, 18, 20, 25, 30, 35, 40, 50, 60, 70, 80, 90, 100, 150, 200, 250 or more). Preferred fragments comprise an epitope from one of SEQ ID NOs: 8 to 67. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of the SEQ ID NO: while retaining at least one epitope of the SEQ ID NO. Other fragments omit one or more protein domains e.g. lacking a signal peptide, etc.

60 proteins have been confirmed as present within blebs of the invention and to be immunoreactive with sera prepared against the blebs. Thus the individual proteins may be used as immunogenic components in purified form, separate from the blebs. Thus the invention also provides a bleb-free immunogenic composition comprising a bleb protein comprising: (a) one or more (e.g. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59 or 60) of amino acid sequences SEQ ID NOs 8 to 67; (b) an amino acid sequence having at least j % identity to one of SEQ ID NOs: 8 to 67, where j is 50 or more (e.g. 60, 65, 70, 75, 80, 85, 90, 91, 92, 93, 94, 95, 96, 97, 98, 99) and/or comprising a fragment of at least n consecutive amino acids of any one of SEQ ID NOs: 8 to 67, wherein n is 7 or more (e.g. 8, 10, 12, 14, 16, 18, 20, 25, 30, 35, 40, 50, 60, 70, 80, 90, 100, 150, 200, 250 or more). Preferred fragments comprise an epitope from one of SEQ ID NOs: 8 to 67, and more preferred fragments are immunogenic fragments. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of a SEQ ID NO: while retaining at least one epitope of the SEQ ID NO. Other fragments omit one or more protein domains e.g. lacking a transmembrane domain, a signal peptide, etc.

The invention also provides a *Shigella* bleb which includes one or more (i.e. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128 or 129) of: (a) a protein consisting of an amino acid sequence selected from SEQ ID NOs: 8 to 136; (b) a protein comprising an amino acid sequence having at least j % identity to one of SEQ ID NOs: 8 to 136, where j is 50 or more (e.g. 60, 65, 70, 75, 80, 85, 90, 91, 92, 93, 94, 95, 96, 97, 98, 99) and/or comprising a fragment of at least n consecutive amino acids of any one of SEQ ID NOs: 8 to 136, wherein n is 7 or more (e.g. 8, 10, 12, 14, 16, 18, 20, 25, 30, 35, 40, 50, 60, 70, 80, 90, 100, 150, 200, 250 or more). Preferred fragments comprise an epitope from one of SEQ ID NOs: 8 to 136. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of the SEQ ID NO: while retaining at least one epitope of the SEQ ID NO. Other fragments omit one or more protein domains e.g. lacking a signal peptide. etc.

129 proteins have been confirmed as present within blebs of the invention and to be immunoreactive with sera prepared against the blebs. Thus the individual proteins may be used as immunogenic components in purified form, separate from the blebs. Thus the invention also provides a bleb-free immunogenic composition comprising a bleb protein comprising: (a) one or more (e.g. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128 or 129) of amino acid sequences SEQ ID NOs 8 to 136; (b) an amino acid sequence having at least j % identity to one of SEQ ID NOs: 8 to 136, where j is 50 or more (e.g. 60, 65, 70, 75, 80, 85, 90, 91, 92, 93, 94, 95, 96, 97, 98, 99) and/or comprising a fragment of at least n consecutive amino acids of any one of SEQ ID NOs: 8 to 136, wherein n is 7 or more (e.g. 8, 10, 12, 14, 16, 18, 20, 25, 30, 35, 40, 50, 60, 70, 80, 90, 100, 150, 200, 250 or more). Preferred fragments comprise an epitope from one of SEQ ID NOs: 8 to 136, and more preferred fragments are immunogenic fragments. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of a SEQ ID NO: while retaining at least one epitope of the SEQ ID NO. Other fragments omit one or more protein domains e.g. lacking a transmembrane domain, a signal peptide, etc.

Within SEQ ID NOs: 8 to 136, a preferred subset in relation to *S. flexneri* is the SEQ ID NOs: listed in "Subset 1" beneath Table 1. Within SEQ ID NOs: 8 to 136, a preferred subset in relation to *S. sonnei* is the SEQ ID NOs: listed in "Subset 2" beneath Table 1

The Tol-Pal System

Like many Gram-negative bacteria, the *Shigella* naturally possess a Tol-Pal system which is made up of TolA, TolB, TolQ, TolR and Pal proteins. According to the invention, the natural Tol-Pal system is disrupted, thereby causing the bacterium to release greater quantities of outer membrane blebs into its culture medium during bacterial replication. Various disruptions can be made.

In some embodiments, at least one of the five Tol-Pal proteins is removed e.g. by deletion or inactivation of the gene encoding the protein. Thus the bacterium may express 0, 1, 2, 3 or 4 of TolA, TolB, TolQ, TolR and Pal proteins. Removal of one of the five proteins can suffice, in which case the bacterium expresses only 4 of these proteins. Preferably the TolR protein is removed e.g. by inactivation of a starting strain's tolR gene. Thus the bacterium may be $tolA^+$ $tolB^+$ $tolQ^+$ $TolR^-$ $Pal^+$.

In some embodiments, the bacterium expresses all five Tol-Pal proteins, but at least one is mutated to cause hyperblebbing. For instance, the TolA, TolQ, TolR and/or Pal protein may be mutated such that the protein retains its membrane localisation but its interactions with other members of the Tol-Pal system are disrupted. The bacterium will thus retain TolA, TolQ and TolR as transmembrane proteins in the inner membrane, and Pal protein as a periplasm-facing lipoprotein in the outer membrane, but at least one of the TolA, TolQ, TolR and/or Pal proteins is mutated.

Examples of wild-type *Shigella* amino acid sequences of the TolA, TolB, TolQ, TolR and Pal proteins are given in the sequence listing as SEQ ID NOs: 1 to 5.

The *Shigella* Bacterium The invention can be used with any of serogroups *S. dysenteriae*, *S. flexneri*, *S. boydii* and *S. sonnei*.

In addition to having a disrupted Tol-Pal system, thereby causing the bacterium to release greater quantities of outer membrane blebs into its culture medium during bacterial replication, a *Shigella* of the invention can advantageously include one or more further changes relative to a wild-type strain. These changes can be used in particular to remove components from the bacterium which would be toxic or undesirable in a human vaccine.

For example, a bacterium may not express native *Shigella* lipopolysaccharide (LPS), thereby reducing endotoxin activity. Various modifications can be made to prevent synthesis of native LPS, and these may disrupt the native lipid A structure, the oligosaccharide core, or the outer O antigen. For example, reference 3 reports LPS mutants caused by inactivation of the de and galU genes, and reference 4 reports LPS mutants caused by inactivation of yihE, galE, galK, galM and galT. Similarly, reference 5 reports defective LPS due to mutations in rfc, rfaL, or galU. Reference 6 reports LPS mutants caused by inactivation of msbB1 and msbB2, reducing acylation in lipid A. As shown herein, another LPS mutant with reduced lipid A acylation can be generated by inactivation of htrB [7, 8].

Absence of O antigen in the LPS is preferred, thereby avoiding serotype-specific responses. In *S. sonnei* the O antigen is absent when the virulence plasmid is removed (see below). The galU gene codes for uridine diphosphoglucose (UDP-glucose) pyrophosphorylase and its inactivation results in synthesis of LPS with no attached O antigen. Inactivation of galU is useful for providing a *Shigella* without uridine diphosphoglucose pyrophosphorylase activity. Inactivation of rfbF and/or rfbG genes can be used to provide a *Shigella* without rhamnosyl transferase activity. Inactivation of rfc can be used to provide a *Shigella* without O antigen polymerase activity. Inactivation of all three of rfbF, rfbG and rfc can provide a useful strain.

Absence of hexa-acylated lipid A in the LPS is preferred. Loss of the virulence plasmid (see below) automatically leads to loss of the msbB2 gene, and the chromosomal msbB1 gene can be inactivated, thereby removing myristoyl transferase activity and providing a penta-acylated lipid A in the LPS. Inactivation of the HtrB lauroyl transferase can provide *Shigella* with mainly tetra-acylated lipid A. Preferred strains have penta- or tetra-acylated LPS.

Preferred strains are inactivated for both galU and msbB1 and also lack the virulence plasmid, thereby providing a strain whose LPS is penta-acylated and lacks attached O antigen.

Some useful strains have penta- or tetra-acylated LPS which includes attached O antigen. More generally, though, preferred strains have penta- or tetra-acylated LPS which lacks attached O antigen. A *S. flexneri*, strain with tolR, rfbG and htrB knockouts (and, optionally, rfbF and/or rfc inactivation) is useful. A useful *S. sonnei* strain has a tolR mutation and lacks a virulence plasmid.

A bacterium may not express an enteric toxin. For instance, a *S. flexneri* strain (particularly a 2a strain) may not express all of the subunits of *Shigella* enterotoxin 1 (ShET-1) e.g. the set1A and/or set1B genes can be inactivated. A *S. dysenteriae* strain may not express both subunits of Shiga toxin e.g. one or both of the stxA and/or stxB genes can be inactivated. A *Shigella*, particularly a *S. sonnei* or *S. flexneri*, may not express enterotoxin 2 (ShET-2) e.g. the ospD3 gene may be inactivated, or the virulence plasmid may be absent. Preferred strains encode none of ShET-1, ShET-2 and Shiga toxin.

*Shigella* bacteria of the invention can be prepared conveniently from wild-type or other starting strains using conventional techniques of mutagenesis e.g. see references 9 to 11. The lambda red recombination system is particularly useful with *Shigella*. Inactivation of a gene can be achieved in various ways e.g. by deletion or mutation in its promoter, by deletion or mutation of its start codon, by introduction of a premature stop codon, by deletion of the complete coding region, by knockout, etc. Isogenic knockout mutants are preferred. In the resulting *Shigella* bacterium, mRNA encoding the desired gene is absent and/or its translation is inhibited (e.g. to less than 1% of wild-type levels).

A *Shigella* bacterium of the invention may contain a marker gene in place of the inactivated gene e.g an antibiotic resistance marker. This can be achieved using homologous recombination. Preferably, though, unmarked deletions (i.e. deletion without introduction of a marker gene) are used.

Virulent *Shigella* strains possess a 220 kb plasmid that mediates virulence properties. This "virulence plasmid" has been shown to encode the genes for several aspects of *Shigella* virulence, including adhesins for target epithelial cells, the invasion plasmid antigens, virF, virG, etc. A *Shigella* of the invention may possess a virulence plasmid but, preferably, it does not possess a virulence plasmid. Absence of the plasmid can stabilise the strain during industrial culture, attenuate the strain by removing virulence factors (thereby increasing safety of manufacture), disrupt the lipopolysaccharide (the biosynthesis genes for the O antigen are on the plasmid in *S. sonnei*), avoid the presence of the ShET-2 enterotoxin (encoded by the ospD3 or sen gene on the plasmid), and avoid the presence of msbB2 which is a second copy of the msbB gene responsible for acylation of lipid A.

A *Shigella* of the invention may express one or more heterologous proteins e.g. proteins which are not naturally found in *Shigella*. If the heterologous protein is an outer membrane protein then blebs from the strain can be used as a delivery system for presenting non-*Shigella* antigens to the immune system.

Culture conditions for growing *Shigella* are well known in the art e.g. see references 12 to 14. For example, they may be grown using an organic nitrogen source (such as amino acid mixtures e.g. containing Ala, Arg, Asn, Asp; casamino acids may be used), glycerol as a carbon source, etc. Inclusion of L-aspartic acid in the medium is particularly useful and may function as both a nitrogen and carbon source.

Advantageously, *Shigella* of the invention may be grown under iron-limiting conditions as this has been shown to up-regulate iron-regulated proteins which are immunogenic and highly-conserved among *Shigella* spp. For instance, the bacteria may be grown in the presence of a compound such as desferal or 2,2'-dipyridyl or 8-hydroxyquinoline. Under these conditions the bacterium may increase expression of proteins such as the FepA outer membrane receptor, the colicin I receptor (CirA), and/or the ferric siderophore receptor (FhuA).

Blebs and Hyperblebbing

*Shigella* bacteria of the invention are, relative to their corresponding wild-type strains, hyperblebbing i.e. they release into their culture medium larger quantities of blebs than the wild-type strain. These blebs are useful as components of *Shigella* vaccines.

The blebs typically have a diameter of 35-120 nm by electron microscopy e.g. 50 nm diameter.

The blebs are released spontaneously during bacterial growth and can be purified from the culture medium. The purification ideally involves separating the blebs from living and/or intact *Shigella* bacteria e.g. by size-based filtration using a filter, such as a 0.22 µm filter, which allows the blebs to pass through but which does not allow intact bacteria to pass through, or by using low speed centrifugation to pellet cells while leaving blebs in suspension.

Thus, unlike the culture medium, bleb-containing compositions of the invention will generally be substantially free from whole bacteria, whether living or dead. The size of the blebs means that they can readily be separated from whole bacteria by filtration e.g. as typically used for filter sterilisation. Although blebs will pass through a standard 0.22 μm filters, these can rapidly become clogged by other material, and so it may be useful to perform sequential steps of filter sterilisation through a series of filters of decreasing pore size before using a 0.22 μm filter. Examples of preceding filters would be those with pore size of 0.8 μm, 0.45 μm, etc.

Separation of spontaneously-released Webs from the culture medium is more convenient than methods which involve deliberate disruption of the outer membrane (e.g. by detergent treatment or sonication) to cause outer membrane vesicles to form. Moreover, they are substantially free from inner membrane and cytoplasmic contamination.

Blebs of the invention contain lipids and proteins. The protein content of the blebs has been analysed, and they include the proteins listed in Table 1 and discussed below.

*Shigella* Outer Membrane Proteins

Table 1 lists the GenBank name and GI number for 129 proteins which were detected in *Shigella* blebs of the invention. These 127 proteins may be used as immunogenic components in purified form, separate from blebs. A preferred subset of the 129 is the first 60 in the list ("Subset 3").

Polypeptides can be prepared by various means e.g. by chemical synthesis (at least in part), by digesting longer polypeptides using proteases, by translation from RNA, by purification from cell culture (e.g. from recombinant expression or from *Shigella* culture). etc. Heterologous expression in an *E. coli* host is a preferred expression route.

Polypeptides of the invention may be attached or immobilised to a solid support. Polypeptides of the invention may comprise a detectable label e.g. a radioactive label, a fluorescent label, or a biotin label. This is particularly useful in immunoassay techniques.

Polypeptides can take various forms (e.g. native, fusions, glycosylated, non-glycosylated, lipidated, disulfide bridges, etc.). Polypeptides are preferably *Shigella* polypeptides.

Polypeptides are preferably prepared in substantially pure or substantially isolated form (i.e. substantially free from other *Shigella* or host cell polypeptides) or substantially isolated form. In general, the polypeptides are provided in a non-naturally occurring environment e.g. they are separated from their naturally-occurring environment. In certain embodiments, the subject polypeptide is present in a composition that is enriched for the polypeptide as compared to a control. As such, purified polypeptide is provided, whereby purified is meant that the polypeptide is present in a composition that is substantially free of other expressed polypeptides, where by substantially free is meant that less than 50%, usually less than 30% and more usually less than 10% of the composition is made up of other expressed polypeptides.

The term "polypeptide" refers to amino acid polymers of any length. The polymer may be linear or branched, it may comprise modified amino acids, and it may be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art. Polypeptides can occur as single chains or associated chains.

Pharmaceutical Compositions

The invention provides a pharmaceutical composition comprising (a) blebs of the invention and (b) a pharmaceutically acceptable carrier. The invention also provides a process for preparing such a composition, comprising the step of admixing blebs of the invention with a pharmaceutically acceptable carrier.

The invention also provides a pharmaceutical composition comprising (a) the bleb-free immunogenic composition defined above and (b) a pharmaceutically acceptable carrier, The immunogenic composition may include a pharmaceutically acceptable carrier, which can be any substance that does not itself induce the production of antibodies harmful to the patient receiving the composition, and which can be administered without undue toxicity. Pharmaceutically acceptable carriers can include liquids such as water, saline, glycerol and ethanol. Auxiliary substances, such as wetting or emulsifying agents, pH buffering substances, and the like, can also be present in such vehicles. A thorough discussion of suitable carriers is available in ref. 15.

*Shigella* infections can affect various areas of the body and so the compositions of the invention may be prepared in various forms. For example, the compositions may be prepared as injectables, either as liquid solutions or suspensions. Solid forms suitable for solution in, or suspension in, liquid vehicles prior to injection can also be prepared. The composition may be prepared for topical administration e.g. as an ointment, cream or powder. The composition be prepared for oral administration e.g. as a tablet or capsule, or as a syrup (optionally flavoured). The composition may be prepared for pulmonary administration e.g. as an inhaler, using a fine powder or a spray. The composition may be prepared as a suppository or pessary. The composition may be prepared for nasal, aural or ocular administration e.g. as drops.

The composition is preferably sterile. It is preferably pyrogen-free. It is preferably buffered e.g. at between pH 6 and pH 8, generally around pH 7. Compositions of the invention may be isotonic with respect to humans.

Immunogenic compositions comprise an immunologically effective amount of immunogen, as well as any other of other specified components, as needed. By 'immunologically effective amount', it is meant that the administration of that amount to an individual, either in a single dose or as part of a series, is effective for treatment or prevention. This amount varies depending upon the health and physical condition of the individual to be treated, age, the taxonomic group of individual to be treated (e.g. non-human primate, primate, etc.), the capacity of the individual's immune system to synthesise antibodies, the degree of protection desired, the formulation of the vaccine, the treating doctor's assessment of the medical situation, and other relevant factors. It is expected that the amount will fall in a relatively broad range that can be determined through routine trials.

Previous work with vesicle vaccines (e.g. for meningococcus) offers pharmaceutical, posological and formulation guidance for administering blebs. The concentration of blebs in compositions of the invention will generally be between 10 and 500 µg/ml, preferably between 25 and 200 µg/ml, and more preferably about 50 µg/ml or about 100 µg/ml (expressed in terms of total protein in the blebs). A dosage volume of 0.5 ml is typical for injection.

The composition may be administered in conjunction with other immunoregulatory agents.

Adjuvants which may be used in compositions of the invention (particularly in bleb-free compositions) include, but are not limited to:

A. Mineral-Containing Compositions

Mineral containing compositions suitable for use as adjuvants in the invention include mineral salts, such as aluminium salts and calcium salts. The invention includes mineral salts such as hydroxides (e.g. oxyhydroxides), phosphates (e.g. hydroxyphosphates, orthophosphates), sulphates, etc. [e.g. see chapters 8 & 9 of ref 19], or mixtures of different mineral compounds, with the compounds taking any suitable form (e.g. gel, crystalline, amorphous, etc.), and with adsorption being preferred. The mineral containing compositions may also be formulated as a particle of metal salt.

The adjuvants known as "aluminium hydroxide" are typically aluminium oxyhydroxide salts, which are usually at least partially crystalline. Aluminium oxyhydroxide, which can be represented by the formula AlO(OH), can be distinguished from other aluminium compounds, such as aluminium hydroxide Al(OH)$_3$, by infrared (IR) spectroscopy, in particular by the presence of an adsorption band at 1070 cm$^{-1}$ and a strong shoulder at 3090-3100 cm$^{-1}$ [chapter 9 of ref. 19]. The degree of crystallinity of an aluminium hydroxide adjuvant is reflected by the width of the diffraction band at half height (WHH), with poorly-crystalline particles showing greater line broadening due to smaller crystallite sizes. The surface area increases as WHH increases, and adjuvants with higher WHH values have been seen to have greater capacity for antigen adsorption. A fibrous morphology (e.g. as seen in transmission electron micrographs) is typical for aluminium hydroxide adjuvants. The pI of aluminium hydroxide adjuvants is typically about 11 i.e. the adjuvant itself has a positive surface charge at physiological pH. Adsorptive capacities of between 1.8-2.6 mg protein per mg Al$^{+++}$ at pH 7.4 have been reported for aluminium hydroxide adjuvants.

The adjuvants known as "aluminium phosphate" are typically aluminium hydroxyphosphates, often also containing a small amount of sulfate (i.e. aluminium hydroxyphosphate sulfate). They may be obtained by precipitation, and the reaction conditions and concentrations during precipitation influence the degree of substitution of phosphate for hydroxyl in the salt. Hydroxyphosphates generally have a PO$_4$/Al molar ratio between 0.3 and 1.2. Hydroxyphosphates can be distinguished from strict AlPO$_4$ by the presence of hydroxyl groups. For example, an IR spectrum band at 3164 cm$^{-1}$ (e.g. at 200° C.) indicates the presence of structural hydroxyls [ch. 9 of ref. 19].

The PO$_4$/Al$^{3+}$ molar ratio of an aluminium phosphate adjuvant will generally be between 0.3 and 1.2, preferably between 0.8 and 1.2, and more preferably 0.95±0.1. The aluminium phosphate will generally be amorphous, particularly for hydroxyphosphate salts. A typical adjuvant is amorphous aluminium hydroxyphosphate with PO$_4$/Al molar ratio between 0.84 and 0.92, included at 0.6 mg Al$^{3+}$/ml. The aluminium phosphate will generally be particulate (e.g. plate-like morphology as seen in transmission electron micrographs). Typical diameters of the particles are in the range 0.5-20 µm (e.g. about 5-10 µm) after any antigen adsorption. Adsorptive capacities of between 0.7-1.5 mg protein per mg Al$^{+++}$ at pH 7.4 have been reported for aluminium phosphate adjuvants.

The point of zero charge (PZC) of aluminium phosphate is inversely related to the degree of substitution of phosphate for hydroxyl, and this degree of substitution can vary depending on reaction conditions and concentration of reactants used for preparing the salt by precipitation. PZC is also altered by changing the concentration of free phosphate ions in solution (more phosphate=more acidic PZC) or by adding a buffer such as a histidine buffer (makes PZC more basic). Aluminium phosphates used according to the invention will generally have a PZC of between 4.0 and 7.0, more preferably between 5.0 and 6.5 e.g. about 5.7.

Suspensions of aluminium salts used to prepare compositions of the invention may contain a buffer (e.g. a phosphate or a histidine or a Tris buffer), but this is not always necessary. The suspensions are preferably sterile and pyrogen-free. A suspension may include free aqueous phosphate ions e.g. present at a concentration between 1.0 and 20 mM, preferably between 5 and 15 mM, and more preferably about 10 mM. The suspensions may also comprise sodium chloride.

In one embodiment, an adjuvant component includes a mixture of both an aluminium hydroxide and an aluminium phosphate. In this case there may be more aluminium phosphate than hydroxide e.g. a weight ratio of at least 2:1 e.g. ≥5:1, ≥6:1, ≥7:1, ≥8:1, ≥9:1, etc.

The concentration of Al$^{+++}$ in a composition for administration to a patient is preferably less than 10 mg/ml e.g. ≤5 mg/ml, ≤4 mg/ml, ≤3 mg/ml, ≤2 mg/ml, ≤1 mg/ml, etc. A preferred range is between 0.3 and 1 mg/ml. A maximum of <0.85 mg/dose is preferred.

B. Oil Emulsions

Oil emulsion compositions suitable for use as adjuvants in the invention include squalene-water emulsions, such as MF59 [Chapter 10 of ref. 19; see also ref 16] (5% Squalene, 0.5% Tween 80, and 0.5% Span 85, formulated into submicron particles using a microfluidizer). Complete Freund's adjuvant (CFA) and incomplete Freund's adjuvant (IFA) may also be used.

Various suitable oin-in-water emulsions are known, and they typically include at least one oil and at least one surfactant, with the oil(s) and surfactant(s) being biodegradable (metabolisable) and biocompatible. The oil droplets in the emulsion are generally less than 5 µm in diameter, and advantageously the emulsion comprises oil droplets with a sub-micron diameter, with these small sizes being achieved with a microfluidiser to provide stable emulsions. Droplets with a size less than 220 nm are preferred as they can be subjected to filter sterilization.

The invention can be used with oils such as those from an animal (such as fish) or vegetable source. Sources for vegetable oils include nuts, seeds and grains. Peanut oil, soybean oil, coconut oil, and olive oil, the most commonly available, exemplify the nut oils. Jojoba oil can be used e.g. obtained from the jojoba bean. Seed oils include safflower oil, cottonseed oil, sunflower seed oil, sesame seed oil and the like. In the grain group, corn oil is the most readily available, but the oil of other cereal grains such as wheat, oats, rye, rice, teff, triticale and the like may also be used. 6-10 carbon fatty acid esters of glycerol and 1,2-propanediol, while not occurring naturally in seed oils, may be prepared by hydrolysis, separation and esterification of the appropriate materials starting from the nut and seed oils. Fats and oils from mammalian milk are metabolizable and may therefore be used in the practice of this invention. The procedures for separation, purification, saponification and other means necessary for obtaining pure oils from animal sources are well known in the art. Most fish contain metabolizable oils which may be readily recovered. For example, cod liver oil, shark liver oils, and whale oil such as spermaceti exemplify several of the fish oils which may be used herein. A number of branched chain oils are synthesized biochemically in 5-carbon isoprene units and are generally referred to as terpenoids. Shark liver oil contains a branched, unsaturated terpenoid known as squalene, 2,6,10,15,19,23-hexamethyl-2,6,10,14,18,22-tetracosahexaene. Other preferred oils are the tocopherols (see below). Oil in water emulsions comprising sqlauene are particularly preferred. Mixtures of oils can be used.

Surfactants can be classified by their 'HLB' (hydrophile/lipophile balance). Preferred surfactants of the invention have a HLB of at least 10, preferably at least 15, and more preferably at least 16. The invention can be used with surfactants including, but not limited to: the polyoxyethylene sorbitan esters surfactants (commonly referred to as the Tweens), especially polysorbate 20 and polysorbate 80; copolymers of ethylene oxide (EO), propylene oxide (PO), and/or butylene oxide (BO), sold under the DOWFAX™ tradename, such as linear BO/PO block copolymers; octoxynols, which can vary in the number of repeating ethoxy (oxy-1,2-ethanediyl) groups, with octoxynol-9 (Triton X-100, or t-octylphenoxypolyethoxyethanol) being of particular interest; (octylphenoxy)polyethoxyethanol (IGEPAL CA-630/NP-40); phospholipids such as phosphatidylcholine (lecithin); polyoxyethylene fatty ethers derived from lauryl, cetyl, stearyl and oleyl alcohols (known as Brij surfactants), such as triethyleneglycol monolauryl ether (Brij 30); and sorbitan esters (commonly known as the SPANs), such as sorbitan trioleate (Span 85) and sorbitan monolaurate. Preferred surfactants for including in the emulsion are Tween 80 (polyoxyethylene sorbitan monooleate), Span 85 (sorbitan trioleate), lecithin and Triton X-100. As mentioned above, detergents such as Tween 80 may contribute to the thermal stability seen in the examples below.

Mixtures of surfactants can be used e.g. Tween 80/Span 85 mixtures. A combination of a polyoxyethylene sorbitan ester such as polyoxyethylene sorbitan monooleate (Tween 80) and an octoxynol such as t-octylphenoxypolyethoxyethanol (Triton X-100) is also suitable. Another useful combination comprises laureth 9 plus a polyoxyethylene sorbitan ester and/or an octoxynol.

Preferred amounts of surfactants (% by weight) are: polyoxyethylene sorbitan esters (such as Tween 80) 0.01 to 1%, in particular about 0.1%; octyl- or nonylphenoxy polyoxyethanols (such as Triton X-100, or other detergents in the Triton series) 0.001 to 0.1%, in particular 0.005 to 0.02%; polyoxyethylene ethers (such as laureth 9) 0.1 to 20%, preferably 0.1 to 10% and in particular 0.1 to 1% or about 0.5%.

Specific oil-in-water emulsion adjuvants useful with the invention include, but are not limited to:

A submicron emulsion of squalene, Tween 80, and Span 85. The composition of the emulsion by volume can be about 5% squalene, about 0.5% polysorbate 80 and about 0.5% Span 85. In weight terms, these ratios become 4.3% squalene, 0.5% polysorbate 80 and 0.48% Span 85. This adjuvant is known as 'MF59' [16-18], as described in more detail in Chapter 10 of ref. 19 and chapter 12 of ref. 20. The MF59 emulsion advantageously includes citrate ions e.g. 10 mM sodium citrate buffer.

An emulsion comprising squalene, an α-tocopherol, and polysorbate 80. These emulsions may have from 2 to 10% squalene, from 2 to 10% tocopherol and from 0.3 to 3% Tween 80, and the weight ratio of squalene: tocopherol is preferably ≤1 (e.g. 0.90) as this provides a more stable emulsion. Squalene and Tween 80 may be present volume ratio of about 5:2, or at a weight ratio of about 11:5. One such emulsion can be made by dissolving Tween 80 in PBS to give a 2% solution, then mixing 90 ml of this solution with a mixture of (5 g of DL-α-tocopherol and 5 ml squalene), then microfluidising the mixture. The resulting emulsion may have submicron oil droplets e.g. with an average diameter of between 100 and 250 nm, preferably about 180 nm.

An emulsion of squalene, a tocopherol, and a Triton detergent (e.g. Triton X-100). The emulsion may also include a 3d-MPL (see below). The emulsion may contain a phosphate buffer.

An emulsion comprising a polysorbate (e.g. polysorbate 80), a Triton detergent (e.g. Triton X-100) and a tocopherol (e.g. an α-tocopherol succinate). The emulsion may include these three components at a mass ratio of about 75:11:10 (e.g. 750 μg/ml polysorbate 80, 110 μg/ml Triton X-100 and 100 μg/ml α-tocopherol succinate), and these concentrations should include any contribution of these components from antigens. The emulsion may also include squalene. The emulsion may also include a 3d-MPL (see below). The aqueous phase may contain a phosphate buffer.

An emulsion of squalane, polysorbate 80 and poloxamer 401 ("Pluronic™ L121"). The emulsion can be formulated in phosphate buffered saline, pH 7.4. This emulsion is a useful delivery vehicle for muramyl dipeptides, and has been used with threonyl-MDP in the "SAF-1" adjuvant [21] (0.05-1% Thr-MDP, 5% squalane, 2.5% Pluronic L121 and 0.2% polysorbate 80). It can also be used without the Thr-MDP, as in the "AF" adjuvant [22] (5% squalane, 1.25% Pluronic L121 and 0.2% polysorbate 80). Microfluidisation is preferred.

An emulsion comprising squalene, an aqueous solvent, a polyoxyethylene alkyl ether hydrophilic nonionic surfactant (e.g. polyoxyethylene (12) cetostearyl ether) and a hydrophobic nonionic surfactant (e.g. a sorbitan ester or mannide ester, such as sorbitan monoleate or 'Span 80'). The emulsion is preferably thermoreversible and/or has at least 90% of the oil droplets (by volume) with a size less than 200 nm [23]. The emulsion may also include one or more of: alditol; a cryoprotective agent (e.g. a sugar, such as dodecylmaltoside and/or sucrose); and/or an alkylpolyglycoside. Such emulsions may be lyophilized.

An emulsion having from 0.5-50% of an oil, 0.1-10% of a phospholipid, and 0.05-5% of a non-ionic surfactant. As described in reference 24, preferred phospholipid components are phosphatidylcholine, phosphatidylethanolamine, phosphatidylserine, phosphatidylinositol, phosphatidylglycerol, phosphatidic acid, sphingomyelin and cardiolipin. Submicron droplet sizes are advantageous.

A submicron oil-in-water emulsion of a non-metabolisable oil (such as light mineral oil) and at least one surfactant (such as lecithin, Tween 80 or Span 80). Additives may be included, such as QuilA saponin, cholesterol, a saponin-lipophile conjugate (such as GPI-0100. described in reference 25, produced by addition of aliphatic amine to desacylsaponin via the carboxyl group of glucuronic acid), dimethyldioctadecylammonium bromide and/or N,N-dioctadecyl-N,N-bis(2-hydroxyethyl)propanediamine.

An emulsion comprising a mineral oil, a non-ionic lipophilic ethoxylated fatty alcohol, and a non-ionic hydrophilic surfactant (e.g. an ethoxylated fatty alcohol and/or polyoxyethylene-polyoxypropylene block copolymer) [26].

An emulsion comprising a mineral oil, a non-ionic hydrophilic ethoxylated fatty alcohol, and a non-ionic lipophilic surfactant (e.g. an ethoxylated fatty alcohol and/or polyoxyethylene-polyoxypropylene block copolymer) [26].

An emulsion in which a saponin (e.g. QuilA or QS21) and a sterol (e.g. a cholesterol) are associated as helical micelles [27].

Antigens and adjuvants in a composition will typically be in admixture at the time of delivery to a patient. The emulsions may be mixed with antigen during manufacture, or extemporaneously, at the time of delivery. Thus the adjuvant and antigen may be kept separately in a packaged or distributed vaccine, ready for final formulation at the time of use. The antigen will generally be in an aqueous form, such that the vaccine is finally prepared by mixing two liquids. The volume ratio of the two liquids for mixing can vary (e.g. between 5:1 and 1:5) but is generally about 1:1.

C. Saponin Formulations [Chapter 22 of Ref. 19]

Saponin formulations may also be used as adjuvants in the invention. Saponins are a heterogeneous group of sterol glycosides and triterpenoid glycosides that are found in the bark, leaves, stems, roots and even flowers of a wide range of plant species. Saponin from the bark of the *Quillaia saponaria* Molina tree have been widely studied as adjuvants. Saponin can also be commercially obtained from *Smilax ornata* (sarsaprilla), *Gypsophilla paniculata* (brides veil), and *Saponaria officianalis* (soap root). Saponin adjuvant formulations include purified formulations, such as QS21, as well as lipid formulations, such as ISCOMs. QS21 is marketed as Stimulon™.

Saponin compositions have been purified using HPLC and RP-HPLC. Specific purified fractions using these techniques have been identified, including QS7, QS17, QS18, QS21, QH-A, QH-B and QH-C. Preferably, the saponin is QS21. A method of production of QS21 is disclosed in ref. 28. Saponin formulations may also comprise a sterol, such as cholesterol [29].

Combinations of saponins and cholesterols can be used to form unique particles called immunostimulating complexs (ISCOMs; see chapter 23 of ref. 19; also refs 30 & 31). ISCOMs typically also include a phospholipid such as phosphatidylethanolamine or phosphatidylcholine. Any known saponin can be used in ISCOMs. Preferably, the ISCOM includes one or more of QuilA, QHA & QHC. Optionally, the ISCOMS may be devoid of additional detergent [32].

A review of the development of saponin based adjuvants can be found in refs. 33 & 34.

D. Bacterial or Microbial Derivatives

Adjuvants suitable for use in the invention include bacterial or microbial derivatives such as non-toxic derivatives of enterobacterial lipopolysaccharide (LPS), Lipid A derivatives, immunostimulatory oligonucleotides and ADP-ribosylating toxins and detoxified derivatives thereof.

Non-toxic derivatives of LPS include monophosphoryl lipid A (MPL) and 3-O-deacylated MPL (3dMPL). 3dMPL is a mixture of 3 de-O-acylated monophosphoryl lipid A with 4, 5 or 6 acylated chains. A preferred "small particle" form of 3 De-O-acylated monophosphoryl lipid A is disclosed in ref. 35. Such "small particles" of 3dMPL are small enough to be sterile filtered through a 0.22 μm membrane [35]. Other non-toxic LPS derivatives include monophosphoryl lipid A mimics, such as aminoalkyl glucosaminide phosphate derivatives e.g. RC-529 [36, 37].

Lipid A derivatives include derivatives of lipid A from *Escherichia coli* such as OM-174. OM-174 is described for example in refs. 38 & 39.

Immunostimulatory oligonucleotides suitable for use as adjuvants in the invention include nucleotide sequences containing a CpG motif (a dinucleotide sequence containing an unmethylated cytosine linked by a phosphate bond to a guanosine). Double-stranded RNAs and oligonucleotides containing palindromic or poly(dG) sequences have also been shown to be immunostimulatory.

The CpG's can include nucleotide modifications/analogs such as phosphorothioate modifications and can be double-stranded or single-stranded. References 40, 41 and 42 disclose possible analog substitutions e.g. replacement of guanosine with 2'-deoxy-7-deazaguanosine. The adjuvant effect of CpG oligonucleotides is further discussed in refs. 43-48.

The CpG sequence may be directed to TLR9, such as the motif GTCGTT or TTCGTT [49]. The CpG sequence may be specific for inducing a Th1 immune response, such as a CpG-A ODN, or it may be more specific for inducing a B cell response, such a CpG-B ODN. CpG-A and CpG-B ODNs are discussed in refs. 50-52. Preferably, the CpG is a CpG-A ODN.

Preferably, the CpG oligonucleotide is constructed so that the 5' end is accessible for receptor recognition. Optionally, two CpG oligonucleotide sequences may be attached at their 3' ends to form "immunomers". See, for example, refs. 53-55.

A particularly useful adjuvant based around immunostimulatory oligonucleotides is known as IC-31™ [56-58]. Thus an adjuvant used with the invention may comprise a mixture of (i) an oligonucleotide (e.g. between 15-40 nucleotides) including at least one (and preferably multiple) CpI motifs (i.e. a cytosine linked to an inosine to form a dinucleotide), and (ii) a polycationic polymer, such as an oligopeptide (e.g. between 5-20 amino acids) including at least one (and preferably multiple) Lys-Arg-Lys tripeptide sequence(s). The oligonucleotide may be a deoxynucleotide comprising 26-mer sequence 5'-(IC)$_{13}$-3' (SEQ ID NO: 7). The polycationic polymer may be a peptide comprising 11-mer amino acid sequence KLKLLLLLKLK (SEQ ID NO: 6). This combination of SEQ ID NOs: 6 and 7 provides the IC-31™ adjuvant.

Bacterial ADP-ribosylating toxins and detoxified derivatives thereof may be used as adjuvants in the invention. Preferably, the protein is derived from *E. coli* (*E. coli* heat labile enterotoxin "LT"), cholera ("CT"), or pertussis ("PT"). The use of detoxified ADP-ribosylating toxins as mucosal adjuvants is described in ref. 59 and as parenteral adjuvants in ref. 60. The toxin or toxoid is preferably in the form of a holotoxin, comprising both A and B subunits. Preferably, the A subunit contains a detoxifying mutation; preferably the B subunit is not mutated. Preferably, the adjuvant is a detoxified LT mutant such as LT-K63, LT-R72, and LT-G192. The use of ADP-ribosylating toxins and detoxified derivatives thereof; particularly LT-K63 and LT-R72, as adjuvants can be found in refs. 61-68. A useful CT mutant is or CT-E29H [69]. Numerical reference for amino acid substitutions is preferably based on the alignments of the A and B subunits of ADP-ribosylating toxins set forth in ref. 70, specifically incorporated herein by reference in its entirety.

E. Human Immunomodulators

Human immunomodulators suitable for use as adjuvants in the invention include cytokines, such as interleukins (e.g. IL-1, IL-2, IL-4, IL-5, IL-6, IL-7, IL-12 [71], etc.) [72], interferons (e.g. interferon-γ), macrophage colony stimulating factor, and tumor necrosis factor. A preferred immunomodulator is IL-12.

F. Bioadhesives and Mucoadhesives

Bioadhesives and mucoadhesives may also be used as adjuvants in the invention. Suitable bioadhesives include esterified hyaluronic acid microspheres [73] or mucoadhesives such as cross-linked derivatives of poly(acrylic acid), polyvinyl alcohol, polyvinyl pyrrolidone, polysaccharides and carboxymethylcellulose. Chitosan and derivatives thereof may also be used as adjuvants in the invention [74].

G. Microparticles

Microparticles may also be used as adjuvants in the invention. Microparticles (i.e. a particle of ~100 nm to ~150 μm in diameter, more preferably ~200 nm to ~30 μm in diameter, and most preferably ~500 nm to ~10 μm in diameter) formed from materials that are biodegradable and non-toxic (e.g. a poly(α-hydroxy acid), a polyhydroxybutyric acid, a polyorthoester, a polyanhydride, a polycaprolactone, etc.), with poly(lactide-co-glycolide) are preferred, optionally treated to have a negatively-charged surface (e.g. with SDS) or a positively-charged surface (e.g. with a cationic detergent, such as CTAB).

H. Liposomes (Chapters 13 & 14 of Ref. 19)

Examples of liposome formulations suitable for use as adjuvants are described in refs. 75-77.

I. Imidazoquinolone Compounds.

Examples of imidazoquinolone compounds suitable for use adjuvants in the invention include Imiquamod and its homologues (e.g. "Resiquimod 3M"), described further in refs. 78 and 79.

The invention may also comprise combinations of aspects of one or more of the adjuvants identified above. For example, the following adjuvant compositions may be used in the invention: (1) a saponin and an oil-in-water emulsion [80]; (2) a saponin (e.g. QS21)+a non-toxic LPS derivative (e.g. 3dMPL) [81]; (3) a saponin (e.g. QS21)+a non-toxic LPS derivative (e.g. 3dMPL)+a cholesterol; (4) a saponin (e.g. QS21)+3dMPL+IL-12 (optionally+a sterol) [82]; (5) combinations of 3dMPL with, for example, QS21 and/or oil-in-water emulsions [83]; (6) SAF, containing 10% squalane, 0.4% Tween 80™, 5% pluronic-block polymer L121, and thr-MDP, either microfluidized into a submicron emulsion or vortexed to generate a larger particle size emulsion. (7) Ribi™ adjuvant system (RAS), (Ribi Immunochem) containing 2% squalene, 0.2% Tween 80, and one or more bacterial cell wall components from the group consisting of monophosphorylipid A (MPL), trehalose dimycolate (TDM), and cell wall skeleton (CWS), preferably MPL+CWS (Detox™); and (8) one or more mineral salts (such as an aluminum salt)+a non-toxic derivative of LPS (such as 3dMPL).

Other substances that act as immunostimulating agents are disclosed in chapter 7 of ref. 19.

An aluminium hydroxide adjuvant is useful, and antigens are generally adsorbed to this salt. Oil-in-water emulsions comprising squalene, with submicron oil droplets, are also preferred, particularly in the elderly. Useful adjuvant combinations include combinations of Th1 and Th2 adjuvants such as CpG & an aluminium salt, or resiquimod & an aluminium salt. A combination of an aluminium salt and 3dMPL may be used.

Immunisation

In addition to providing immunogenic compositions as described above, the invention also provides a method for raising an antibody response in a mammal, comprising administering an immunogenic composition of the invention to the mammal. The antibody response is preferably a protective antibody response. The invention also provides compositions of the invention for use in such methods.

The invention also provides a method for protecting a mammal against a *Shigella* infection and/or disease (e.g. against shigellosis, Reiter's syndrome, and/or hemolytic uremic syndrome), comprising administering to the mammal an immunogenic composition of the invention.

The invention provides compositions of the invention for use as medicaments (e.g. as immunogenic compositions or as vaccines). It also provides the use of vesicles of the invention in the manufacture of a medicament for preventing a *Shigella* infection in a mammal e.g. for preventing shigellosis, Reiter's syndrome, and/or hemolytic uremic syndrome. It also provides the use of a bleb protein (as defined above) in the manufacture of a bleb-free medicament for preventing a *Shigella* infection in a mammal e.g. for preventing shigellosis.

The mammal is preferably a human. The human may be an adult or, preferably, a child. Where the vaccine is for prophylactic use, the human is preferably a child (e.g. a toddler or infant); where the vaccine is for therapeutic use, the human is preferably an adult. A vaccine intended for children may also be administered to adults e.g. to assess safety, dosage, immunogenicity, etc.

The uses and methods are particularly useful for preventing/treating diseases including, but not limited to, shigellosis, Reiter's syndrome, and/or hemolytic uremic syndrome Efficacy of therapeutic treatment can be tested by monitoring *Shigella* infection after administration of the composition of the invention. Efficacy of prophylactic treatment can be tested by monitoring immune responses against immunogenic proteins in the blebs or other antigens after administration of the composition. Immunogenicity of compositions of the invention can be determined by administering them to test subjects (e.g. children 12-16 months age) and then determining standard serological parameters. These immune responses will generally be determined around 4 weeks after administration of the composition, and compared to values determined before administration of the composition. Where more than one dose of the composition is administered, more than one post-administration determination may be made.

Compositions of the invention will generally be administered directly to a patient. Direct delivery may be accomplished by parenteral injection (e.g. subcutaneously, intraperitoneally, intravenously, intramuscularly, or to the interstitial space of a tissue), or by rectal, oral, vaginal, topical, transdermal, intranasal, ocular, aural, pulmonary or other mucosal administration. Intramuscular administration to the thigh or the upper arm is preferred. Injection may be via a needle (e.g. a hypodermic needle), but needle-free injection may alternatively be used. A typical intramuscular dose is about 0.5 ml.

The invention may be used to elicit systemic and/or mucosal immunity.

Dosage treatment can be a single dose schedule or a multiple dose schedule. Multiple doses may be used in a primary immunisation schedule and/or in a booster immunisation schedule. A primary dose schedule may be followed by a booster dose schedule. Suitable timing between priming doses (e.g. between 4-16 weeks), and between priming and boosting, can be routinely determined.

General

The term "comprising" encompasses "including" as well as "consisting" e.g. a composition "comprising" X may consist exclusively of X or may include something additional e.g. X+Y.

The term "about" in relation to a numerical value x is optional and means, for example, x±10%.

The word "substantially" does not exclude "completely" e.g. a composition which is "substantially free" from Y may be completely free from Y. Where necessary, the word "substantially" may be omitted from the definition of the invention.

References to a percentage sequence identity between two amino acid sequences means that, when aligned, that percentage of amino acids are the same in comparing the two sequences. This alignment and the percent homology or sequence identity can be determined using software programs known in the art, for example those described in section 7.7.18 of reference 84. A preferred alignment is determined by the Smith-Waterman homology search algorithm using an affine gap search with a gap open penalty of 12 and a gap extension penalty of 2, BLOSUM matrix of 62. The Smith-Waterman homology search algorithm is well known and is disclosed in reference 85.

"GI" numbering is used above. A GI number, or "GenInfo Identifier", is a series of digits assigned consecutively to each sequence record processed by NCBI when sequences are added to its databases. The GI number bears no resemblance to the accession number of the sequence record. When a sequence is updated (e.g. for correction, or to add more annotation or information) then it receives a new GI number. Thus the sequence associated with a given GI number is never changed.

Where the invention concerns an "epitope", this epitope may be a B-cell epitope and/or a T-cell epitope. Such epitopes can be identified empirically (e.g. using PEPSCAN [86, 87] or similar methods), or they can be predicted (e.g. using the Jameson-Wolf antigenic index [88], matrix-based approaches [89], MAPITOPE [90], TEPITOPE [91, 92], neural networks [93], OptiMer & EpiMer [94, 95], ADEPT [96], Tsites [97], hydrophilicity [98], antigenic index [99] or the methods disclosed in references 100-101, etc.). Epitopes are the parts of an antigen that are recognised by and bind to the antigen binding sites of antibodies or T-cell receptors, and they may also be referred to as "antigenic determinants".

BRIEF DESCRIPTION OF DRAWINGS

FIG. 7A, S. sonneiG53 wt; FIG. 7B, S. sonnei G53 DGalU/DTolR; FIG. 7C, S. flexneri2a DGalU; FIG. 7D, S. flexneriM90TDGalU; FIG. 7E, S. flexneri2a; FIG. 7F, S. flexneri2a.

MODES FOR CARRYING OUT THE INVENTION

Preparation of Mutant of S. sonnei

Figure 1:
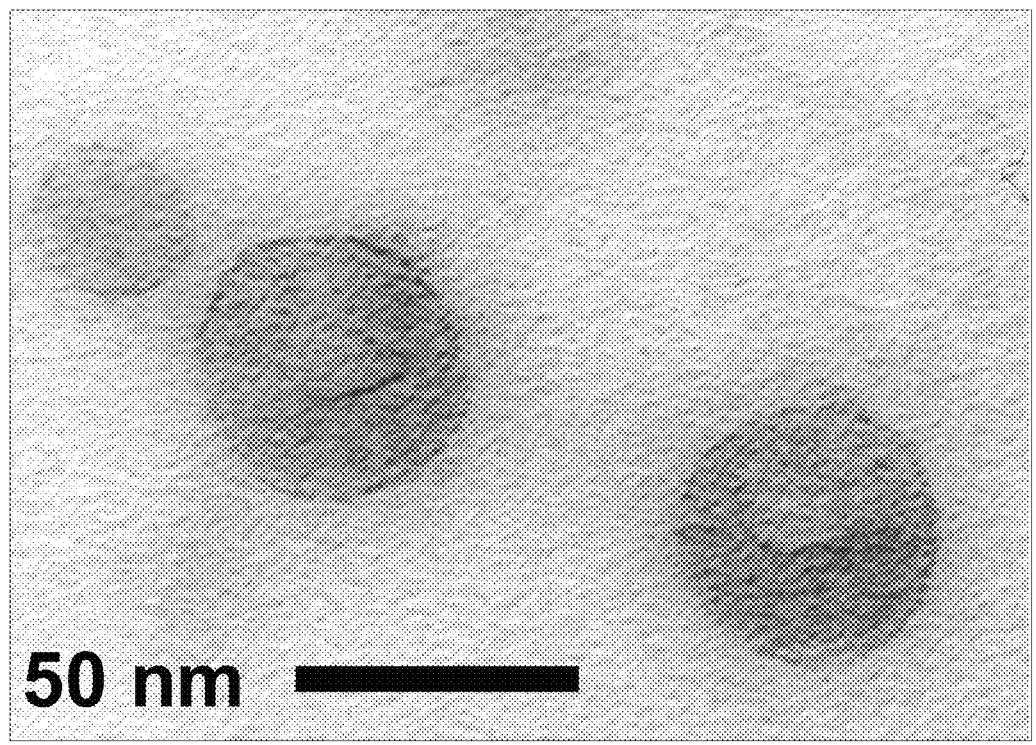
FIG. 1 shows an electron micrograph of blebs of the invention purified from culture.

The tolR gene of wild-type S. sonnei 53G was deleted using the λ Red system [11, 102]. Competent cells transformed with the λ Red plasmids are prepared and then transformed with a linear fragment designed to swap the tolR gene for an antibiotic resistance gene by homologous recombination. Clones that have integrated the fragment into the chromosome are selected by resistance to the antibiotic and deletion of the tolR is verified by PCR or other techniques. The temperature sensitive λ Red plasmids can then be removed by growth of the new clones at 37° C.

The lack of TolR expression in this ΔtolR mutant was confirmed and, compared to the original wild-type isolate, it was confirmed to release more blebs into culture medium during growth.

The galU gene was also deleted in a similar way, to provide a ΔgalU single mutant and a ΔtolRΔgalU double mutant. Blebs released by mutants are confirmed to have a defective LPS lacking O antigen.

A ΔtolRΔmsbB double mutant strain with modified LPS is prepared in the same way.

The virulence plasmid has also been removed from the ΔtolR and ΔtolRΔmsbB strains.

Preparation of Mutant of S. flexneri

The tolR gene of S. flexneri was deleted using the λ Red system as described above for S. sonnei. O antigen biosynthesis in S. flexneri was abolished by deletion of a chromosomal fragment comprising the complete rfbG gene and as well as parts of rfbF and rfc, resulting in activation of all three genes. The deletion was generated using the λ Red system and is abbreviated as ΔrfbG.

A ΔtolRΔrfbG double mutant has been generated in the same way.

A ΔtolRΔhtrB double mutant containing modified LPS has been generated in the same way.

The virulence plasmid has also been removed from these strains.

Purification of Blebs

Fermentation of the double mutant ΔtolRΔgalU strain was run under the following conditions: pH 7.1, 37° C., dissolved oxygen maintained at 30% saturation by controlling agitation and setting maximum aeration. The pH was controlled by addition of 4M ammonium hydroxide. The foam was controlled by addition of 10% PPG during the run. The medium consisted of the following components: $KH_2PO_4$ 5 g/l, $K_2HPO_4$ 20 g/l and yeast extract 30 g/l. After the medium was sterilized by autoclaving, glycerol 15 g/l and $MgSO_4$ 2 mM were added prior to inoculation. The culture inoculum was 5% of the fermentor volume. The fermentation process took approximately 13 hours and cell concentration was measured as optical density at 600 nm.

The fermentation process of the S. sonnei ΔtolRΔmsbB double mutant strain was performed with defined medium: glycerol 30 g/l, $KH_2PO_4$ 13.3 g/l, $(NH_4)_2HPO_4$ 4 g/l, $MgSO_4.7H_2O$ (1M) 2 ml, citric acid 1.7 g/l, $CoCl_2.6H_2O$ 2.5 mg/l, $MnCl_2.4H_2O$ 15 mg/l, $CuCl_2.2H_2O$ 1.5 mg/l, $H_3BO_3$ 3 mg/l, Na₂MoO₄.2H₂O 2.5 mg/l, Zn(CH₃COO)₂.2H₂O 13 mg/l, ferric citrate 2 μM, thiamine 50 mg/l, nicotinic acid 10 mg/l, L-acid aspartic 2.5 g/l.

Vesicles produced in the fermentation broth were purified using two consecutive TFF (tangential flow filtration) steps: micro-filtration at 0.22 μm and then a second micro-filtration at 0.1 μm. During the first filtration step the vesicles were separated from biomass by TFF through a 0.22 μm pore size cassette. The biomass was first concentrated 4-fold and, after five diafiltration steps against PBS, the vesicles were collected in the filtrate. In the second filtration step the filtrate from the 0.22 μm TFF was further micro-filtered trough a 0.1 μm cut-off cassette, in order to purify the vesicles from soluble proteins. The vesicles could not pass through the filter cassette. After five diafiltration steps, the retentate containing the vesicles was collected.

The final purified product was observed with TEM (FIG. 1). The blebs have a homogenous size of about 50 nm in diameter.

Blebs from *S. flexneri* mutants were purified in the same way after growing the various strains in yeast extract medium as used for *S. sonnei* ΔtolRΔgalU.

Bleb Characterisation

A proteomic approach confirmed that the blebs are essentially pure outer membranes. Unlike conventional outer membrane vesicles (OMV) derived by disruption of the outer membrane, the blebs conserve lipophilic proteins and are essentially free of cytoplasmic and inner membrane components.

Figure 2:
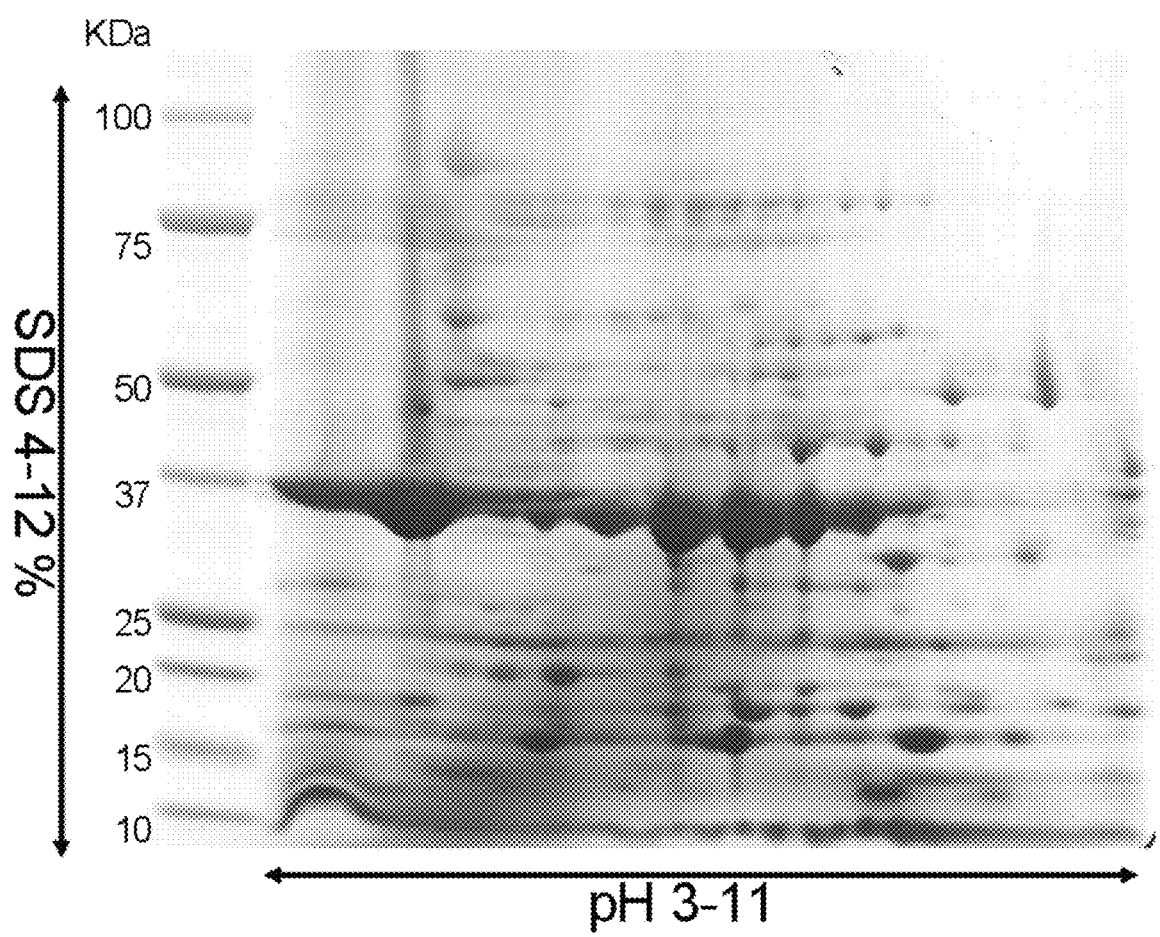
FIG. 2 shows 2D SDS-PAGE of blebs from S. sonnei ΔtolR ΔgalU.

Blebs from *S. sonnei* and *S. flexneri* strains were denatured with a detergent and proteins were identified with a LC-MS/MS approach. Alternatively, blebs were separated with SDS page or 2D gel electrophoresis (FIG. 2). Visible bands and spots were excised from the gel and proteins identified via protein mass fingerprint. The relative amount of different proteins was studied with densitometer analysis of SDS-PAGE bands or spots from the 2D gel.

Figure 3:
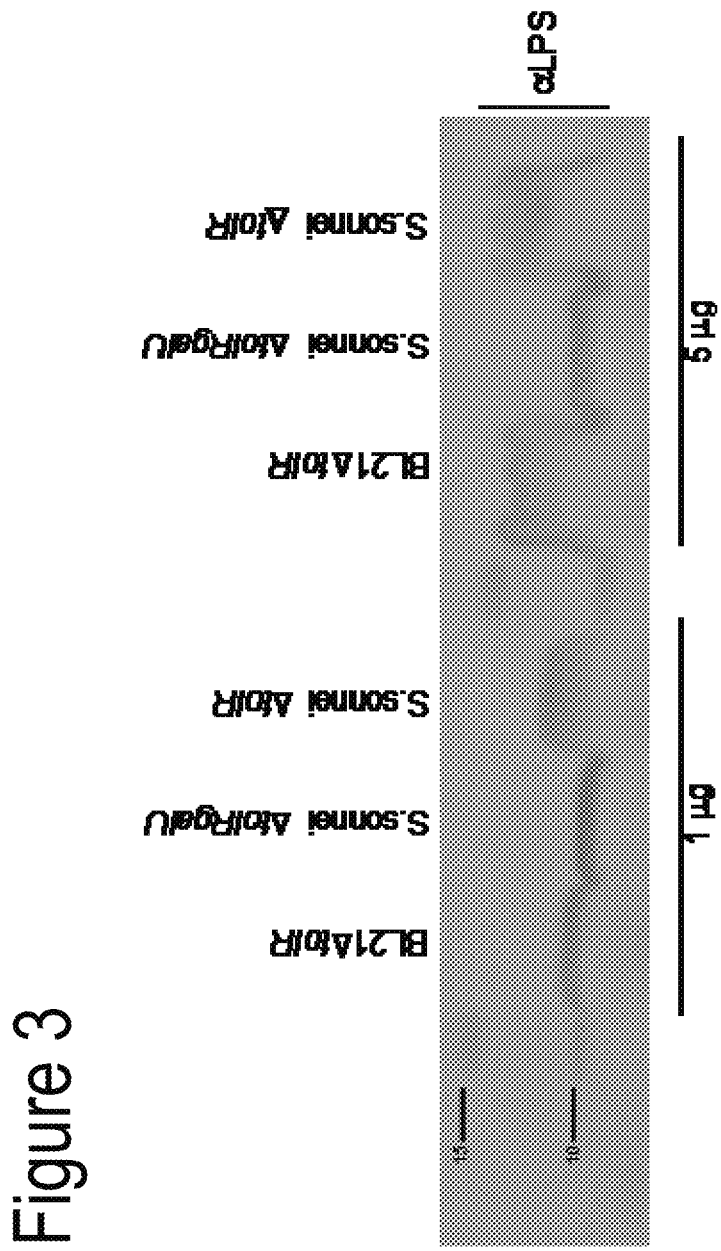
FIG. 3 shows LPS of blebs in various indicated strains, stained with anti-core antibody.

FIG. 3 shows a shift in LPS mobility in the ΔgalU mutant strain compared to wildtype *Shigella* and *E. coli* (all strains are in a ΔtolR background).

A second proteomic approach, based on surface digestion, was used to characterize exposed portions of membrane proteins. A set of proteins was identified as reactive with sera from mice immunized with the blebs and many of these have been found to be conserved in a large panel of strains. Little is known about the structure of most integral outer membrane proteins. The surfome of blebs was investigated by treatment with a protease and recovery and identification via LC-MS/MS of released peptides. As blebs should represent the surface of the whole living bacterial cell, this map should be representative of exposed proteins on the surface of *S. sonnei*.

By these and other approaches the 129 proteins listed in Table 1 have been seen in the blebs.

Bleb Immunogenicity

Figure 4:
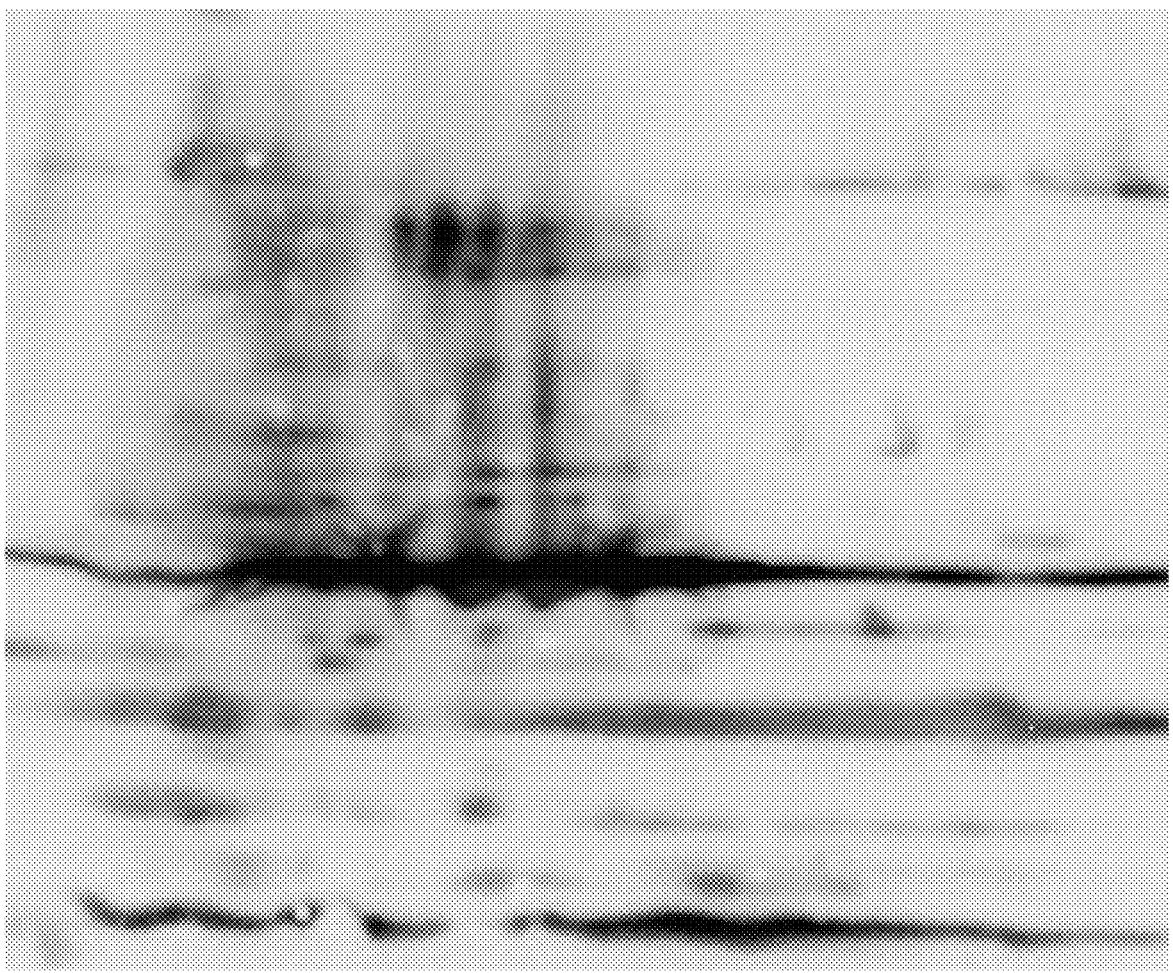
FIG. 4 shows an immunoblot of 2D-separated proteins of blebs using serum from immunised mice.

Mice immunised with the blebs from the ΔtolRΔgalU strain produce serum which reacts with a 2D gel of the blebs as shown in FIG. 4. Thus the blebs are immunogenic.

Mice received 2 μg or 10 μg *S. sonnei* ΔtolRΔgalU blebs (measured as total protein), with or without adjuvant (aluminium hydroxide or Freund's complete). A classical ELISA method was performed to analyze IgG production in sera obtained from immunization studies. Sera from all groups of mice demonstrated a high level production of bleb-specific IgG. No significant differences in IgG production were detected when blebs were used alone or in combination with an adjuvant. The group immunized with the lower dose of 2 μg showed the same level of bleb-specific IgG as the group immunized with 10 μg, showing that a low dose vaccine may be achievable i.e. more doses per dollar. Blebs from other *S. sonnei* as well as *S. flexneri* strains were similarly immunogenic.

Sera raised against the blebs were tested for reactivity with three different bacteria: *S. sonnei* G53, *S. flexneri* 2a 2457T or *S. flexneri* 5 M90T. The samples were than stained with a labeled secondary Ab and were analyzed by flow cytometry. As shown in FIG. 7, the *S. sonnei* and *S. flexneri* strains cross-react with the sera.

Therefore the bleb approach has a strong potential to produce effective and low-cost vaccines and can be extended to different *Shigella* strains towards a broad spectrum vaccine.

Bleb Adsorption

Figure 6:
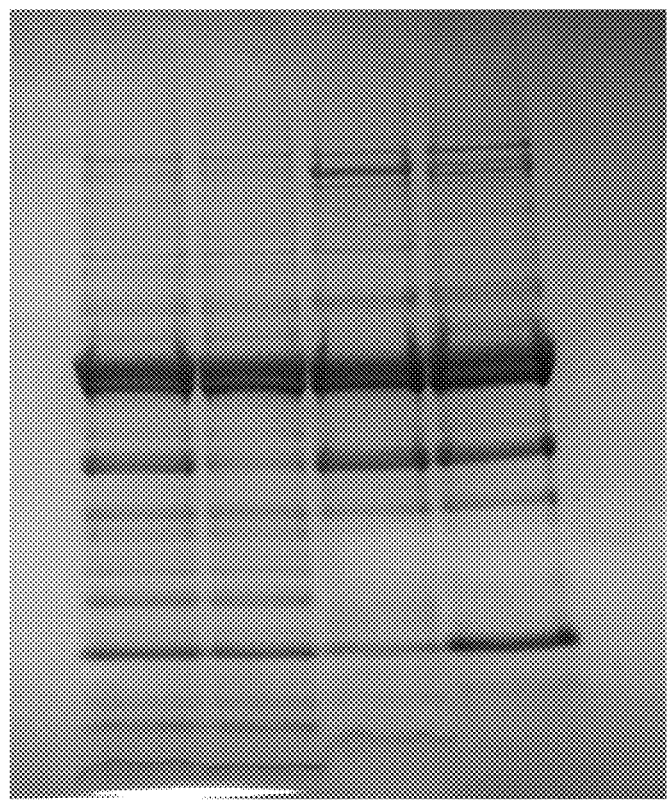
FIG. 6 shows adsorbed proteins in blebs. Lanes from left to right: 1) protein molecular weight marker, 2) Ss OMB 10 µg, 3) Ss OMB 2 µg, 4) Ss OMB 10 µg adsorbed on alum for 1 month.
Figure 7A:
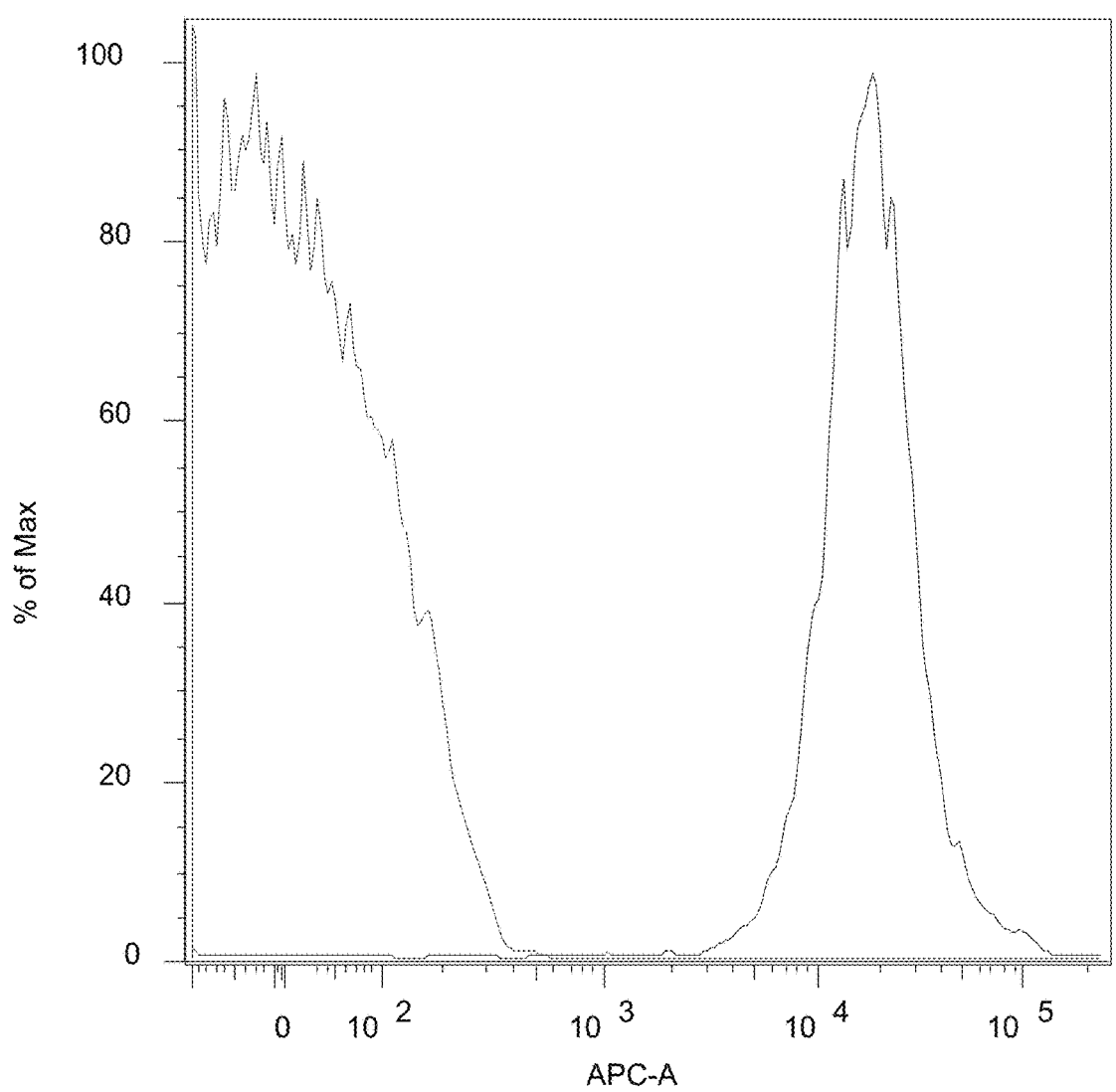
FIGS. 7A-F show FACS data for indicated strains.
Figure 7B:
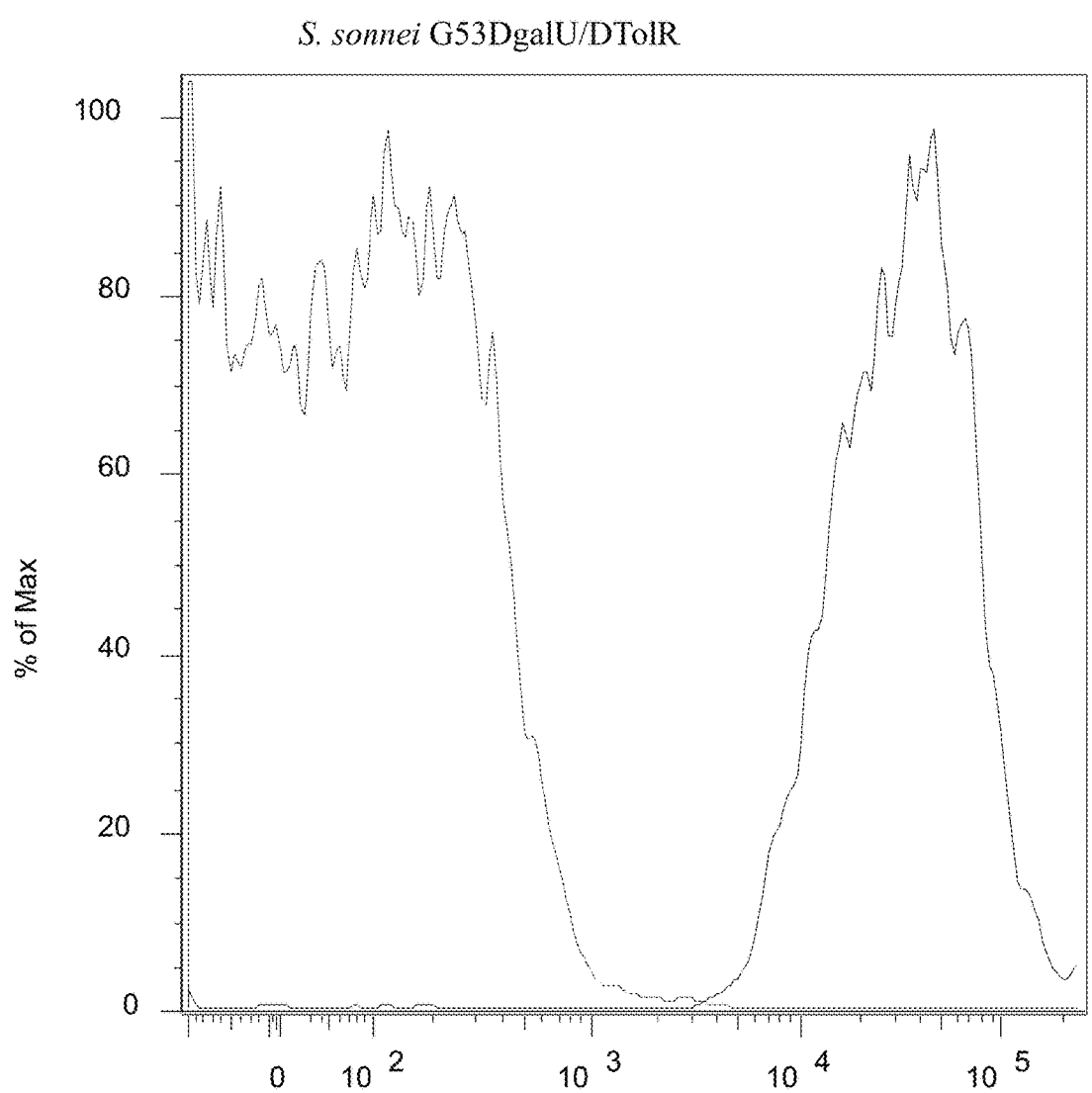
Figure 7C:
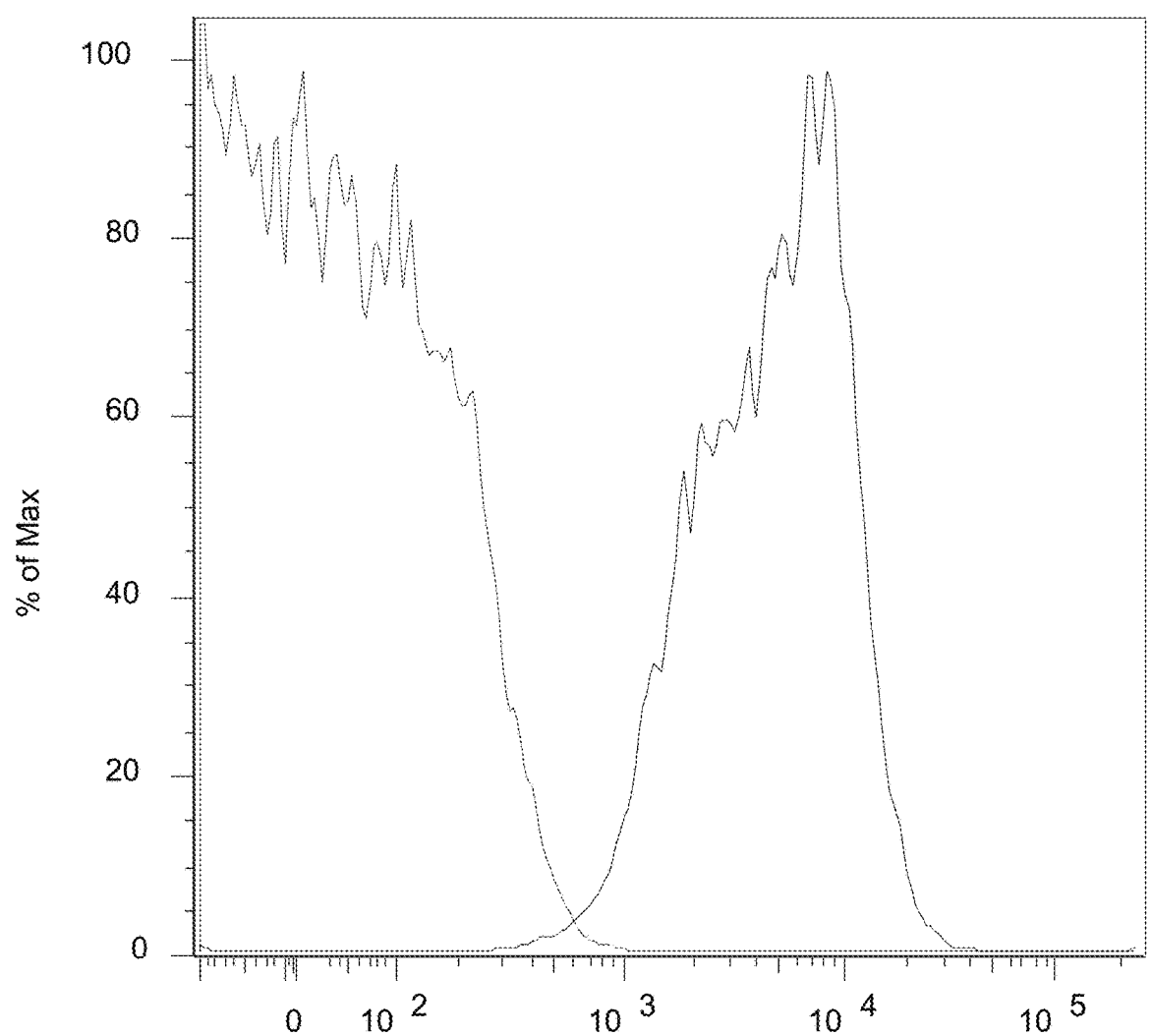
Figure 7D:
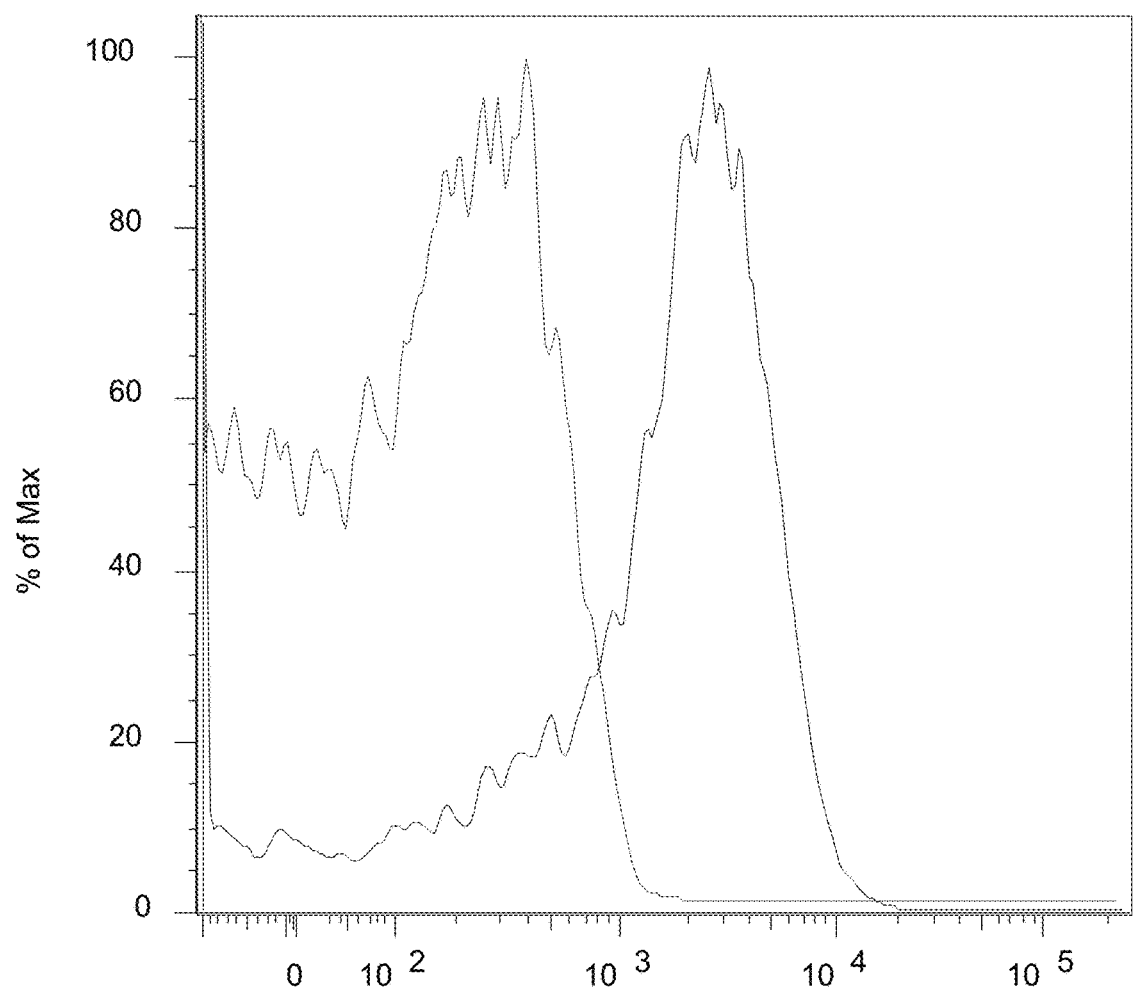
Figure 7E:
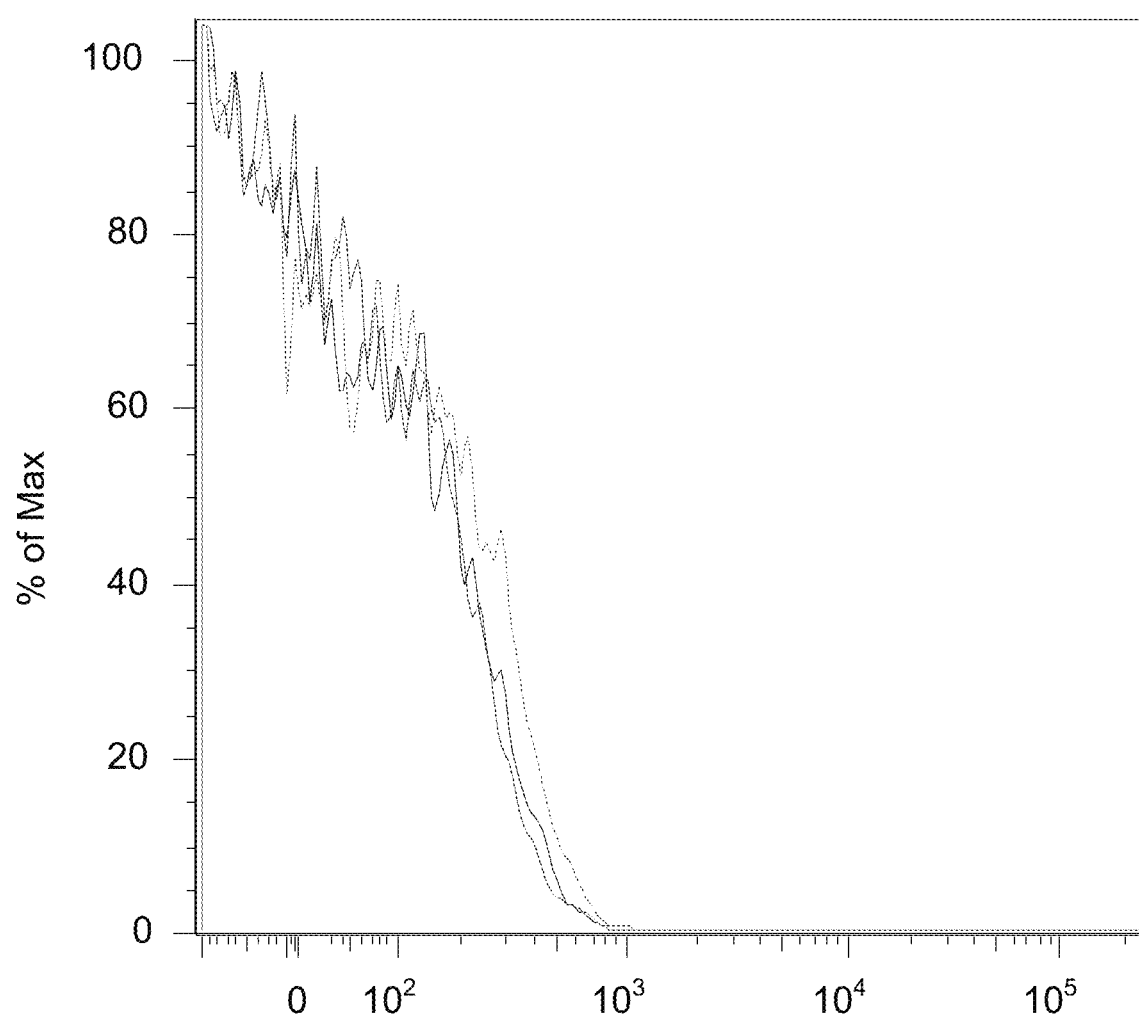
Figure 7F:
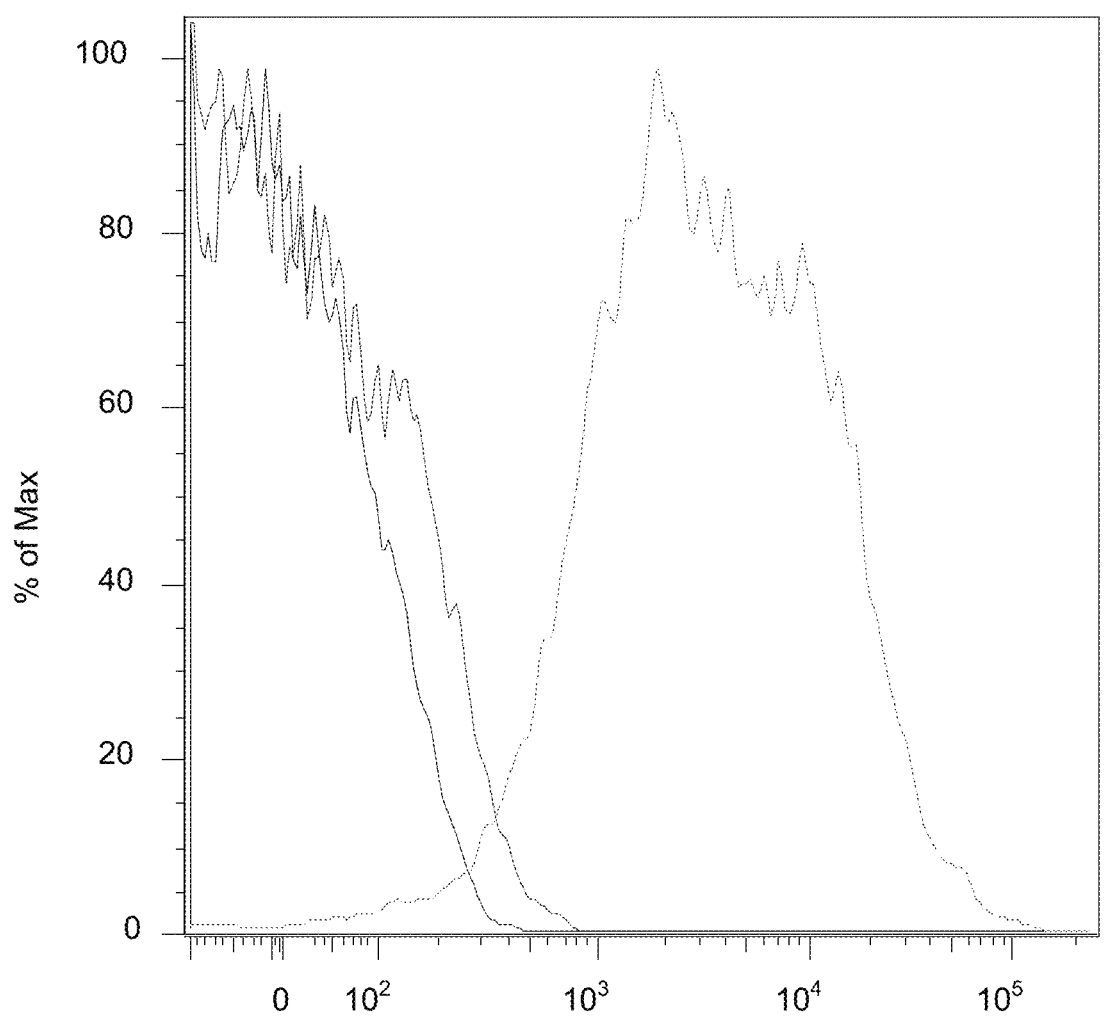

Blebs were combined with aluminium hydroxide (2 mg/ml) for adsorption. The adsorbed material was stored at 4° C. for 1 day, 1 week or 1 month. The blebs were totally adsorbed after 1 day and there was no evidence of desorption even after 1 month (FIG. 6).

Iron-Limiting Growth

Figure 5:
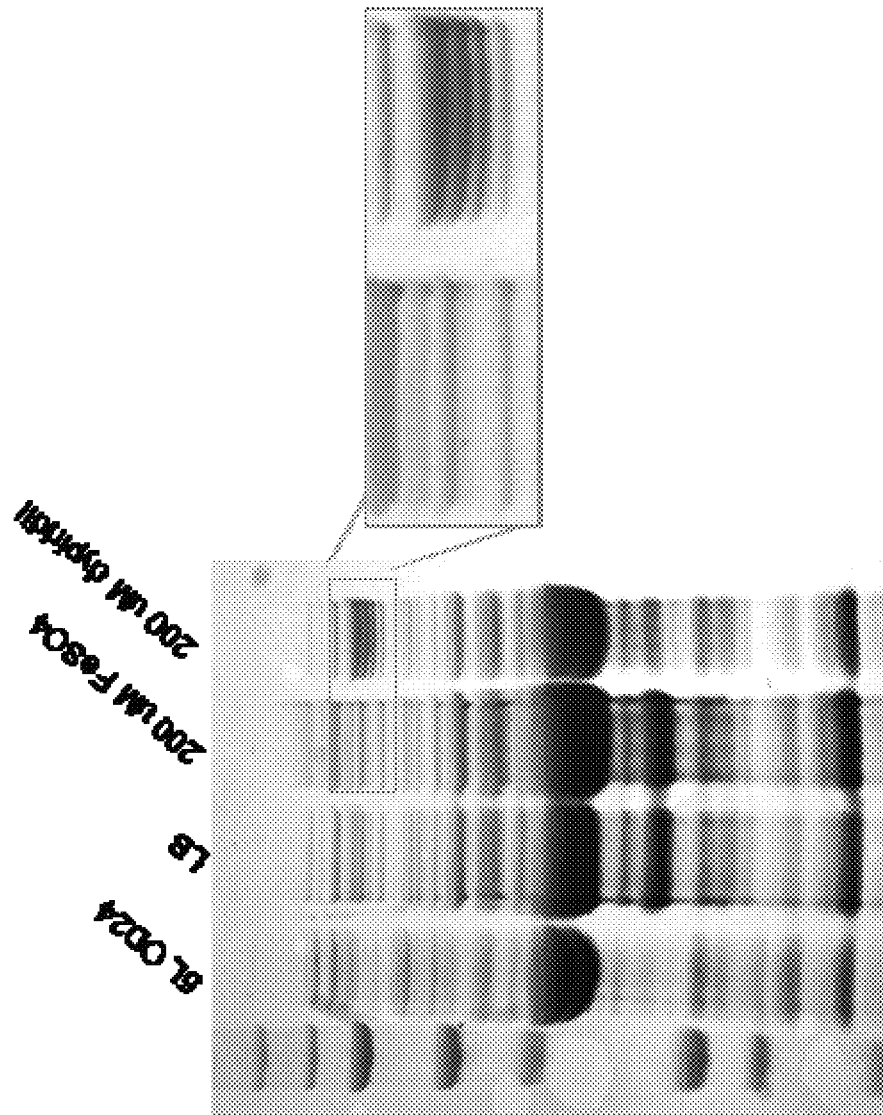
FIG. 5 shows SDS-PAGE of bacteria grown in different conditions.

FIG. 5 shows proteins expressed by *Shigella* grown under various conditions. In lane 4 the bacteria were grown in the presence of 200 μM FeSO₄ whereas in lane 5 the culture had 200 μM dypiridyl. The inset shows that three proteins are up-regulated under the iron-limiting conditions. These three proteins were identified as the FepA outer membrane receptor (GI 74311118), the colicin I receptor (GI 74312677), and the putative ferric siderophore receptor (GI 74313972). These proteins are well-conserved among *Shigella* spp. and enterobacteriaceae and are potentially highly immunogenic. Thus growth of *Shigella* under iron-limiting conditions can lead to the release of blebs which are, compared to normal growth conditions, enriched for these proteins.

It will be understood that the invention has been described by way of example only and modifications may be made whilst remaining within the scope and spirit of the invention.

TABLE 1

| SEQ ID NO: | GI | Gene name | Definition |
|---|---|---|---|
| 8 | 56480244 | tolC | outer membrane channel protein [*Shigella flexneri* 2a str. 301] |
| 9 | 74312736 | ompC | outer membrane porin protein C [*Shigella sonnei* Ss046] |
| 10 | 74311514 | ompA | outer membrane protein A [*Shigella sonnei* Ss046] |
| 11 | 110807342 | SFV_3519 | hypothetical protein SFV_3519 [*Shigella flexneri* 5 str. 8401] |
| 12 | 56479734 | ompX | outer membrane protein X [*Shigella flexneri* 2a str. 301] |
| 13 | 24113033 | slyB | putative outer membrane protein [*Shigella flexneri* 2a str. 301] |
| 14 | 24112608 | lolB | outer membrane lipoprotein LolB [*Shigella flexneri* 2a str. 301] |
| 15 | 24111612 | yaeT | outer membrane protein assembly factor YaeT [*Shigella flexneri* 2a str. 301] |
| 16 | 187733369 | | outer membrane protein C [*Shigella boydii* CDC 3083-94] |

TABLE 1-continued

| SEQ ID NO: | GI | Gene name | Definition |
|---|---|---|---|
| 17 | 24113066 | Lpp | murein lipoprotein [*Shigella flexneri* 2a str. 301] |
| 18 | 56479690 | pal | peptidoglycan-associated outer membrane lipoprotein [*Shigella flexneri* 2a str. 301] |
| 19 | 24115506 | ecnB | entericidin B membrane lipoprotein [*Shigella flexneri* 2a str. 301] |
| 20 | 30063370 | yedD | hypothetical protein S2067 [*Shigella flexneri* 2a str. 2457T] |
| 21 | 30064374 | ygiW | hypothetical protein S3269 [*Shigella flexneri* 2a str. 2457T] |
| 22 | 30065519 | yjeI | hypothetical protein S4565 [*Shigella flexneri* 2a str. 2457T] |
| 23 | 24111837 | ybaY | hypothetical protein SF0398 [*Shigella flexneri* 2a str. 301] |
| 24 | 24113773 | SF2485 | hypothetical protein SF2485 [*Shigella flexneri* 2a str. 301] |
| 25 | 74313380 | SSON_2966 | hypothetical protein SSON_2966 [*Shigella sonnei* Ss046] |
| 26 | 30063856 | nlpB | lipoprotein [*Shigella flexneri* 2a str. 2457T] |
| 27 | 145294038 | exc | entry exclusion protein 2 [*Shigella sonnei* Ss046] |
| 28 | 82775909 | rlpB | LPS-assembly lipoprotein RplB [*Shigella dysenteriae* Sd197] |
| 29 | 74311310 | ybhC | putative pectinesterase [*Shigella sonnei* Ss046] |
| 30 | 24114611 | fkpA | FKBP-type peptidyl-prolyl cis-trans isomerase [*Shigella flexneri* 2a str. 301] |
| 31 | 74312826 | hisJ | histidine-binding periplasmic protein of high-affinity histidine transport system [*Shigella sonnei* Ss046] |
| 32 | 24111599 | htrA | serine endoprotease [*Shigella flexneri* 2a str. 301] |
| 33 | 30062097 | tolB | translocation protein TolB [*Shigella flexneri* 2a str. 2457T] |
| 34 | 24111968 | modA | molybdate transporter periplasmic protein [*Shigella flexneri* 2a str. 301] |
| 35 | 24114628 | ppiA | peptidyl-prolyl cis-trans isomerase A (rotamase A) [*Shigella flexneri* 2a str. 301] |
| 36 | 24111499 | surA | peptidyl-prolyl cis-trans isomerase SurA [*Shigella flexneri* 2a str. 301] |
| 37 | 30062764 | oppA | periplasmic oligopeptide binding protein [*Shigella flexneri* 2a str. 2457T] |
| 38 | 30065614 | osmY | periplasmic protein [*Shigella flexneri* 2a str. 2457T] |
| 39 | 74311404 | artJ | arginine 3rd transport system periplasmic binding protein [*Shigella sonnei* Ss046] |
| 40 | 74311061 | ushA | bifunctional UDP-sugar hydrolase/5'-nucleotidase periplasmic precursor [*Shigella sonnei* Ss046] |
| 41 | 74311733 | fliY | cystine transporter subunit [*Shigella sonnei* Ss046] |
| 42 | 110805056 | mdoG | glucan biosynthesis protein G [*Shigella flexneri* 5 str. 8401] |
| 43 | 74312961 | cysP | thiosulfate transporter subunit [*Shigella sonnei* Ss046] |
| 44 | 24114441 | yraP | hypothetical protein SF3191 [*Shigella flexneri* 2a str. 301] |
| 45 | 74312191 | SSON_1681 | putative receptor [*Shigella sonnei* Ss046] |
| 46 | 74312061 | ydgA | hypothetical protein SSON_1546 [*Shigella sonnei* Ss046] |
| 47 | 24111764 | proC | pyrroline-5-carboxylate reductase [*Shigella flexneri* 2a str. 301] |
| 48 | 24112431 | SF1022 | hypothetical protein SF1022 [*Shigella flexneri* 2a str. 301] |
| 49 | 110806822 | yggE | hypothetical protein SFV_2968 [*Shigella flexneri* 5 str. 8401] |
| 50 | 74312071 | ydgH | hypothetical protein SSON_1556 [*Shigella sonnei* Ss046] |
| 51 | 74313729 | yrbC | hypothetical protein SSON_3340 [*Shigella sonnei* Ss046] |
| 52 | 24115498 | groEL | chaperonin GroEL [*Shigella flexneri* 2a str. 301] |
| 53 | 56479605 | lpdA | dihydrolipoamide dehydrogenase [*Shigella flexneri* 2a str. 301] |
| 54 | 24112862 | osmE | DNA-binding transcriptional activator OsmE [*Shigella flexneri* 2a str. 301] |
| 55 | 30065622 | deoD | purine nucleoside phosphorylase [*Shigella flexneri* 2a str. 2457T] |
| 56 | 24111996 | sucC | succinyl-CoA synthetase subunit beta [*Shigella flexneri* 2a str. 301] |
| 57 | 24113762 | Crr | glucose-specific PTS system component [*Shigella flexneri* 2a str. 301] |
| 58 | 24111463 | dnaK | molecular chaperone DnaK [*Shigella flexneri* 2a str. 301] |
| 59 | 74311033 | | glycoprotein-polysaccharide metabolism |
| 60 | 30064444 | yqjD | hypothetical protein S3349 |
| 61 | 82777539 | ycbO | alkanesulfonate transporter substrate-binding |
| 62 | 74313684 | yraM | putative glycosylase |
| 63 | 24113841 | SF2558 | OM protein assembly complex subunit YfgL |
| 64 | 24112186 | ybiS | hypothetical protein SF0769 |
| 65 | 24111697 | tauA | taurine transporter substrate binding subunit |
| 66 | 24115105 | yifL | putative outer membrane lipoprotein |
| 67 | 24113718 | vacJ | lipoprotein precursor |
| 68 | 1679580 | phoN | nonspecific phosphatase precursor [*Shigella flexneri*] |
| 69 | 13449092 | mxiD | Type III secretion protein |
| 70 | 24112703 | pspA | phage shock protein PspA [*Shigella flexneri* 2a str. 301] |
| 71 | 24112822 | yeaF | hypothetical protein SF1441 [*Shigella flexneri* 2a str. 301] |
| 72 | 24113297 | SF1963 | cystine transporter subunit |
| 73 | 24113931 | SF2652 | outer membrane protein assembly complex subunit YfiO [*Shigella flexneri* 2a str. 301] |
| 74 | 24114232 | sigA | serine protease [*S. flexneri* 2a str. 301] |
| 75 | 24115037 | ATP-synt_ab_C | F0F1 ATP synthase subunit alpha |
| 76 | 24115158 | glnA | glutamine synthetase [*Shigella flexneri* 2a str. 301] |
| 77 | 30061681 | aceF | dihydrolipoamide acetyltransferase |
| 78 | 30062108 | sucD | succinyl-CoA synthetase subunit alpha |
| 79 | 30062110 | sucB | dihydrolipoamide succinyltransferase |
| 80 | 30062117 | gltA | type II citrate synthase |
| 81 | 30062179 | dacA | D-alanyl-D-alanine carboxypeptidase fraction A |
| 82 | 30062295 | glnH | glutamine ABC transporter periplasmic protein |

TABLE 1-continued

| SEQ ID NO: | GI | Gene name | Definition |
|---|---|---|---|
| 83 | 30062539 | agp | Glucose-1-phosphate/inositol phosphatase |
| 84 | 30062760 | adhE | bifunctional acetaldehyde-CoA/alcohol dehydrogenase |
| 85 | 30062895 | mdoD | glucan biosynthesis protein D |
| 86 | 30062959 | gapA | glyceraldehyde-3-phosphate dehydrogenase |
| 87 | 30063091 | rspA | starvation sensing protein |
| 88 | 30063194 | S1842 | bifunctional cysteine desulfurase/selenocysteine lyase |
| 89 | 30063263 | zwf | glucose-6-phosphate 1-dehydrogenase |
| 90 | 30063276 | aspS | aspartyl-tRNA synthetase |
| 91 | 30063294 | sitA | Iron transport protein |
| 92 | 30063449 | yeeX | hypothetical protein S2177 |
| 93 | 30063472 | hisB | imidazole glycerol-phosphate dehydratase/histidinol phosphatase |
| 94 | 30063593 | mglB | Galactose-binding transport protein; receptor for galactose taxis |
| 95 | 30064126 | eno | phosphopyruvate hydratase |
| 96 | 30064248 | tktA | transketolase |
| 97 | 30064278 | ansB | L-asparaginase II |
| 98 | 30064289 | S3169 | superfamily I DNA helicase |
| 99 | 30064503 | yhbM | lipoprotein NlpI |
| 100 | 30064729 | rpoC | DNA-directed RNA polymerase subunit beta' |
| 101 | 30064730 | rpoB | DNA-directed RNA polymerase subunit beta |
| 102 | 30064872 | udp | uridine phosphorylase |
| 103 | 30064882 | pldA | phospholipase A |
| 104 | 30064963 | atpD | F0F1 ATP synthase subunit beta |
| 105 | 30065048 | iutA | putative ferric siderophore receptor |
| 106 | 30065119 | lldD | L-lactate dehydrogenase |
| 107 | 30065247 | nikA | Periplasmic binding proteins for nickel |
| 108 | 30065291 | glpD | glycerol-3-phosphate dehydrogenase |
| 109 | 30065404 | rpoA | DNA-directed RNA polymerase subunit alpha |
| 110 | 30065544 | hfq | RNA-binding protein Hfq |
| 111 | 56479788 | yccZ | exopolysaccharide export protein [Shigella flexneri 2a str. 301] |
| 112 | 56480532 | lamB | maltoporin [Shigella flexneri 2a str. 301] |
| 113 | 58045130 | sepA | SepA [Shigella flexneri] |
| 114 | 74310732 | aceE | pyruvate dehydrogenase subunit E1 [Shigella sonnei Ss046] |
| 115 | 74310771 | fhuA | ferrichrome outer membrane transporter [Shigella sonnei Ss046] |
| 116 | 74311118 | fepA | outer membrane receptor FepA [Shigella sonnei Ss046] |
| 117 | 74311859 | prc | Carboxy-terminal protease [Shigella sonni Ss046] |
| 118 | 74312394 | yciD | outer membrane protein W [Shigella sonnei Ss046] |
| 119 | 74312453 | prsA | ribose-phosphate pyrophosphokinase [Shigella sonnei Ss046] |
| 120 | 74312677 | cirA | colicin I receptor [Shigella sonnei Ss046] |
| 121 | 74312761 | glpQ | glycerophosphodiester phosphodiesterase [Shigella sonnei Ss046] |
| 122 | 74312989 | talA | transaldolase A [Shigella sonnei Ss046] |
| 123 | 74313764 | degQ | serine endoprotease [Shigella sonnei Ss046] |
| 124 | 74314527 | malE | maltose ABC transporter periplasmic protein [Shigella sonnei Ss046] |
| 125 | 82543910 | SBO_1406 | major capsid protein [Shigella boydii Sb227] |
| 126 | 82544504 | ycdO | hypothetical protein SBO_2040 [Shigella boydii Sb227] |
| 127 | 82545484 | dsbC | thiol:disulfide interchange protein DsbC [Shigella boydii Sb227] |
| 128 | 82777619 | ybjP | putative lipoprotein [Shigella dysenteriae Sd197] |
| 129 | 110807066 | yhbN | hypothetical protein SFV_3230 [Shigella flexneri 5 str. 8401] |
| 130 | 161486535 | yajG | hypothetical protein S0385 |
| 131 | 187427808 | tolC | outer membrane protein TolC [Shigella boydii CDC 3083-94] |
| 132 | 187731061 | SbBS512_E3369 | peptidase, M48B family [Shigella boydii CDC 3083-94] |
| 133 | 187731375 | SbBS512_E3904 | outer membrane lipoprotein, Slp family [Shigella boydii CDC 3083-94] |
| 134 | 187733898 | osmY | osmotically inducible protein Y [Shigella boydii CDC 3083-94] |
| 135 | 187734005 | bglX | beta-glucosidase, periplasmic [Shigella boydii CDC 3083-94] |
| 136 | 30065453 | pepA | leucyl aminopeptidase |

SEQ ID NOs: 70, 71, 73, 74, 76, 111, 112, 114-129 & 131-135 were identified from S. sonnei ΔtolR blebs. SEQ ID NOs: 8-15 & 17-58 were identified from S. sonnei ΔtolRΔgalU blebs. SEQ ID NOs: 83, 94, 97 & 107 were identified from S. flexneri ΔtolR blebs. SEQ ID NOs: 68, 69, 72, 75, 77-82, 84-93, 95, 96, 98-106, 108-10, 113, 130 & 136 were identified from S. flexneri ΔtolRΔrfbG blebs. SEQ ID NOs: 60-67 were identified from surface digestion of S. sonnei.

Subset 1:

SEQ ID NOs: 68, 69, 72, 75, 77-110, 113, 130 & 136.

Subset 2:

SEQ ID NOs: 8-15, 17-58, 60-67, 70, 71, 73, 74, 76, 111, 112, 114-129 & 131-135.

Subset 3:

SEQ ID NOs: 1-60.

NB: SEQ ID NO: 18 is the same as SEQ ID NO: 5; SEQ ID NO: 33 is the same as SEQ ID NO: 2; SEQ ID NOs: 9 & 16 are related (~97% identity); SEQ ID NOs: 23 & 59 are related (~98% identity).

REFERENCES

[1] Kweon (2008) Curr Opin Infect Dis. 21(3):313-8.
[2] Henry et al. (2004) Res Microbiol 155:437-46.
[3] Sandlin et al. (1995) Infect. Inzmun., 63:229-37.
[4] Edwards-Jones et al. (2004) Microbiol 150:1079-84.
[5] Köhler et al. (2002) Infect Immun 70:1150-8.
[6] d'Hauteville et al. (2002) J ImmunoL 168: 5240-51.
[7] Clementz et al. (1997) J. Biol. Chem. 16:10353-60.
[8] Nichols et al. (1997) J. Endotoxin Res. 4:163-72.
[9] Liu et al. (2005) Sci China C Life Sci. 48(3):228-40.
[10] Beloin et al. (2003) Mol Genet Genomics. 270(1):66-77.

[11] Day et al. (2001) *Infect Immun* 69:7471-80.
[12] Erlandson & Mackey (1958) *J Bacteriol* 75(3): 253-7.
[13] U.S. Pat. No. 5,681,736.
[14] Uyttendaele et at (2001) *International journal of food microbiology* 70(3):255-65.
[15] Gennaro (2000) *Remington: The Science and Practice of Pharmacy.* 20th edition, ISBN: 0683306472.
[16] WO90/14837.
[17] Podda & Del Giudice (2003) *Expert Rev Vaccines* 2:197-203.
[18] Podda (2001) *Vaccine* 19: 2673-2680.
[19] *Vaccine Design: The Subunit and Adjuvant Approach* (eds. Powell & Newman) Plenum Press 1995 (ISBN 0-306-44867-X).
[20] *Vaccine Adjuvants: Preparation Methods and Research Protocols* (Volume 42 of *Methods in Molecular Medicine* series). ISBN: 1-59259-083-7. Ed. O'Hagan.
[21] Allison & Byars (1992) *Res Immunol* 143:519-25.
[22] Hariharan et al. (1995) *Cancer Res* 55:3486-9.
[23] US-2007/014805.
[24] WO95/11700.
[25] U.S. Pat. No. 6,080,725.
[26] WO2006/113373.
[27] WO2005/097181.
[28] U.S. Pat. No. 5,057,540.
[29] WO96/33739.
[30] EP-A-0109942.
[31] WO96/11711.
[32] WO00/07621.
[33] Barr et al. (1998) *Advanced Drug Delivery Reviews* 32:247-271.
[34] Sjolanderet et al. (1998) *Advanced Drug Delivery Reviews* 32:321-338.
[35] EP-A-0689454.
[36] Johnson et al. (1999) *Bioorg Med Chem Lett* 9:2273-2278.
[37] Evans et al. (2003) *Expert Rev Vaccines* 2:219-229.
[38] Meraldi et al. (2003) *Vaccine* 21:2485-2491.
[39] Pajak at al. (2003) *Vaccine* 21:836-842.
[40] Kandimalla et al. (2003) *Nucleic Acids Research* 31:2393-2400.
[41] WO02/26757.
[42] WO99/62923.
[43] Krieg (2003) *Nature Medicine* 9:831-835.
[44] McCluskie et al. (2002) *FEMS Immunology and Medical Microbiology* 32:179-185.
[45] WO98/40100.
[46] U.S. Pat. No. 6,207,646.
[47] U.S. Pat. No. 6,239,116.
[48] U.S. Pat. No. 6,429,199.
[49] Kandimalla et al. (2003) *Biochemical Society Transactions* 31 (part 3):654-658.
[50] Blackwell et al. (2003) *J Immunol* 170:4061-4068.
[51] Krieg (2002) *Trends Immunol* 23:64-65.
[52] WO01/95935.
[53] Kandimalla et al. (2003) *BBRC* 306:948-953.
[54] Bhagat et al. (2003) *BBRC* 300:853-861.
[55] WO03/035836.
[56] Schellack et al. (2006) *Vaccine* 24:5461-72.
[57] Lingnau et al. (2007) *Expert Rev Vaccines* 6:741-6.
[58] WO2004/084938.
[59] WO95/17211.
[60] WO98/42375.
[61] Beignon et al. (2002) *Infect Immun* 70:3012-3019.
[62] Pizza et al. (2001) *Vaccine* 19:2534-2541.
[63] Pizza at al. (2000) *Int J Med Microbiol* 290:455-461.
[64] Scharton-Kersten et al. (2000) *Infect Immun* 68:5306-5313.
[65] Ryan et al. (1999) *Infect Immun* 67:6270-6280.
[66] Partidos at al. (1999) *Immunol Lett* 67:209-216.
[67] Peppoloni et al. (2003) *Expert Rev Vaccines* 2:285-293.
[68] Pine et at (2002) *J Control Release* 85:263-270.
[69] Tebbey et al. (2000) *Vaccine* 18:2723-34.
[70] Domenighini et al. (1995) *Mol Microbiol* 15:1165-1167.
[71] WO99/40936.
[72] WO99/44636.
[73] Singh et al] (2001) *J Cont Release* 70:267-276.
[74] WO99/27960.
[75] U.S. Pat. No. 6,090,406.
[76] U.S. Pat. No. 5,916,588.
[77] EP-A-0626169.
[78] Stanley (2002) *Clin Exp Dermatol* 27:571-577.
[79] Jones (2003) *Curr Opin Investig Drugs* 4:214-218.
[80] WO99/11241.
[81] WO94/00153.
[82] WO98/57659.
[83] European patent applications 0835318, 0735898 and 0761231.
[84] *Current Protocols in Molecular Biology* (F. M. Ausubel et al., eds., 1987) Supplement 30.
[85] Smith & Waterman (1981) *Adv. Appl. Math.* 2:482-489.
[86] Geysen at al. (1984) *PNAS USA* 81:3998-4002.
[87] Carter (1994) *Methods Mol Biol* 36:207-23.
[88] Jameson, B A et al. 1988, *CABIOS* 4(1):181-186.
[89] Raddrizzani & Hammer (2000) *Brief Bioinform* 1(2): 179-89.
[90] Bublil at al. (2007) *Proteins* 68(1):294-304.
[91] De Lalla et al. (1999) *J. Immunol.* 163:1725-29.
[92] Kwok et al. (2001) *Trends Immunol* 22:583-88.
[93] Brusic at al. (1998) *Bioinformatics* 14(2):121-30
[94] Meister et al. (1995) *Vaccine* 13(6):581-91.
[95] Roberts et al. (1996) *AIDS Res Hum Retroviruses* 12(7):593-610.
[96] Maksyutov & Zagrebelnaya (1993) *Comput Appl Biosci* 9(3):291-7.
[97] Feller & de la Cruz (1991) *Nature* 349(6311):720-1.
[98] Hopp (1993) *Peptide Research* 6:183-190.
[99] Welling et al. (1985) *FEBS Lett.* 188:215-218.
Davenport et al. (1995) *Immunogenetics* 42:392-297.
Chen et al. (2007) *Amino Acids* 33(3):423-8.
Murphy & Campellone (2003) *BMC Molecular Biology* 4:11.

The invention claimed is:

1. A *Shigella* bacterium which expresses TolA, TolB, TolQ, and Pal proteins, does not express TolR protein, and does not express a native *Shigella lipopolysaccharide*, wherein the bacterium is *Shigella sonnei* or *Shigella flexneri*, and, during growth in culture medium, releases greater quantities of outer membrane blebs into the medium than the same bacterium expressing all of TolA, TolB, TolQ, TolR, and Pal proteins.

2. The *Shigella* bacterium of claim 1, which is a ΔtolR strain of *Shigella*.

3. The *Shigella* bacterium of claim 2, wherein the bacterium does not express a native *Shigella lipopolysaccharide* and does not express a native *Shigella* O antigen.

4. The *Shigella* bacterium of claim 1, wherein the TolA, TolQ, and/or Pal protein is located in the bacterium's inner or outer membrane.

5. The *Shigella* bacterium of claim 1, wherein the *Shigella* bacterium additionally does not express a *Shigella* enteric toxin.

6. The *Shigella* bacterium of claim 1, which does not express the functional HtrB enzyme.

7. The *Shigella* bacterium of claim 6, which is a htrB knockout.

8. The *Shigella* bacterium of claim 2, wherein the bacterium is of a ΔtolRΔgalU strain.

9. The *Shigella* bacterium of claim 2, wherein a stxA and/or stxB gene is inactivated.

10. Culture medium comprising a bacterium of claim 5, which has been grown under conditions which permit the release of blebs into the medium by the bacterium.

11. A method of producing *Shigella sonnei* or *Shigella flexneri* blebs, comprising culturing the bacterium of claim 1 in a culture medium under conditions which permit the release of blebs into the medium by the bacterium and separating the released blebs from the culture medium.

12. The method of claim 11, wherein the bacterium has been grown under iron-limiting conditions.

* * * * *